US011591592B2

(12) United States Patent
Belgrader et al.

(10) Patent No.: US 11,591,592 B2
(45) Date of Patent: Feb. 28, 2023

(54) COMPOSITIONS, METHODS, MODULES AND INSTRUMENTS FOR AUTOMATED NUCLEIC ACID-GUIDED NUCLEASE EDITING IN MAMMALIAN CELLS USING MICROCARRIERS

(71) Applicant: Inscripta, Inc., Boulder, CO (US)

(72) Inventors: Phillip Belgrader, Pleasanton, CA (US); Nathan Bade, Boulder, CO (US); Christian Siltanen, Boulder, CO (US); Aamir Mir, Boulder, CO (US); Xi-Jun Chen, Boulder, CO (US); Janine Mok, Boulder, CO (US); Burak Dura, Boulder, CO (US); Bruce Chabansky, Boulder, CO (US); David Stumbo, Boulder, CO (US); Eric Smith, Boulder, CO (US); Jorge Bernate, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 17/239,540

(22) Filed: Apr. 23, 2021

(65) Prior Publication Data
US 2021/0332389 A1 Oct. 28, 2021

Related U.S. Application Data

(60) Provisional application No. 63/092,499, filed on Oct. 15, 2020, provisional application No. 63/014,944, filed on Apr. 24, 2020.

(51) Int. Cl.
| *C12N 15/11* | (2006.01) |
| *C12N 15/10* | (2006.01) |
| *C12M 1/34* | (2006.01) |
| *C12M 1/26* | (2006.01) |
| *C12N 15/113* | (2010.01) |
| *C12N 15/86* | (2006.01) |
| *C12M 3/00* | (2006.01) |
| *C12M 3/04* | (2006.01) |
| *C12M 1/00* | (2006.01) |
| *C12N 5/074* | (2010.01) |
| *C12N 15/88* | (2006.01) |
| *C12N 15/90* | (2006.01) |

(Continued)

(52) U.S. Cl.
CPC .... *C12N 15/1082* (2013.01); *B01L 3/502761* (2013.01); *B01L 7/00* (2013.01); *C12M 23/12* (2013.01); *C12M 23/16* (2013.01); *C12M 23/42* (2013.01); *C12M 23/50* (2013.01); *C12M 27/10* (2013.01); *C12M 29/04* (2013.01); *C12M 33/14* (2013.01); *C12M 41/36* (2013.01); *C12M 43/00* (2013.01); *C12M 47/02* (2013.01); *C12M 47/04* (2013.01); *C12N 5/0696* (2013.01); *C12N 15/1065* (2013.01); *C12N 15/1068* (2013.01); *C12N 15/11* (2013.01); *C12N 15/113* (2013.01); *C12N 15/86* (2013.01); *C12N 15/88* (2013.01); *C12N 15/907* (2013.01); *B01L 2200/0647* (2013.01); *B01L 2300/0681* (2013.01); *B01L 2300/123* (2013.01); *B01L 2300/161* (2013.01); *B01L 2400/0415* (2013.01); *B01L 2400/0421* (2013.01); *B01L 2400/0424* (2013.01); *C12N 9/22* (2013.01); *C12N 2310/20* (2017.05); *C12N 2510/00* (2013.01); *C12N 2740/10011* (2013.01); *C12N 2740/15011* (2013.01); *C12N 2750/14111* (2013.01); *C12N 2800/80* (2013.01)

(58) Field of Classification Search
CPC .............. C12N 15/907; C12N 15/1065; C12N 15/1068; C12N 15/11; C12N 15/88; C12N 5/0696; C12N 9/22; C12N 2310/20; C12N 2510/00; C12N 2800/80; C12M 23/42; C12M 27/10; C12M 43/00; C12M 47/02; C12M 29/04
See application file for complete search history.

(56) References Cited

U.S. PATENT DOCUMENTS

| 4,833,080 A | 5/1989 | Brent et al. |
| 4,959,317 A | 9/1990 | Sauer et al. |
| 5,464,764 A | 11/1995 | Capecchi et al. |
| 5,487,992 A | 1/1996 | Capecchi et al. |
| 5,627,059 A | 5/1997 | Capecchi et al. |
| 5,631,153 A | 5/1997 | Capecchi et al. |

(Continued)

FOREIGN PATENT DOCUMENTS

| CN | 2397122 Y | 9/2000 |
| EP | 2135626 A1 | 12/2009 |

(Continued)

OTHER PUBLICATIONS

Sivalingam et al. Superior Red Blood Cell Generation from Human Pluripotent Stem Cells Through a Novel Microcarrier-Based Embryoid Body Platform. Tissue Engineering Part C: Methods. vol. 22, No. 8, pp. 765-780 (Year: 2016).*

(Continued)

*Primary Examiner* — Nancy J Leith
*Assistant Examiner* — Khaleda B Hasan
(74) *Attorney, Agent, or Firm* — Bookoff McAndrews, PLLC

(57) ABSTRACT

This invention relates to compositions of matter, methods, modules and automated, end-to-end closed instruments for automated mammalian cell growth, reagent bundle creation and mammalian cell transfection followed by nucleic acid-guided nuclease editing in live mammalian cells. The disclosed compositions and method entail making "reagent bundles" comprising many (hundreds of thousands to millions) clonal copies of an editing cassette and delivering or co-localizing the reagent bundles with live mammalian cells such that the editing cassettes edit the cells and the edited cells continue to grow.

30 Claims, 60 Drawing Sheets

(51) Int. Cl.
  *B01L 3/00* (2006.01)
  *B01L 7/00* (2006.01)
  *C12M 1/32* (2006.01)
  *C12M 3/06* (2006.01)
  *C12N 9/22* (2006.01)

(56) References Cited

U.S. PATENT DOCUMENTS

| | | |
|---|---|---|
| 5,654,182 A | 8/1997 | Wahl et al. |
| 5,677,177 A | 10/1997 | Wahl et al. |
| 5,710,381 A | 1/1998 | Atwood et al. |
| 5,792,943 A | 8/1998 | Craig |
| 5,885,836 A | 3/1999 | Wahl et al. |
| 5,888,732 A | 3/1999 | Hartley et al. |
| 6,074,605 A | 6/2000 | Meserol et al. |
| 6,127,141 A | 10/2000 | Kopf |
| 6,143,527 A | 11/2000 | Pachuk et al. |
| 6,150,148 A | 11/2000 | Nanda et al. |
| 6,204,061 B1 | 3/2001 | Capecchi et al. |
| 6,277,608 B1 | 8/2001 | Hartley et al. |
| 6,391,582 B2 | 5/2002 | Ying et al. |
| 6,482,619 B1 | 11/2002 | Rubinsky et al. |
| 6,509,156 B1 | 1/2003 | Stewart |
| 6,654,636 B1 | 11/2003 | Dev et al. |
| 6,689,610 B1 | 2/2004 | Capecchi et al. |
| 6,746,441 B1 | 6/2004 | Hofmann et al. |
| 6,774,279 B2 | 8/2004 | Dymecki |
| 6,916,632 B2 | 7/2005 | Chesnut et al. |
| 6,956,146 B2 | 10/2005 | Wahl et al. |
| 7,029,916 B2 | 4/2006 | Dzekunov et al. |
| 7,112,715 B2 | 9/2006 | Chambon et al. |
| 7,141,425 B2 | 11/2006 | Dzekunov et al. |
| 7,422,889 B2 | 9/2008 | Sauer et al. |
| 8,110,122 B2 | 2/2012 | Alburty et al. |
| 8,110,360 B2 | 2/2012 | Serber et al. |
| 8,153,432 B2 | 4/2012 | Church et al. |
| 8,332,160 B1 | 12/2012 | Platt et al. |
| 8,569,041 B2 | 10/2013 | Church et al. |
| 8,584,535 B2 | 11/2013 | Page et al. |
| 8,584,536 B2 | 11/2013 | Page et al. |
| 8,667,839 B2 | 3/2014 | Kimura |
| 8,667,840 B2 | 3/2014 | Lee et al. |
| 8,677,839 B2 | 3/2014 | Page et al. |
| 8,677,840 B2 | 3/2014 | Page et al. |
| 8,697,359 B1 | 4/2014 | Zhang et al. |
| 8,726,744 B2 | 5/2014 | Alburty et al. |
| 8,758,623 B1 | 6/2014 | Alburty et al. |
| 8,921,332 B2 | 12/2014 | Choulika et al. |
| 8,926,977 B2 | 1/2015 | Miller et al. |
| 8,932,850 B2 | 1/2015 | Chang et al. |
| 9,029,109 B2 | 5/2015 | Hur et al. |
| D731,634 S | 6/2015 | Page et al. |
| 9,063,136 B2 | 6/2015 | Talebpour et al. |
| 9,175,259 B2 | 11/2015 | Nankervis |
| 9,260,505 B2 | 2/2016 | Weir et al. |
| 9,361,427 B2 | 6/2016 | Hillson |
| 9,499,855 B2 | 11/2016 | Hyde et al. |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill |
| 10,017,760 B2 | 7/2018 | Gill et al. |
| 10,179,898 B2 | 1/2019 | Khan |
| 10,227,576 B1 | 3/2019 | Cameron et al. |
| 10,240,117 B2 | 3/2019 | Dahlberg et al. |
| 10,266,851 B2 | 4/2019 | Chen |
| 10,294,447 B2 | 5/2019 | Reif et al. |
| 10,370,629 B2 | 8/2019 | Mietzner et al. |
| 10,577,576 B2 | 3/2020 | Nankervis et al. |
| 10,633,625 B2 | 4/2020 | Nankervis et al. |
| 10,669,519 B2 | 6/2020 | Stanton, IV et al. |
| 10,837,021 B1 | 11/2020 | Tian et al. |
| 10,927,385 B2 | 2/2021 | Kannan et al. |
| 2003/0059945 A1 | 3/2003 | Dzekunov et al. |
| 2003/0073238 A1 | 4/2003 | Dzekunov et al. |
| 2003/0104588 A1 | 6/2003 | Orwar et al. |
| 2004/0110253 A1 | 6/2004 | Kappler et al. |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2005/0118705 A1 | 6/2005 | Rabbitt et al. |
| 2006/0001865 A1 | 1/2006 | Bellalou et al. |
| 2006/0224192 A1 | 10/2006 | Dimmer et al. |
| 2007/0020761 A1* | 1/2007 | Yu .................. C12N 15/87 435/459 |
| 2007/0042427 A1 | 2/2007 | Gerdes et al. |
| 2007/0105206 A1 | 5/2007 | Lu et al. |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2010/0055790 A1 | 3/2010 | Simon |
| 2010/0076057 A1 | 3/2010 | Sontheimer et al. |
| 2011/0002812 A1 | 1/2011 | Asogawa et al. |
| 2011/0003303 A1 | 1/2011 | Pagano et al. |
| 2011/0009807 A1 | 1/2011 | Kjeken et al. |
| 2011/0065171 A1 | 3/2011 | Dzekunov et al. |
| 2011/0213288 A1 | 9/2011 | Choi et al. |
| 2011/0236962 A1 | 9/2011 | Loebbert et al. |
| 2012/0156786 A1 | 6/2012 | Bebee |
| 2013/0005025 A1 | 1/2013 | Church et al. |
| 2013/0196441 A1 | 8/2013 | Rubinsky et al. |
| 2013/0236970 A1 | 9/2013 | Anneren et al. |
| 2014/0068797 A1 | 3/2014 | Doudna et al. |
| 2014/0121728 A1 | 5/2014 | Dhillon et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2014/0350456 A1 | 11/2014 | Caccia |
| 2015/0071898 A1 | 3/2015 | Liu et al. |
| 2015/0072413 A1 | 3/2015 | Zenhausern et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0297887 A1 | 10/2015 | Dhillon et al. |
| 2015/0344549 A1 | 12/2015 | Muir et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0272961 A1 | 9/2016 | Lee |
| 2016/0281047 A1 | 9/2016 | Chen et al. |
| 2016/0281053 A1 | 9/2016 | Sorek et al. |
| 2016/0289673 A1 | 10/2016 | Huang et al. |
| 2016/0298074 A1 | 10/2016 | Dai |
| 2016/0298134 A1 | 10/2016 | Chen et al. |
| 2016/0310943 A1 | 10/2016 | Woizenko et al. |
| 2016/0313366 A1 | 10/2016 | Ingber et al. |
| 2016/0354487 A1 | 12/2016 | Zhang et al. |
| 2016/0367991 A1 | 12/2016 | Cepheid |
| 2017/0002339 A1 | 1/2017 | Barrngou et al. |
| 2017/0022499 A1 | 1/2017 | Lu et al. |
| 2017/0029805 A1 | 2/2017 | Li et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0218355 A1 | 8/2017 | Buie et al. |
| 2017/0240922 A1 | 8/2017 | Gill et al. |
| 2017/0283761 A1 | 10/2017 | Corso |
| 2017/0307606 A1 | 10/2017 | Hallock |
| 2017/0349874 A1 | 12/2017 | Jaques et al. |
| 2017/0369870 A1 | 12/2017 | Gill et al. |
| 2018/0023045 A1 | 1/2018 | Hallock et al. |
| 2018/0028567 A1 | 2/2018 | Li et al. |

(56) References Cited

U.S. PATENT DOCUMENTS

| | | | |
|---|---|---|---|
| 2018/0051327 | A1 | 2/2018 | Blainey et al. |
| 2018/0052176 | A1 | 2/2018 | Holt et al. |
| 2018/0073013 | A1 | 3/2018 | Lorenz et al. |
| 2018/0112235 | A1 | 4/2018 | Li et al. |
| 2018/0142196 | A1 | 5/2018 | Coppeta et al. |
| 2018/0155665 | A1 | 6/2018 | Zenhausern et al. |
| 2018/0169148 | A1 | 6/2018 | Adair et al. |
| 2018/0179485 | A1 | 6/2018 | Borenstein et al. |
| 2018/0187149 | A1 | 7/2018 | Ma et al. |
| 2018/0200342 | A1 | 7/2018 | Bikard et al. |
| 2018/0230460 | A1 | 8/2018 | Gill et al. |
| 2019/0017072 | A1 | 1/2019 | Ditommaso et al. |
| 2019/0136230 | A1 | 5/2019 | Sather et al. |
| 2019/0169605 | A1 | 6/2019 | Masquelier et al. |
| 2019/0194650 | A1* | 6/2019 | Gill ..................... C12N 15/102 |
| 2019/0225928 | A1* | 7/2019 | Masquelier ............ C12M 41/46 |
| 2020/0263197 | A1 | 8/2020 | Cheng et al. |

FOREIGN PATENT DOCUMENTS

| | | |
|---|---|---|
| EP | 2240238 | 10/2010 |
| EP | 2395087 | 12/2011 |
| EP | 3030652 | 6/2016 |
| EP | 1766004 | 8/2016 |
| EP | 3199632 | 8/2017 |
| EP | 2459696 | 11/2017 |
| WO | WO 2003/057819 | 7/2001 |
| WO | WO2002/010183 | 2/2002 |
| WO | WO 2003/087341 | 10/2003 |
| WO | WO 2009/091578 | 7/2009 |
| WO | WO 2010/079430 | 7/2010 |
| WO | WO 2011/072246 | 6/2011 |
| WO | WO2011/143124 | 11/2011 |
| WO | WO 2012/012779 A3 | 1/2012 |
| WO | WO2013/142578 | 9/2013 |
| WO | WO 2013/176772 | 11/2013 |
| WO | WO2014/018423 | 1/2014 |
| WO | WO2014/144495 | 9/2014 |
| WO | WO 201/5021270 | 2/2015 |
| WO | WO 2016/003485 | 1/2016 |
| WO | WO 2016/054939 | 4/2016 |
| WO | WO2016/110453 | 7/2016 |
| WO | WO 2016/110453 | 7/2016 |
| WO | WO 2016/145290 | 9/2016 |
| WO | WO2017/053902 | 3/2017 |
| WO | WO 2017/078631 | 5/2017 |
| WO | WO2017/083722 | 5/2017 |
| WO | WO2017/106414 | 6/2017 |
| WO | WO 2017/106414 | 6/2017 |
| WO | WO2017/161371 | 9/2017 |
| WO | WO2017/174329 | 10/2017 |
| WO | WO2017/186718 | 11/2017 |
| WO | WO2017/212400 | 12/2017 |
| WO | WO2017/216392 | 12/2017 |
| WO | WO 2017/216392 | 12/2017 |
| WO | WO 2017/223330 | 12/2017 |
| WO | WO2017/223330 | 12/2017 |
| WO | WO 2018/015544 | 1/2018 |
| WO | WO2018/031950 | 2/2018 |
| WO | WO2018/071672 | 4/2018 |
| WO | WO2018/083339 | 5/2018 |
| WO | WO 2018/191715 | 10/2018 |
| WO | WO2019/006436 | 1/2019 |
| WO | WO2019/046766 | 3/2019 |
| WO | WO 2019/200004 A1 | 10/2019 |
| WO | WO2019/209926 | 10/2019 |
| WO | WO 2020/005383 A1 | 1/2020 |
| WO | WO2020/021045 | 1/2020 |
| WO | WO-2020005383 A1 * | 1/2020 ............. C12N 15/87 |

OTHER PUBLICATIONS

Unciti-Broceta et al. Combining Nebulization-Mediated Transfection and Polymer Microarrays for the Rapid Determination of Optimal Transfection Substrates. Journal of Combinatorial Chemistry. 10 (2), pp. 179-184 (Year: 2008).*

Yu et al. Improved delivery of Cas9 protein/gRNA complexes using lipofectamine CRISPRMAX. Biotechnol Lett. 38, pp. 919-929 (Year: 2016).*

Chen et al. Human Pluripotent Stem Cell Culture: Considerations for Maintenance, Expansion, and Therapeutics. Cell Stem Cell. vol. 14, Issue 1, Jan. 2, 2014, pp. 13-26 (Year: 2014).*

Bao, et al., "Genome-scale engineering of *Saccharomyces cerevisiae* with single-nucleotide precision", Nature Biotechnology, doi:10.1038/nbt.4132, pp. 1-6 (May 7, 2018).

Dicarlo, et al., "Genome engineering in *Saccharomyces cervisiae* using CRISPR-Case systems", Nucleic Acids Research, 41(7):4336-43 (2013).

Eklund, et al., "Altered target site specificity variants of the I-Ppol His-Cys bis homing endonuclease" Nucleic Acids Research, 35(17):5839-50 (2007).

Garst, et al., "Genome-wide mapping of mutations at singie-nucleotide resolution for protein, metabolic and genome engineering", Nature Biotechnology, 35(1):48-59 (2017).

Boles, et al., "Digital-to-biological converter for on-demand production of biologies", Nature Biotechnology, doi:10.1038/nbt.3859 (May 29, 2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Pines, et al., "Codon Compression Algorithms for Saturation Mutagenesis", ACS Synthetic Biology, 4:604-14 (2015).

Verwaal, et al., "CRISPR/Cpfl enables fast and simple genome editing of *Saccharamyces cerevisiae*", Yeast, 35:201-11 (2018).

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

Roy, et cl., "Multiplexed precision genome editing with trackable genomic barcodes in yeast", Nature Biotechnolgy, doi:10.1038/nbt.4137, pp. 1-16 (2018).

Bessa et al., "Improved gap repair cloning in yeast: treatment of the gapped vector with Taq DNA polymerase avoids vector self-ligation," Yeast, 29(10):419-23 (2012).

Boch, "TALEs of genome targeting," Nature Biotechnology vol. 29, pp. 135-136 (2011).

Campbell et al., "Targeting protein function: the expanding toolkit for conditional disruption," Biochem J., 473(17):2573-2589 (2016).

Casini et al., "Bricks and blueprints: methods and standards for DNA assembly," Nat Rev Mol Cell Biol., (9):568-76 (2015).

Chica et al., "Semi-rational approaches to engineering enzyme activity: combining the benefits of directed evolution and rational design," Current Opinion in Biotechnology, 16(4): 378-384 (2005).

Cramer et al., "Functional association between promoter structure and transcript alternative splicing," PNAS USA, 94(21):11456-60 (1997).

Dalphin et al., "Transterm: A Database of Translational Signals," Nucl. Acids Res., 24(1): 216-218 (1996).

Datsenko and Wanner, "One-step inactivation of chromosomal genes in *Escherichia coli* K-12 using PCR products", PNAS USA, 97(12):6640-5 (2000).

De Kok et al., "Rapid and reliable DNA assembly via ligase cycling reaction," ACS Synth Biol., 3(2):97-106 (2014).

Desmet et al., "Human Splicing Finder: an online bioinformatics tool to predict splicing signals," Nucleic Acids Res., 37(9):e67 (2009).

Divina et al., "Ab Initio prediction of mutation-induced cryptic splice-site activation and exon skipping," European Journal of Human Genetics, 17:759-765 (2009).

Dong, "Establishment of a highly efficient virus-inducible CRISPR/Cas9 system in insect cells," Antiviral Res., 130:50-7(2016).

(56) References Cited

OTHER PUBLICATIONS

Durai et al., "Zinc finger nucleases: custom-designed molecular scissors for genome engineering of plant and mammalian cells", Nucleic Acids Res., 33(18):5978-90 (2005).
Engler et al., "PLoS One, A One Pot, One Step, Precision Cloning Method with High Throughput Capability," 3(11):e3647 (2008).
Epinat et al., "A novel engineered meganuclease induces homologous recombination in eukaryotic cells, e.g., yeast and mammalian cells", Nucleic Acids Research, 31(11): 2952-2962.
Faber et al., "Genome-wide prediction of splice-modifying SNPs in human genes using a new analysis pipeline called AASsites," BMC Bioinformatics, 12(suppl 4):S2 (2011).
Farasat et al., "A Biophysical Model of CRISPR/Cas9 Activity for Rational Design of Genome Editing and Gene Regulation," PLoS Comput Biol., 29:12(1):e1004724 (2016).
Adamo, et al., "Flow-through comb electroporation device for delivery of macromolecules", Analytical Chemistry, 85(3):1637-41 (2015).
Greger et al., "Balancing transcriptional interference and initiation on the GAL7 promoter of Saccharomyces cerevisiae," PNAS, 97(15):8415-20 (2000).
Juan et al., "Histone deacetylases specifically down-regulate p53-dependent gene activation," Journal of Biological Chemistry 275.27 (2000): 20436-20443.
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20(1): 81-9 (2009).
Lefevre et al., "Alanine-stretch scanning mutagenesis: a simple and efficient method to probe protein structure and function, "Nucleic Acids Research, vol. 25(2):447-448 (1997).
Liu et al., "A chemical-inducible CRISPR-Cas9 system for rapid control of genome editing", Nature Chemical Biology, 12:980-987(2016).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Mullick et al., "The cumate gene-switch: a system for regulated expression in mammalian cells", BMC Biotechnology, 6:43 (2006).
Nalla et al., "Automated splicing mutation analysis by information theory," Hum. Mutat., 25:334-342 (2005).
No et al., "Ecdysone-inducible gene expression in mammallan cells and transgenic mice," PNAS, 93(8):3346-3351 (1996).
Ohtsuka, "Lantibiotics: mode of action, biosynthesis and bioengineering," Curr Pharm Biotechnol, 10(2):244-51 (2009).
Patron, "DNA assembly for plant biology: techniques and tools," Curr Opinion Plant Biol., 19:14-9 (2014).
Sands et al., "Overview of Post Cohen-Boyer Methods for Single Segment Cloning and for Multisegment DNA Assembly," Curr Protoc Moi Biol., 113:3.26.1-3.26.20 (2016).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
West et al., "Molecular Dissection of Mammalian RNA Polymerase II Transcriptional Termination," Mol Cell. 29(5):600-10 (2008).
West et al., "Transcriptional Termination Enhances Protein Expression in Human Cells," Mol Cell.; 33(3-9); 354-364 (2009).
International Search Report and Written Opinion for International Application No. PCT/US2018/040519, dated Sep. 26, 2018, p. 1-8.
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Nov. 23, 2018, p. 1-12.
International Search Report and Written Opinion for International Application No. PCT/US2019/023342 dated Jun. 6, 2019, p. 1-12.
International Search Report and Written Opinion for International Application No. PCT/US2019/026836 dated July 2, 2019, p. 1-10.
International Search Report and Written Opinion for International Application No. PCT/US2019/028821 dated August 2, 2019, p. 1-14.
International Search Report and Written Opinion for Interational Application No. PCT/US2019/028883 dated Aug. 16, 2019, p. 1-12.
International Search Report and Written Opinion for International Application No. PCT/US2019/030085 dated Jul. 23, 2019, p. 1-14.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication for U.S. Appl. No. 16/024,831, dated Feb. 12, 2019, p. 1-37.
First Office Action Interview Pilot Program Pre-Interview Communication for U.S. Appl. No. 16/360,404 dated Jul. 1, 2019, p. 1-27.
First Office Action Interview Pilot Program Pre-Interview Communication for U.S. Appl. No. 16/360,423 dated Jul. 1, 2019, p. 1-27.
Non Final Office Action for U.S. Appl. No. 16/399,988 dated Jul. 31, 2019, p. 1-20.
First Office Action Interview Pilot Program Pre-Interview Communication for U.S. Appl. No. 16/454,865 dated Aug. 16, 2019, p. 1-36.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
Yoshioka, et al., "Development for a mono-promoter-driven CRISPR/CAS9 system in mammalian cells", Scientific Reports, Jul. 3, 2015, p. 1-8.
Remaut, et al., "Plasmid vectors for high-efficiency expression controlled by the PL promoter of coliphage lambda", Laboratory of Molecular Biology, Apr. 15, 1981, p. 81-93.
International Search Report and Written Opinion for International Application No. PCT/US19/46515, dated Oct. 28, 2019, p. 1-11.
International Search Report and Written Opinion for International Application No. PCT/US19/49735, dated Nov. 18, 2019, p. 1-13.
International Search Report and Written Opinion for International Application No. PCT/US19/46526, dated Dec. 18, 2019, p. 1-17.
International Search Report and Written Opinion for International Application No. PCT/US18/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US20/24341, dated Jun. 19, 2020, p. 1-9.
International Search Report and Written Opinion for International Application No. PCT/US19/47135, dated Jun. 11, 2020, p. 1-15.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.

(56) References Cited

OTHER PUBLICATIONS

Anzalone et al., "Search-and-replace genome editing without doubles-strand breaks or donor DNA," Nature, Oct. 21, 2019, vol. 576, No. 7785, pp. 149-157.

International Search Report and Written Opinion for International Application No. PCT/US2020/038345, dated Nov. 23, 2020, p. 1-13.

International Search Report and Written Opinion for International Application No. PCT/US21/29008, dated Aug. 24, 2021, p. 1-19.

International Search Report and Written Opinion for International Application No. PCT/US21/29011, dated Aug. 24, 2021, p. 1-20.

Sivalingam, et al., "Superior Red Blood Cell Generation from Human Pluripotent Stem Cells Through a Novel Microcarrier-Based Embryoid Body Platform", Tissue Engineering: Part C. Aug. 2016, vol. 22, No. 8, p. 765-780.

Kim, et al., "Formation of Thermoresponsive Poly(Nisopropylacrylamide)/Dextran Particles by Atom Transfer Radical Polymerization". Macromolecular Rapid Communications. May 19, 2003, vol. 24, No. 8, p. 517-521.

Jacobi, et al., "Simplified CRISPR tools for the efficient genome editing and streamlined protocols for their delivery into mammalian cells and mouse zygotes". Methods. May 15, 2017, vol. 121-122, p. 16-28.

Nienow, et al., "A potentially scalable method for the harvesting of hMSCs from microcarriers". Biochemical Engineering Journal. Apr. 15, 2014, vol. 85, p. 79-88.

Bauer, et al., "Cell-Microcarrier Adhesion to Gas-Liquid interfaces and Foam". Biotechnology Progress. Jan.-Feb. 2000, vol. 16, p. 125-132.

GE Healthcare Life Sciences, "Microcarrier Cell Culture Principles and Methods". Nov. 2013, <URL:https://www.cytivalifesciences.co.kr/wp-content/uploads/2020/04/AC-Microcarrier-cell-culture.pdf<, m p. 19.

Fayazpour, et al., "Evaluation of Digitally Encoded Layer-by-layer Coated Microparticles as Cell Carriers", Advanced Functional Materials, Sep. 1, 2008, 18, doi: 10.1002/adfm.200800255, pp. 2716-2723.

Fayazpour, "Exploring New Applications For Photophysically Encoded Microcarriers", Ghent University Faculty of Pharmaceutical Sciences, Thesis submitted Sep. 2008, pp. 1-159.

Bengali, et al., "Gene Delivery Through Cell Culture Substrate Adsorbed DNA Complexes", Biotechnol Bioeng., May 5, 2005; doi:10.1002/bit.20393; pp. 1-23.

Segura, et al., "Substrate-mediated DNA delivery: role of the cationic polymer structure and extent of modification", Journal of Controlled Release, 93, Aug. 9, 2003, pp. 69-84.

\* cited by examiner

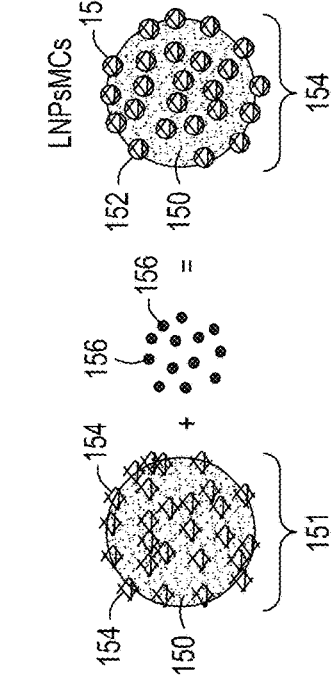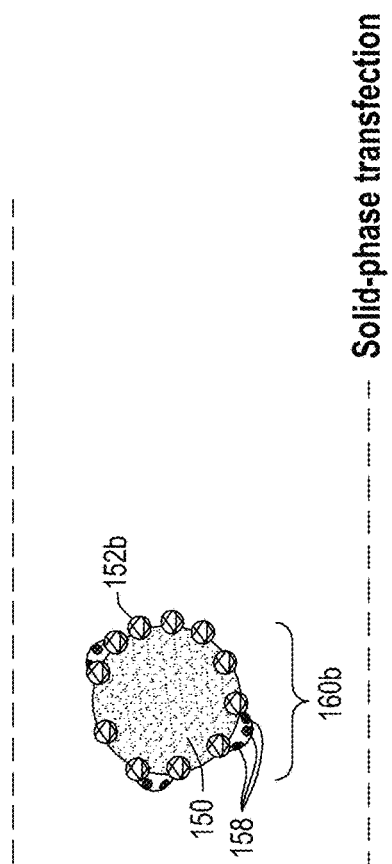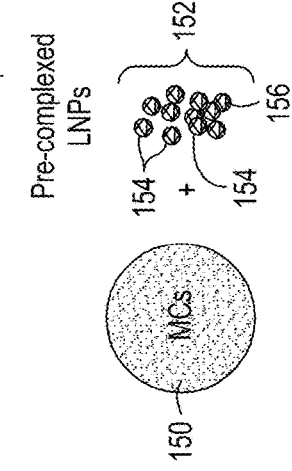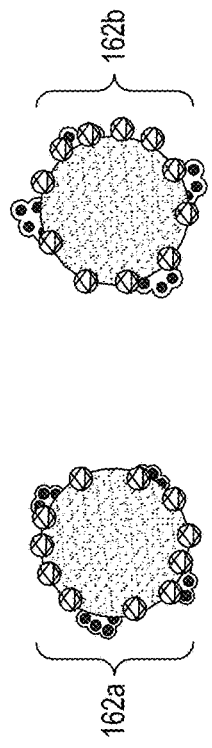
FIG. 1B

CREATING BEADS WITH HIGH COPY NUMBER LINEAR AMPLICONS ON BEAD SURFACE

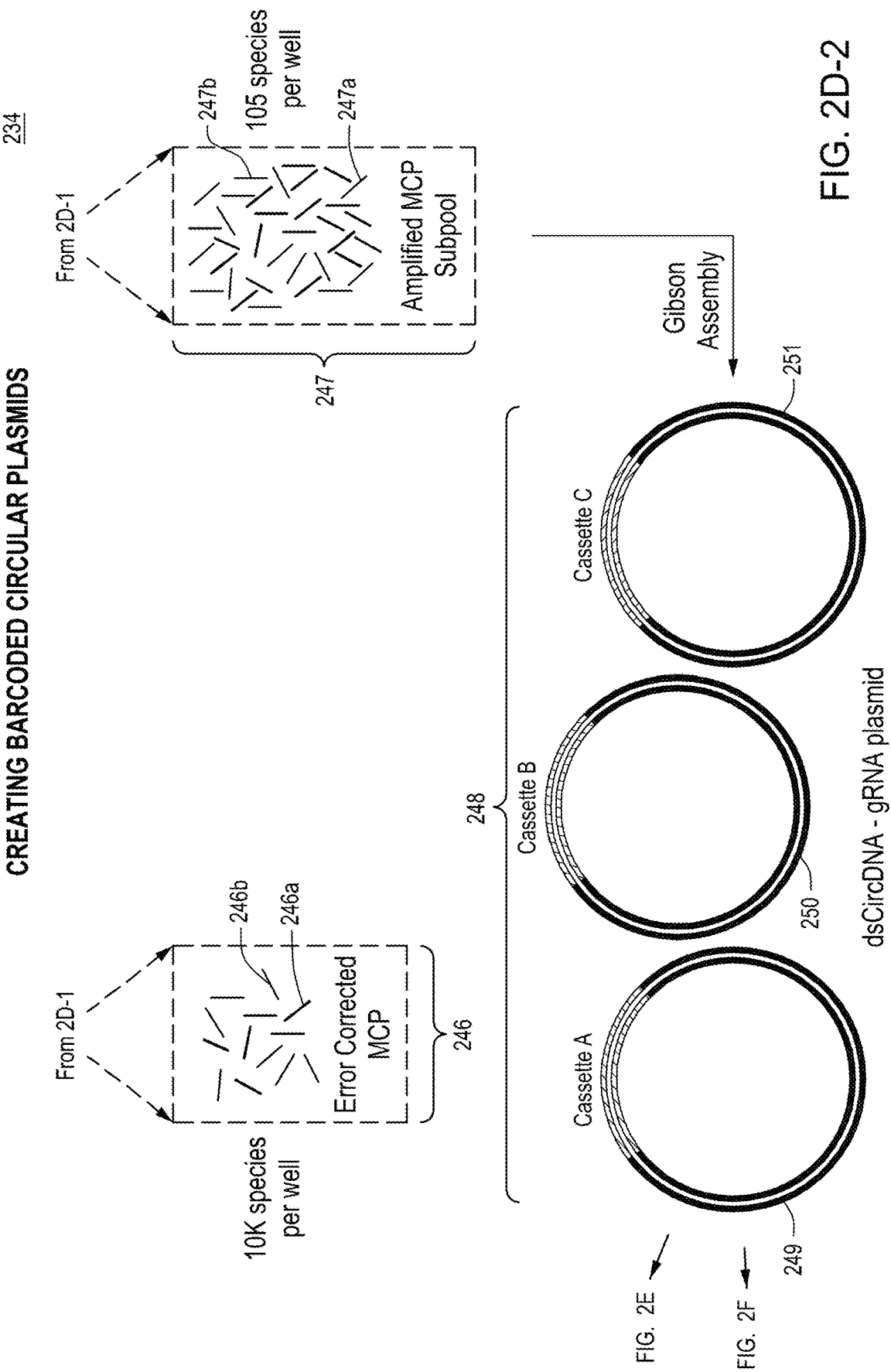

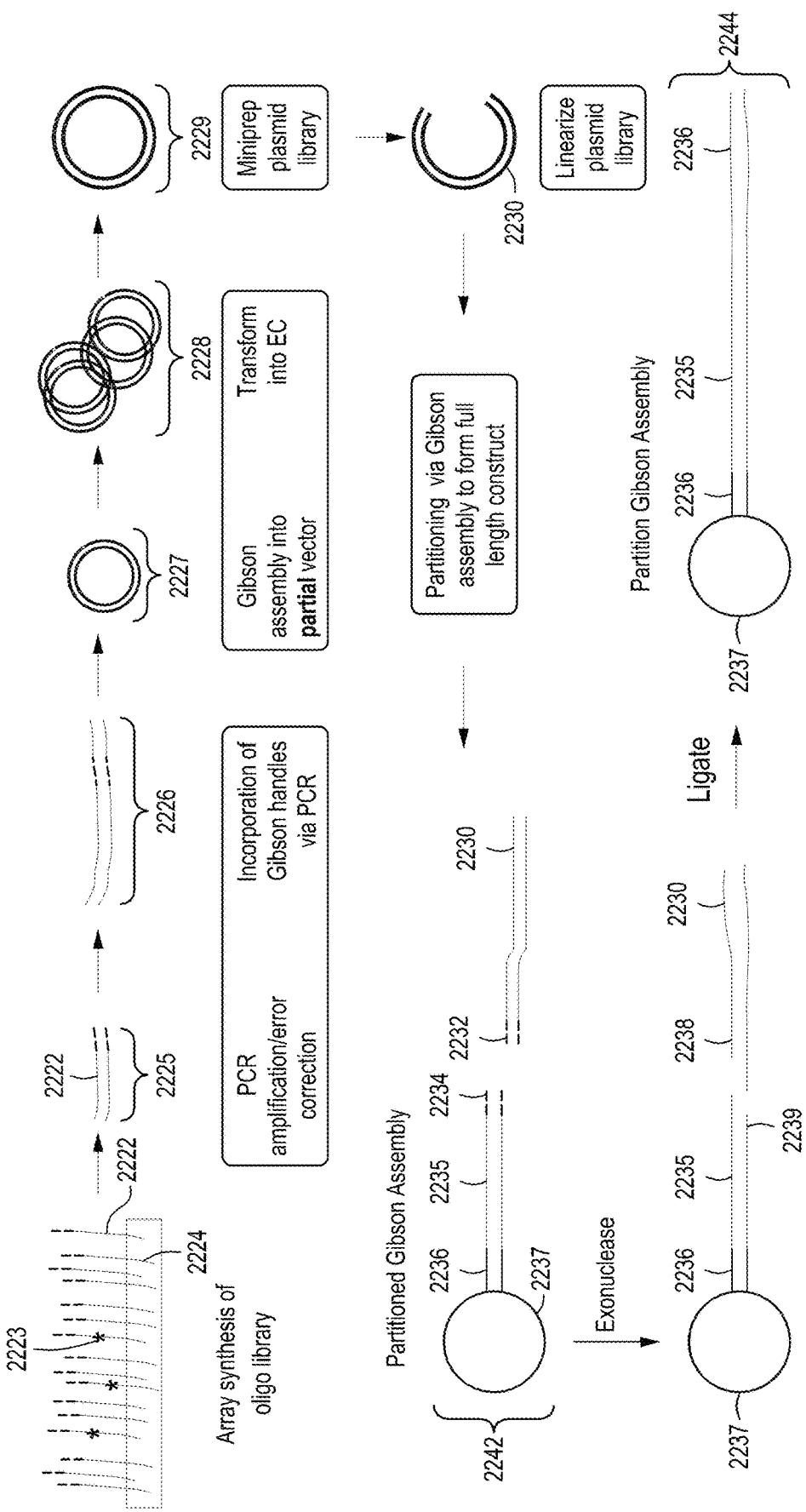

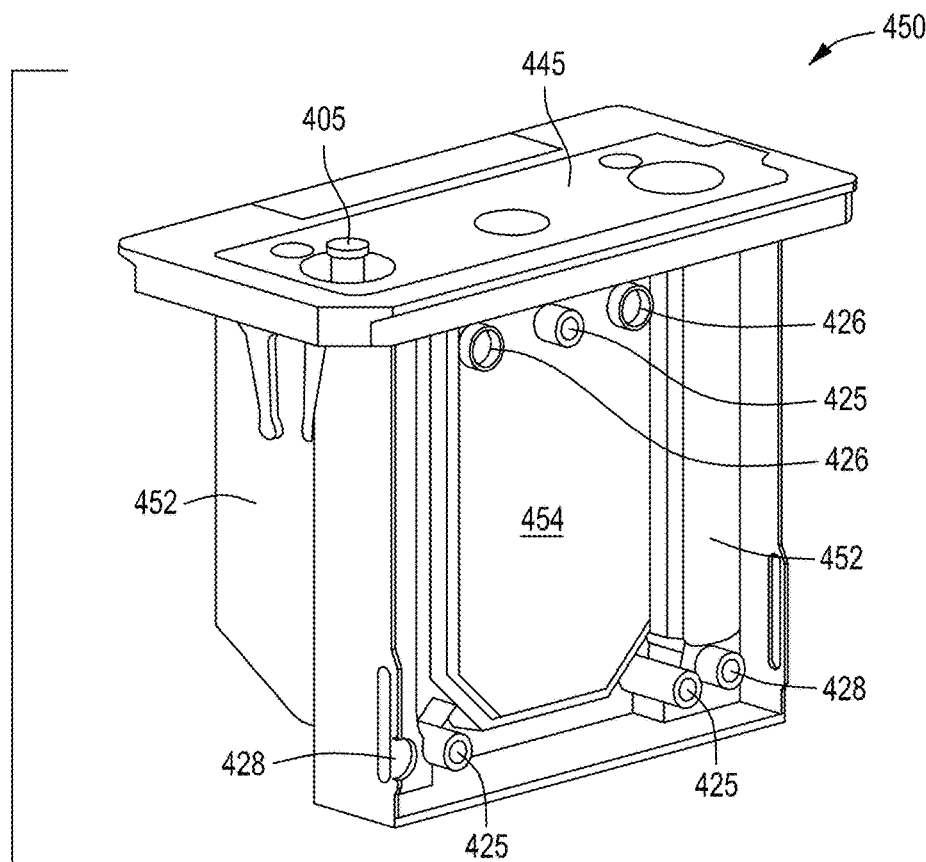
FIG. 4B
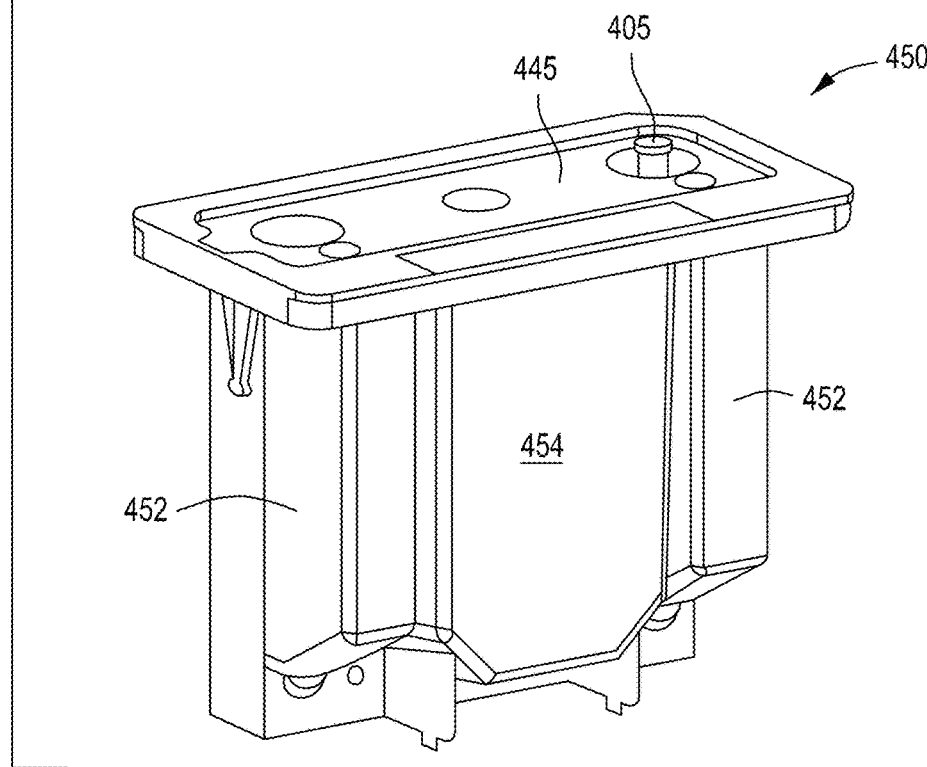

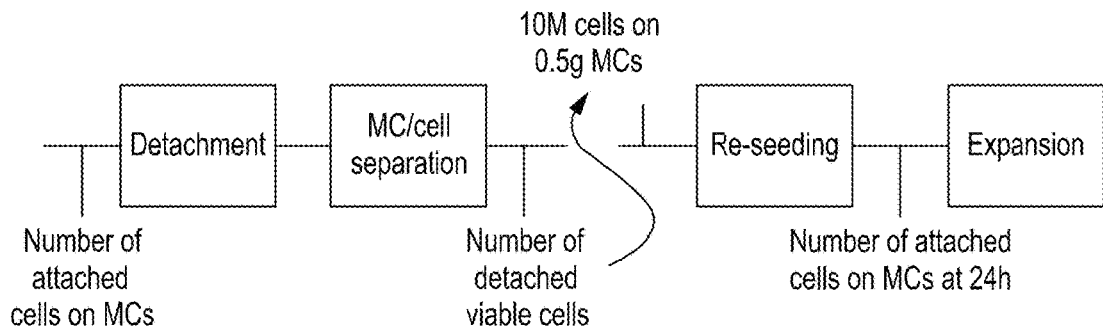
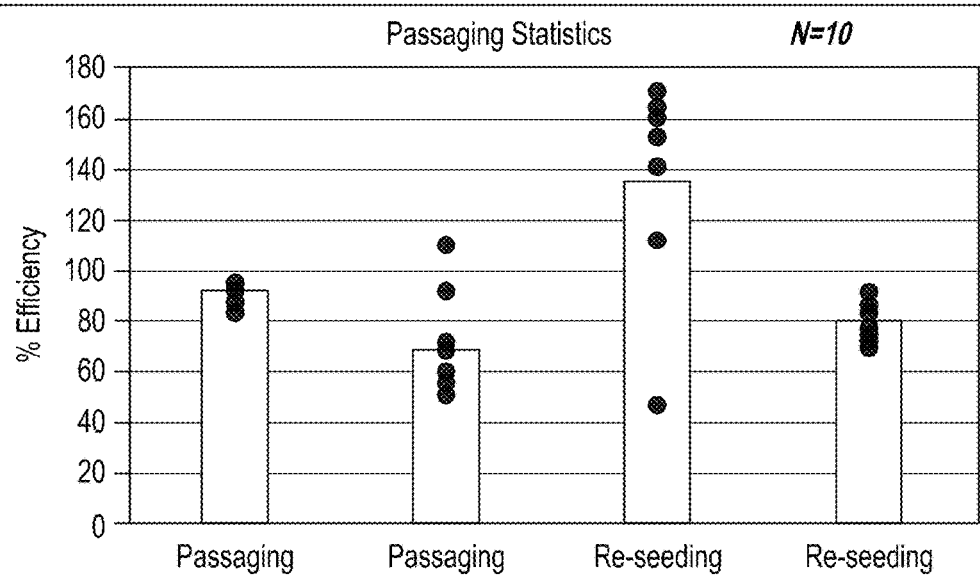
FIG. 20

COMPOSITIONS, METHODS, MODULES AND INSTRUMENTS FOR AUTOMATED NUCLEIC ACID-GUIDED NUCLEASE EDITING IN MAMMALIAN CELLS USING MICROCARRIERS

RELATED CASES

This application claims priority to U.S. Ser. No. 63/092, 499 filed 15 Oct. 2020, entitled "Compositions, Methods, Modules and Instruments for Automated Nucleic Acid-Guided Nuclease Editing in Mammalian Cells" and U.S. Ser. No. 63/014,944, filed 24 Apr. 2020, also entitled "Compositions, Methods, Modules and Instruments for Automated Nucleic Acid-Guided Nuclease Editing in Mammalian Cells."

FIELD OF THE INVENTION

This invention relates to compositions of matter, methods, modules and automated end-to-end instruments for automated mammalian cell growth, reagent bundle creation and mammalian cell transfection followed by nucleic acid-guided nuclease editing in live mammalian cells.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently various nucleases have been identified that allow manipulation of gene sequence; hence, gene function. The nucleases include nucleic acid-guided nucleases, which enable researchers generate permanent edits in live cells. Editing efficiencies frequently correlate with the concentration of guide RNAs (gRNAs) and repair templates (e.g., donor DNAs or homology arms) in the cell, particularly in mammalian cells. That is, the higher the concentration of gRNA and repair templates, the better the editing efficiency. Further, it is desirable to be able to perform many different edits in a population of mammalian cells simultaneously and to do so in an automated fashion, minimizing manual or hands-on cell manipulation.

There is thus a need in the art of nucleic acid-guided nuclease gene editing for improved compositions, methods, modules and instrumentation for increasing nucleic acid-guided nuclease editing efficiency and throughput in live mammalian cells, particularly in an end-to-end, closed and fully automated instrument. The present invention satisfies this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure relates to compositions, methods, modules and instrumentation for making edits in a mammalian genome. Efficient editing requires many excess copies of editing cassettes—comprising a gRNA and a repair template (e.g., donor DNA)—in the cell nucleus. In order to perform highly-multiplexed editing in a single reaction, it is necessary to co-localize the cells with many clonal copies of each editing cassette. Thus, the present compositions and method entail making "reagent bundles" comprising many (hundreds of thousands to millions) clonal copies of an editing cassette and delivering or co-localizing the reagent bundles with live mammalian cells such that the editing cassettes edit the cells and the edited cells continue to grow. In addition, it is preferable to use a fully-automated, end-to-end closed instrument that does not require human hands or intervention to establish and provide consistent results in the workflow and to enhance uniformity of processing between "batches" while maintaining sample integrity.

Thus, in one embodiment there is provided a method for transfecting and performing nucleic acid-guided nuclease editing in mammalian cells in an automated closed cell editing instrument comprising the steps of comprising the steps of: synthesizing a library of editing cassettes off instrument, wherein each editing cassette comprises a different gRNA and donor DNA pair; amplifying each editing cassette in the library of editing cassettes in a partition separate from other editing cassettes; adding nuclease to each partition with an amplified editing cassette; adding LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) to each amplified editing cassette and nuclease to form a library of LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease complexes; adding microcarriers to each LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease complex in the library of LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease complexes, wherein the microcarriers are coated in extracellular matrix or a cell adhesion molecule coating and wherein the LIPOFECTAMINE™ (a composition of 3:1 DOSPA (2,3-dioleoyloxy-N-[2(sperminecarboxamido) ethyl]-N,N-dimethyl-1-propaniminium trifluoroacetate) to DOPE (1,2-dioleoyl-sn-glycerophosphotheanolamine))/nucleic acid/nuclease complexes bind to the microcarriers; transferring cell growth medium, the microcarriers and mammalian cells to a growth module in the automated closed cell editing instrument via a liquid handling system; allowing the cells to seed on the coated microcarriers in the growth module; providing conditions for the cells to take-up the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease payloads in the growth module; providing conditions for the nucleic acids and nuclease to edit the cells in the growth module; and detaching the edited cells from the microcarriers.

Yet another embodiment provides a method for transfecting and performing nucleic acid-guided nuclease editing in mammalian cells in an automated closed cell editing instrument comprising the steps of comprising the steps of: synthesizing a library of editing cassettes off instrument, wherein each editing cassette comprises a different gRNA and donor DNA pair; amplifying each editing cassette in the library of editing cassettes in a partition separate from other editing cassettes; adding nuclease to each partition with an amplified editing cassette; adding microcarriers to each partition comprising an amplified editing cassette and nuclease to form nucleic acid/nuclease complexes on the microcarriers, wherein the microcarriers are coated in extracellular matrix or a cell adhesion molecule coating; adding LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) to each microcarrier to form a library of microcarriers with LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease complexes; transferring cell growth medium, the microcarriers with LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease complexes, and mammalian cells to a growth module in the automated closed cell editing instrument via a liquid handling system; allowing the cells to seed on the coated microcarriers in the growth module; providing conditions for the cells to take-up the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease payloads in the growth module; providing conditions for the nucleic acids and nuclease to edit the cells in the growth module; and detaching the edited cells from the microcarriers.

In some aspects of these embodiments, the growth module is a rotating growth module, a tangential flow filtration module, or a bioreactor. In some aspects of these embodiments, the liquid handling system comprises an air displacement pipettor, and in some aspects, the automated closed cell editing instrument comprises a reagent cartridge. In alternative aspects, the liquid handing system comprises a manifold with one or more connections to the bioreactor, or the liquid handling system comprises reagent receptacles individually connected to the growth module.

In some aspects of these embodiments, the mammalian cells are iPSCs and in some aspects, the mammalian cells are primary cells such as NK or T cells.

In some aspects of these embodiments, the microcarriers are fabricated from natural organic materials, biocompatible synthetic polymers, or inorganic materials, and in some aspects, the microcarriers are fabricated from polystyrene or a polyacrylate. In some aspects, the microcarriers are coated with laminin, and in some aspects, the microcarriers are coated with laminin L-521. In certain aspects, the microcarriers range in size from 30-1200 microns in diameter, or from 50-150 microns in diameter.

In some aspects, between the enriching and second delivering step, the mammalian cells are detached from the microcarriers, the medium is exchanged and fresh microcarriers are added to the growth module. In some aspects, the growth module is a rotating growth module and the mammalian cells are detached from the microcarriers by increasing rotation of the rotating growth vial. In alternative aspects, the growth module is a rotating growth module comprising fins, wherein the fins comprise frits. In yet other aspects, the growth module is a tangential flow filtration module and the mammalian cells are detached from the microcarriers by bubbling or the growth module is a tangential flow filtration module and the mammalian cells are detached from the microcarriers by passing the mammalian cells through a conduit between reservoirs, wherein the conduit comprises at least one frit. In yet another aspect the growth module is a bioreactor with at least one impeller and the mammalian cells are detached from the microcarriers by increasing revolutions per minute of the at least one impeller, and in some instances, the growth module is a bioreactor with at least two impellers and the mammalian cells are detached from the microcarriers by increasing revolutions per minute of the at least two impellers.

In some aspects of these embodiments, the nuclease is provided as a protein, and in other aspects, the nuclease is provided as a nucleic acid coding sequence under the control of a promoter. Preferably, when each editing cassette in the library of editing cassettes comprises a barcode, different editing cassettes comprise different barcodes.

In some aspects of these embodiments, the steps of providing conditions for the cells to take-up the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease payloads in the growth module and providing conditions for the nucleic acids and nuclease to edit the cells in the growth module may take up to 2 days, and in some aspects, the steps of providing conditions for the cells to take-up the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease payloads in the growth module and providing conditions for the nucleic acids and nuclease to edit the cells in the growth module may take up to 24 hours.

In some aspects of these embodiments, the editing cassettes comprise from 5' to 3': a first primer binding region; a spacer region of the gRNA; a scaffold region of the gRNA; the donor DNA; a barcode; a second primer binding region; and a third primer binding region.

Other embodiments provide a method for transfecting and performing nucleic acid-guided nuclease editing in mammalian cells comprising the steps of: synthesizing a library of editing cassettes, wherein each editing cassette comprises a different gRNA and donor DNA pair, and wherein each gRNA/donor DNA pair comprises a unique handle; amplifying the library of editing cassettes; providing microcarriers with DNA tags complementary to the unique handles on the editing cassettes; loading the amplified editing cassettes onto the microcarriers resulting in reagent bundles; coating the reagent bundles in an extracellular matrix; loading mammalian cells onto the extracellular matrix on the reagent bundles; providing a nucleic acid-guided nuclease or nuclease fusion or a coding sequence for a nucleic acid-guided nuclease or nuclease fusion and transfection reagents to the mammalian cells on the reagent bundles under conditions that allow for cell transfection and editing; removing the edited cells from the reagent bundles; and pooling the cells.

Yet other method embodiments herein provide a method of creating reagent bundles for editing mammalian cells comprising the steps of: synthesizing a library of editing cassettes, wherein each editing cassette comprises a different gRNA and donor DNA pair; providing microcarriers in partitions, wherein the microcarriers comprise cleavable groups on an outer surface of the microcarriers, and each partition further comprises copies of an oligonucleotide, wherein each oligonucleotide comprises a moiety that complexes with the cleavable group on the outer surface of the microcarriers, a barcode unique to the well and a region complementary to the editing cassettes; adding an editing cassette to each partition; amplifying the editing cassettes in each partition; and capturing the amplified editing cassettes onto the surface of the microcarrier via the oligonucleotide.

Additional method embodiments provide a method of creating reagent bundles for editing mammalian cells comprising the steps of: synthesizing a library of linear constructs, wherein each linear construct comprises from 5' to 3', a noncoding region, a promoter, an editing cassette wherein each editing cassette comprises a different gRNA and donor DNA pair, a terminator and a pull-down handle; amplifying the library of linear constructs; cutting the amplified linear constructs with a restriction endonuclease leaving 5' overhangs at the 5' and 3' ends of the amplified linear constructs; adding nucleic acid loop constructs to the 5' and 3' ends of the amplified linear constructs; ligating the nucleic acid loop constructs to the 5' and 3' ends of the amplified linear constructs to form amplified linear loop constructs; adding microcarriers to the amplified linear constructs to form amplified linear loop constructs, wherein the microcarriers comprise surface oligonucleotides complementary to the pull-down handle; allow binding of the microcarriers to the amplified linear loop constructs; and performing rolling circle amplification of the amplified linear loop constructs.

Further provided is a method of creating reagent bundles for editing mammalian cells comprising the steps of: synthesizing a library of editing cassettes wherein each editing cassette comprises a different gRNA and donor DNA pair; adding the editing cassettes from the library of editing cassettes to partitions where each partition comprises a construct with a unique first barcode; amplifying the editing cassettes to add the first barcodes to the editing cassettes to form first amplicons; pooling the first amplicons; adding the first amplicons to partitions comprising unique second barcodes, wherein each partition comprises at least 100 unique barcodes and the unique barcodes in each partition are different than the unique second barcodes in all other partitions; amplifying the first amplicons to add the second barcodes to the first amplicons to form second amplicons; providing a vector backbone; inserting the second amplicons into the vector backbone to produce first double-strand circular vectors; nicking one strand of the first double-strand circular vectors; digesting 5' or 3' to produce single-stranded vectors; providing microcarriers comprising surface oligonucleotides with regions complementary to the second barcodes on the single-stranded vectors; allow binding of the surface oligonucleotides on the microcarriers to the single-stranded vectors via the complementary regions; extending the complementary regions to produce second double-strand circular vectors; and ligating the double-strand circular vectors.

Another embodiment provides a method of creating reagent bundles for editing mammalian cells comprising the steps of: synthesizing a library of editing cassettes wherein each editing cassette comprises a different gRNA and donor DNA pair; adding the editing cassettes from the library of editing cassettes to partitions where each partition comprises a construct with a unique first barcode; amplifying the editing cassettes to add the first barcode nucleic acids to the editing cassettes to form first amplicons; pooling the first amplicons; adding the first amplicons to partitions comprising unique second barcode nucleic acids, wherein each partition comprises at least 100 unique second barcode nucleic acids and the unique second barcode nucleic acids in each partition are different than the unique second barcode nucleic acids in all other partitions; amplifying the first amplicons to add the second barcodes to the first amplicons to form second amplicons; inserting the second amplicons into the vector backbone to produce first double-strand circular vectors; nicking one strand of the first double-strand circular vectors; adding unique third barcode nucleic acids with sequences that recognize unique sequences in the editing cassettes and bind to the nicked double-strand circular vectors forming a mismatch; extending the third barcode nucleic acids along the circular vector thereby displacing one strand of the nicked double-strand circular vectors; ligating the nicked strand of the nicked double-strand circular vectors for form ligated double-strand circular vectors; providing microcarriers, wherein the microcarriers have surface nucleic acids complementary to the mismatch in the third barcode nucleic acids; using the microcarriers to pull-down the ligated double-strand circular vectors; extending the surface nucleic acids resulting in a captured double-stranded editing vector on the microcarrier.

Other embodiments for creating reagent bundles provide a method comprising the steps of: synthesizing a library of editing cassette constructs wherein each editing cassette comprises from 5' to 3' an editing cassette, wherein each editing cassette construct comprises a different gRNA and donor DNA pair, a T7 promoter; and a unique barcode; providing 5'-capped RNA barcoded microcarriers; allowing binding of the editing cassette constructs to the 5'-capped RNA barcoded microcarriers; transcribing the editing cassette constructs on the microcarriers to form gRNA/DNA duplexes; digesting the gRNA/DNA duplexes with DNase to render gRNA/mRNA constructs attached to the microcarrier; and polyadenylating the gRNA/mRNA constructs.

Further provided is a method of creating reagent bundles for editing mammalian cells comprising the steps of: synthesizing a library of editing cassettes wherein each editing cassette comprises a different gRNA and donor DNA pair and a barcode; amplifying the library of editing cassettes, incorporating handles for insertion into vector backbones; inserting the library of editing cassettes into the vector backbones to create editing vectors; transforming the editing vectors into bacteria; isolating the editing vector from the bacteria; linearizing the isolated editing vectors; adding microcarriers to the isolated linearized editing vectors, wherein the microcarriers comprise a surface-lined nucleic acid comprising a cleavable region, a region comprising episomal elements, and a region complementary to the barcodes in the editing vectors; treating the microcarriers and isolated linearized editing vectors with an exonuclease, generating sticky ends for ligation; and ligating the microcarriers and isolated linearized editing vectors.

Additionally provided is a method of creating reagent bundles for editing mammalian cells comprising the steps of: synthesizing a library of editing cassettes wherein each editing cassette comprises a different gRNA and donor DNA pair and a barcode; amplifying the library of editing cassettes, incorporating a promoter region and restriction endonuclease recognition site; digest the amplified library of editing cassettes using the restriction endonuclease; in vitro transcribe the digested library of editing cassettes into RNA-based editing cassettes; partitioning the RNA-based editing cassettes; adding microcarriers to the RNA-based editing cassettes, wherein the microcarriers comprise a linker; a poly-A tract; a long RNA tract, wherein the long RNA tract comprises an episomal element region including a promoter and an origin of replication; coupling the microcarriers to the RNA-based editing cassettes via a splint oligonucleotide comprising a sequence complementary to the episomal element region and a sequence complementary to the barcode on the RNA-based editing cassettes.

Also provided is a method for transfecting and performing nucleic acid-guided nuclease editing in mammalian cells comprising the steps of: synthesizing a library of editing cassettes, wherein each editing cassette comprises a different gRNA and donor DNA pair; amplifying each editing cassette in the library of editing cassettes in a partition separate from other editing cassettes; adding nuclease to each amplified editing cassette; adding LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) to each amplified editing cassette to form a library of LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease payloads; adding microcarriers to LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid payload in the library of LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease payloads, wherein the microcarriers are coated in laminin; seeding cells on the laminin-coated microcarriers; allowing the cells to take-up the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid/nuclease payloads; and providing conditions for the nucleic acids and nuclease to edit the cells.

All embodiments for creating reagent bundles may include a step of error correcting the editing cassettes before amplification.

Yet another embodiment of the present disclosure provides a method of growing cells, passaging the cells, editing the cells via nucleic acid-guided nuclease editing, and detaching the cells in a bioreactor, comprising the steps of: providing a bioreactor comprising: a growth vessel comprising a tapered main body, a lid assembly comprising ports, at least one driving impeller, and an impeller shaft, wherein there is at least one liquid-in port; at least one liquid-out port; at least one gas-in port; at least one gas-out port; at least one rupture disc; and at least one sensor port; and wherein the lid assembly makes an air-tight fitting on the tapered main body; and a bioreactor stand assembly comprising a frame, a stand main body disposed in the frame, wherein the stand main body accommodates the tapered main body of the growth vessel during operation, and wherein the stand main body comprises a heating element to heat the tapered main body; providing cell growth medium and reagent bundle microcarriers to the tapered main body of the growth vessel, wherein the reagent bundle microcarriers comprise editing cassettes, a selection a selection marker and a lipofection agent; allowing the cells to attach to and grow on the reagent bundle microcarriers; providing conditions for the editing cassettes to transfect the cells; monitoring growth of the cells on the reagent bundle microcarriers; selecting for transfected cells via the selection marker; detaching the cells from the reagent bundle microcarriers by increasing revolutions per minute of the impeller; stopping or slowing the impeller; allowing the reagent bundle microcarriers to settle in the tapered main body of the growth vessel; removing the reagent bundle microcarriers from the tapered main body of the growth vessel or transferring the detached cells to a second main tapered body in a second growth vessel; adding first microcarriers to the tapered main body of the growth vessel; allowing the cells to attach to and grow on the first microcarriers; monitoring growth of the cells on the first microcarriers; adding LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) and nuclease to the tapered main body of the growth vessel; providing conditions for the nuclease to transfect the cells; and providing conditions for nucleic acid-guided nuclease editing of the cells.

In one aspect of this embodiment, the method further comprises the steps of, after the step of monitoring growth of the cells on the first microcarriers and before the step of adding LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) and nuclease to the tapered main body of the growth vessel: detaching the cells from the first microcarriers by increasing revolutions per minute of the impeller; stopping or slowing the impeller; allowing the first microcarriers to settle in the tapered main body of the growth vessel; removing the first microcarriers from the tapered main body of the growth vessel or transferring the detached cells to a second main tapered body in a second growth vessel; adding second microcarriers to the tapered main body of the growth vessel; and allowing the cells to attach to and grow on the second microcarriers.

In yet another embodiment there is provided a method of growing cells, passaging the cells, editing the cells via nucleic acid-guided nuclease editing and detaching the cells in a bioreactor, comprising the steps of: providing a bioreactor comprising: a growth vessel comprising a tapered main body, a lid assembly comprising ports, at least one driving impeller, and an impeller shaft, wherein there is at least one liquid-in port; at least one liquid-out port; at least one gas-in port; at least one gas-out port; at least one rupture disc; and at least one sensor port; and wherein the lid assembly makes an air-tight fitting on the tapered main body; and a bioreactor stand assembly comprising a frame, a stand main body disposed in the frame, wherein the stand main body accommodates the tapered main body of the growth vessel during operation, and wherein the stand main body comprises a heating element to heat the tapered main body; providing cell growth medium and reagent bundle microcarriers to the tapered main body of the growth vessel, wherein the reagent bundle microcarriers comprise editing cassettes, a selection a selection marker, a lipofection agent and a nuclease; allowing the cells to attach to and grow on the reagent bundle microcarriers; providing conditions for the editing cassettes and nuclease to transfect the cells; monitoring growth of the cells on the reagent bundle microcarriers; selecting for transfected cells via the selection marker;

providing conditions for the editing cassettes and nuclease to transfect the cells; and providing conditions for nucleic acid-guided nuclease editing of the cells; detaching the edited cells from the reagent bundle microcarriers by increasing revolutions per minute of the impeller; stopping or slowing the impeller; allowing the reagent bundle microcarriers to settle in the tapered main body of the growth vessel; removing the reagent bundle microcarriers from the tapered main body of the growth vessel; and harvesting the edited cells.

In some aspects of either of these embodiments, the lid assembly further comprises a motor integration port for a motor to control the impeller, and in some aspects, the bioreactor comprises a second impeller.

In some aspects of either of these embodiments, the at least one sensor port in the lid assembly is configured to accommodate a monitor capacitance of the cells and medium in the tapered main body of the growth vessel; a sensor to measure O2 concentration of the cells and medium in the tapered main body of the growth vessel; a sensor to measure CO2 of the cells and medium in the tapered main body of the growth vessel; a sensor to measure pH of the cells and medium in the tapered main body of the growth vessel; a sensor to measure lactate concentration of the cells and medium in the tapered main body of the growth vessel; a sensor to measure glucose concentration of the cells and medium in the tapered main body of the growth vessel; a sensor to measure biomass of the cells and medium in the tapered main body of the growth vessel; or a sensor to measure optical density of the cells and medium in the tapered main body of the growth vessel., and in some embodiments, there are at least two, at least three or at least four sensor ports in the lid assembly each configured to monitor capacitance of the cells and medium in the tapered main body of the growth vessel; a sensor to measure O2 concentration of the cells and medium in the tapered main body of the growth vessel; a sensor to measure CO2 of the cells and medium in the tapered main body of the growth vessel; a sensor to measure pH of the cells and medium in the tapered main body of the growth vessel; a sensor to measure lactate concentration of the cells and medium in the tapered main body of the growth vessel; a sensor to measure glucose concentration of the cells and medium in the tapered main body of the growth vessel; a sensor to measure biomass of the cells and medium in the tapered main body of the growth vessel; or a sensor to measure optical density of the cells and medium in the tapered main body of the growth vessel.

In some aspects of either of these embodiments, the lid assembly further comprises a temperature probe, and in some aspects, the lid assembly further comprises a camera port. In some aspects the heating element of the stand main body is a heat jacket, and in some aspects, the heat jacket comprises LED lights and may also comprise a camera port. In some aspects, the at least one liquid-out port comprises a filter. In some aspects, there is more than one liquid-out port and/or more than one liquid-in port.

In some aspects of either of these embodiments, the tapered main body of the growth vessel accommodates cell culture volumes of 25 ml to 500 ml. In some aspects, during cell growth impeller revolutions per minute is approximately 40-80 rpm, and in some aspects during cell detachment impeller revolutions per minute is approximately 2700 rpm. In some aspects of either of these embodiments, the tapered main body is optically transparent and in some aspects, the tapered main body is optically transparent in UV and IR ranges.

In some aspects of these embodiments, a chemical agent is added to the tapered main body of the growth vessel to aid in detaching the cells, and in some aspects, the chemical agent is hemagglutinin, collagenase, dispase or trypsin.

In some aspects of these embodiments, the nuclease is provided as a protein and in other aspects, the nuclease is provided as a nucleic acid coding sequence under control of a promoter.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 1B depicts alternative methods for populating microcarriers with a LIPO-FECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine))/nucleic acid payload and cells.

FIG. 4B depicts two side perspective views of a reservoir assembly of a tangential flow filtration module.

FIGS. 5H-1 and 5H-2 depict an exemplary fluidic diagram for the bioreactor described in relation to FIGS. 5A-5G. FIG. 5I depicts an exemplary control system block diagram for the bioreactor described in relation to FIGS. 5A-5G.

FIG. 20 shows a workflow at top right, a table reporting percent efficiency at various steps in the workflow at center, and a graph showing the replicates measuring the percent efficiency at various steps in the workflow at bottom.

FIG. 22 at bottom left is a bar graph showing a stemness panel (FACS % positive) for cells in the bioreactor described herein, on laminin plates and on MATRIGEL® plates (CORNING® BIOCOAT™ MATRIGEL® 6-well plates (Corning, Inc., Glendale, Ariz.)). FIG. 22 at bottom right is a bar graph showing a stemness panel (FACS median fluorescence) for cells in the bioreactor described herein, on laminin plates and on MATRIGEL® plates (CORNING® BIOCOAT™ MATRIGEL® 6-well plates (Corning, Inc., Glendale, Ariz.)).

It should be understood that the drawings are not necessarily to scale, and that like reference numbers refer to like features.

DETAILED DESCRIPTION

Figure 1A:
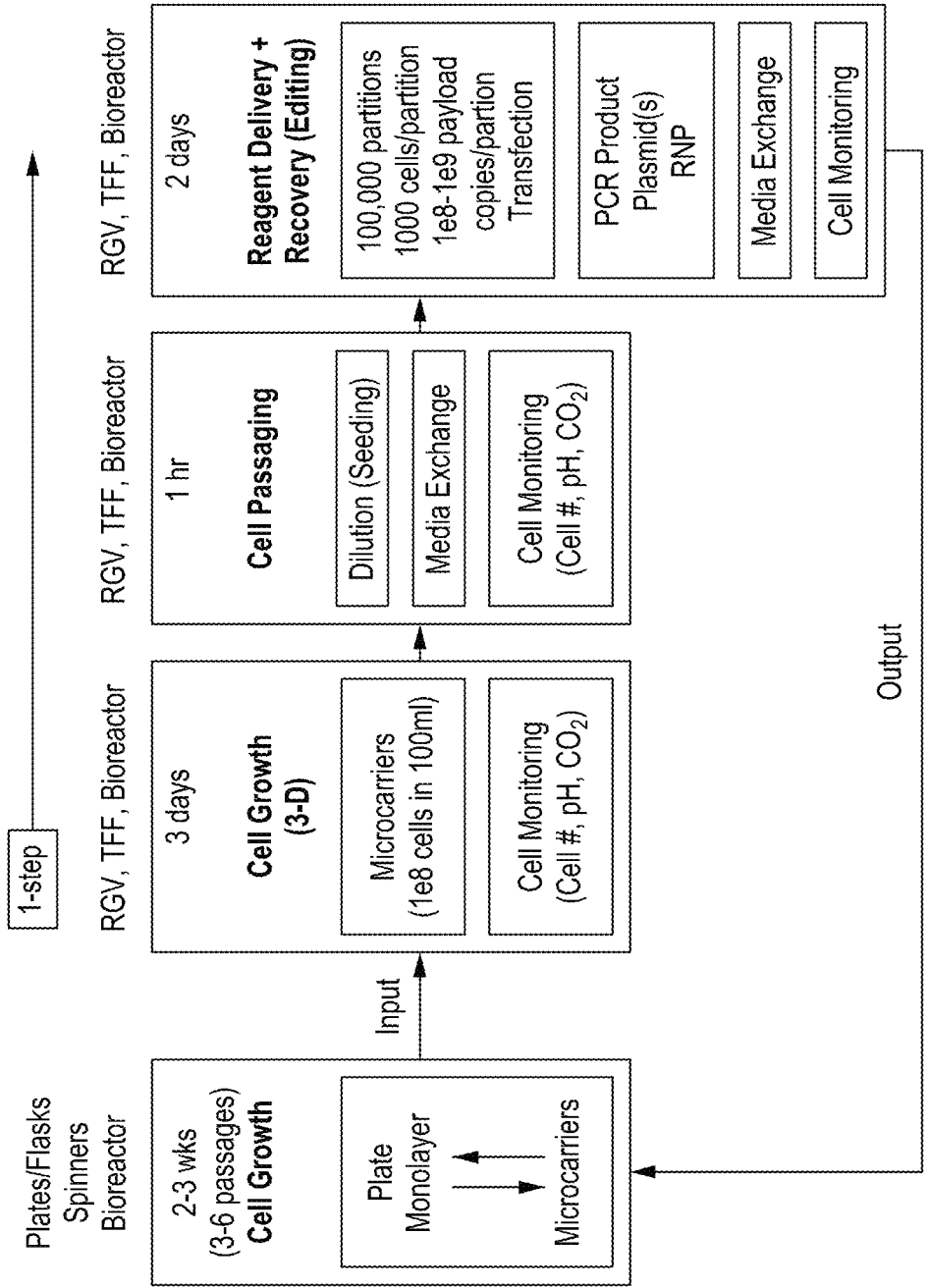
FIG. 1A depicts an exemplary workflow employing microcarrier-partitioned delivery for editing mammalian cells grown in suspension.

All of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual; Mount* (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual (all from* Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* 3$^{rd}$ Ed., W. H. Freeman Pub., New York, N.Y.; Viral Vectors (Kaplift & Loewy, eds., Academic Press 1995); all of which are herein incorporated in their entirety by reference for all purposes. For mammalian/stem cell culture and methods see, e.g., *Basic Cell Culture Protocols*, Fourth Ed. (Helgason & Miller, eds., Humana Press 2005); *Culture of Animal Cells*, Seventh Ed. (Freshney, ed., Humana Press 2016); *Microfluidic Cell Culture*, Second Ed. (Borenstein, Vandon, Tao & Charest, eds., Elsevier Press 2018); *Human Cell Culture* (Hughes, ed., Humana Press 2011); *3D Cell Culture* (Koledova, ed., Humana Press 2017); *Cell and Tissue Culture: Laboratory Procedures in Biotechnology* (Doyle & Griffiths, eds., John Wiley & Sons 1998); *Essential Stem Cell Methods*, (Lanza & Klimanskaya, eds., Academic Press 2011); *Stem Cell Therapies: Opportunities for Ensuring the Quality and Safety of Clinical Offerings: Summary of a Joint Workshop* (Board on Health Sciences Policy, National Academies Press 2014); *Essentials of Stem Cell Biology*, Third Ed., (Lanza & Atala, eds., Academic Press 2013); and *Handbook of Stem Cells*, (Atala & Lanza, eds., Academic Press 2012). Information on use of microcarriers in cell culture include *Microcarriers for Animal Cell Culture*, 1$^{st}$ ed., PM Conn, Academic Press (1990); Huang, et al., *Biopolymer-Based Microcarriers for Three-Dimensional Cell Culture and Engineered Tissue Formation*, Int. J. Molecular Sci., 21:1895 (2020); and Park, et al., *Microcarriers designed for cell culture and tissue engineering*, Tissue Eng. Part B Rev., 12(2):172-90 (2013). CRISPR-specific techniques can be found in, e.g., *Genome Editing and Engineering from TALENs and CRISPRs to Molecular Surgery*, Appasani and Church (2018); and CRISPR: *Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" or "homology arm" or "repair arm" refers to nucleic acid that is designed to introduce a DNA sequence modification (insertion, deletion, substitution) into a locus by homologous recombination using nucleic acid-guided nucleases or a nucleic acid that serves as a template (including a desired edit) to be incorporated into target DNA by reverse transcriptase in a CREATE fusion editing (CFE) system. For homology-directed repair, the donor DNA must have sufficient homology to the regions flanking the "cut site" or the site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "editing cassette", "CREATE cassette", "CREATE editing cassette", "CREATE fusion editing cassette" or "CFE editing cassette" refers to a nucleic acid molecule comprising a coding sequence for transcription of a guide nucleic acid or gRNA covalently linked to a coding sequence for transcription of a donor DNA or homology arm.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "microcarrier" refers to nonporous, microporous, and macroporous microcarriers comprising natural organic materials such as, e.g., gelatin, collagen, alginate, agarose, chitosan, and cellulose; synthetic polymeric materials such as, e.g., polystyrene, polyacrylates such as polyacrylamide, polyamidoamine (PAMAM), polyethylene oxide (PEO/PEG), poly(N-isopropylacrylamide) (PNIPAM), polycaprolactone (PCL), polylactic acid (PLA), and polyglycolic acid (PGA); inorganic materials such as, e.g., silica, silicon, mica, quartz and silicone; as well as mixtures of natural, polymeric materials, crossed-linked materials, and inorganic materials etc., on which animal cells can grow. The term "reagent vehicle microcarrier", "rvMC", "reagent bundle microcarrier", "RBMC", "LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) and nucleic acid microcarriers" or "LNPsMCs" refers to a microcarrier with a payload; as used herein a payload of nucleic acids, proteins or proteins complexes to be transfected into cells and/or transfection reagents and/or cells.

"Nucleic acid-guided editing components" refers to one, some, or all of a nucleic acid-guided nuclease or nickase fusion enzyme, a guide nucleic acid and a donor nucleic acid.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "PAM mutation" refers to one or more edits to a target sequence that removes, mutates, or otherwise renders inactive a PAM or spacer region in the target sequence.

As used herein, a "partition" is an isolated region (e.g., a feature surrounded by an interstitial region) or an isolate depression (e.g., a well) on a substrate. Partitions are used, in relation to the present disclosure, to separate a plurality to many different nucleic acids (e.g., editing cassettes) into a plurality or many compartments (i.e., separate droplets comprising nucleic acids).

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA. Promoters may be constitutive or inducible.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, nourseothricin N-acetyl transferase, erythromycin, tetracycline, gentamicin, bleomycin, streptomycin, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+ cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); rhamnose; and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

The terms "transformation", "transfection" and "transduction" are used interchangeably herein to refer to the process of introducing exogenous DNA into cells.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, BACs, YACs, PACs, synthetic chromosomes, and the like. In some embodiments, a coding sequence for a nucleic acid-guided nuclease is provided in a vector, referred to as an "engine vector." In some embodiments, the editing cassette may be provided in a vector, referred to as an "editing vector." In some embodiments, the coding sequence for the nucleic acid-guided nuclease and the editing cassette are provided in the same vector.

A "viral vector" as used herein is a recombinantly produced virus or viral particle that comprises an editing cassette to be delivered into a host cell. Examples of viral vectors include retroviral vectors, lentiviral vectors, adenovirus vectors, adeno-associated virus vectors, alphavirus vectors and the like.

Nuclease-Directed Genome Editing Generally

The compositions, methods, modules and automated instruments described herein are employed to allow one to perform nucleic acid nuclease-directed genome editing to introduce desired edits to a population of live mammalian cells in a closed, end-to-end automated instrument. The compositions and methods entail creating reagent bundle microcarriers (RBMCs) comprising many clonal (e.g., identical) copies of editing cassettes—that is, the editing cassettes on a single microcarrier will be clonal copies of one another—followed by co-localizing the RBMCs with live mammalian cells to effect editing of the genome of the mammalian cells by the editing cassettes. The RBMCs are manufactured off-instrument and are co-located with the cells on-instrument for automated cell editing.

Generally, a nucleic acid-guided nuclease or nickase fusion complexed with an appropriate synthetic guide nucleic acid in a cell can cut the genome of the cell at a desired location. The guide nucleic acid helps the nucleic acid-guided nuclease or nickase fusion recognize and cut the DNA at a specific target sequence. By manipulating the nucleotide sequence of the guide nucleic acid, the nucleic acid-guided nuclease or nickase fusion may be programmed to target any DNA sequence for cleavage as long as an appropriate protospacer adjacent motif (PAM) is nearby. In certain aspects, the nucleic acid-guided nuclease or nickase fusion editing system may use two separate guide nucleic acid molecules that combine to function as a guide nucleic acid, e.g., a CRISPR RNA (crRNA) and trans-activating CRISPR RNA (tracrRNA). In other aspects and preferably, the guide nucleic acid is a single guide nucleic acid construct that includes both 1) a guide sequence capable of hybridizing to a genomic target locus, and 2) a scaffold sequence capable of interacting or complexing with a nucleic acid-guided nuclease or nickase fusion.

In general, a guide nucleic acid (e.g., gRNA) complexes with a compatible nucleic acid-guided nuclease or nickase fusion and can then hybridize with a target sequence, thereby directing the nuclease or nickase fusion to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. Preferably and typically, the guide nucleic acid comprises RNA and the gRNA is encoded by a DNA sequence on an editing cassette along with the coding sequence for a donor DNA. Covalently linking the gRNA and donor DNA allows one to scale up the number of edits that can be made in a population of cells tremendously. Methods and compositions for designing and synthesizing editing cassettes (e.g., CREATE cassettes) are described in U.S. Pat. No. 10,240,167; 10,266,849; 9,982,278; 10,351,877; 10,364,442; 10,435,715; 10,669,559; 10,711,284; 10,731,180, all of which are incorporated by reference herein.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease or nickase fusion to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In general, to generate an edit in the target sequence, the gRNA/nuclease or gRNA/nickase fusion complex binds to a target sequence as determined by the guide RNA, and the nuclease or nickase fusion recognizes a protospacer adjacent motif (PAM) sequence adjacent to the target sequence. The target sequence can be any polynucleotide endogenous or exogenous to the cell, or in vitro. For example, in the case of mammalian cells the target sequence is typically a polynucleotide residing in the nucleus of the cell. A target sequence can be a sequence encoding a gene product (e.g., a protein) or a non-coding sequence (e.g., a regulatory polynucleotide, an intron, a PAM, a control sequence, or "junk" DNA). The proto-spacer mutation (PAM) is a short nucleotide sequence recognized by the gRNA/nuclease complex. The precise preferred PAM sequence and length requirements for different nucleic acid-guided nucleases or nickase fusions vary; however, PAMs typically are 2-7 base-pair sequences adjacent or in proximity to the target sequence and, depending on the nuclease or nickase, can be 5' or 3' to the target sequence.

In most embodiments, genome editing of a cellular target sequence both introduces a desired DNA change to a cellular target sequence, e.g., the genomic DNA of a cell, and removes, mutates, or renders inactive a proto-spacer mutation (PAM) region in the cellular target sequence (e.g., thereby rendering the target site immune to further nuclease binding). Rendering the PAM at the cellular target sequence inactive precludes additional editing of the cell genome at that cellular target sequence, e.g., upon subsequent exposure to a nucleic acid-guided nuclease or nickase fusion complexed with a synthetic guide nucleic acid in later rounds of editing. Thus, cells having the desired cellular target sequence edit and an altered PAM can be selected for by using a nucleic acid-guided nuclease or nickase fusion complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM alteration will not be cut, as these edited cells no longer contain the necessary PAM site and will continue to grow and propagate.

As for the nuclease or nickase fusion component of the nucleic acid-guided nuclease editing system, a polynucleotide sequence encoding the nucleic acid-guided nuclease or nickase fusion can be codon optimized for expression in particular cell types, such as bacterial, yeast, and, here, mammalian cells. The choice of the nucleic acid-guided nuclease or nickase fusion to be employed depends on many factors, such as what type of edit is to be made in the target sequence and whether an appropriate PAM is located close to the desired target sequence. Nucleases of use in the methods described herein include but are not limited to Cas 9, Cas 12/CpfI, MAD2, or MAD7, MAD 2007 or other MADzymes (see U.S. Pat. Nos. 9,982,279; 10,337,028; 10,604,746; 10,665,114; 10,640,754, 10,876,102; 10,883,077; 10,704,033; 10,745,678; 10,724,021; 10,767,169; and 10,870,761 for sequences and other details related to MADzymes). Nickase fusion enzymes typically comprise a CRISPR nucleic acid-guided nuclease engineered to cut one DNA strand in the target DNA rather than making a double-stranded cut, and the nickase portion is fused to a reverse transcriptase. For more information on nickases and nickase fusion editing see U.S. Pat. No. 10,689,669 and U.S. Ser. Nos. 16/740,418; 16/740,420 and 16/740,421, both filed 11 Jan. 2020. Here, a coding sequence for a desired nuclease or nickase fusion is typically on an "engine vector" along with other desired sequences such as a selective marker.

Another component of the nucleic acid-guided nuclease or nickase fusion system is the donor nucleic acid comprising homology to the cellular target sequence. For the present compositions, methods, modules and instruments the donor nucleic acid is in the same editing cassette as (e.g., is covalently-linked to) the guide nucleic acid and typically is under the control of the same promoter as the gRNA (that is, a single promoter driving the transcription of both the editing gRNA and the donor nucleic acid). The donor nucleic acid is designed to serve as a template for homologous recombination with a cellular target sequence cleaved or nicked by the nucleic acid-guided nuclease or nickase fusion, respectively, as a part of the gRNA/nuclease complex. A donor nucleic acid polynucleotide may be of any suitable length, such as about or more than about 20, 25, 50, 75, 100, 150, 200, 500, or 1000 nucleotides in length, and up to 2, 3, 4, 5, 6, 7, 8, 9, 10, 11, 12, 13 and up to 20 kb in length if combined with a dual gRNA architecture as described in U.S. Pat. No. 10,711,284.

In certain preferred aspects, the donor nucleic acid can be provided as an oligonucleotide of between 20-300 nucleotides, more preferably between 50-250 nucleotides. The donor nucleic acid comprises a region that is complementary to a portion of the cellular target sequence (e.g., a homology arm(s)). When optimally aligned, the donor nucleic acid overlaps with (is complementary to) the cellular target sequence by, e.g., about as few as 4 (in the case of nickase fusions) and as many as 20, 25, 30, 35, 40, 50, 60, 70, 80, 90 or more nucleotides (in the case of nucleases). The donor nucleic acid comprises two homology arms (regions complementary to the cellular target sequence) flanking the mutation or difference between the donor nucleic acid and the cellular target sequence. The donor nucleic acid comprises at least one mutation or alteration compared to the cellular target sequence, such as an insertion, deletion, modification, or any combination thereof compared to the cellular target sequence.

As described in relation to the gRNA, the donor nucleic acid is provided as part of a rationally-designed editing cassette along with a promoter to drive transcription of both the gRNA and donor DNA. As described below, the editing cassette may be provided as a linear editing cassette, or the editing cassette may be inserted into an editing vector. Moreover, there may be more than one, e.g., two, three, four, or more editing gRNA/donor nucleic acid pair rationally-designed editing cassettes linked to one another in a linear "compound cassette" or inserted into an editing vector; alternatively, a single rationally-designed editing cassette may comprise two to several editing gRNA/donor DNA pairs, where each editing gRNA is under the control of separate different promoters, separate promoters, or where all gRNAs/donor nucleic acid pairs are under the control of a single promoter. In some embodiments the promoter driving transcription of the editing gRNA and the donor nucleic acid (or driving more than one editing gRNA/donor nucleic acid pair) is an inducible promoter. In many if not most embodiments of the compositions, methods, modules and instruments described herein, the editing cassettes make up a collection or library editing gRNAs and of donor nucleic acids representing, e.g., gene-wide or genome-wide libraries of editing gRNAs and donor nucleic acids.

Figure 15:
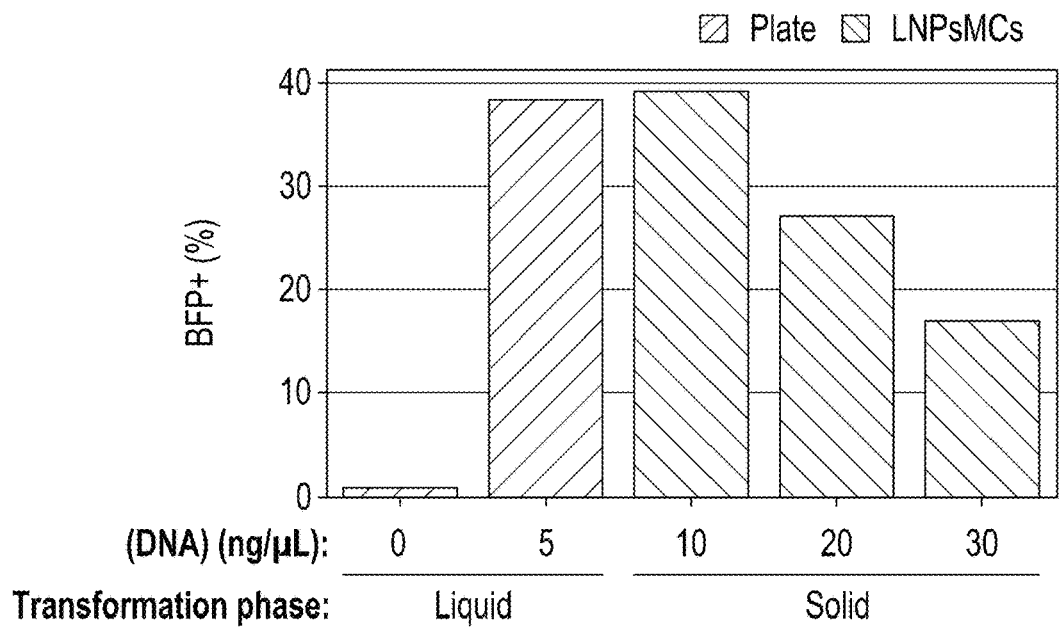
FIG. 15 is a bar graph showing data demonstrating that green-to-blue editing on LNPsMCs is equivalent to reverse transcription on a tissue culture plate.

In addition to the donor nucleic acid, the editing cassettes comprise one or more primer binding sites to allow for PCR amplification of the editing cassettes. The primer binding sites are used to amplify the editing cassette by using oligonucleotide primers as described infra (see, e.g., FIG. 15B), and may be biotinylated or otherwise labeled. In addition, the editing cassette may comprise a barcode. A barcode is a unique DNA sequence that corresponds to the donor DNA sequence such that the barcode serves as a proxy to identify the edit made to the corresponding cellular target sequence. The barcode typically comprises four or more nucleotides. Also, in preferred embodiments, an editing cassette or editing vector or engine vector further comprises one or more nuclear localization sequences (NLSs), such as about or more than about 1, 2, 3, 4, 5, 6, 7, 8, 9, 10, or more NLSs.

Mammalian Cell Growth, Reagent Bundle Creation Transformation and Editing

In the present methods, mammalian cells are often grown in culture off-instrument for several passages before entry into a close, end-to-end automated, closed process. Cell culture is the process by which cells are grown under controlled conditions, almost always outside the cell's natural environment. For mammalian cells, culture conditions typically vary somewhat for each cell type but generally include a medium and additives that supply essential nutrients such as amino acids, carbohydrates, vitamins, minerals, growth factors, hormones, and gases such as, e.g., $O_2$ and $CO_2$. In addition to providing nutrients, the medium typically regulates the physio-chemical environment via a pH buffer, and most cells are grown at 37° C. Many mammalian cells require or prefer a surface or artificial substrate on which to grow (e.g., adherent cells), whereas other cells such as hematopoietic cells and some adherent cells can be grown in or adapted to grow in suspension. Adherent cells often are grown in 2D monolayer cultures in petri dishes or flasks, but some adherent cells can grow in suspension cultures to higher density than would be possible in 2D cultures. "Passages" generally refers to transferring a small number of cells to a fresh substrate with fresh medium, or, in the case of suspension cultures, transferring a small volume of the culture to a larger volume of medium.

Mammalian cells include primary cells, which are cultured directly from a tissue and typically have a limited lifespan in culture, including T cells and NK cells; established or immortalized cell lines, which have acquired the ability to proliferate indefinitely either through random mutation or deliberate modification such as by expression of the telomerase gene; and stem cells, of which there are undifferentiated stem cells or partly-differentiated stem cells that can both differentiate into various types of cells and divide indefinitely to produce more of the same stem cells.

Primary cells can be isolated from virtually any tissue. Immortalized cell lines can be created or may be well-known, established cell lines such as human cell lines DU145 (derived from prostate cancer cells); H295R (derived from adrenocortical cancer cells); HeLa (derived from cervical cancer cells); KBM-7 (derived from chronic myelogenous leukemia cells); LNCaP (derived from prostate cancer cells); MCF-7 (derived from breast cancer cells); MDA-MB-468 (derived from breast cancer cells); PC3 (derived from prostate cancer cells); SaOS-2 (derived from bone cancer cells); SH-SY5Y (derived from neuroblastoma cells); T-047D (derived from breast cancer cells); TH-1 (derived from acute myeloid leukemia cells); U87 (derived from glioblastoma cells); and the National Cancer Institute's 60 cancer line panel NCI60; and other immortalized mammalian cell lines such as Vero cells (derived from African green monkey kidney epithelial cells); the mouse line MC3T3; rat lines GH3 (derived from pituitary tumor cells) and PC12 (derived from pheochromocytoma cells); and canine MDCK cells (derived from kidney epithelial cells).

Stem cells are of particular interest in the methods and compositions described herein. Generally speaking, there are three general types of mammalian stem cells: adult stem cells (ASCs), which are undifferentiated cells found living within specific differentiated tissues including hematopoietic, mesenchymal, neural, and epithelial stem cells; embryonic stem cells (ESCs), which in humans are isolated from a blastocyst typically 3-5 days following fertilization and which are capable of generating all the specialized tissues that make up the human body; and induced pluripotent stem cells (iPSCs), which are adult stem cells that are created using genetic reprogramming with, e.g., protein transcription factors.

Once the cells of choice have been grown and passaged several times—in most embodiments off-instrument—in a first step the mammalian cells that are to be edited are transferred to an automated instrument where the cells are grown in cell culture and the growth of the cells is monitored. Growth modules envisioned in the automated instrument include a rotating growth module, a tangential filtration module, and a bioreactor, all of which are described in detail infra. Moreover, these growth modules may be used for the transfection or reverse transfection steps performed to initiate editing. Monitoring is usually performed by imaging the cells as described infra and/or by, e.g., measuring pH of the medium using a medium comprising a pH indicator. As opposed to 2D culture of cells as described above, the present methods envision culturing the cells in suspension. Growing cells in suspension can be effected in various configurations. Adherent cells that typically are grown in 2D cultures when grown in suspension often aggregate into "clumps." For example, some iPSCs grow well as aggregates in suspension, and are most healthy growing in aggregates of 50-300 microns in size, starting off as smaller aggregates 30-50 microns in size. iPSCs are typically grown in culture 3-5 days between passaging and the larger aggregates are broken into smaller aggregates by filtering them, e.g., through a cell strainer (e.g., a sieve or frit) with a 37 micron filter. The iPSCs can grow indefinitely in 3D aggregates as long as they are passaged into smaller aggregates when the aggregates become approximately 300-400 microns in size.

An alternative to growing cells in 3D aggregates and in a preferred embodiment is growing cells on microcarriers. Generally, microcarriers are nonporous (comprising pore sizes range from 0-20 nm), microporous (comprising pore sizes range from 20 nm-1 micron), and macroporous (comprising pore sizes range from 1-50 microns). Microcarriers may be fabricated from natural organic materials such as, e.g., gelatin, collagen, alginate, agarose, chitosan, and cellulose; biocompatible synthetic polymeric materials such as, e.g., polystyrene, polyacrylates such as polyacrylamide, polyamidoamine (PAMAM), polyethylene oxide (PEO/PEG), poly(N-isopropylacrylamide) (PNIPAM), polycaprolactone (PCL), polylactic acid (PLA), and polyglycolic acid (PGA); inorganic materials such as, e.g., silica, silicon, mica, quartz and silicone; as well as mixtures of natural, polymeric materials, cross-linked polymeric materials, and inorganic materials etc. on which animal cells can grow. Microcarriers useful in the methods herein typically range in size from 30-1200 microns in diameter and more typically range in size from 40-200 or from 50-150 microns in diameter.

Finally, another option for growing mammalian cells for editing in the compositions, methods, modules and automated instruments described herein is growing single cells in suspension using a specialized medium such as that developed by ACCELLTA™ (Haifa, Israel). Cells grown in this medium must be adapted to this process over many cell passages; however, once adapted the cells can be grown to a density of >40 million cells/ml and expanded 50-100× in approximately a week, depending on cell type. For cells grown in suspension, liquid delivery of the editing components such as shown in FIG. 6C may be used.

There are three exemplary modules—as an alternative to classic culture in flasks or tissue culture plates—for growing and monitoring cells off-instrument or in the automated instruments described herein. One module is a rotating growth module, which is depicted in FIGS. 3A-3E, another module is a tangential flow filtration module (TFF), which is depicted in FIGS. 4A-4E and finally another growth module is a bioreactor, which is depicted in FIGS. 5A-5G. These modules can be adapted to dissociate cells (if required) as well, which process is described in detail in relation to these figures.

The cells grown off-instrument or, more typically, in a growth module of the automated instrument as well as reagents needed for cell growth, nucleic acid amplification, cell transfection (e.g., the RBMCs), cell editing and enrichment may be provided in a reagent cartridge, particularly is a closed, fully-automated instrument as described herein. The cells and reagents are moved from the reagent cartridge and between modules by a robotic liquid handling system including the gantry. As an example, the robotic liquid handling system may include an automated liquid handling system such as those manufactured by Tecan Group Ltd. of Mannedorf, Switzerland, Hamilton Company of Reno, Nev. (see, e.g., WO2018015544A1 to Ott, entitled "Pipetting device, fluid processing system and method for operating a fluid processing system"), or Beckman Coulter, Inc. of Fort Collins, Colo. (see, e.g., US20160018427A1 to Striebl et al., entitled "Methods and systems for tube inspection and liquid level detection"), and typically includes an air displacement pipettor.

Reagent cartridges, such as those described in U.S. Pat. Nos. 10,376,889; 10,406,525; 10,478,222; 10,576,474; 10,639,637 and 10,738,271 allow for particularly easy integration with liquid handling instrumentation. In some embodiments, only the air displacement pipettor is moved by the gantry and the various modules and reagent cartridge remain stationary. In alternative embodiments, an automated mechanical motion system (actuator) additionally supplies XY axis motion control or XYZ axis motion control to one or more modules and/or cartridges of the automated multi-module cell processing system. Used pipette tips, for example, may be placed by the robotic handling system in a waste repository. For example, an active module may be raised to come into contact-accessible positioning with the robotic handling system or, conversely, lowered after use to avoid impact with the robotic handling system as the robotic handling system is moving materials to other modules within the automated multi-module cell processing instrument. Alternatively, the cells may be transferred to the growth module by the user.

Alternatively, in some embodiments, a gantry and/or an air displacement pump is not used; instead, in one embodiment reagents are individually connected to the bioreactor, typically via tubing or microfluidic circuits; in another embodiment, reagents may be connected to a manifold that has a single connection to the bioreactor. In some embodiments, the bioreactor is a completely closed fluidic system; that is, e.g., no pipets piercing reagent tubes and transferring liquid.

In addition, any of the growth modules described herein may reside in the same automated instrument; that is, one automated instrument may comprises two or more rotating growth modules, two or more tangential flow filtration modules and/or two or more bioreactors and/or combinations of these modules for processing cells in parallel.

In a next step, the cells that have been grown in suspension or on microcarriers are dissociated or, if grown on microcarriers, may be dissociated from the microcarrier and/or transferred to fresh microcarriers. Dissociation is required if the cells grown as cell aggregates. In one embodiment, dissociation may be via mechanical means such as agitation or by a filter, frit or sieve. Such a filter, frit or sieve may be adapted to be part of the rotating growth module, tangential flow filtration module, or bioreactor module as described in relation to FIGS. 3A-3E, 4A-4E, and 5A-5G or may be a separate "dissociation only module." For example, cells grown in a rotating growth module may be transferred to the tangential flow filtration module (TFF) for dissociation.

As an alternative, aggregates of cells may be dissociated by enzymes such as hemagglutinin, collagenase, dispase and trypsin, which can be added to the medium of the growing cells in the rotating growth module, tangential flow filtration module or bioreactor. If the cells are grown on microcarriers, the cells can be dissociated from the microcarriers using enzymes that are typically used in cell culture to dissociate cells in 2D culture, such as collagenase, trypsin or pronase or by non-enzymatic methods including EDTA or other chelating chemicals. In a bioreactor, dissociation can be performed mechanically using, e.g., an impeller or by bubbling, or cells grown in a bioreactor may be transferred to a dissociation module. Example IX herein describes the results of cells having been detached in a bioreactor via turbulence created by an impeller. In the rotating growth module, cells may be dissociated by turbulence in the culture caused by rotation and/or by inclusion of "fins" (as described infra) or fins with an integrated frit of sieve.

Finally, in some methods and instruments, the population of cells after editing are enriched for edited cells by, e.g., magnetic beads, antibiotic selection, co-edit selection, or FACS sorting, all of which are described in more detail infra.

Exemplary Embodiments for Delivery of Reagent Bundles to Mammalian Cells

I. Microcarrier-Partitioned Reagent Delivery for Editing Cells Grown in Suspension FIG. 1A depicts an exemplary workflow employing microcarrier-partitioned delivery for editing mammalian cells grown in suspension where the cells are co-localized on RBMCs comprising the nucleic acids to be transfected into the cell. In a first step, the cells to be edited are grown for several passages, e.g., off instrument, to assure cell health. The cells may be grown in 2D culture, in 3D culture (if the cells are viable when grown in or adapted to 3D culture) or on microcarriers. This initial cell growth typically takes place off the automated instrument. If necessary, the cells are dissociated and added to medium in, e.g., a rotating growth vial, TFF reservoir or bioreactor comprising cell growth medium such as MEM, DMEM, RPMI, or, for stem cells, mTeSR™Plus serum-free, feeder-free cell culture medium (STEMCELL Technologies Canada INC., Vancouver, BC) and cell growth microcarriers. If the cells are grown initially on microcarriers, the microcarriers are transferred to a rotating growth vial, TFF reservoir or bioreactor comprising cell growth medium such as mTeSR™Plus serum-free, feeder-free cell culture medium (STEMCELL Technologies Canada INC., Vancouver, BC) and additional microcarriers. Approximately 1e7 cells are transferred to the cell growth module on the automated instrument for growth.

In parallel with the off-instrument cell growth, reagent bundle microcarriers (RBMCs) are manufactured, also off-instrument. The present description provides several methods for manufacturing RBMCs that may be used to edit the cells in the automated instrument in relation to FIGS. 1B, 1C and 1D, 1F, and 2B-2J.

The cells are grown in 3D culture on microcarriers in the RGV, TFF or bioreactor for, e.g., three days or until a desired number of cells, e.g., 1e8, cells are present. Note that all processes in this FIG. 1A may take place in the rotating growth module, the TFF or the bioreactor or a combination thereof; e.g., if the TFF module is a cell dissociation module only. During this growth cycle, the cells are monitored for cell number, pH, and optionally other parameters. As described above, cell growth monitoring can be performed by imaging, for example, by allowing the microcarriers to settle and imaging the bottom of the rotating growth vial, TFF retentate reservoir or bioreactor. Alternatively, an aliquot of the culture may be removed and run through a separate flow cell, e.g., in a separate module, for imaging. In another alternative, the cells may express a fluorescent protein and fluorescence in the cell culture is measured. This microcarrier-based workflow can be performed in the rotating growth device, the TFF device or the bioreactor with most if not all steps performed in the same device; thus, several rotating growth and/or TFF devices and/or bioreactors may be deployed in parallel for two to many samples simultaneously. In yet another alternative, permittivity or capacitance is used to monitor cell coverage on the microcarriers. In yet another embodiment, an aliquot of cells is manually removed and counted on a commercial cell counter (i.e., Thermofisher Countess, Waltham, Mass.).

The microcarriers used for initial cell growth can be nonporous (where pore sizes are typically <20 nm in size), microporous (with pores between >20 nm to <1 μm in size), or macroporous (with pores between >1 μm in size, e.g. 20 μm). In microcarrier culture, cells grow as monolayers on the surface of nonporous or microporous microcarriers, which are typically spherical in morphology; alternatively, the cells grow on the surface and as multilayers in the pores of macroporous microcarriers. The microcarriers preferably have a density slightly greater than that of the culture medium to facilitate easy separation of cells and medium for, e.g., medium exchange and imaging; yet the density of the microcarriers is also sufficiently low to allow complete suspension of the microcarriers at a minimum stirring or bubbling rate. Maintaining a low stirring or bubbling rate is preferred so as to avoid hydrodynamic damage to the cells.

The microcarriers used for cell growth depend on cell type and desired cell numbers, and typically include a coating of a natural or synthetic extracellular matrix or cell adhesion promoters (e.g., antibodies to cell surface proteins or poly-L-lysine) to promote cell growth and adherence. Microcarriers for cell culture are widely commercially available from, e.g., Millipore Sigma, (St. Louis, Mo., USA); Thermo Fisher (Waltham, Mass., USA); Pall Corp. (Port Washington, N.Y., USA); GE Life Sciences (Marlborough, Mass., USA); and Corning Life Sciences (Tewkesbury, Mass., USA). As for the extracellular matrix, natural matrices include collagen, fibrin and vitronectin (available, e.g., from ESBio, Alameda, Calif., USA), and synthetic matrices include Matrigel® (Corning Life Sciences, Tewkesbury, Mass., USA), Geltrex™ (Thermo Fisher Scientific, Waltham, Mass., USA), Cultrex® (Trevigen, Gaithersburg, Md., USA), biomemetic hydrogels available from Cellendes (Tubingen, Germany); and tissue-specific extracellular matrices available from Xylyx (Brooklyn, N.Y., USA); further, denovoMatrix (Dresden, Germany) offers screenMATRIX™, a tool that facilitates rapid testing of a large variety of cell microenvironments (e.g., extracellular matrices) for optimizing growth of the cells of interest.

Following cell growth, medium exchange is performed by, e.g., stopping rotation of the rotating growth vial, stopping bubbling in the retentate reservoir of the TFF, or stopping the impeller rotation or bubbling action in the bioreactor and allowing the microcarriers to settle. In one method, the cells are removed from the microcarriers using enzymes such as collagenase, trypsin or pronase, or by non-enzymatic methods including EDTA or other chelating chemicals, and once removed from the carriers, medium is added to dilute the enzyme to inhibit enzymatic action. Once medium is added, then the cells are separated from the microcarriers and are optionally dissociated via a filter, sieve or by agitation. Alternatively, cells can be removed from microcarriers by dissolving the microcarriers. Next, microcarriers comprising the manufactured reagent bundles (RBMCs) are added to the dissociated cells. Alternatively, instead of removing cells from the cell growth microcarriers and re-seeding on RBMCs, the cells are transferred from the cell growth microcarriers to RBMCs via microcarrier bridge passaging. Bridge passaging involves allowing a new microcarrier (e.g. an RBMC) to come into physical contact with a cell-laden microcarrier, such that cells on the latter microcarrier can migrate to the RBMC.

RBMCs are not prepared on-instrument but are pre-manufactured. The microcarriers used for reagent bundles may be microporous microcarriers, which, due to the plethora of micropores, can carry a larger reagent payload per carrier diameter than nonporous or macroporous microcarriers. Preferred RBMCs are microporous, to provide increased surface area for reagent delivery, and functionalized on the surface so as to be able to bind reagents. Preferred microcarriers for RBMC include Pierce™ Streptavidin UltraLink™ Resin, a cross-linked polyacrylamide carrier functionalized with streptavidin comprising a pore size of 50 to 100 nm; Pierce™ NeutrAvidin™ Plus Ultra-Link™ Resin, cross-linked polyacrylamide carrier functionalized with avidin comprising a pore size of 50 to 100 nm; and UltraLink™ Hydrazide Resin, a cross-linked polyacrylamide carrier functionalized with hydrazine comprising a pore size of 50 to 100 nm, all available from Thermo Fisher (Waltham, Mass., USA); cross-linked agarose resins with alkyne, azide, photo-cleavable azide and disulfide surface functional groups available from Click Chemistry Tools (Scottsdale, Ariz., USA); Sepharose™ Resin, cross-linked agarose with amine, carboxyl, carbodiimide, N-hydroxysuccinimide (NHS), and epoxy surface functional groups available from GE Health (Chicago, Ill., USA).

The microcarriers are loaded with amplified editing cassettes or amplified editing plasmids, engine plasmids, nuclease or nuclease fusion proteins, mRNAs or ribonucleoproetins (RNPs) depending on, e.g., the functionalized group, via, e.g., via chemical or photo linkage or depending on a surface coating on the microcarrier, if present. RBMCs are prepared by 1) partitioning and amplifying a single copy of an editing cassette to produce clonal copies in an RBMC, or by 2) pooling and amplifying editing cassettes, followed by dividing the editing cassettes into sub-pools and "pulling down" the amplified editing cassettes with microcarriers comprising nucleic acids specific to and complementary to unique sequences on the editing cassettes. The step of sub-pooling acts to "de-multiplex" the editing cassette pool, thereby increasing the efficiency and specificity of the "pull down" process. De-multiplexing thus allows for amplification and error correction of the editing cassettes to be performed in bulk followed by efficient loading of clonal copies of the editing cassettes onto a microcarrier.

FIG. 1B depicts alternative methods for populating microcarriers with a LIPOFECTAMINE™ (a composition of 3:1 DOSPA (2,3-dioleoyloxy-N-[2(sperminecarboxamido) ethyl]-N,N-dimethyl-1-propaniminium trifluoroacetate) to DOPE (1,2-dioleoyl-sn-glycerophosphotheanolamine))/nucleic acid payload and cells. At top left, partitioned LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) and nucleic acid payloads 152 ("LNPs") are formed in solution from nucleic acids 154 and LIPOFECTAMINE™ (a composition of 3:1 DOSPA (2,3-dioleoyloxy-N-[2(sperminecarboxamido) ethyl]-N,N-dimethyl-1-propaniminium trifluoroacetate) to DOPE (1,2-dioleoyl-sn-glycerophosphotheanolamine)) 156 prior to being adsorped onto micocarriers 150 ("MCs") comprising a coating such as laminin 521 to foster LNP adsorption and cell attachment. The microcarriers 150 are added to the solution of pre-formed or pre-complexed LNPs 152 comprising nucleic acids (e.g., editing cassettes) 154 and LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) 156. The LNPs 152 adsorb onto the microcarriers 150 to form LNPsMCs 157. The processes of forming RBMCs to this point are typically performed off-instrument. Following adsorption of the LNPs 152 onto the microcarriers 150, the microcarriers 150 are provided on-instrument where they are seeded with cells 158 to form microcarriers 160a with both LNPs 152 and cells 158 on the surface. The cells begin to take up the nucleic acids 154 complexed with the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) 156 on microcarriers 160a, where these cells+LNP complexes are denoted at 152a, a process which take several hours up to several days. At the end of the uptake process, transfected cells will reside on the surface of the microcarriers, denoted at 162a.

FIG. 1B at top right shows a process where the microcarriers 150 first adsorb the nucleic acids 154 (e.g., editing cassettes) to form microcarriers 151. Microcarriers 151 are then incubated with LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) 156, where the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) 156 is adsorbed onto the microcarrier 151 and the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) 156 will complex with the nucleic acids 154 to form LNP-nucleic acid complexes 152 resulting in LNPsMCs 154, i.e., the same complex as in the process shown on the left of FIG. 1B. Again, these processes typically take place off-instrument. As with the process at left, following adsorption of the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) 156 onto the microcarriers 151 comprising nucleic acids 154, the microcarriers 151 are seeded with cells 158 to form microcarriers 160b with both LNPs 152 and cells 158 on the surface. The cells begin to take up the nucleic acids 154 complexed with the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) 156 on microcarriers 160b, where these cells+LNP complexes are denoted at 152b, a process which may take several hours up to several days. At the end of the uptake process, transfected cells will reside on the surface of the microcarriers, denoted at 162b.

Figure 1C:
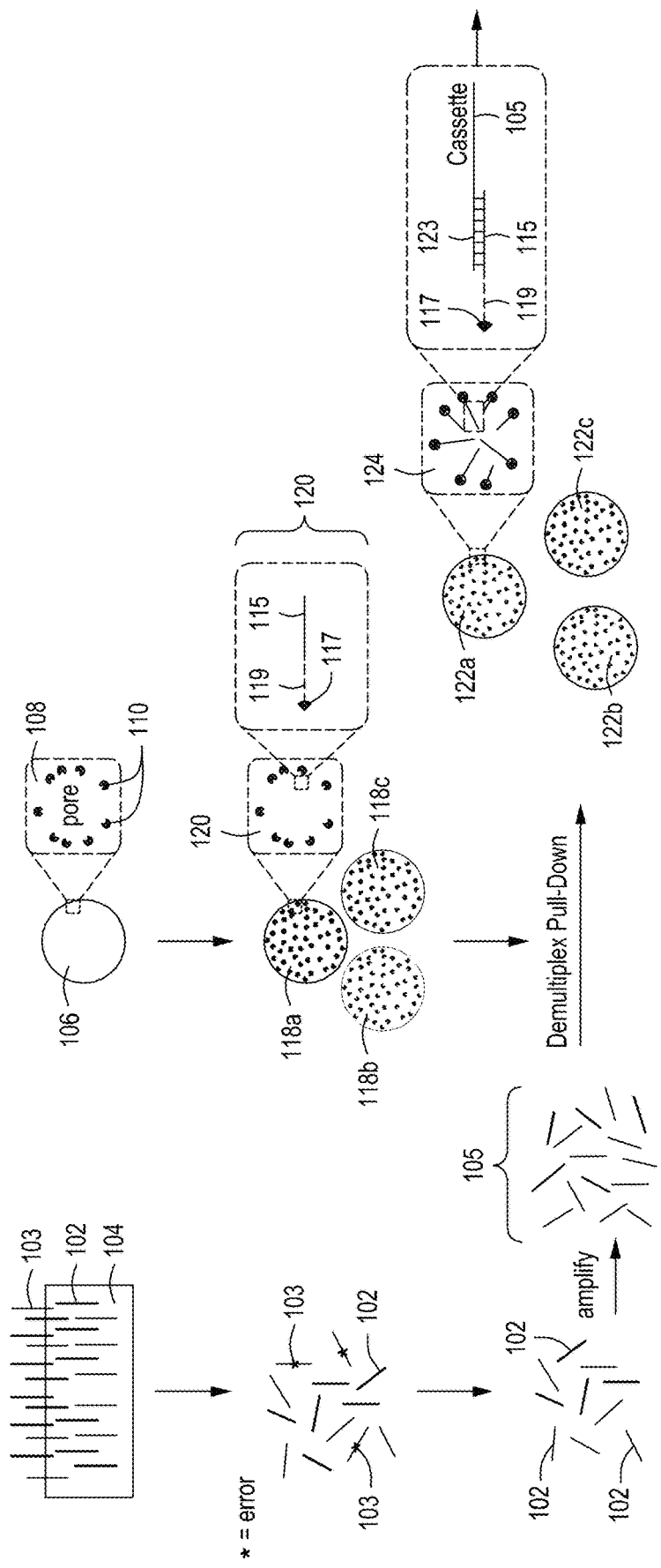
FIG. 1C depicts manufacture of high copy number reagent bundles via a "pull down" method and FIG. 1D depicts co-localizing the reagent bundles with live mammalian cells.

FIG. 1C, described in detail infra, depicts one method for loading editing cassettes onto RBMCs to assure the editing cassettes on any one bead are clonal copies of one another. Again, the formation or manufacture of RBMCs typically takes place off-instrument. The nuclease or nuclease fusion in protein form may be encapsulated inside gel bead RBMCs or the nuclease or nuclease fusion may be bound to the RBMCs using, e.g., a bait gRNA or form an RNP with a gRNA. Once the reagents are loaded onto the RBMCs, the RBMCs are coated with an extracellular matrix or other bio-macromolecules as described above to allow the cells to adhere and grow on the RBMCs.

Once the RBMCs have been prepared, the dissociated cells (or microcarriers with cells) are mixed with the RBMCs in medium and the cells are allowed to populate the RBMCs and grow. For example, at least 100,000 different RBMCs (that is, a population of RBMCs with at least 100,000 different editing cassettes attached) comprising 1e8-1e9 copies of a clonal editing cassette or editing plasmid per RBMC is mixed with at least 1000 cells per RBMC. After the cells grow to a desired density on the RBMCs, medium exchange is performed wherein the medium comprises LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) or polycationic polymer for transfection, and a release trigger such as, e.g., UV light; enzymes such as USER, proteinase; reductants such as β-mercaptoethanol, DTT; etc. allows the editing cassettes or editing vector and engine vector or nuclease, nuclease fusion or RNP to be released from the RBMC and transfect the cells grown on the RBMC. Once sufficient time has passed to allow transfection, medium exchange is performed once again to remove the unreacted reagents and conditions are provided to allow the cells on the RBMCs to edit and divide. These edited cells are then removed from the RBMCs such as, e.g., using enzymes such as collagenase, trypsin or pronase, and transferred off-instrument to 2D or 3D culture to recover and grow; alternatively, the cells may be enriched for edited cells by selection in antibiotics or via magnetic beads.

Figure 1D:
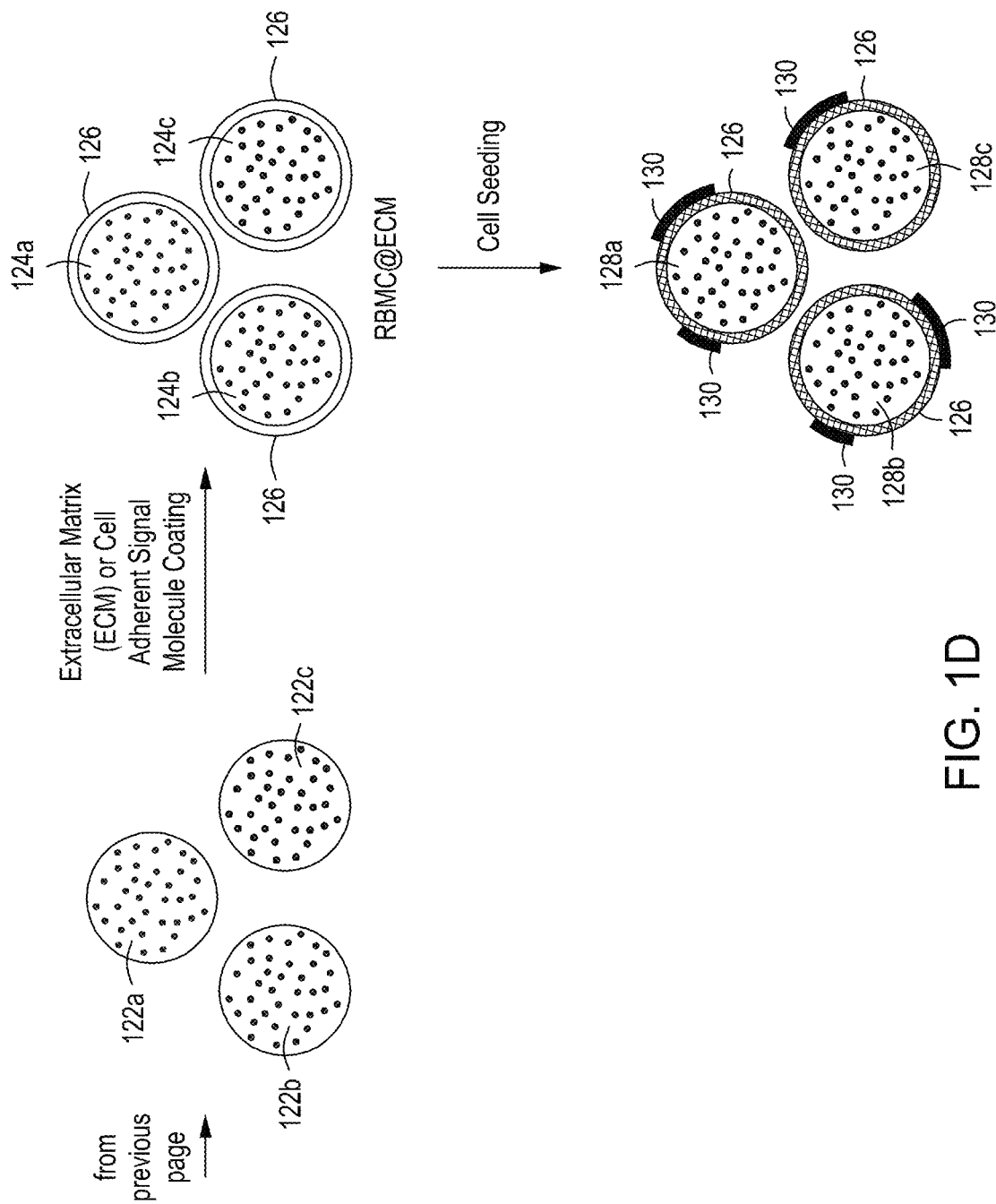

FIGS. 1C and 1D depict one method for loading editing cassettes onto an RBMC and delivering or co-localizing the RBMC to live cells. Looking at FIG. 1C top left, editing cassettes 102, 103 are synthesized on a substrate. The editing cassettes all have different gRNA and donor DNA pairs. Once synthesized, the editing cassettes are removed from substrate 104. During most oligonucleotide synthesis procedures, some oligonucleotides will comprise one or more sequence errors. The oligonucleotides are processed so as to remove oligonucleotides with errors 103, leaving only oligonucleotides, e.g., error-corrected editing cassettes 102, which were synthesized properly. At a next step, the error-corrected editing cassettes 102 are amplified to produce a pool 105 of error-corrected editing cassettes 102.

In parallel, looking at the top middle of FIG. 1C, porous microcarriers 106 comprising pores 108 with functionalized reagent groups 110 are provided. In a next step, the porous microcarriers 118a, 118b, and 118c, are "loaded" with capture oligonucleotides 120 each comprising a functionalized group 117 compatible with the functionalized reagent group 110 on the porous microcarrier, a cleavable group 119 and a DNA barcode 115 where the DNA barcode 115 has a sequence compatible with one of the editing cassettes. The capture oligonucleotides 120 are loaded on the porous microcarriers 118a, 118b and 118c where the functionalized groups 117 and cleavable groups 119 are universal to the capture oligonucleotides on the microcarriers; however, the DNA barcode 115 is different for each porous microcarrier. A batch of porous microcarriers each with functionalized group 117 and cleavable group 119 and DNA barcode 115; a batch of porous microcarriers each with functionalized group 117 and cleavable group 119 and a different DNA barcode 115; and porous microcarriers each with functionalized group 117 and cleavable group 119 and yet a different DNA barcode 115 can be manufactured in advance, with aliquots of each batch mixed prior to loading with the amplified editing cassettes.

At a next step, the pool 105 of error-corrected editing cassettes is added to the mixed batches or mixed sub-pools of porous microcarriers, and the DNA barcodes 115 hybridize to a barcode portion 123 of the editing cassettes 105. Each different editing cassette 105 has a different barcode; thus, porous microcarrier 118a will hybridize to an editing cassette 105 with a complementary barcode portion 123; porous microcarrier 118b will hybridize to an editing cassette 105 with a complementary barcode portion 123; and porous microcarrier 118c will hybridize to an editing cassette 105 with a complementary barcode portion 123, resulting in loaded porous microcarriers 122a, 122b, and 122c with clonal copies of a single editing cassette attached. The microcarriers comprising the functionalized/cleavable/barcode-complementary nucleic acids are separated into sub-pools to "de-multiplex" the pull-down process. That is, to each sub-pool of microcarriers a mixture of the amplified editing cassettes if added. Sub-pooling increases the efficiency and specificity of hybridization of the barcodes on the editing cassettes to the complementary sequence on the nucleic acids on the microcarrier surface.

FIG. 1D depicts adding an extracellular matrix to the loaded porous microcarriers 122a, 122b, and 122c. In a first step, the extracellular matrix (or alternatively, a cell adhesion promoter molecule coating) 126 is added to the loaded porous microcarriers 122a, 122b, and 122c to coat the surface of the loaded porous microcarriers, resulting in RBMCs 124a, 124b, and 124c. Next, cells 130 are added to the RBMCs 124a, 124b, and 124c resulting in cell-populated RBMCs 128a, 128b and 128c.

Figure 1E:
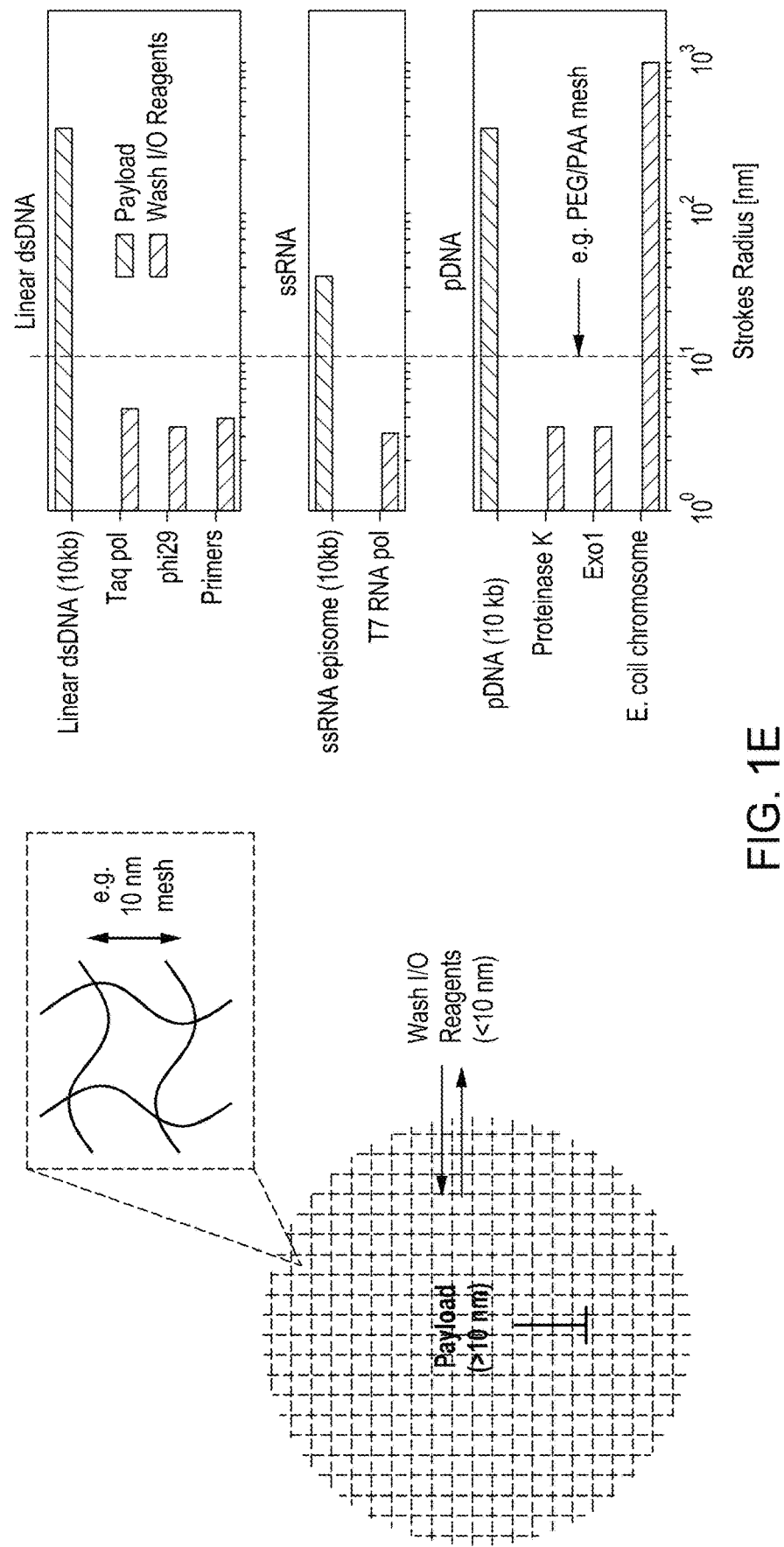
FIG. 1E depicts parameters for creating high copy number reagent bundles via encapsulation in a size-selective porous microcarrier.

FIG. 1E depicts a "tunable" gel bead, where the bead is formed such that it can carry a payload of, e.g., linear single- or double-strand DNA or single-strand RNA—which is effectively encapsulated within the gel bead—however, pores in the bead "mesh" allow nucleic acid amplification reagents to penetrate the gel bead. The gel matrix forming a microcarrier typically comprises at least one polymer and a linker. A microcarrier may be porous, non-porous, solid, semi-solid, and/or semi-fluidic. In the gel bead depicted in FIG. 1E, the bead is degradable, dissolvable or disruptable. The gel bead may be a hydrogel bead, formed from molecular precursors such as a polymeric or monomeric species. Gel beads may be of uniform size or heterogeneous size. In some cases, the diameter of a gel bead is at least about 1 micrometer (µm), 5 µm, 10 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 150 µm, 200 µm, 250 µm, 300 µm, 400 µm, 500 µm, 1 mm, or greater. Typically, in the present methods the gel beads are provided as a population or plurality of gel beads having a relatively monodisperse size distribution as it is desirable to provide relatively consistent amounts of reagents within the gel beads.

Gel beads for use herein contain molecular precursors (e.g., monomers or polymers) that form the polymer network via polymerization of the molecular precursors. In some embodiments, a precursor may be an already polymerized species capable of undergoing further polymerization via, for example, a chemical cross-linkage. For example, a precursor may comprise one or more of an acrylamide or a methacrylamide monomer, oligomer, or polymer. In some cases, the gel bead may comprise pre-polymers, which are oligomers capable of further polymerization; for example, polyurethane beads may be prepared using prepolymers.

Alternatively, the gel bead may contain individual polymers that may be further polymerized together. In some embodiments, gel beads may be generated via polymerization of different precursors, such that they comprise mixed polymers, co-polymers, and/or block co-polymers. In some embodiments, the gel bead may comprise covalent or ionic bonds between polymeric precursors (e.g., monomers, oligomers, linear polymers) and other entities. In some aspects, the covalent bonds can be carbon-carbon bonds or thioether bonds. In the present methods, cross-linking preferably is reversible, which allows for the polymer to linearize or dissociate under appropriate conditions. In some aspects of the present methods, reversible cross-linking may also allow for reversible attachment of a material bound to the surface of a gel bead.

In some aspects, disulfide linkages can be formed between molecular precursor units (e.g., monomers, oligomers, or linear polymers) incorporated into the gel bead. For example, cystamine and modified cystamines are organic agents comprising a disulfide bond that may be used as a crosslinker agent between individual monomeric or polymeric precursors of a gel bead. Polyacrylamide may be polymerized in the presence of cystamine or a species comprising cystamine to generate polyacrylamide gel beads comprising disulfide linkages; that is, chemically degradable beads comprising chemically-reducible cross-linkers. The disulfide linkages permit the bead to be degraded (or dissolved) upon exposure of the bead to a reducing agent.

Functionalization of microcarriers for, e.g., attachment of the editing cassettes or other moieties to the gel bead may be achieved through a number of different approaches, including activation of chemical groups within a polymer, incorporation of active functional groups in the polymer structure, or attachment at the pre-polymer or monomer stage in gel bead production.

In some of the embodiments herein, the editing cassettes, editing vectors, nuclease or nickase fusion coding sequence, engine vector, PCR reagents, transformation or transfection reagents, etc. are encapsulated in gel beads during gel bead generation (e.g., during polymerization of precursors) and the gel beads are not permeable to the nucleic acid amplification reagents. In other embodiments, small molecules such as lipofect or PCR reagents (e.g., primers, polymerases, dNTPs, co-factors) and buffers may be added to the gel beads after formation such as with the gel bead in FIGS. 1E and 1F. The encapsulation of reagents and the addition of reagents after gel bead formation is controlled by the polymer network density. The porosity of gel beads can be controlled by adjusting the polymer concentration or degree of crosslinking, effectively creating a tunable molecular cut-off size for transport through the gel. The porosity can then be adjusted to physically retain large molecules of interest while allowing smaller molecules or buffers to be freely exchanged. (See, e.g., Rehmann, et al., Biomacromolecules, 18(10):3131-42 (2017); Goodrich, et al., Nat. Communications, 9:4348 (2018); and Tsuji, et al., Gels, doi: 103390/gel4020050 (2018).) Alternatively, the polymer network may be chemically modified to conjugate specifically with a target molecule for retention. As described herein infra, encapsulated reagents and molecules may be released from a gel bead upon degradation of the gel bead.

In FIG. 1E, nucleic acids are encapsulated in size-selective gel beads and nucleic acid amplification reagents may traverse the gel bead "mesh", where the mesh has a pore size of approximately 10 nm. At right are three bar graphs showing the Stokes radius in nm of linear dsDNA ($>10^2$ nm), ssRNA ($>10^{15}$ nm) and amplification and reverse transcription reagents ($<10^1$ nm), as well as plasmid DNA and the *E. coli* chomosome.

Figure 1F:
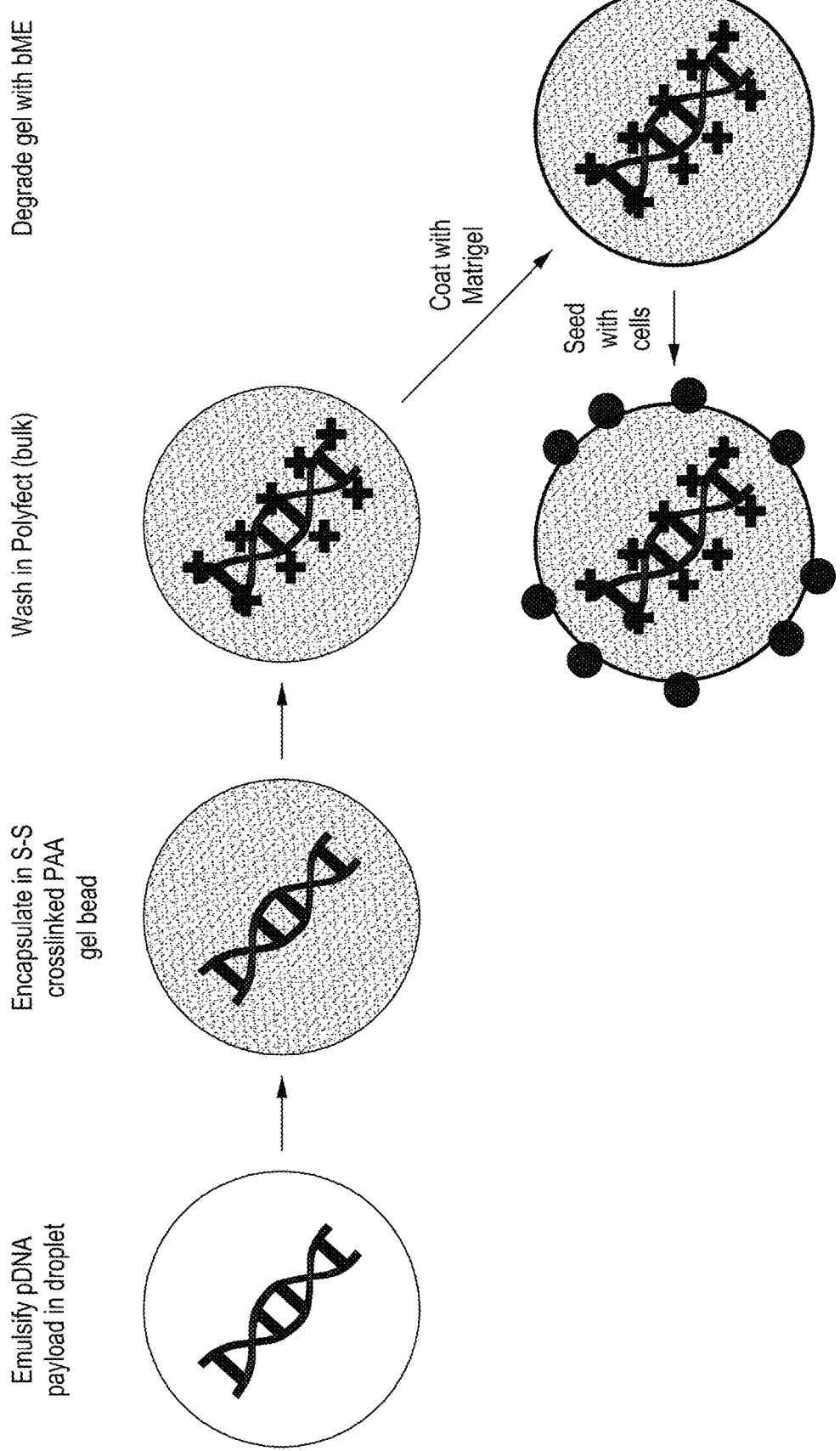
FIG. 1F depicts a method of using nucleic acids encapsulated in a size-selective porous microcarrier to add a transfection agent then co-localize the reagent bundle microcarriers with live mammalian cells.

FIG. 1F depicts the embodiment for combining amplified editing cassettes and transformation or transfection agents in a gel bead where the transformation or transfection agents are added after the droplet has been polymerized and the gel bead formed. As described in relation to FIG. 1E, reagents may be added to the gel beads after polymerization as long as the polymer network density of the gel bead is appropriate (denoted here by a single helix). In this process, first clonal copies of editing vectors are partitioned into droplets. Following partitioning into droplets, the droplets are polymerized into, e.g., a disulfide crosslinked polyacrylic acid (PAA) gel bead, where the size of the DNA payload is approximately 1e5-1e6 kDA. The gel beads are demulsified—where the oil carrier fluid is removed and the gel beads are washed in buffer—then the gel beads are washed in bulk with transformation or transfection reagents such as a transfection agent, with an approximate size of less than 1e2 kDA. The gel beads are then co-localized with cells much like seen in FIG. 1D where an extracellular matrix (or alternatively, a cell adhesion promoter coating) is added to the RBMC to coat the surface of the RBMC then cells are added to the RBMC in a cell-populated RBMC.

Figure 1G:
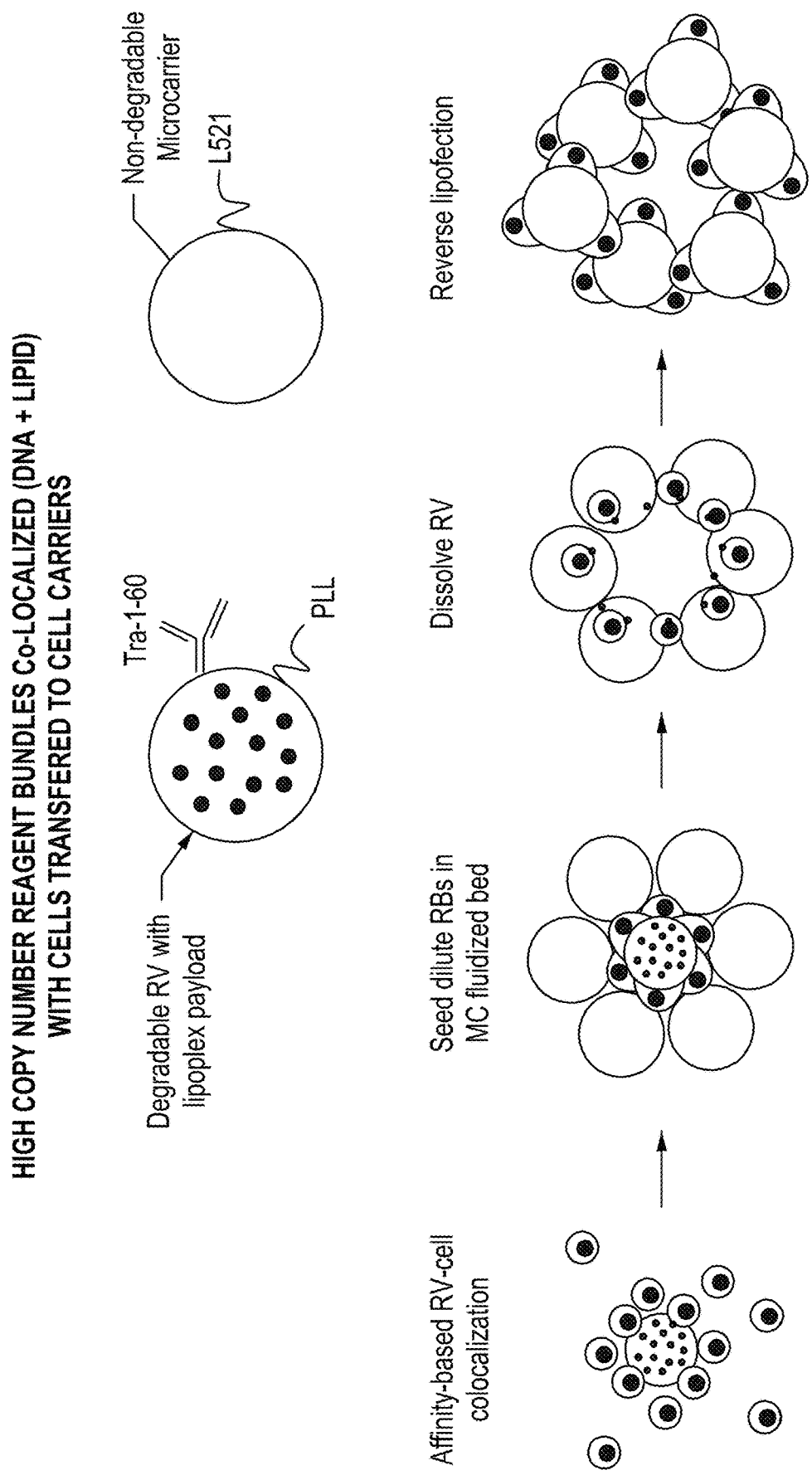
FIG. 1G depicts at top a degradable reagent bundle microcarrier and a non-degradable microcarrier, both of which are used in the method at bottom; first co-localizing live mammalian cells with the degradable reagent bundle microcarrier and then co-localizing the reagent bundle microcarrier and live mammalian cells with the non-degradable microcarrier on which the cells can grow.

FIG. 1G depicts at top a degradable loaded RBMC, such as the loaded microcarrier seen in FIG. 1F, as well as a non-degradable microcarrier, both of which are used in the method for transfecting cells at bottom. In this embodiment, the loaded RBMC, in addition to comprising a DNA payload and a transfection agent, comprises a cell adherent signal molecule, such as a cell surface protein-specific antibody (such as, e.g., the anti-human TRA-1-60 antibody) or other cell adhesion promoter such as poly-L-lysine or poly-D-lysine. The non-degradable microcarrier also comprises a cell adherent signal molecule, in this case biolaminin 521. In the embodiment shown in this FIG. 1G, live cells are co-localized to the degradable RBMC by the cell adhesion promoters on the surface of the RBMC. Next, the cell-loaded RBMCs are seeded on a densely-packed solution of the non-degradable microcarriers.

After seeding the cell-loaded RBMCs onto the non-degradable microcarriers, the RBMCs are degraded. The gel beads used in the method depicted in this FIG. 1G are dissolvable or degradable upon exposure to one or more stimuli; for example, pH changes, a change in temperature, exposure to light, or exposure to a certain chemical species such as a reducing agent. The degradable gel bead may comprise one or more species with a labile bond such that, when the gel bead is exposed to the appropriate stimuli, the labile bond is broken, and the gel bead degrades. The labile bond may be a chemical bond or another type of physical interaction such as, e.g., van der Waals interaction, dipole-dipole interaction, or the like. In some cases, the crosslinker used to generate the gel bead may comprise a labile bond, where, upon exposure to the appropriate conditions, the labile bond can be broken and the gel bead degraded. For example, upon exposure of a polyacrylamide gel bead comprising disulfide crosslinkers to a reducing agent, the disulfide bonds can be broken and the bead degraded. Examples of reducing agents include β-mercaptoethanol, dithiothreitol (DTT), (2S)-2-amino-1,4-dimercaptobutane (dithiobutylamine or DTBA), tris(2-carboxyethyl) phosphine (TCEP), or combinations thereof. Thus, in the method depicted in FIG. 1G, a reducing agent may be delivered to the densely-packed mix of cell-loaded RBMCs and the non-degradable microcarriers to dissolve the RBMC thus releasing the nucleic acid and Polyfect (Qiagen, Inc., Hilden, Germany) payload in the proximity of the cells. Although the RBMC is dissolved, the cells can adhere to the cell adherent signal molecules, e.g., biolaminin 521, on the surface of the non-degradable microcarriers on which the cells can grow.

Creating Reagent Bundles in a Scalable Manner

In addition to the RBMC fabrication shown in relation to FIGS. 1B-1D and 1F along with cell co-localization, the following figures FIGS. 2B-2J depict processes for fabricating RBMCs, which again, typically occurs off-instrument. FIG. 2A depicts a decision matrix for different types of microcarriers available for RBMCs, including gel beads, which can be prepared as depicted in FIG. 1E, infra, commercial microcarriers (functionalized microparticles), and commercial microparticles. Again, preferred microcarriers for RBMC include PIERCE™ Streptavidin ULTRALINK™ Resin, a cross-linked polyacrylamide carrier functionalized with streptavidin comprising a pore size of 50 to 100 nm; PIERCE™ NEUTRAVIDIN™ Plus ULTRALINK™ Resin, cross-linked polyacrylamide carrier functionalized with avidin comprising a pore size of 50 to 100 nm; and ULTRALINK™ Hydrazide Resin, a cross-linked polyacrylamide carrier functionalized with hydrazine comprising a pore size of 50 to 100 nm, all available from Thermo Fisher (Waltham, Mass., USA); cross-linked agarose resins with alkyne, azide, photo-cleavable azide and disulfide surface functional groups available from Click Chemistry Tools (Scottsdale, Ariz., USA); SEPHAROSE™ Resin, cross-linked agarose with amine, carboxyl, carbodiimide, N-hydroxysuccinimide (NHS), and epoxy surface functional groups available from GE Health (Chicago, Ill., USA).

FIGS. 2B-2J demonstrate exemplary methods for creating RBMCs and delivering or co-localizing the RBMCs with live mammalian cells. In addition to the methods for creating RBMCs described in relation to transfection strategies FIGS. 1B-1G, FIGS. 2B-2J describe additional methods for creating RBMCs in a scalable manner. In one scheme, single editing cassettes or editing cassette constructs are partitioned, then each partitioned single editing cassette or editing cassette construct is amplified to make thousands, tens of thousands, hundreds of thousands or more partitioned copies for delivery to cells. In the other scheme, editing cassettes are synthesized, error corrected and amplified in a pool, followed by de-multiplexing of the pool of amplified editing cassettes or editing cassette constructs. Both methods result in RBMCs with hundreds of thousands to millions of clonal copies of editing cassettes in or on a partition (e.g., droplet, gel bead or microcarrier).

Figure 2A:
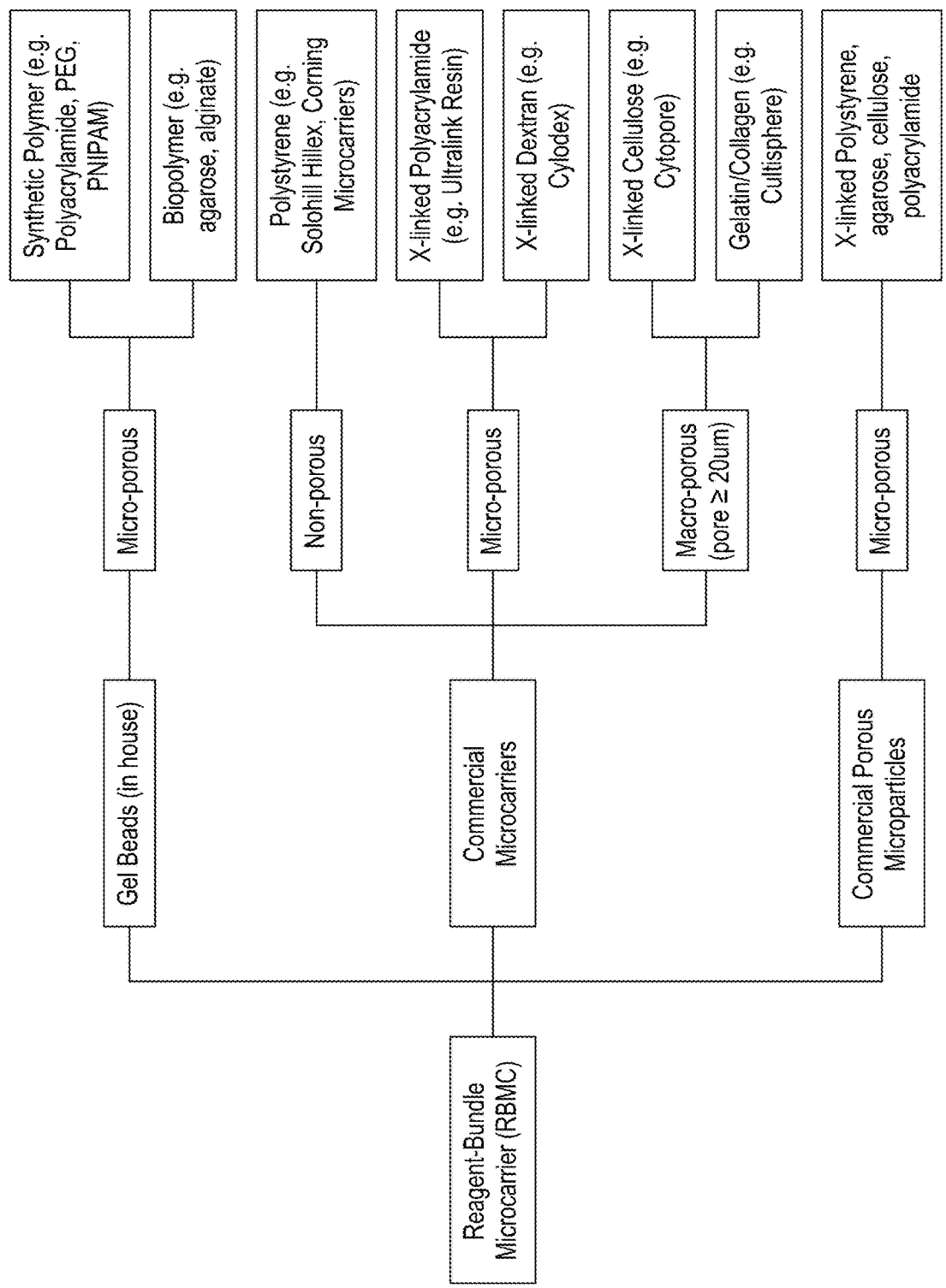
FIG. 2A depicts options for microcarriers useful in microcarrier-partitioned delivery.
Figure 2B:
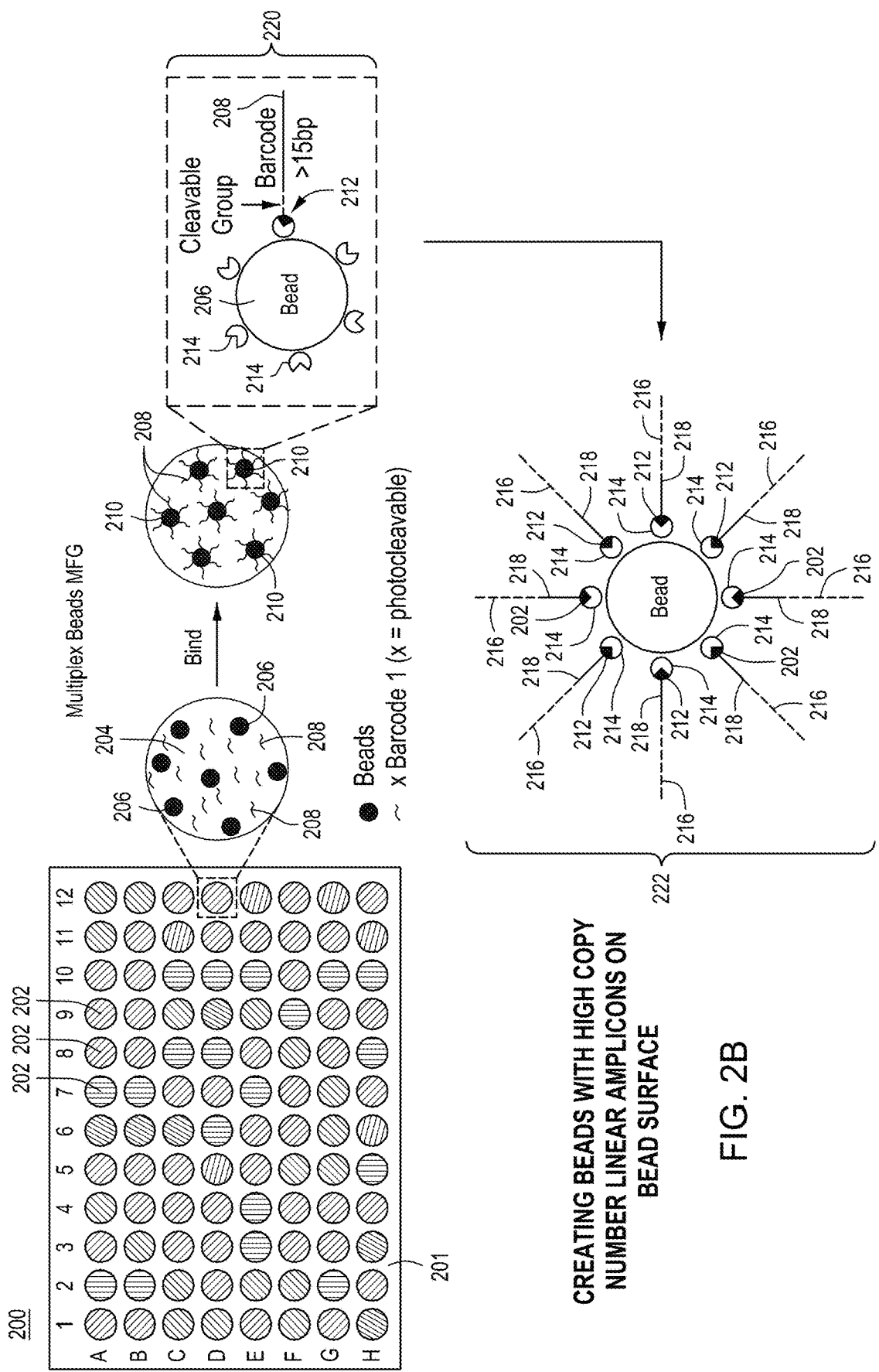
FIG. 2B depicts creating high copy number reagent bundles via pull-down of linear amplicons on a microcarrier surface.

FIG. 2B depicts manufacture 200 of high copy number RBMCs via pull-down of linear amplicons to the microcarrier surface. In a first step, wells 202 in a substrate 201 are filled with microcarriers having functional groups on their surface. The number of microcarriers distributed per well will differ depending on well size; however, a range of 50-1e4, 50-1e5, 50-1e6, 50-1e7, 50-1e8, 50-1e9, 50-1e10 depending on well size and working well volume is contemplated. The microcarriers 206 may be nonporous or microporous formed from, e.g., polystyrene or any other material that is compatible with functionalization and the surface functional groups 214 may be any group that can conjugate with a molecule that can bind to a nucleic acid such as avidin/biotin, avidin/desthiobiotin, amine/carboxylic acid, and thiol/acrylate. In a next step, nucleic acid cleavable barcode molecules 208 are added to each well, where the cleavable barcode molecules in different wells have different barcodes. The barcode molecules 208 are preferably greater than 15 bp in length and can be comprised of nucleic acids and xeno derivatives such as, e.g., DNA, RNA, PNA, LNA, morpholino DNA, 2'-O-methyl RNA, TNA, HAN, ANA, GNA or GANA. In addition to a functional group 212 capable of binding to the functional group 214 on the microcarriers 206, the cleavable barcode molecules 208 comprise a cleavable group 220 that allows the barcode molecules 208 to be cleaved from the microcarrier 206 later in the manufacturing process. Exemplary cleavable groups include avidin/biotin and avidin/desthiobiotin, which dissociate due to competition, and disulfide (redox) and nitrobenzyl (photocleavable) groups. The microcarriers 206 are loaded with the barcode molecules via the functional groups 212/214 forming a microcarrier complex 210.

After the microcarrier complexes 210 are formed in each well, amplified editing cassettes are added to each well. Because the barcode molecules 208 on the microcarrier complex 210 also comprise a sequence 218 complementary to a sequence on amplified editing cassettes 216 (e.g., to a barcode or to the gRNA or donor DNA sequence on the editing cassette), the barcode molecules 208 bind the editing cassettes 216 in the next step forming RBMCs 2222. This method is another approach to "de-multiplexing" the editing cassette pool. Again, the editing cassettes are amplified in a single pool; however, by having only one barcode sequence per well, only a single species of editing cassette is pulled down per well. Although a single editing cassette 218 is shown on microcarrier complex 210 and eight editing cassettes are shown populating RBMC 222, in practice the RBMC would comprise hundreds of thousands to millions of clonal copies of an editing cassette. Once the RBMCs 222 are formed, they can be co-localized with cells via the method shown in FIGS. 1A-1G (assuming the microcarriers further comprise cell adhesion promoters such as, e.g., an antibody to a cell surface protein or poly-L-lysine).

Figure 2C:
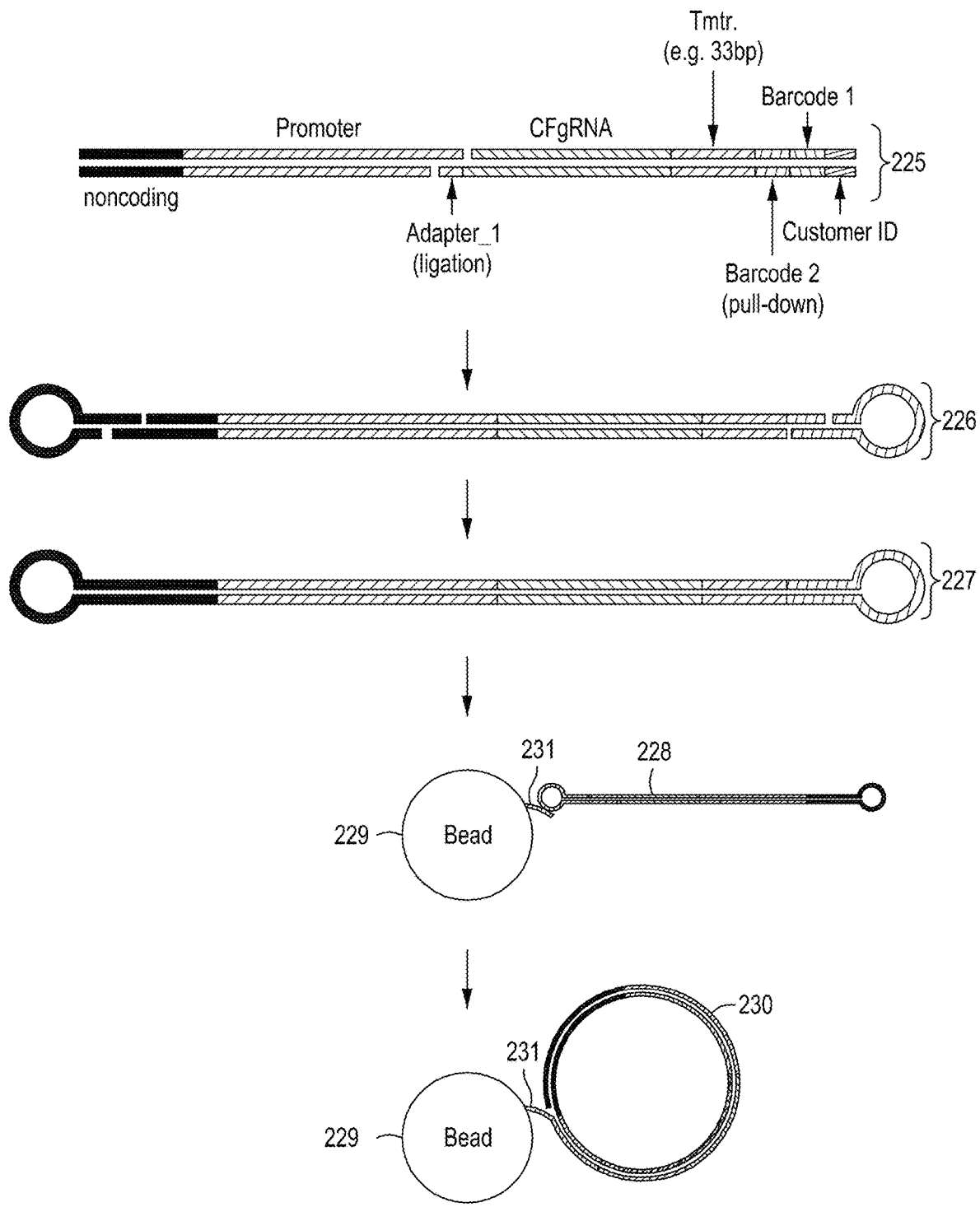
FIG. 2C depicts creating of high copy number reagent bundles via pull-down of linear amplicons with loop adapters onto a microcarrier surface.

FIG. 2C depicts an alternative method for manufacturing high copy number RBMCs, in this embodiment via pull-down onto the microcarrier surface linear amplicons having loop adapters. In this method, linear constructs 225 resulting from, e.g., restriction digests of amplified editing cassettes are hybridized to loop nucleic acid sequences at the 3' and 5' ends to form structures 226, then are ligated to form constructs 227. The loop-adapted constructs are then introduced to microcarriers 229 comprising nucleic acids 231 on the surface of the microcarriers, where the nucleic acids 231 are complementary to a sequence on one of the loops that have been ligated to the amplified editing cassettes to form surface-bound loop nucleic acids 228. Optionally, the surface-bound nucleic acids also comprise a cleavable group.

Extension of the hybridized loop and the complementary nucleic acid on the surface of the microcarrier results in circular constructs 230 comprising the editing cassettes to form RBMCs. For example, a non-processive DNA polymerase with high fidelity can be used to make the complementary strand on the beads. The barcode on the beads is attached via an internally functionalized nucleotide, with 5' and 3' ends free, where the 5' is phosphorylated, and the newly synthesized DNA strand extends from the 3' end of the barcode, and then stop the replication process when it hits the 5' phosphorylated end of the barcode. A ligation step can then be performed using a DNA ligase to yield double-stranded circular plasmids bundled on the bead surface. Note that although only one nucleic acid on the microcarrier and only one loop construct is pictured in this FIG. 2C (and the figure is not to scale), in practice each microcarrier would comprise hundreds of thousands to a million or more nucleic acids capable of hybridizing to the loop sequences of the editing cassette constructs; thus, hundreds to thousands of editing cassettes constructs would populate each RBMC.

In the embodiment described in this FIG. 2C, circular DNA molecules are used instead of linear DNA molecules, as it has been observed that circular DNA molecules are more efficient than linear DNA molecules in transfecting mammalian cells. As with other high copy number RBMCs described herein, once the RBMCs are formed they can be co-localized with cells via the method shown in FIGS. 1B-1G (assuming the microcarriers further comprise cell adhesion promoters such as, e.g., an antibody to a cell surface protein or poly-L-lysine).

Figures 1, 2D:
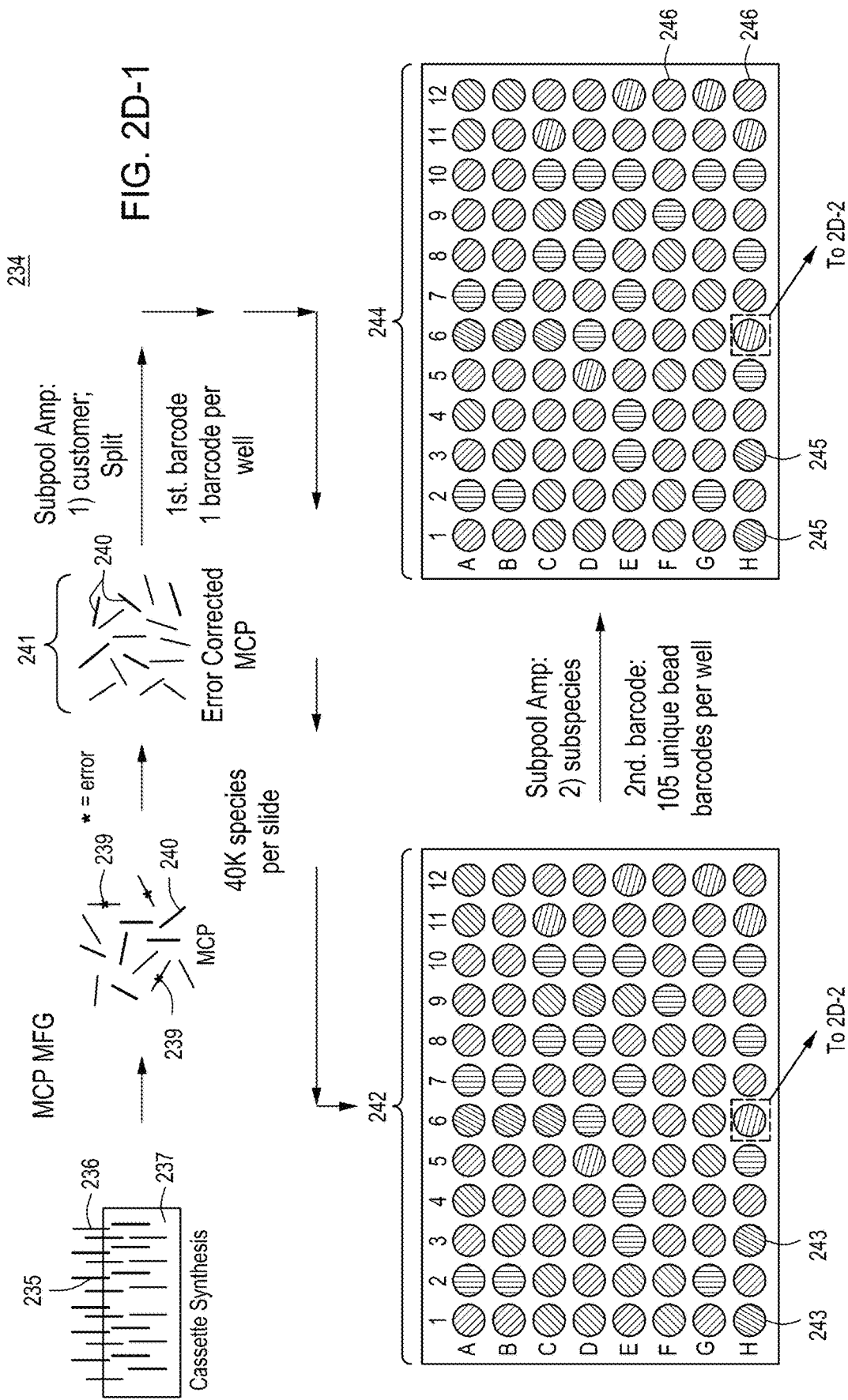
FIGS. 2D-1 and 2D-2 depict a process for creating circular plasmids comprising barcoded editing cassettes, which are used in the manufacturing processes of FIGS. 2E and 2F to produce reagent bundle microcarriers (RBMCs).

FIG. 2D-1 depicts another method 234 for creating circular plasmids to populate microcarriers to form RBMCs using the process of "de-multiplexing." In FIG. 2D-1, editing cassettes 235, 236 are synthesized on substrate 237. The editing cassettes all have different gRNA and donor DNA pairs. Once synthesized, the editing cassettes are removed from substrate 237 and pooled. As discussed previously, during most oligonucleotide synthesis procedures, some oligonucleotides will comprise one or more sequence errors. The oligonucleotides are processed so as to remove oligonucleotides with errors 235, leaving only error-corrected editing cassettes 240, which were synthesized properly; thus producing a pool 241 of error-corrected editing cassettes. The error-corrected editing cassette pool is then amplified, and the amplified pool of the error-corrected editing cassettes 240 are aliquoted into wells 243 in substrate 242 where the error-corrected editing cassettes are amplified with barcoded primers adding a first barcode to each editing cassette. After amplification, each well 243 will contain error-corrected editing cassettes 240 comprising barcode 1. The barcodes in different wells are different but within each well each barcode is the same barcode.

After the initial amplification, the amplified, barcoded editing cassettes are split among wells 245 in substrate 244, where each well comprises multiple to many (e.g., 100 or more) second barcoded primers, where each well has a different set of barcoded primers. Amplification of the barcoded primers with other barcoded primers produces an amplified subpool 246 of 105 species of barcoded editing cassettes comprising, e.g., barcoding editing cassettes, 246a, 246b and so on (see FIG. 2D-2). In this example, again de-multiplexing is used to more specifically and efficiently "pull down" the amplified editing cassettes onto the microcarriers. Following the second amplification with the second set of barcodes, the amplified, twice-barcoded editing cassettes 247a, 247b, and so on in pool 247 are assembled into vector backbones via, Gibson Assembly, thereby producing a set of editing vectors 248, comprising, e.g., vectors 249 comprising cassette A, 250 comprising cassette B and 251 comprising cassette C and so on. Each vector in addition to an editing cassette comprises two barcodes.

Figure 2E:
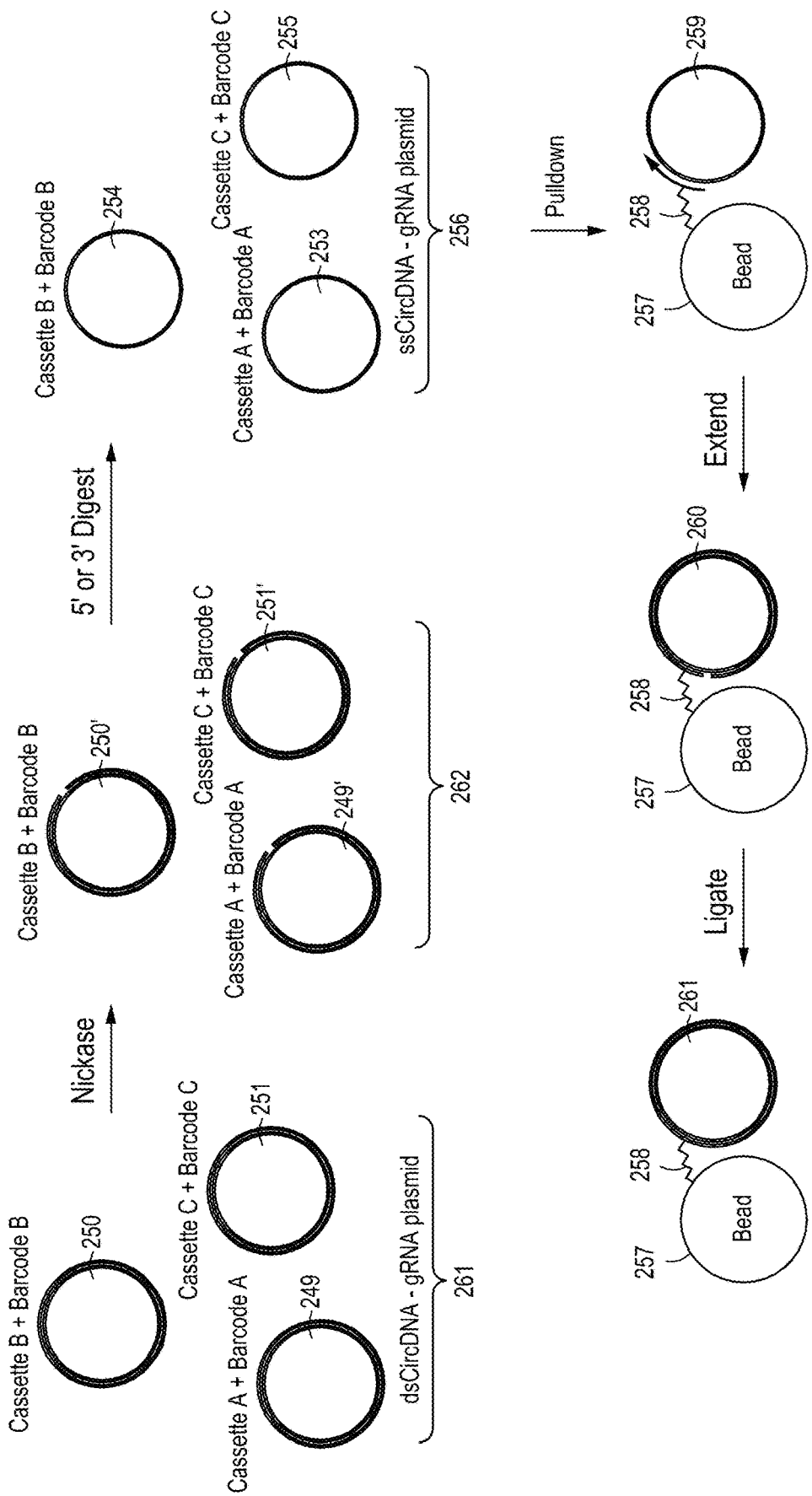
FIG. 2G depicts manufacture of high copy number reagent bundles via pull-down of DNA editing cassettes followed by transcription of the DNA into mRNAs.
FIG. 2H depicts manufacture of high copy number "lariat" episome reagent bundles via pull-down onto a microcarrier.
FIG. 2I depicts manufacture of high copy number RNA episome reagent bundles via pull-down onto a microcarrier.
FIG. 2J depicts creating of high copy number reagent bundles of plasmid DNA via encapsulation of *E. coli* cells.
Figure 5A:
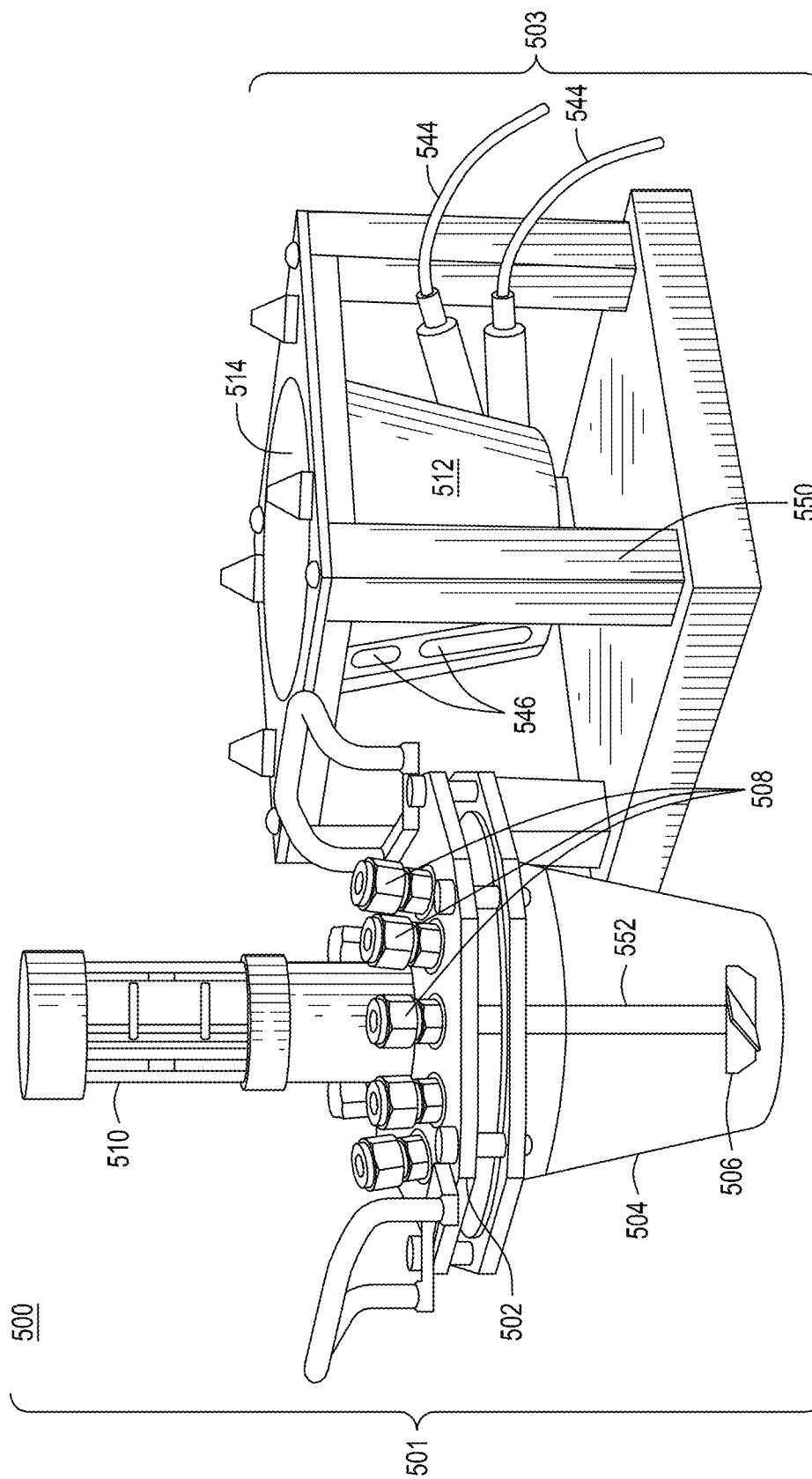
FIGS. 5A-5G depict various components of an embodiment of a bioreactor useful for growing and transducing mammalian cells by the methods described herein.
Figure 5B:
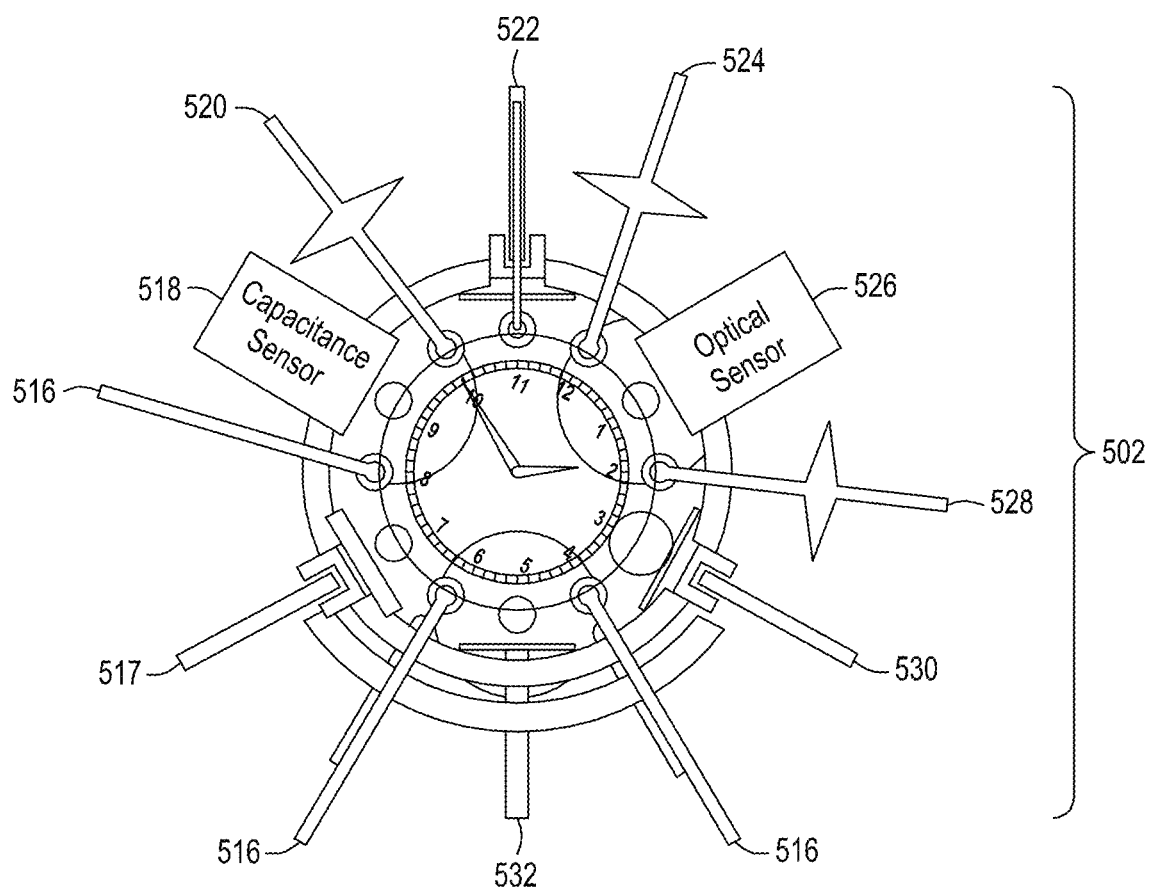
Figure 5C:
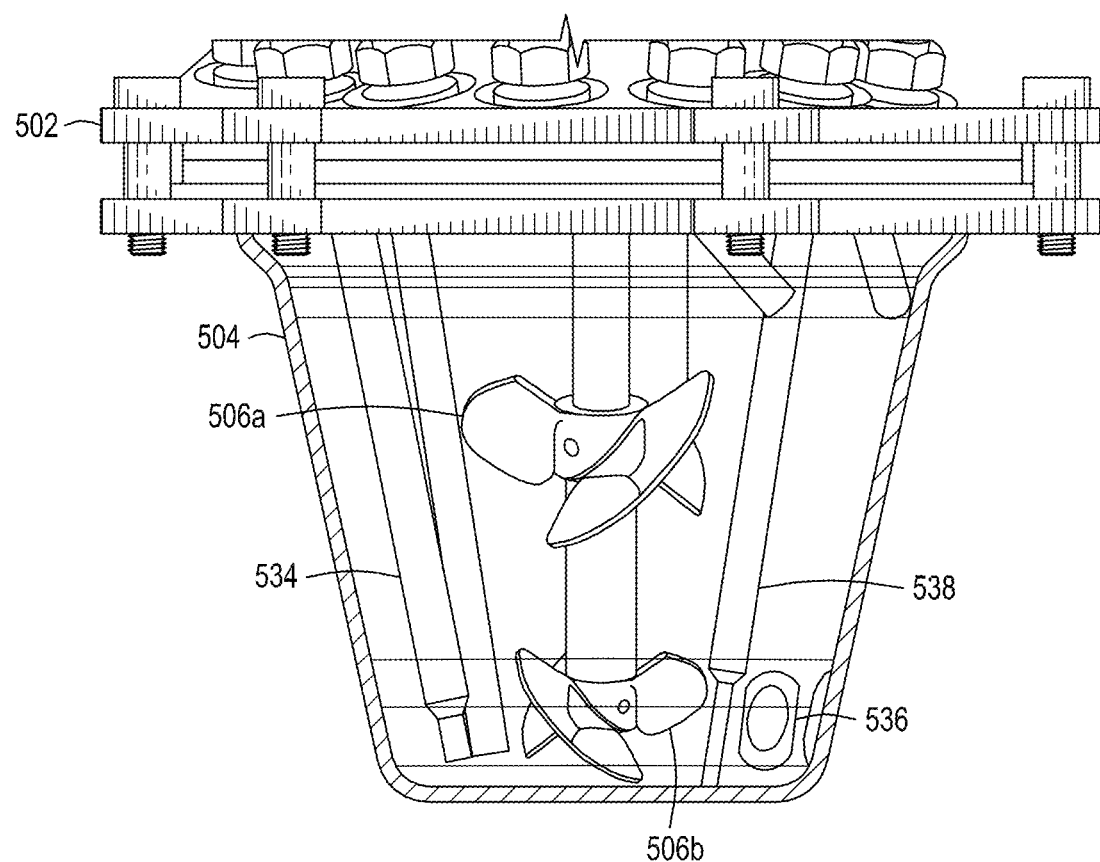
Figure 5D:
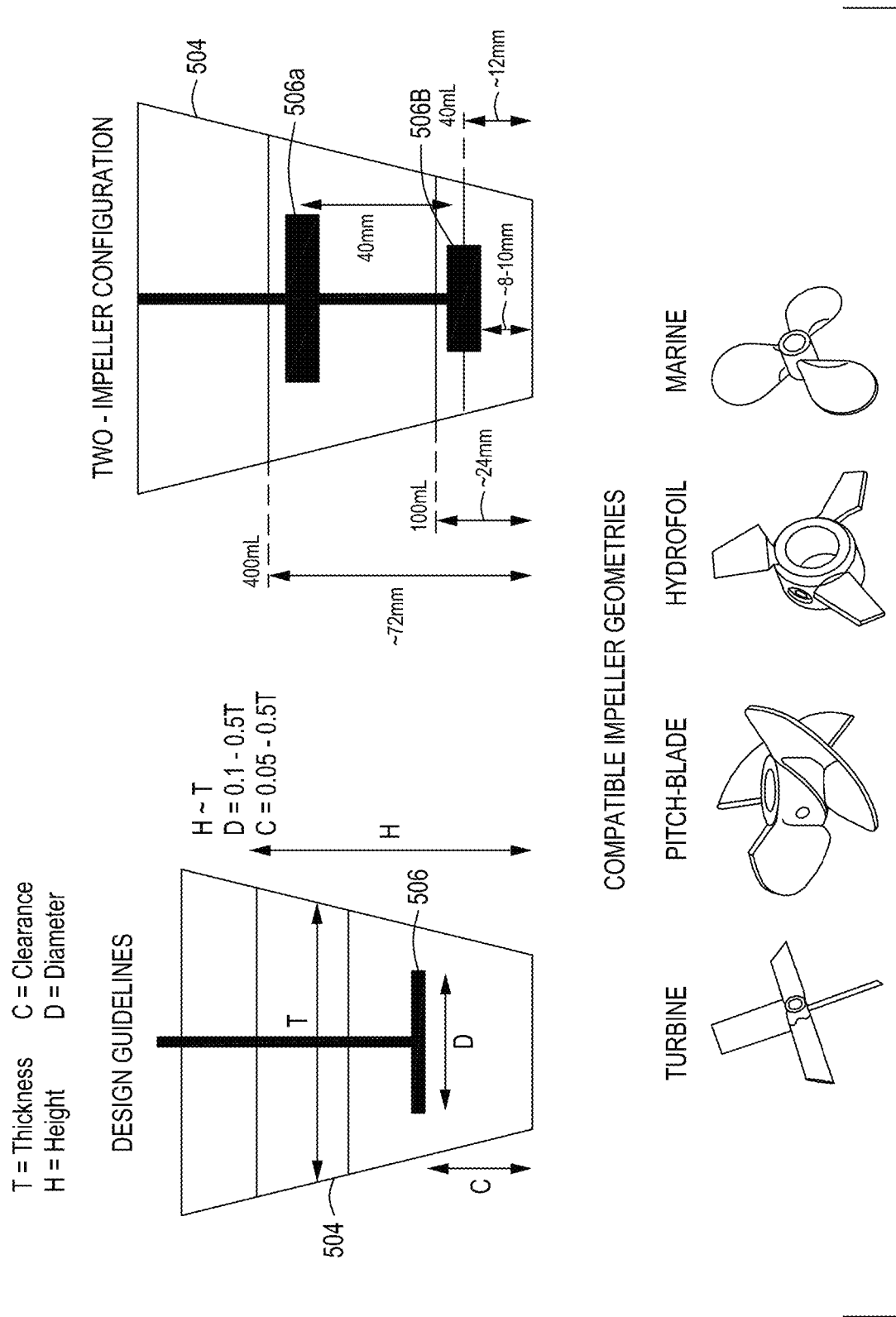
Figure 5E:
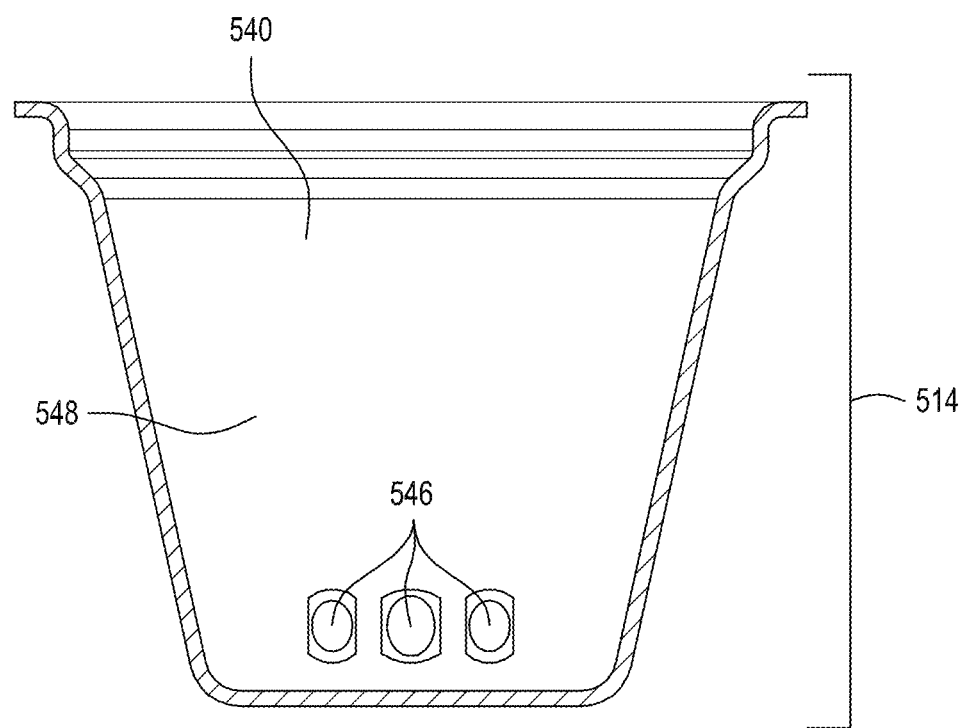
Figure 5F:
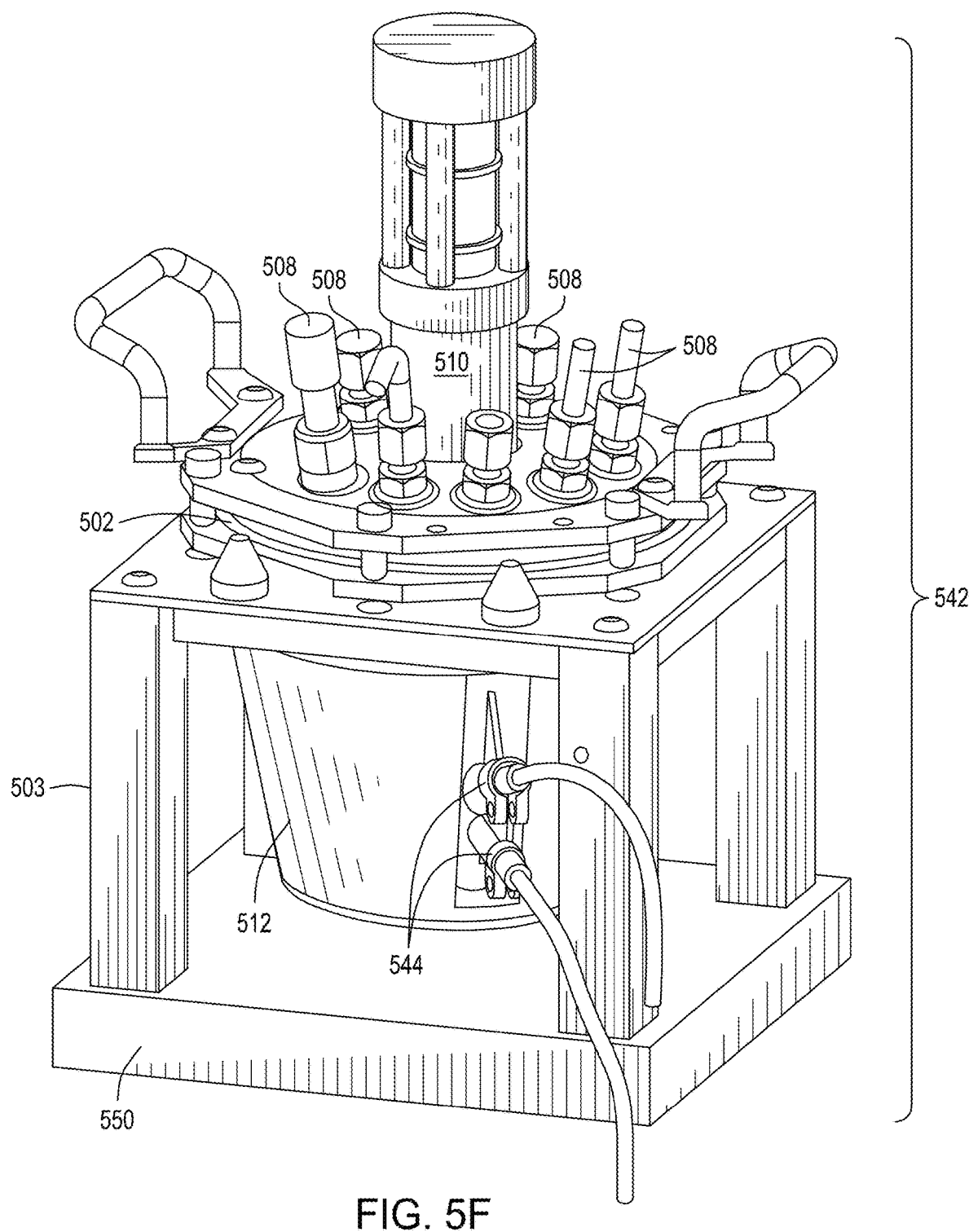
Figure 5G:
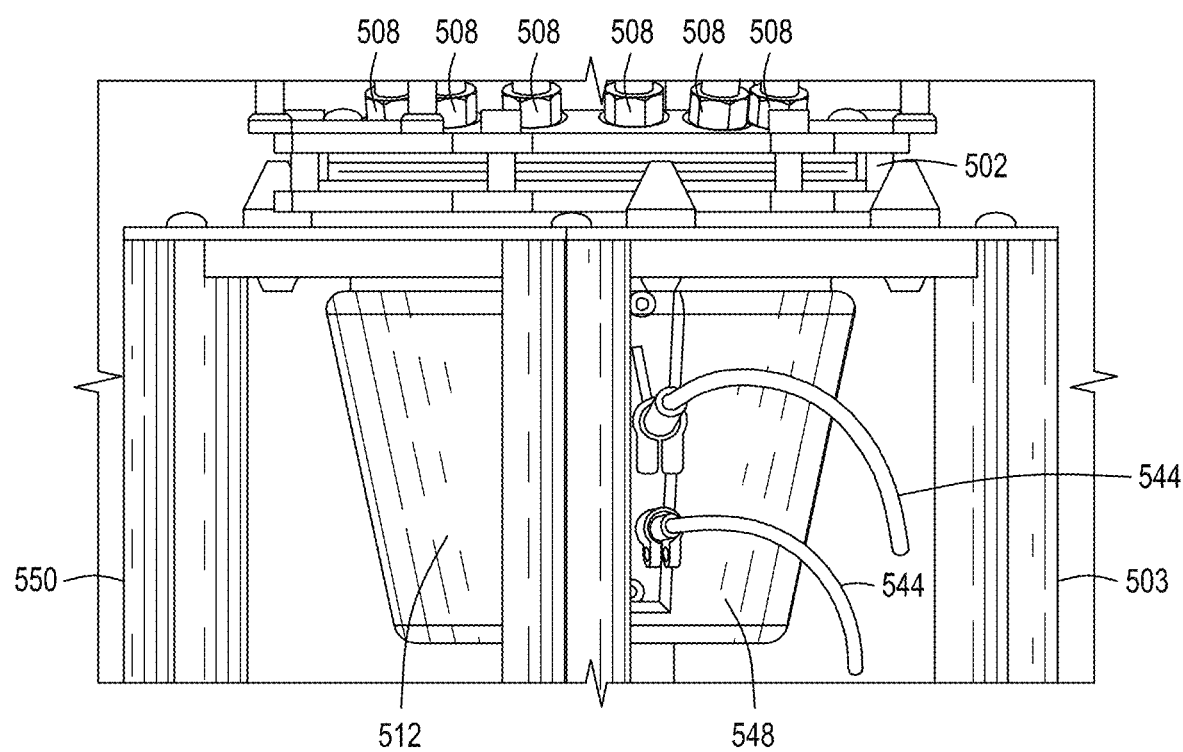
Figures 1, 5H:
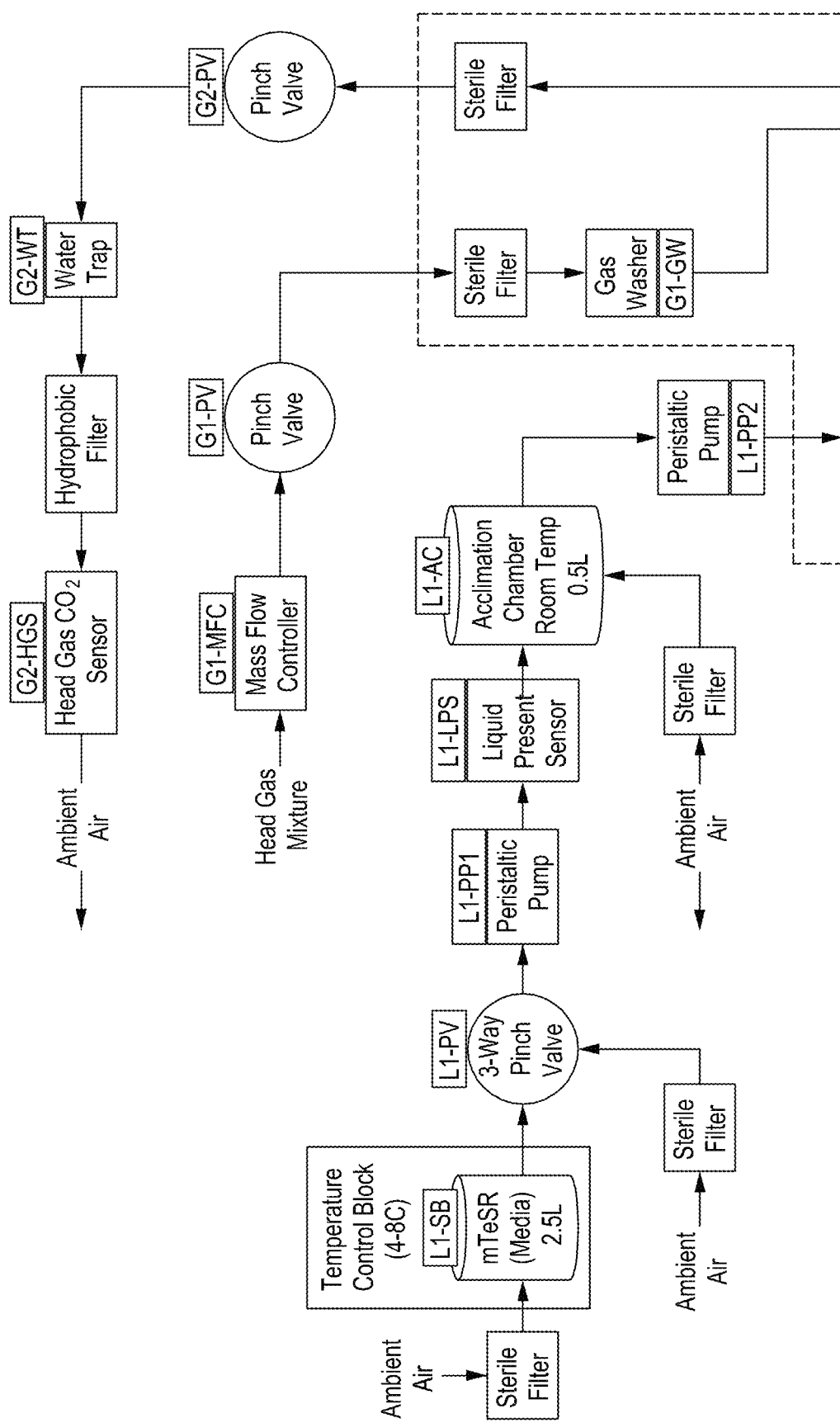
Figures 2, 5H:
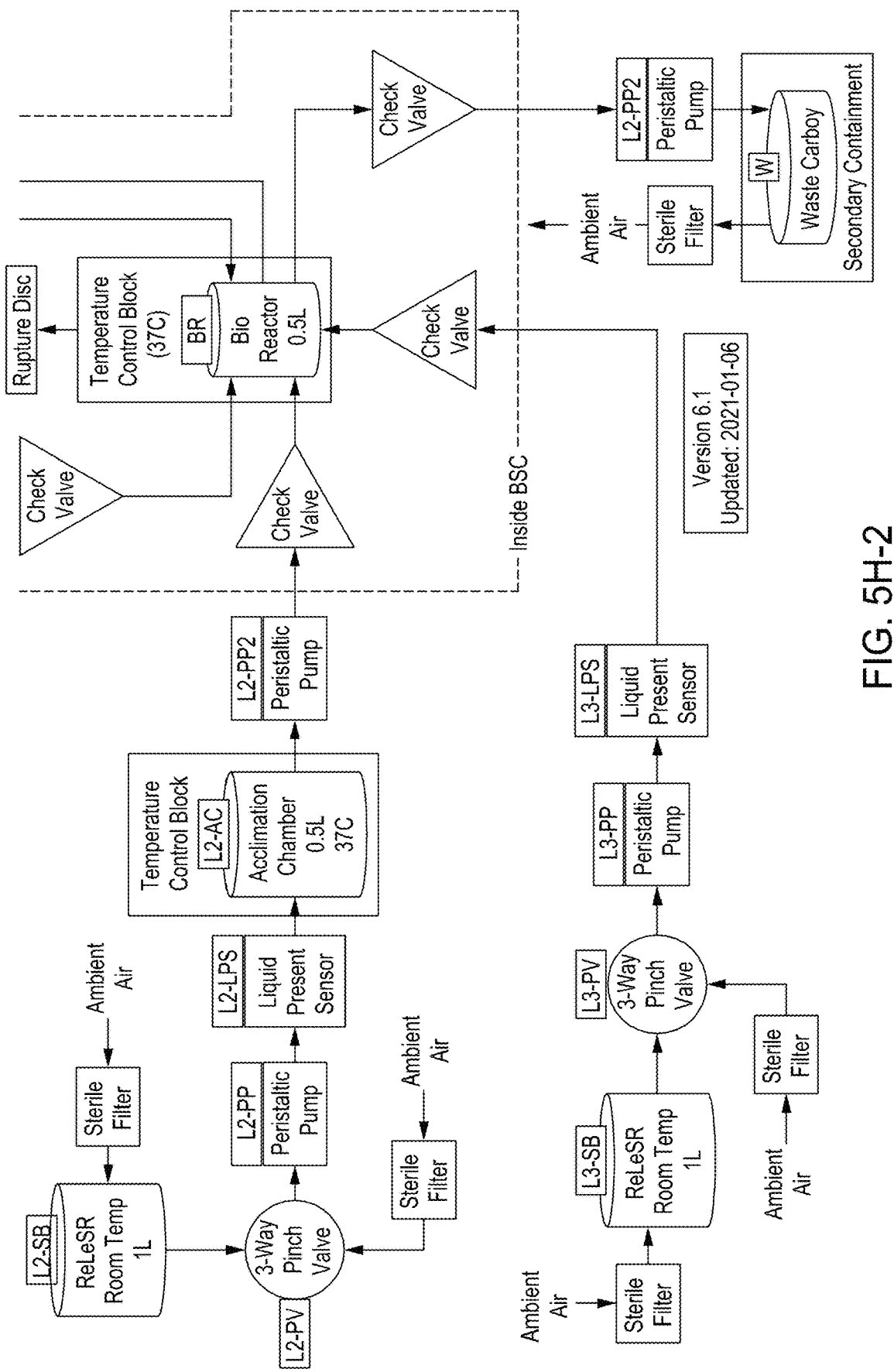
Figure 51:
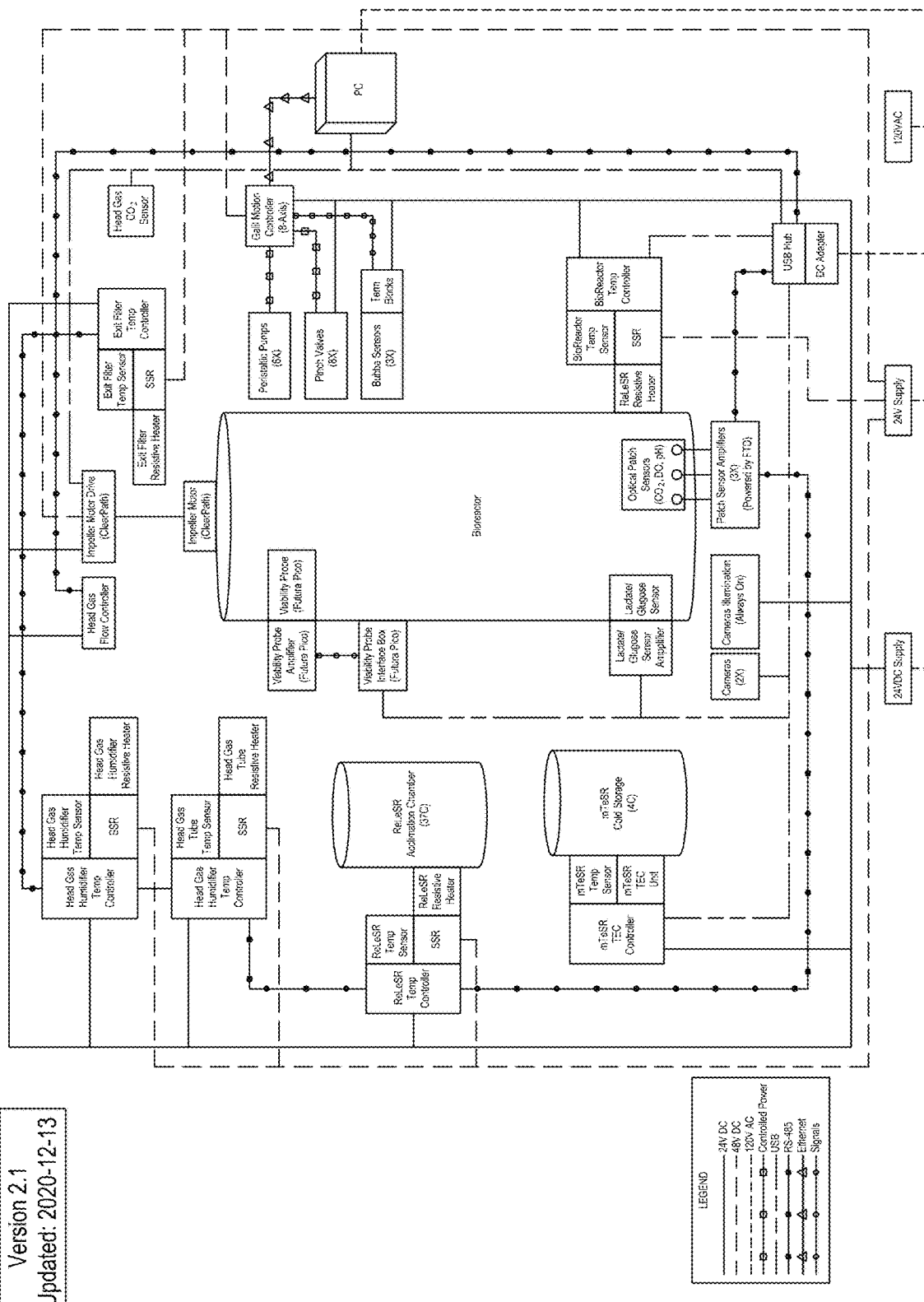

FIG. 2E depicts one method 252 for creating RBMCs from the editing vectors from FIG. 2D-2. In FIG. 2E, the set of editing vectors 261, comprising, e.g., vectors 249 comprising cassette A, 250 comprising cassette B, and 251 comprising cassette C are nicked to create as set 262 of nicked double-stranded editing vectors comprising 249' comprising cassette A, 250' comprising cassette B, and 251' comprising cassette C. The barcodes would be present after the process depicted in FIGS. 2E-1 and 2D-2 where the barcodes would be at one of the ends (likely 3') of the cassette; note, however, barcodes could also be introduced during oligo synthesis of the cassette (e.g., by extending the design barcode customarily included for barcode readout). Following treatment with nickase, the editing vectors are 5' or 3' digested to render the set 256 of editing vectors (253, 254 and 255) single-stranded or primarily single-stranded (e.g., a full digest to single-stranded circular DNA is envisioned for plasmids from 0.5 kb-3 kb, and partial digestion is envisioned for plasmids larger than 5 kb, where the barcoded area is exposed as single-strand while the rest of the plasmids remain as double-stranded to avoid introduction of error through long-range amplification of larger plasmids). The single-stranded editing vectors are then captured or "pulled down" by microcarriers 257 comprising surface nucleic acids 258 complementary to the barcode sequences in the editing cassettes 259.

After capture, the surface nucleic acid that is hybridized to the barcode 2 sequence on the single-strand editing vector is extended to produce a nicked double-stranded circular construct 260, which is then ligated to produce a double-stranded construct 261 tethered to microcarrier 257 via surface nucleic acid 258. Note that although only one nucleic acid on the microcarrier and only one double-stranded editing construct is pictured in this FIG. 2E (and the various components are not drawn to scale, in practice each microcarrier would comprise hundreds of thousands to millions of surface nucleic acids capable of hybridizing to the single-stranded editing cassette constructs; thus, hundreds to thousands of double-stranded editing cassettes constructs would populate each RBMC. Moreover, as with other high copy number RBMCs described herein, once the RBMCs are formed they can be co-localized with cells via the method shown in FIGS. 1B-1G (assuming the microcarriers further comprise cell adhesion promoters such as, e.g., an antibody to a cell surface protein or poly-L-lysine).

Figure 2F:
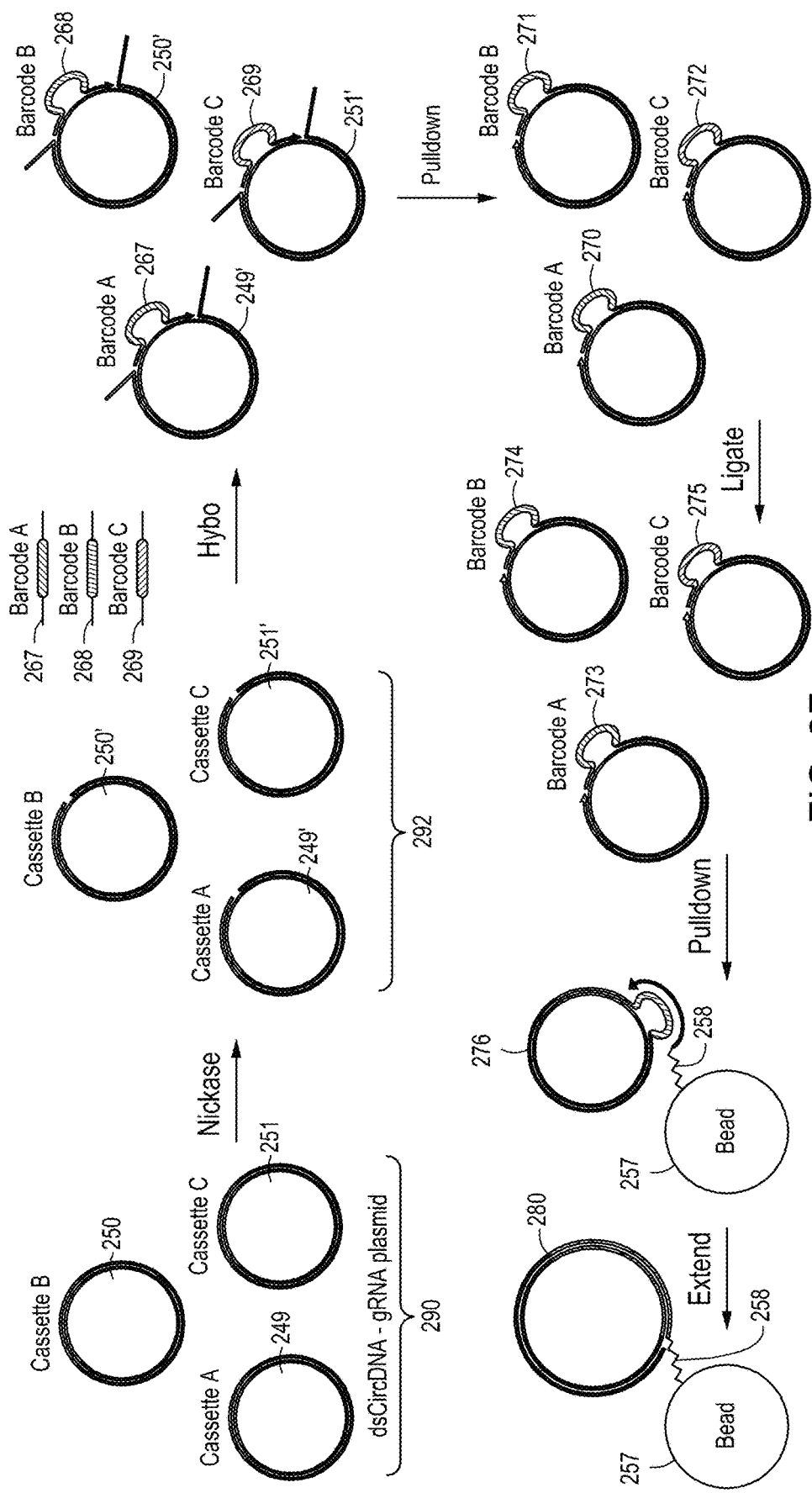

FIG. 2F depicts yet another method 265 for creating RBMCs from the editing vectors from FIG. 2E. In FIG. 2F like FIG. 2E, the set of editing vectors 290, comprising, e.g., vectors 249 comprising cassette A, 250 comprising cassette B, and 251 comprising cassette C are nicked to create a set 292 of nicked double-stranded editing vectors comprising vectors 249' comprising cassette A, 250' comprising cassette B, and 251' comprising cassette C. As in FIG. 2E, the editing vectors (249, 250, 251) are treated with a nickase; however, in this present method nucleic acids comprising third barcode nucleic acids 267, 268 and 269 are combined with the nicked editing vectors 249', 250' and 251' such that the third barcode nucleic acids 267, 268 and 269 hybridize to the nicked editing vectors. The third barcode nucleic acids are extended along the circular template thereby displacing one strand of the nicked editing vectors 249', 250' and 251' resulting in third barcoded editing vectors 270, 271 and 272. Following ligation, double-stranded editing vectors 273, 274 and 275 are formed with a mismatch portion or "bubble" where the third barcodes are located. The double-stranded "bubble" editing vectors are captured or pulled down by microcarriers 257 having surface nucleic acids 258 complementary to the third "bubble" barcodes in the double-stranded editing vectors 276.

After capture, the surface nucleic acid is extended thereby displacing one strand of double-stranded editing vector 276, resulting in captured double-stranded editing vector 280 on microcarrier 257. As described previously, although only one double-stranded nucleic acid 280 is shown on microcarrier 257 forming a RMBC, in practice each RBMC would comprise hundreds to thousands of surface nucleic acids capable of hybridizing to the double-stranded editing cassette constructs; thus, hundreds of thousands to millions of double-stranded editing cassettes constructs would populate each RBMC. Also, as with other high copy number RBMCs described herein, once the RBMCs are formed they can be co-localized with cells via the method shown in FIGS. 1B-1G (assuming the microcarriers further comprise cell adhesion promoters such as, e.g., an antibody to a cell surface protein or poly-L-lysine).

Figure 2G:
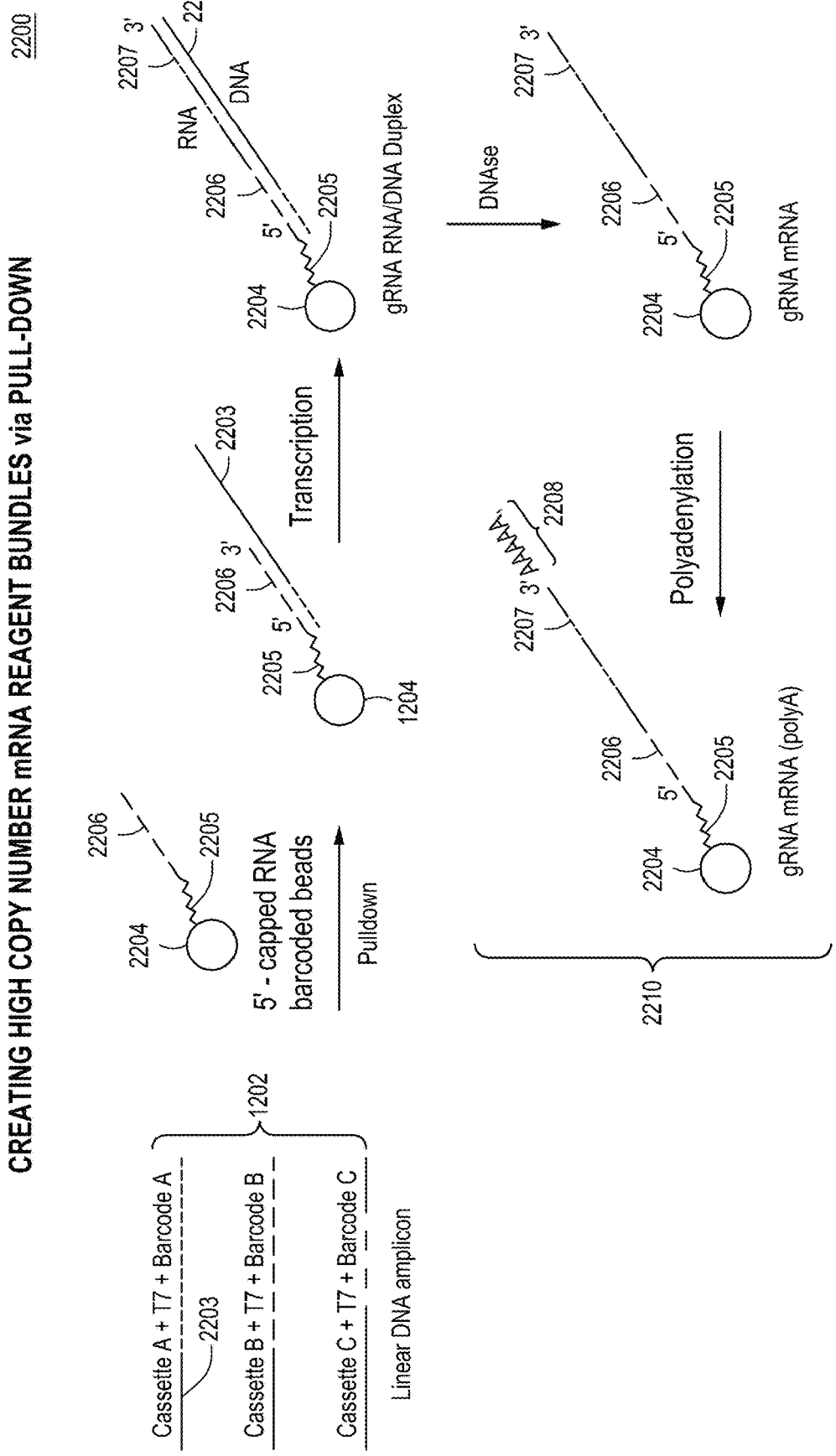

FIG. 2G depicts yet another mode of manufacture 2200 to produce RBMCs of high copy number mRNA reagent bundles via pull-down. In this method 2200, error-corrected editing cassettes 2202 with mRNA payloads comprising a promoter sequence (here, a T7 promoter) and a barcode specific to the editing cassette are amplified. In an example, cassette A is covalently linked to the T7 promoter and to barcode A 2203. Next, microcarriers 2204 comprising surface-linked 2205 5'-capped barcoded RNAs 2206 are added to the editing cassettes, where the surface-linked 5'-capped barcoded RNAs 2206 have complementarity to the barcodes on the amplified editing cassettes. Optionally, linker 2205 may be a cleavable linker. After capture, the barcoded editing cassettes 2203 are transcribed into mRNAs 2207, then treated with DNase to digest the editing cassette DNA 2203, thereby leaving the transcribed mRNA 2207 comprising the barcode complement 2206, linker 2205 and microcarrier 2204.

After polyadenylation, RBMCs 2210 are formed comprising the microcarrier 2204, linker 2205, barcode complement 2206, mRNA 2207 and poly-A tract 2208. In this FIG. 2G, though only one linked and barcoded mRNA 2209 is shown on microcarrier 2204 forming RMBC 2210, in practice each RBMC 2210 would comprise hundreds to thousands of surface mRNAs; thus, hundreds of thousands to millions of linked and barcoded mRNAs would populate each RBMC 2210. Also, as with other high copy number RBMCs described herein, once the RBMCs 2210 are formed they can be co-localized with cells via the method shown in FIGS. 1B-1G (assuming the microcarriers further comprise cell adhesion promoters such as, e.g., an antibody to a cell surface protein or poly-L-lysine).

FIG. 2H depicts manufacture 2220 of high copy number "lariat" episome reagent bundles via pull-down onto a microcarrier. The present method involves creation of RBMCs having very large, self-replicating editing cassette constructs as payload. In the method 2220 depicted in FIG. 2H, editing cassettes 2222, 2223 are synthesized on a substrate 2224. The editing cassettes all have different gRNA and donor DNA pairs. Once synthesized, the editing cassettes are removed from substrate 2224. As described above, during most oligonucleotide synthesis procedures, some oligonucleotides will comprise one or more sequence errors. The oligonucleotides are processed so as to remove oligonucleotides with errors 2223 leaving only error-corrected editing cassettes 2222, thereby producing a pool 2225 of error-corrected editing cassettes 2222. The error-corrected editing cassettes 2222 are then amplified to form amplified editing cassettes 2226 and in a next step Gibson Assembly handles are added to the error-corrected editing cassettes via PCR and the editing cassettes are assembled into a vector backbone 2227 or a partial vector; that is, the portion of the vector that sits as part of the bead probe can be variable, assuming whatever is added via the cassette piece reconstitutes a full construct. In the present depiction the vector is a partial vector because of the large size of the construct and where the cassette is positioned to sit within the final construct.

Following Gibson Assembly, the partial vector is transformed into *E. coli* 2228, allowed to replicate and a plasmid prep is performed to isolate the plasmids 2229. At this point the plasmids 2229 will comprise the editing cassettes from the error-corrected editing cassette pool. Following plasmid prep, the plasmids are linearized to partial vectors 2230 and combined with microcarriers 2242 comprising a bead 2237, surface-linked nucleic acids comprising optionally a cleavable moiety 2236, a region 2235 comprising episomal elements, and a region 2234 complementary to the barcodes 2232 on the partial vectors 2230 comprising the editing cassettes. Next, both the microcarriers 2242 and linearized plasmids 2230 are treated with exonuclease to generate sticky ends 2238, 2239 for ligation. Ligation of the linearized plasmids 2230 to the microcarriers 2242 results in RBMCs 2244. As with the other RBMC manufacturing protocols described herein, though only one linked and barcoded double-stranded editing cassette construct 2230 is shown on microcarrier 2237 forming RMBC 2244, in practice each RBMC 2244 would comprise hundreds to thousands of surface-linked double-stranded editing cassette constructs; thus, hundreds of thousands to millions of linked and barcoded editing cassette constructs would populate each RBMC 2244. Additionally—as with other high copy number RBMCs described herein—once the RBMCs 2244 are formed they can be co-localized with cells via the method shown in FIGS. 1B-1G (assuming the microcarriers further comprise cell adhesion promoters such as, e.g., an antibody to a cell surface protein or poly-L-lysine).

FIG. 2I depicts an alternative mode to manufacture high copy number RNA episome reagent bundles via pull-down onto a microcarrier. In the method 2250 depicted in FIG. 2I, editing cassettes 2252, 2253 are synthesized on a substrate 2254. The editing cassettes all have different gRNA and donor DNA pairs. Once synthesized, the editing cassettes are removed from substrate 2254. As described above, during most oligonucleotide synthesis procedures, some oligonucleotides will comprise one or more sequence errors. The oligonucleotides are processed so as to remove oligonucleotides with errors 2253 leaving only error-corrected editing cassettes 2252, thereby producing a pool 2255 of error-corrected editing cassettes. The error-corrected editing cassettes are then amplified and promoters and restriction endonuclease sites are added to the amplicons via PCR. The editing cassette constructs are then digested with the restriction endonuclease to remove the primer 2 (P2) site used to amplify the editing cassettes 2252, resulting in editing cassette constructs 2256. Editing cassette constructs 2256 are then in vitro transcribed into a pool of RNAs 2258 where each RNA 2257 comprises a 5' end cap 2259, RNA cassette region 2257 and barcode 2265.

In a next step, the pool of RNA-based editing cassettes 2258 are partitioned for de-multiplexing. Following partitioning, microcarriers 2270 are added to the RNA-based editing cassette constructs 2258. Microcarriers 2270 comprise a bead 2264; a linker 2263 (optionally a cleavable linker); a poly-A tract 2262, and a long RNA tract comprising episomal elements such as a promoter, origin(s) of replication and the like (including, e.g., components necessary for viral vector delivery). The nucleic acids linked to the microcarriers 2270 are coupled with the RNA-based editing cassette constructs 2258 via a splint 2260 comprising a sequence complementary to the episomal element region of the RNA coupled to the microcarrier and a sequence complementary to the barcode on the RNA-based editing cassette constructs 2258. As with the other RBMC creation protocols described herein, though only one linked RNA-based editing cassette construct 2258 is shown on microcarrier construct 2270 forming RMBC 2272, in practice each RBMC 2272 would comprise hundreds to thousands of surface-linked RNA-based editing cassette constructs 2258; thus, hundreds of thousands to millions of linked and barcoded editing cassette constructs would populate each RBMC 2272. Additionally—as with other high copy number RBMCs described herein—once the RBMCs 2272 are formed they can be co-localized with cells via the method shown in FIGS. 1G-1G (assuming the microcarriers further comprise cell adhesion promoters such as, e.g., an antibody to a cell surface protein or poly-L-lysine).

Figure 2J:
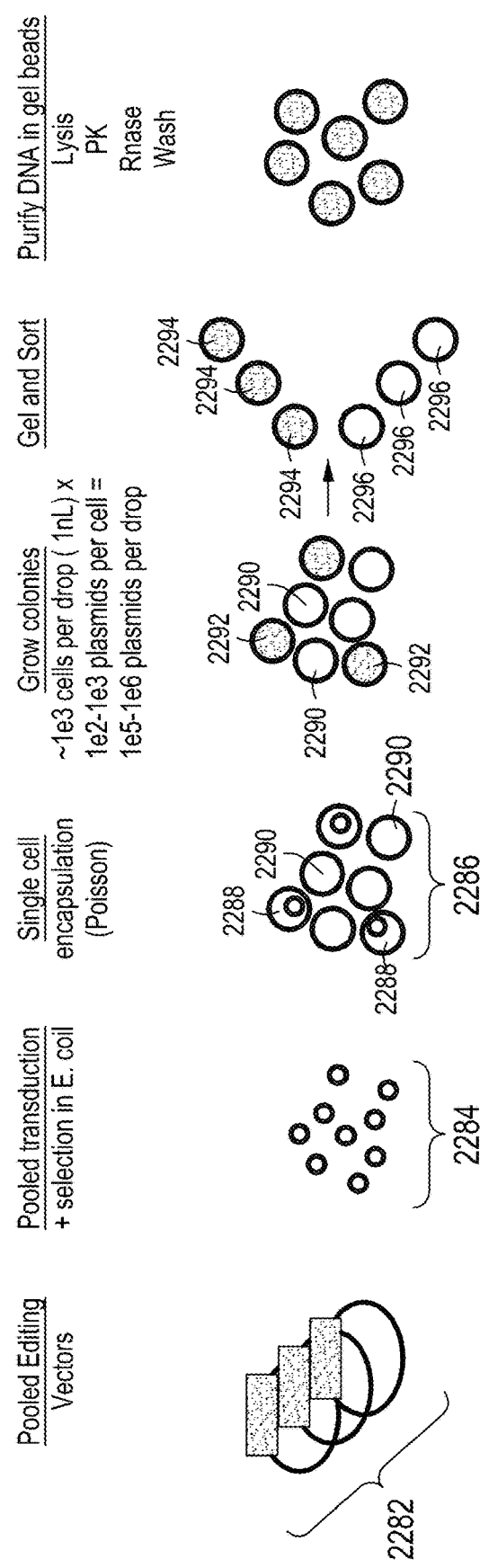

FIG. 2J depicts a method 2280 for manufacturing high copy number reagent bundles of plasmid DNA via encapsulation of *E. coli* cells where a single editing cassette construct is partitioned, with the clonal copies of the editing cassette construct created within the partition. Linear editing cassettes are amenable to cell-free amplification to produce clonal copies of the editing cassette in a droplet or partition; however, making clonal copies of editing vectors in a massively parallel and scalable manner requires cells; in this case, *E. coli*. First, a library of editing vectors 2282 (e.g., a library of editing cassettes each inserted into a vector backbone) is provided. The library of editing cassettes (e.g., CREATE cassettes) may comprise tens, hundreds, thousands, tens of thousands, hundreds of thousands or more different gRNA/donor DNA pairs, in single gRNA/donor DNA cassettes or in compound gRNA/donor DNA cassettes comprising two to many gRNA/donor DNA cassettes. The library of editing vectors 2282 is then transformed, transfected or transduced into *E. coli*. Preferably, the editing vector comprises a selectable marker that allows one to select for *E. coli* cells 2284 that have been properly transformed.

Once the transformed cells have been selected, microfluidic droplet formation is performed to encapsulate individual cells in polymerizable droplets 2288. Preferably this process results in a Poisson distribution of droplets 2286 with one cell 2288 or no cell 2290. Conditions are provided to allow the individual cells to grow in the droplets 2292 (see also droplets 2290 in which no cells grow), thereby producing clonal copies of the cells and therefore the editing vectors in the cells. After a predetermined amount of time, e.g., 12 to 36 hours, or 24 to 48 hours, the droplets are polymerized, thereby forming gel beads 2294 and 2296, and sorted into gel beads 2294 with nucleic acids and gel beads 2296 without nucleic acids. In the present embodiment, the cells may constitutively express a GFP or other marker that allows gel beads containing cells to be sorted from gel beads without cells. Once sorted, the editing vectors in the gel beads 2298 can be isolated by, e.g., lysing the cells and treating the gel beads with reagents such as proteinase K, RNase, and other reagents.

In this embodiment, addition of the reagents used to lyse the cells and purify the editing cassettes are added to the gel bead after gel bead formation. As stated above and described in relation to FIG. 1E, smaller molecules and reagents may be added to the gel beads following polymerization depending on the polymer network density. If the gel beads have an appropriate polymer network density, the cells—and editing vectors released from the cells after lysis of the cells—will remain in the gel bead, and reagents for cell lysis, protein degradation (e.g., proteinase K), RNase, and wash buffers can enter the gel bead. Because genomic DNA from the bacterial cells is relatively large in size as compared to the amplified editing plasmid DNA, genomic DNA is unlikely to enter the mammalian cells upon transfection. Once the cells in the gel beads have been lysed and the contents of the gel beads treated and washed, transformation or transfection agents can be delivered to the gel beads, and the gel beads can then be delivered to cells and dissolved thereby releasing the transfection or transformation agents and editing vectors to the cells.

Cell Growth and Editing Modules
The Rotating Growth Module

Figure 3A:
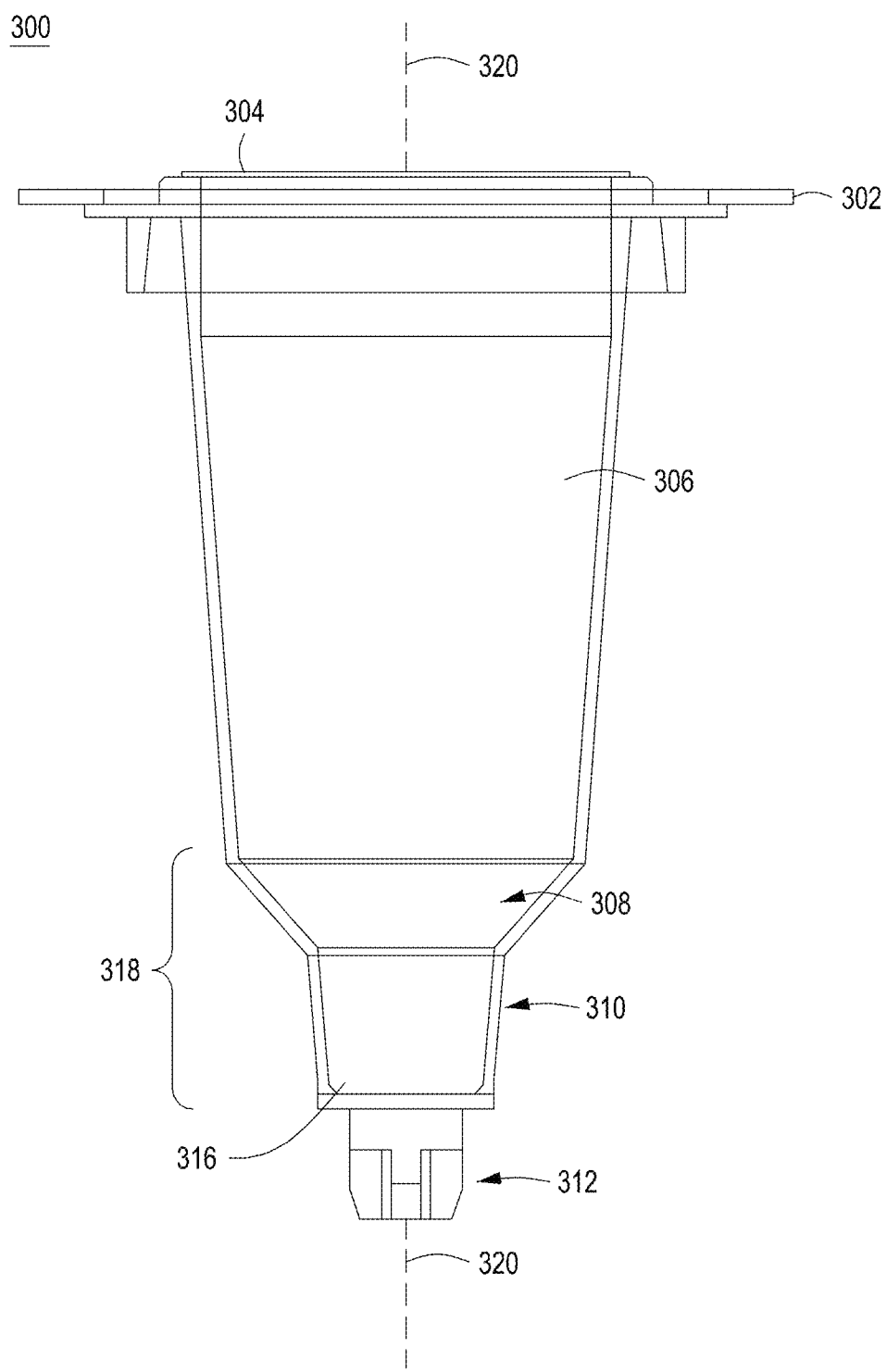
FIG. 3A depicts one embodiment of a rotating growth vial for use with the cell growth module described herein and in relation to FIGS. 3C-3E.

In one embodiment of the fully-automated, end-to-end closed instrument disclosed herein, the instrument comprises a rotating growth module. The fully automated instrument does not require human hands or intervention. Full automation establishes and provides consistent results in the workflow and enhances uniformity of processing between "batches" while maintaining sample integrity. FIG. 3A shows one embodiment of a rotating growth vial 300 for use with a rotating growth module and in the automated multi-module cell processing instruments described herein. The rotating growth module can be used for both cell growth, and for cell transduction and transfection. The rotating growth vial 300 is an optically-transparent container having an open end 304 for receiving liquid media and cells, a central vial region 306 that defines the primary container for growing cells, a tapered-to-constricted region 318 defining at least one light path 310, a closed end 316, and a drive engagement mechanism 312. The rotating growth vial 300 has a central longitudinal axis 320 around which the vial rotates, and the light path 310 is generally perpendicular to the longitudinal axis of the vial. The first light path 310 is positioned in the lower constricted portion of the tapered-to-constricted region 318. Optionally, some embodiments of the rotating growth vial 300 have a second light path 308 in the tapered region of the tapered-to-constricted region 318. Both light paths in this embodiment are positioned in a region of the rotating growth vial that is constantly filled with the cell culture (cells+growth media) and are not affected by the rotational speed of the growth vial. The first light path 310 is shorter than the second light path 308 allowing for, e.g., sensitive measurement of OD values when the OD values of the cell culture in the vial are at a high level (e.g., later in the cell growth process), whereas the second light path 308 allows for, e.g., sensitive measurement of OD values when the OD values of the cell culture in the vial are at a lower level (e.g., earlier in the cell growth process).

The drive engagement mechanism 312 engages with a motor (not shown) to rotate the vial. In some embodiments, the motor drives the drive engagement mechanism 312 such that the rotating growth vial 300 is rotated in one direction only, and in other embodiments, the rotating growth vial 300 is rotated in a first direction for a first amount of time or periodicity, rotated in a second direction (i.e., the opposite direction) for a second amount of time or periodicity, and this process may be repeated so that the rotating growth vial 300 (and the cell culture contents) are subjected to an oscillating motion. Further, the choice of whether the culture is subjected to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial 300 may be oscillated at a first periodicity (e.g., every 60 seconds), and then a later stage of cell growth the rotating growth vial 300 may be oscillated at a second periodicity (e.g., every one second) different from the first periodicity.

The rotating growth vial 300 may be reusable or, preferably, the rotating growth vial is consumable. In some embodiments, the rotating growth vial is consumable and is presented to the user pre-filled with growth medium, where the vial is hermetically sealed at the open end 304 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial. Open end 304 may optionally include an extended lip 302 to overlap and engage with the cell growth device. In automated systems, the rotating growth vial 300 may be tagged with a barcode or other identifying means that can be read by a scanner or camera (not shown) that is part of the automated system.

The volume of the rotating growth vial 300 and the volume of the cell culture (including growth medium) may vary, but the volume of the rotating growth vial 300 must be large enough to generate a specified total number of cells. In practice, the volume of the rotating growth vial 300 may range from 5-1000 mL, 10-500 mL, or from 20-250 mL. Likewise, the volume of the cell culture (cells+growth media) should be appropriate to allow proper aeration and mixing in the rotating growth vial 300. Proper aeration promotes uniform cellular respiration within the growth medium. Thus, the volume of the cell culture should be approximately 5-85% of the volume of the growth vial or from 20-60% of the volume of the growth vial. For example, for a 300 mL growth vial, the volume of the cell culture would be from about 15 mL to about 260 mL, or from 6 mL to about 180 mL.

The rotating growth vial 300 preferably is fabricated from a bio-compatible optically transparent material—or at least the portion of the vial comprising a light path for imaging is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyetheretherketone (PEEK), polypropylene, polycarbonate, poly(methyl methacrylate (PMMA)), polysulfone, poly(dimethylsiloxane), and co-polymers of these and other polymers. Preferred materials include polypropylene, polycarbonate, or polystyrene. In some embodiments, the rotating growth vial is inexpensively fabricated by, e.g., injection molding or extrusion.

Figure 3B:
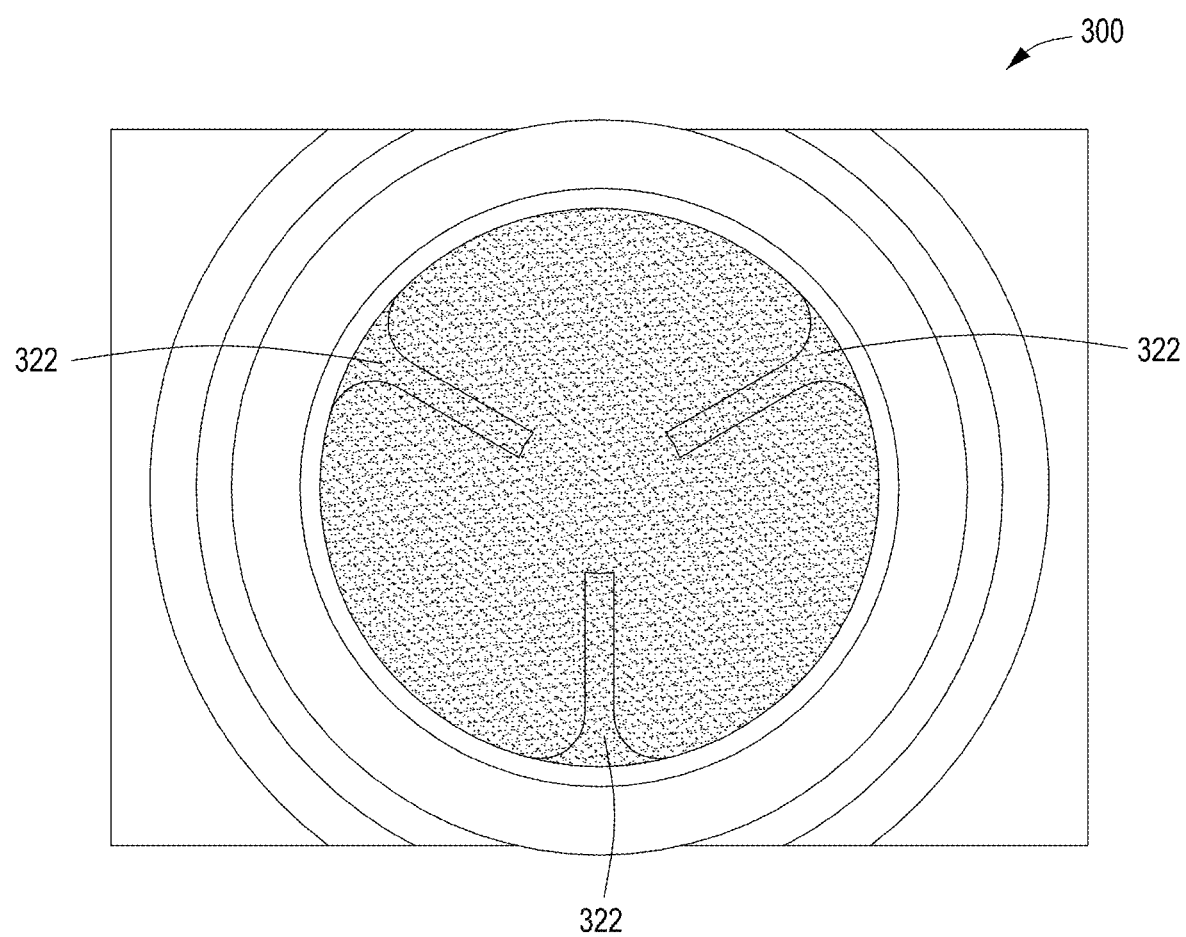
FIG. 3B illustrates a top-down view of the rotating growth vial depicted in FIG. 3A, showing optional internal "fins" or "paddles" for growing mammalian cells.

FIG. 3B illustrates a top view of a rotating growth vial 300. In some examples, the vial 300 may include one or more fins or paddles 322 affixed to an inner surface of the vial wall, where the paddles protrude toward the center of the vial 300. The vial 300 shown in FIG. 3B includes three paddles 322 that are substantially equally spaced around the periphery of the vial 300, but in other examples vial 300 may include two, four, or more paddles 322. The paddles, in some implementations, provide increased mixing and aeration within the vial 300 rotating within a cell growth device, which facilitates cell growth. In other configurations, there may be concentric rows of raised features disposed on the inner surface of the rotating growth vial and the features may be arranged horizontally or vertically; and in other aspects, there may be a spiral configuration of raised features disposed on the inner surface of the rotating growth vial. In alternative aspects, the fins or paddles or concentric rows of raised features may be disposed upon a post or center structure of a rotating growth vial, where the paddles or features radiate out from the center of the vial toward the inner walls of the vial. In some aspects, the width of the paddles or interior features varies with the size or volume of the rotating growth vial, and may range from ⅛ to just under ½ the radius of the rotating growth vial, or from ¼ to ⅓ the radius of the rotating growth vial. The length of the paddles varies with the size or volume of the rotating growth vial and may range from ¼ to ⅘ the length of the rotating growth vial, or from ⅓ to ¾ the length of the rotating growth vial.

The paddles themselves—depending on the speed of rotation of the vial—may provide adequate turbulence to either dissociate cell aggregates or to detach cells from microcarriers. In addition, the paddles may be modified to comprise strainers, frits or sieves for dissociating cell aggregates. That is, the paddles may comprise pores that dissociate the cell aggregates, where the pores range in size from 10 to 400 microns in size, or from 20 to 200 microns in size, or from 30 to 100 microns in size. In some embodiments of the automated instruments, there may be two different types of rotating growth vials present, one type without fins and/or strainers or sieves present for cell growth, and one with fins or features and with strainers or sieves for cell dissociation where cells and medium are transferred to and between the growth vial and dissociation vial by an automated liquid handling system.

Figure 3C:
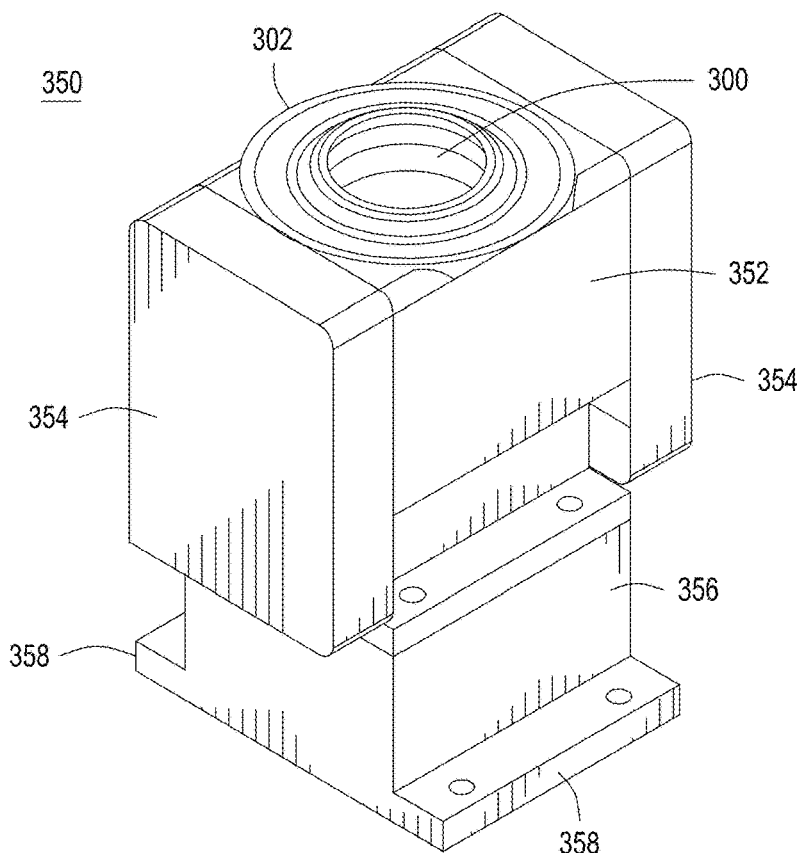
FIG. 3C is a perspective view of one embodiment of a rotating growth vial in a cell growth module housing.
Figure 3D:
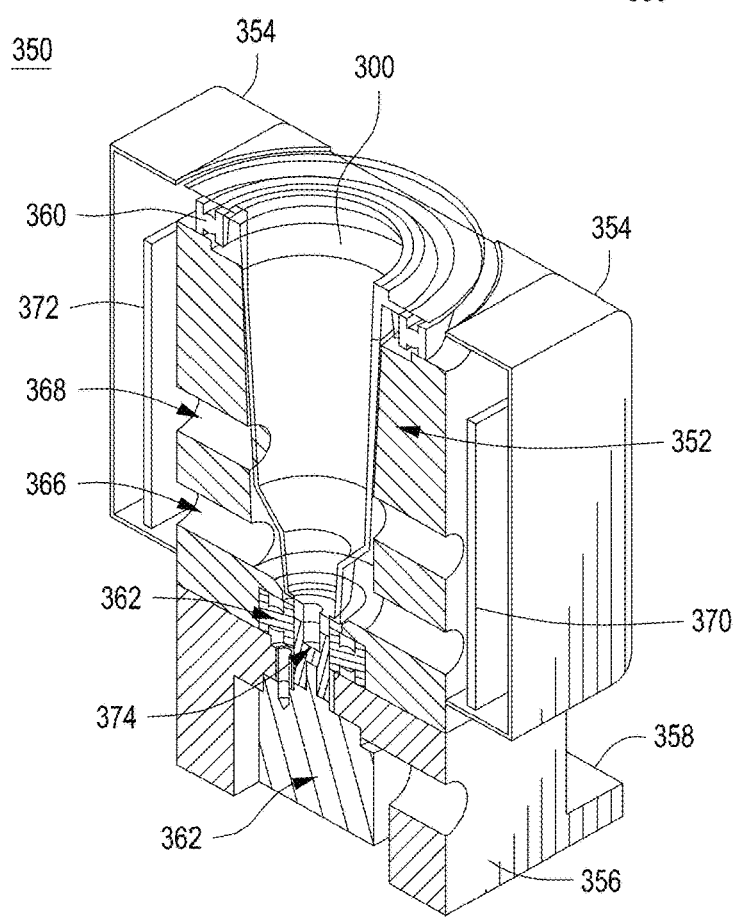
FIG. 3D depicts a cut-away view of the cell growth module from FIG. 3C.

FIG. 3C is a perspective view of one embodiment of a cell growth device 350. FIG. 3D depicts a cut-away view of the cell growth device 350 from FIG. 3C. In both figures, the rotating growth vial 300 is seen positioned inside a main housing 336 with the extended lip 302 of the rotating growth vial 300 extending above the main housing 336. Additionally, end housings 352, a lower housing 332 and flanges 334 are indicated in both figures. Flanges 334 are used to attach the cell growth device 350 to heating/cooling means or other structure (not shown). FIG. 3D depicts additional detail. In FIG. 3D, upper bearing 342 and lower bearing 340 are shown positioned within main housing 336. Upper bearing 342 and lower bearing 340 support the vertical load of rotating growth vial 300. Lower housing 332 contains the drive motor 338. The cell growth device 350 of FIG. 3C may comprise two light paths; a primary light path 344, and a secondary light path 350. Light path 344 corresponds to light path 310 positioned in the constricted portion of the tapered-to-constricted portion of the rotating growth vial 300, and light path 350 corresponds to light path 308 in the tapered portion of the tapered-to-constricted portion of the rotating growth via 316. Light paths 310 and 308 are not shown in FIG. 3D but may be seen in FIG. 3A. In addition to light paths 344 and 340, there is an emission board 348 to illuminate the light path(s), and detector board 346 to detect the light after the light travels through the cell culture liquid in the rotating growth vial 300.

Cell growth monitoring can be performed by imaging, for example, by allowing the microcarriers to settle and imaging the bottom of the rotating growth vial. Alternatively, an aliquot of the culture is removed and run through a flow cell for imaging. In yet another alternative, the cells may express a fluorescent protein and fluorescence is measured. In yet another alternative, the cell density may be measured by light absorbance at 250-350 nm at light path 310.

The motor 328 engages with drive mechanism 312 and is used to rotate the rotating growth vial 300. In some embodiments, motor 338 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 338 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 336, end housings 352 and lower housing 332 of the cell growth device 350 may be fabricated from any suitable, robust material including aluminum, stainless steel, or other thermally conductive materials, including plastics. These structures or portions thereof can be created through various techniques, e.g., metal fabrication, injection molding, creation of structural layers that are fused, etc. Whereas the rotating growth vial 300 is envisioned in some embodiments to be reusable, but preferably is consumable, the other components of the cell growth device 350 are preferably reusable and function as a stand-alone benchtop device or as a module in a multi-module cell processing system.

Figure 3E:
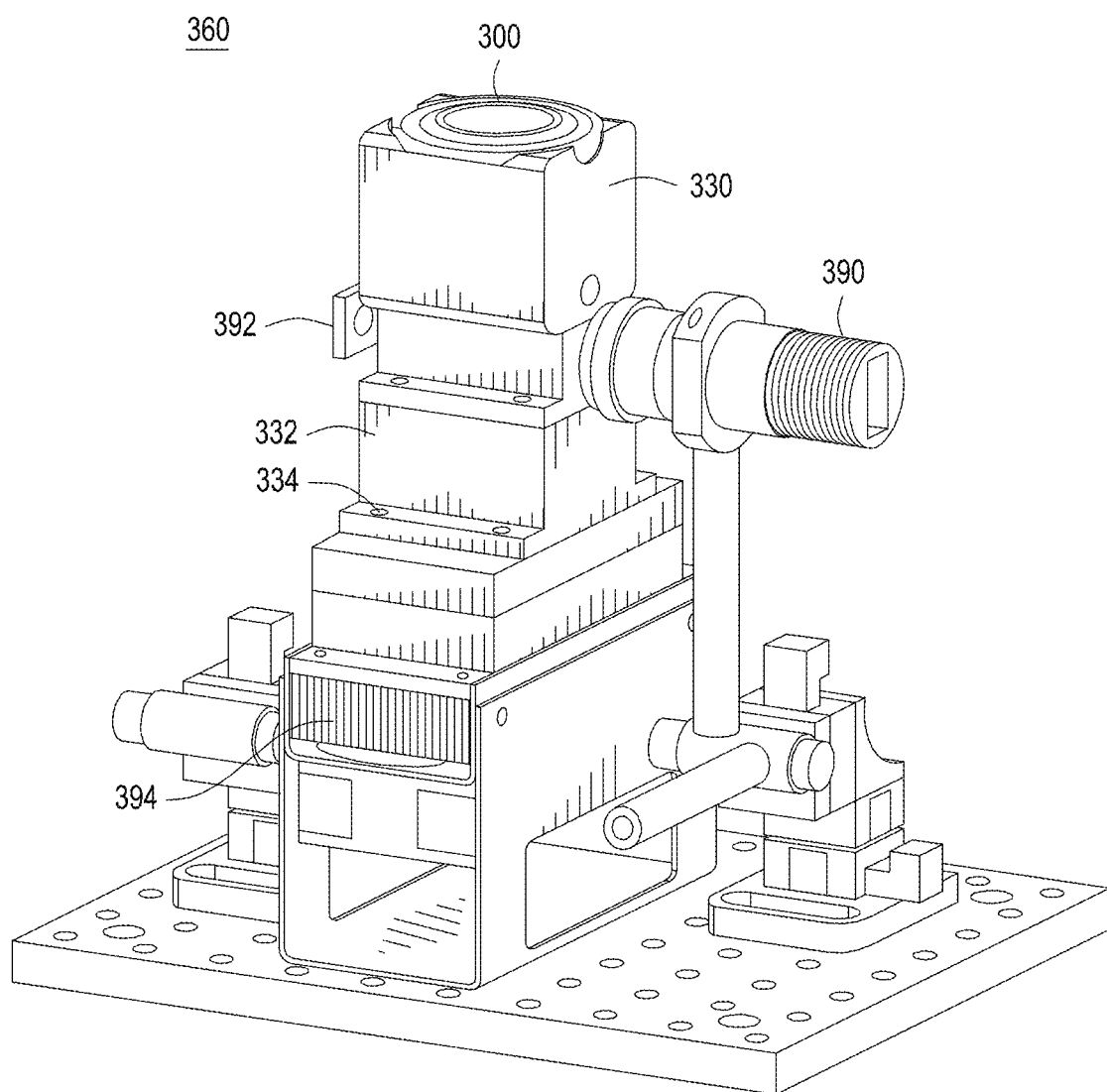
FIG. 3E illustrates the cell growth module of FIG. 3C coupled to LED, detector, and temperature regulating components.

FIG. 3E illustrates a cell growth device 350 as part of an assembly comprising the cell growth device 350 of FIG. 3C coupled to light source 390, detector 392, and thermal components 394. The rotating growth vial 300 is inserted into the cell growth device. Components of the light source 390 and detector 392 (e.g., such as a photodiode with gain control to cover 5-log) are coupled to the main housing of the cell growth device. The lower housing 332 that houses the motor that rotates the rotating growth vial 300 is illustrated, as is one of the flanges 334 that secures the cell growth device 350 to the assembly. Also, the thermal components 394 illustrated are a Peltier device or thermoelectric cooler. In this embodiment, thermal control is accomplished by attachment and electrical integration of the cell growth device 350 to the thermal components 394 via the flange 334 on the base of the lower housing 332. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 300 is controlled to approximately +/−0.5° C. In yet another alternative, the detector is replaced with an imaging camera. The geometry of the constricted portion of the rotating growth vial 300 containing light path 310 is further tapered to collect settled cell aggregates or microcarriers coated with cells when rotation is paused. The stacked cell aggregates or microcarriers with cells are imaged. Total cell number can be derived from the height of the stacked cell aggregates. Total cell number can be derived from the combined height of the microcarriers coated with cells and the observed confluency of cells on a subset of microcarriers.

In use, cells are inoculated (cells can be pipetted, e.g., from an automated liquid handling system or by a user) into pre-filled growth media of a rotating growth vial 300 by piercing though the foil seal or film. The programmed software of the cell growth device 350 sets the control temperature for growth, typically 30° C., then slowly starts the rotation of the rotating growth vial 300. The cell/growth media mixture slowly moves vertically up the wall due to centrifugal force allowing the rotating growth vial 300 to expose a large surface area of the mixture to an $O_2$ or $CO_2$ environment. If enhanced mixing is required, e.g., to optimize growth conditions, the speed of the vial rotation can be varied to cause an axial precession of the liquid, and/or a complete directional change can be performed at programmed intervals.

In addition to imaging, other cell growth parameters can be measured. Other optional measures of cell growth may be made including spectroscopy using visible, UV, or near infrared (NIR) light, measuring, e.g., the concentration of nutrients and/or wastes in the cell culture and/or other spectral properties can be measured via, e.g., dielectric impedance spectroscopy, visible fluorescence, fluorescence polarization, or luminescence. Additionally, the cell growth device 350 may include additional sensors for measuring, e.g., dissolved oxygen, carbon dioxide, pH, conductivity, and the like. For additional details regarding rotating growth vials and cell growth devices see U.S. Pat. No. 10,435,662; and 10,443,031; and U.S. Ser. No. 16/552,981, filed 7 Aug. 2019; and Ser. No. 16/780,640, filed 3 Feb. 2020.

The Tangential Flow Filtration Module

An alternative to the rotating growth module in the fully automated, closed, end-to-end instrument is a tangential flow filtration (TFF) module as shown in FIGS. 4A-4G. The TFF module shown in FIGS. 4A-4G is a module that can grow, perform buffer exchange, concentrate cells and dissociate cells or detach cells from microcarriers so that the cells may be transfected or transduced with the nucleic acids needed for engineering or editing the cell's genome. The TFF module also supports cell transduction and cell transfection or reverse transfection.

Figure 4A:
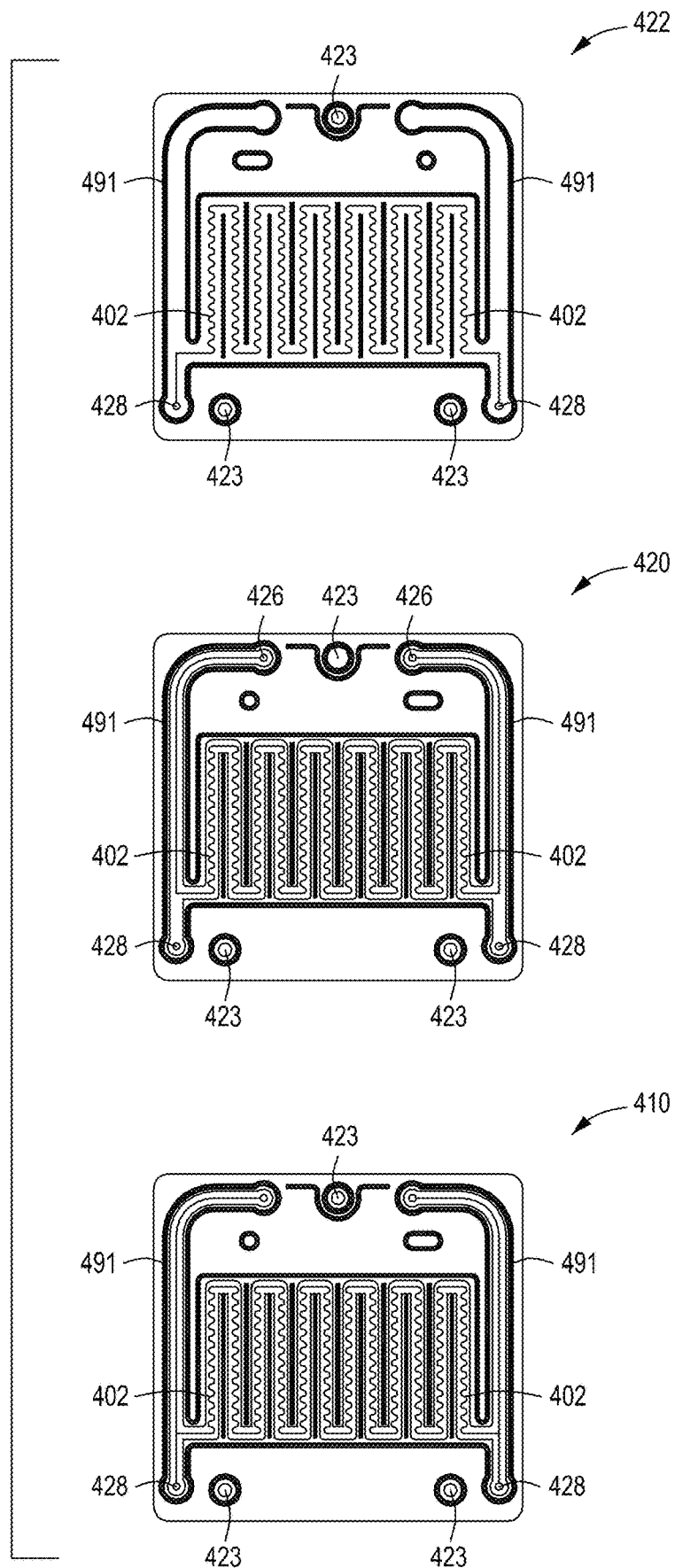
FIG. 4A depicts retentate (top) and permeate (middle) members for use in a tangential flow filtration module (e.g., cell growth and/or concentration module), as well as the retentate and permeate members assembled into a tangential flow assembly (bottom).

FIG. 4A shows a retentate member 422 (top), permeate member 420 (middle) and a tangential flow assembly 410 (bottom) comprising the retentate member 422, membrane 424 (not seen in FIG. 4A), and permeate member 420 (also not seen). In FIG. 4A, retentate member 422 comprises a tangential flow channel 402, which has a serpentine configuration that initiates at one lower corner of retentate member 422—specifically at retentate port 428—traverses across and up then down and across retentate member 422, ending in the other lower corner of retentate member 422 at a second retentate port 428. Also seen on retentate member 422 are energy directors 491, which circumscribe the region where a membrane or filter (not seen in this FIG. 4A) is seated, as well as interdigitate between areas of channel 402. Energy directors 491 in this embodiment mate with and serve to facilitate ultrasonic welding or bonding of retentate member 422 with permeate/filtrate member 420 via the energy director component 491 on permeate/filtrate member 420 (at right). Additionally, countersinks 423 can be seen, two on the bottom one at the top middle of retentate member 422. Countersinks 423 are used to couple and tangential flow assembly 410 to a reservoir assembly (not seen in this FIG. 4A but see FIG. 4B).

Permeate/filtrate member 420 is seen in the middle of FIG. 4A and comprises, in addition to energy director 491, through-holes for retentate ports 428 at each bottom corner (which mate with the through-holes for retentate ports 428 at the bottom corners of retentate member 422), as well as a tangential flow channel 402 and two permeate/filtrate ports 426 positioned at the top and center of permeate member 420. The tangential flow channel 402 structure in this embodiment has a serpentine configuration and an undulating geometry, although other geometries may be used. Permeate member 420 also comprises countersinks 423, coincident with the countersinks 423 on retentate member 420.

At bottom is a tangential flow assembly 410 comprising the retentate member 422 and permeate member 420 seen in this FIG. 4A. In this view, retentate member 422 is "on top" of the view, a membrane (not seen in this view of the assembly) would be adjacent and under retentate member 422 and permeate member 420 (also not seen in this view of the assembly) is adjacent to and beneath the membrane. Again countersinks 423 are seen, where the countersinks in the retentate member 422 and the permeate member 420 are coincident and configured to mate with threads or mating elements for the countersinks disposed on a reservoir assembly (not seen in FIG. 4A but see FIG. 4B).

A membrane or filter is disposed between the retentate and permeate members, where fluids can flow through the membrane but cells cannot and are thus retained in the flow channel disposed in the retentate member. Filters or membranes appropriate for use in the TFF module are those that are solvent resistant, are contamination free during filtration, and are able to retain the types and sizes of cells of interest. For example, in order to retain small cell types, pore sizes can be as low as 0.5 µm, however for other cell types, the pore sizes can be as high as 20 µm. Indeed, the pore sizes useful in the TFF module include filters with sizes from 0.50 µm and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching.

The length of the channel structure 402 may vary depending on the volume of the cell culture to be grown. The length of the channel structure typically is from 60 mm to 300 mm, or from 70 mm to 200 mm, or from 80 mm to 100 mm. The cross-section configuration of the flow channel 402 may be round, elliptical, oval, square, rectangular, trapezoidal, or irregular. If square, rectangular, or another shape with generally straight sides, the cross section may be from about 10 µm to 1000 µm wide, or from 200 µm to 800 µm wide, or from 300 µm to 700 µm wide, or from 400 µm to 600 µm wide; and from about 10 µm to 1000 µm high, or from 200 µm to 800 µm high, or from 300 µm to 700 µm high, or from 400 µm to 600 µm high. If the cross section of the flow channel 302 is generally round, oval or elliptical, the radius of the channel may be from about 50 µm to 1000 µm in hydraulic radius, or from 5 µm to 800 µm in hydraulic radius, or from 200 µm to 700 µm in hydraulic radius, or from 300 µm to 600 µm wide in hydraulic radius, or from about 200 to 500 µm in hydraulic radius. Moreover, the volume of the channel in the retentate 422 and permeate 420 members may be different depending on the depth of the channel in each member.

FIG. 4B shows front perspective (right) and rear perspective (left) views of a reservoir assembly 450 configured to be used with the tangential flow assembly 410 seen in FIG. 4A. Seen in the front perspective view (e.g., "front" being the side of reservoir assembly 450 that is coupled to the tangential flow assembly 410 seen in FIG. 4A) are retentate reservoirs 452 on either side of permeate reservoir 454. Also seen are permeate ports 426, retentate ports 428, and three threads or mating elements 425 for countersinks 423 (countersinks 423 not seen in this FIG. 4B). Threads or mating elements 425 for countersinks 423 are configured to mate or couple the tangential flow assembly 410 (seen in FIG. 4A) to reservoir assembly 450. Alternatively, or in addition, fasteners, sonic welding or heat stakes may be used to mate or couple the tangential flow assembly 410 to reservoir assembly 450. In addition is seen gasket 445 covering the top of reservoir assembly 450. Gasket 445 is described in detail in relation to FIG. 4E. At left in FIG. 4B is a rear perspective view of reservoir assembly 450, where "rear" is the side of reservoir assembly 450 that is not coupled to the tangential flow assembly. Seen are retentate reservoirs 452, permeate reservoir 454, and gasket 445.

The TFF module may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF module is disposable, preferably it is made of plastic. In some embodiments, the material used to fabricate the TFF module is thermally-conductive so that the cell culture may be heated or cooled to a desired temperature. In certain embodiments, the TFF module is formed by precision mechanical machining, laser machining, electro discharge machining (for metal devices); wet or dry etching (for silicon devices); dry or wet etching, powder or sand-blasting, photostructuring (for glass devices); or thermoforming, injection molding, hot embossing, or laser machining (for plastic devices) using the materials mentioned above that are amenable to this mass production techniques.

Figure 4C:
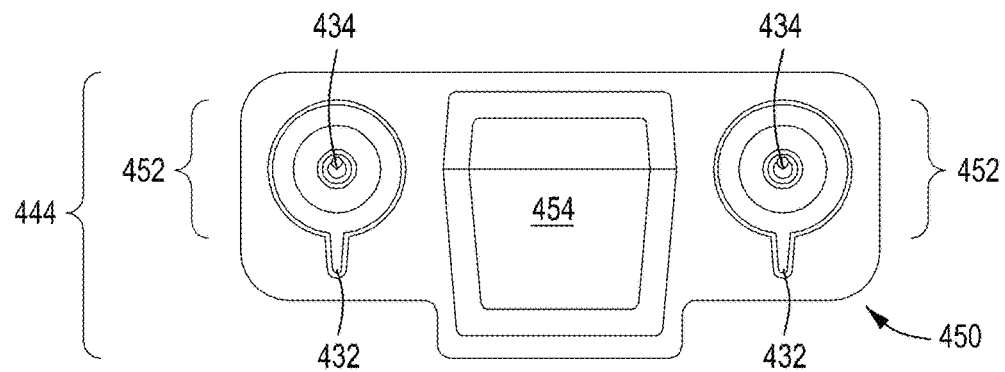
FIGS. 4C-4E depict an exemplary top, with fluidic and pneumatic ports and gasket suitable for the reservoir assemblies shown in FIG. 4B.
Figure 4D:
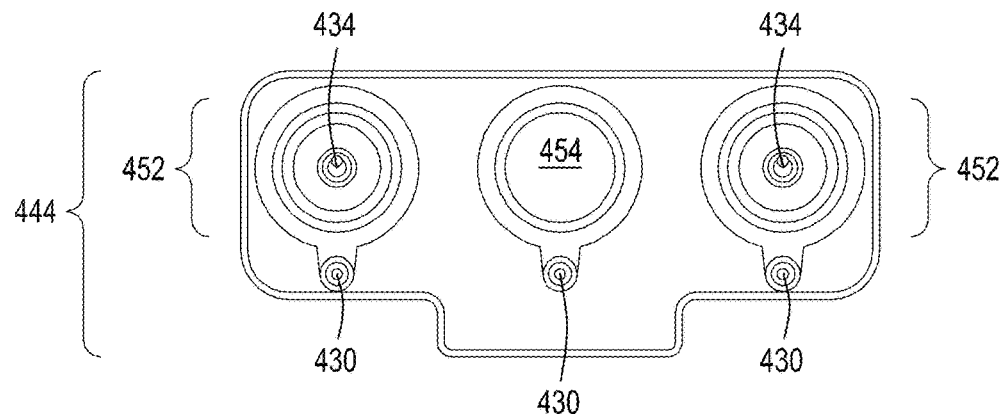
Figure 4E:
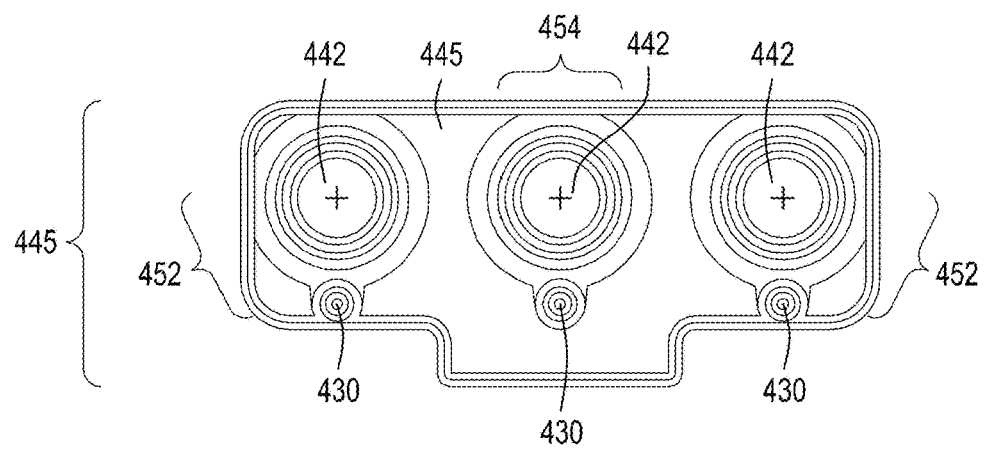

FIG. 4C depicts a top-down view of the reservoir assemblies 450 shown in FIG. 4B. FIG. 4D depicts a cover 444 for reservoir assembly 450 shown in FIGS. 4B and 4E depicts a gasket 445 that in operation is disposed on cover 444 of reservoir assemblies 450 shown in FIG. 4B. FIG. 4C is a top-down view of reservoir assembly 450, showing the tops of the two retentate reservoirs 452, one on either side of permeate reservoir 454. Also seen are grooves 432 that will mate with a pneumatic port (not shown), and fluid channels 434 that reside at the bottom of retentate reservoirs 452, which fluidically couple the retentate reservoirs 452 with the retentate ports 428 (not shown), via the through-holes for the retentate ports in permeate member 420 and membrane 424 (also not shown). FIG. 4D depicts a cover 444 that is configured to be disposed upon the top of reservoir assembly 450. Cover 444 has round cut-outs at the top of retentate reservoirs 452 and permeate/filtrate reservoir 454. Again, at the bottom of retentate reservoirs 452 fluid channels 434 can be seen, where fluid channels 434 fluidically couple retentate reservoirs 452 with the retentate ports 428 (not shown). Also shown are three pneumatic ports 430 for each retentate reservoir 452 and permeate/filtrate reservoir 454. FIG. 4E depicts a gasket 445 that is configures to be disposed upon the cover 444 of reservoir assembly 450. Seen are three fluid transfer ports 442 for each retentate reservoir 452 and for permeate/filtrate reservoir 454. Again, three pneumatic ports 430, for each retentate reservoir 452 and for permeate/filtrate reservoir 454, are shown.

The overall work flow for cell growth comprises loading a cell culture to be grown into a first retentate reservoir, preferably bubbling air or an appropriate gas through the cell culture, passing or flowing the cell culture through the first retentate port then tangentially through the TFF channel structure while collecting medium or buffer through one or both of the permeate ports 426, collecting the cell culture through a second retentate port 428 into a second retentate reservoir, optionally adding additional fresh or different medium to the cell culture and optionally bubbling air or gas through the cell culture, then repeating the process, all while measuring, e.g., the optical density of the cell culture in the retentate reservoirs continuously or at desired intervals. Again, cell growth monitoring can be performed by imaging, for example, by allowing the microcarriers to settle and imaging the bottom of the TFF retentate reservoir. Alternatively, an aliquot of the culture is removed and run through a flow cell for imaging. In yet another alternative, the cells may express a fluorescent protein and fluorescence is measured.

In the channel structure, the membrane bifurcating the flow channels retains the cells on one side of the membrane (the retentate side 422) and allows unwanted medium or buffer to flow across the membrane into a filtrate or permeate side (e.g., permeate member 420) of the device. Bubbling air or other appropriate gas through the cell culture both aerates and mixes the culture to enhance cell growth. During the process, medium that is removed during the flow through the channel structure is removed through the permeate/filtrate ports 426. Alternatively, cells can be grown in one reservoir with bubbling or agitation without passing the cells through the TFF channel from one reservoir to the other.

The overall workflow for cell concentration using the TFF module involves flowing a cell culture or cell sample tangentially through the channel structure. As with the cell growth process, the membrane bifurcating the flow channels retains the cells on one side of the membrane and allows unwanted medium or buffer to flow across the membrane into a permeate/filtrate side (e.g., permeate member 420) of the device. In this process, a fixed volume of cells in medium or buffer is driven through the device until the cell sample is collected into one of the retentate ports 428, and the medium/buffer that has passed through the membrane is collected through one or both of the permeate/filtrate ports 426. All types of prokaryotic and eukaryotic cells—both adherent and non-adherent cells—can be grown in the TFF module. Adherent cells may be grown on beads or other cell scaffolds suspended in medium that flow through the TFF module.

The medium or buffer used to suspend the cells in the TFF module may be any suitable medium or buffer for the type of cells being transformed or transfected, such as MEM, DMEM, IMDM, RPMI, Hanks', PBS and Ringer's solution, where the media may be provided in a reagent cartridge as part of a kit. For culture of adherent cells, cells may be disposed on microcarriers or other type of scaffold suspended in medium. The microcarriers of particular use typically have a diameter of 50-500 µm and have a density slightly greater than that of the culture medium thus facilitating an easy separation of cells and medium for, e.g., medium exchange yet the density must also be sufficiently low to allow complete suspension of the carriers at a minimum stirring rate in order to avoid hydrodynamic damage to the cells.

In both the cell growth and concentration processes, passing the cell sample through the TFF module and collecting the cells in one of the retentate ports 428 while collecting the medium in one of the permeate/filtrate ports 426 is considered "one pass" of the cell sample. The transfer between retentate reservoirs "flips" the culture. The retentate and permeate ports collecting the cells and medium, respectively, for a given pass reside on the same end of TFF module with fluidic connections arranged so that there are two distinct flow layers for the retentate and permeate/filtrate sides, but if the retentate port 428 resides on the retentate member of device/module (that is, the cells are driven through the channel above the membrane and the filtrate (medium) passes to the portion of the channel below the membrane), the permeate/filtrate port 426 will reside on the permeate member of device/module and vice versa (that is, if the cell sample is driven through the channel below the membrane, the filtrate (medium) passes to the portion of the channel above the membrane). Due to the high pressures used to transfer the cell culture and fluids through the flow channel of the TFF module, the effect of gravity is negligible.

At the conclusion of a "pass" in either of the growth and concentration processes, the cell sample is collected by passing through the retentate port 428 and into the retentate reservoir (not shown). To initiate another "pass", the cell sample is passed again through the TFF module, this time in a flow direction that is reversed from the first pass. The cell sample is collected by passing through the retentate port 428 and into retentate reservoir (not shown) on the opposite end of the device/module from the retentate port 428 that was used to collect cells during the first pass. Likewise, the medium/buffer that passes through the membrane on the second pass is collected through the permeate port 426 on the opposite end of the device/module from the permeate port 426 that was used to collect the filtrate during the first pass, or through both ports. This alternating process of passing the retentate (the concentrated cell sample) through the device/module is repeated until the cells have been grown to a desired optical density, and/or concentrated to a desired volume, and both permeate ports (i.e., if there are more than one) can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell growth may (and typically do) take place simultaneously, and buffer exchange and cell concentration may (and typically do) take place simultaneously. For further information and alternative embodiments on TFFs see, e.g., U.S. Ser. No. 16/798,302, filed 22 Feb. 2020.

Figure 4F:
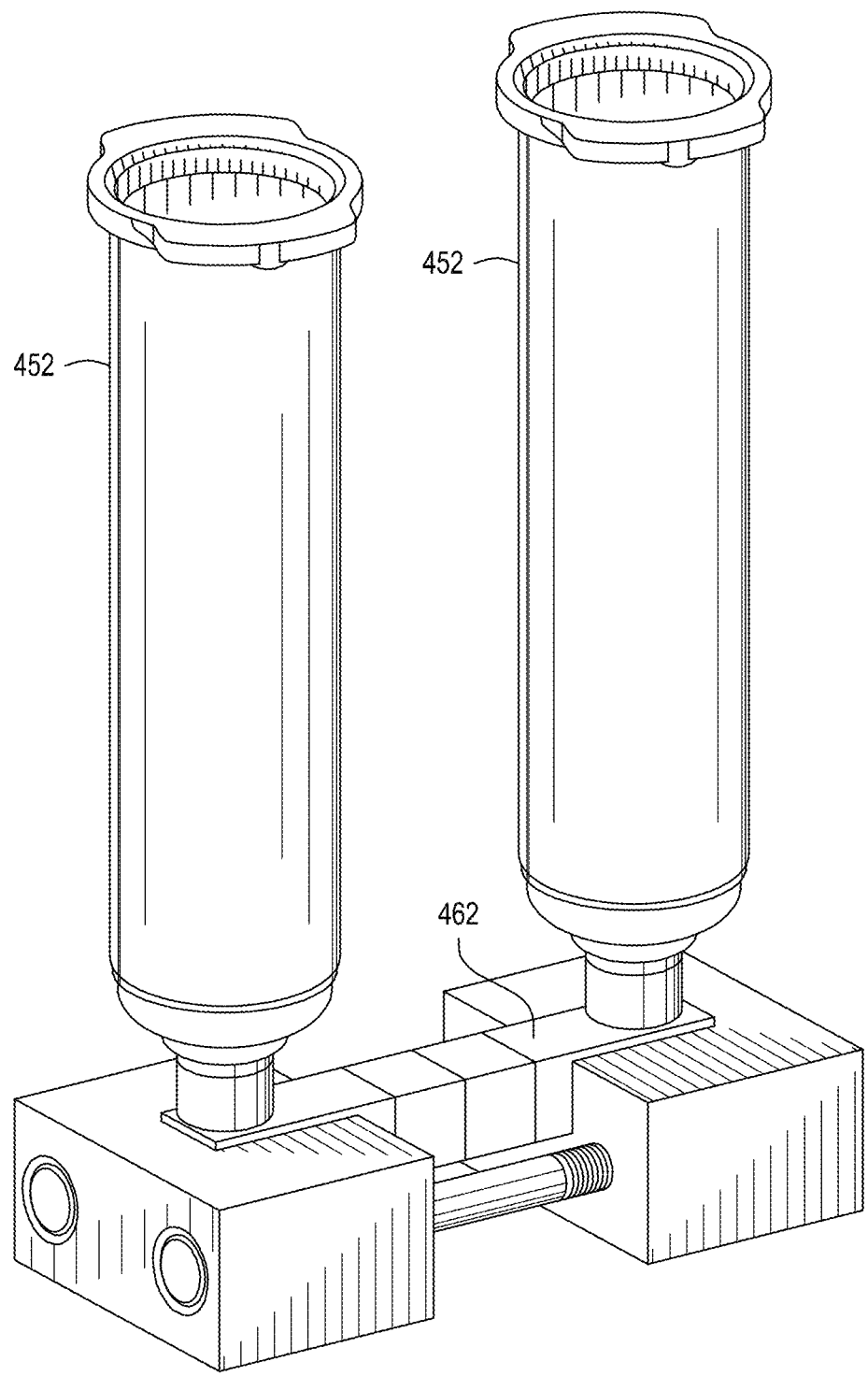
FIGS. 4F and 4G depict a retentate reservoir assembly comprising one or more strainers, frits or sieves which may be used to dissociate cells in the tangential flow filtration module.
Figure 4G:
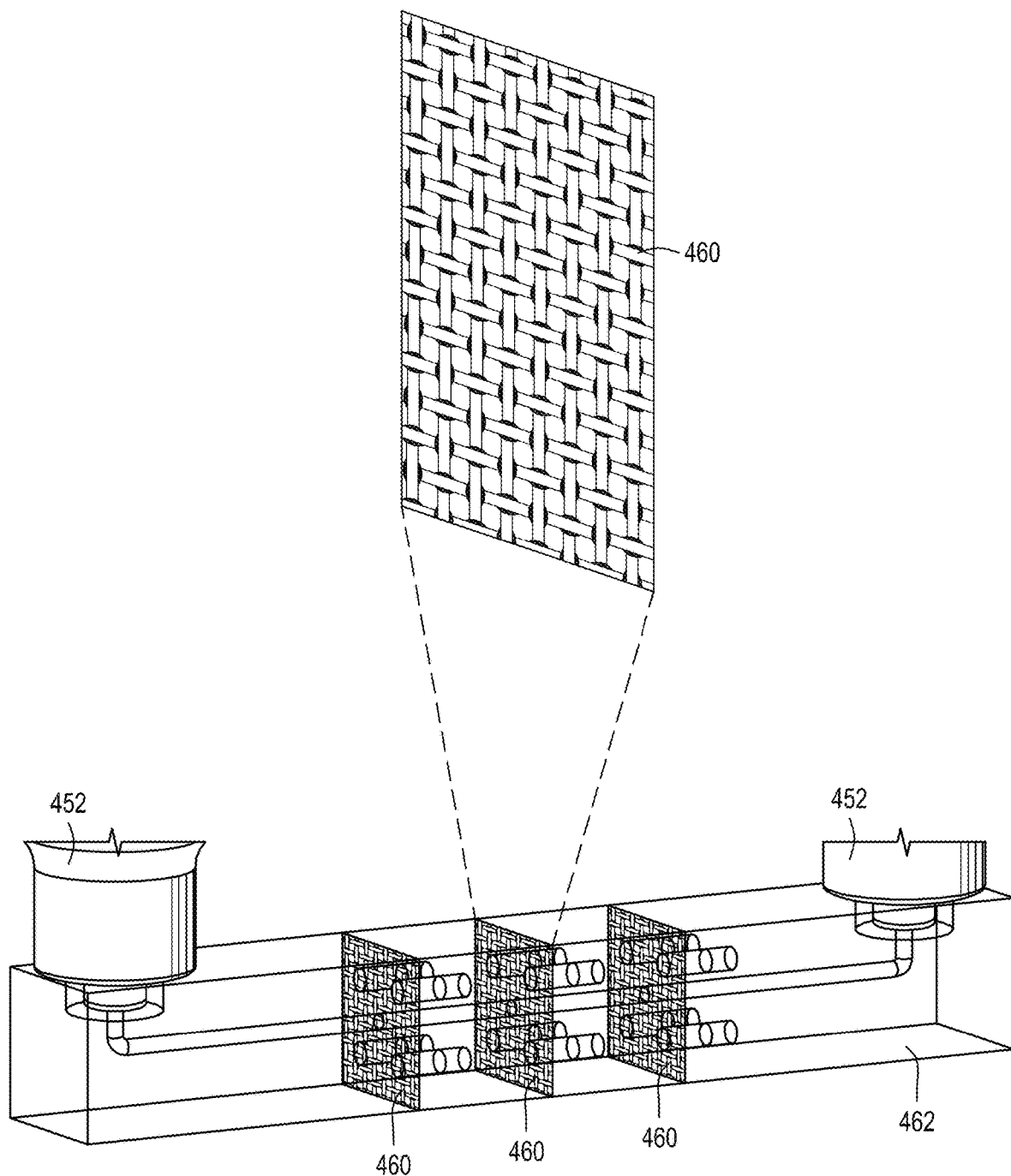

In addition, the TFF module may be modified to dissociate cells, as shown in FIGS. 4F and 4G. That is, the TFF may be modified such that the retentate reservoirs, in addition to being connected through the flow channel that courses through the TFF module, are connected directly by a conduit where the cells are passed from one retentate reservoir to another without being sent through the flow channel. In FIG. 4F, retentate reservoirs 452 are shown, connected by conduit 462. In conduit 462 are placed one to many (e.g., in FIG. 4G, there are three) strainers, frits or sieves 460 through which aggregates of cells are passed to dissociate the aggregates. As with the modified paddles or features in the rotating growth vial, strainers, frits or sieves 460 comprise pores or openings from 10 to 400 microns in size, or from 20 to 200 microns in size, or from 30 to 100 microns in size configured to dissociate the cell aggregates. That is, the TFF may be used to grow the cells—either as aggregates or on microcarriers—passage the cells to increase the number of cells, concentrate the cells and then finally the cells may be routed through the direct conduit between the retentate reservoirs to dissociate the cells for transfection/transduction.

The Bioreactor

In addition to the rotating growth vial module shown in FIGS. 3A-3E and described in the related text, and the tangential flow filtration (TFF) module shown FIGS. 4A-4G and described in the related text, a bioreactor can be used to grow cells off-instrument or to allow for cell growth and recovery on-instrument; e.g., as one module of the multi-module fully-automated closed instrument. Further, the bioreactor supports cell selection/enrichment, via expressed antibiotic markers in the growth process or via expressed antibodies coupled to magnetic beads and a magnet associated with the bioreactor. There are many bioreactors known in the art, including those described in, e.g., WO 2019/046766; 10,699,519; 10,633,625; 10,577,576; 10,294,447; 10,240,117; 10,179,898; 10,370,629; and 9,175,259; and those available from Lonza Group Ltd. (Basel, Switzerland); Miltenyi Biotec (Bergisch Gladbach, Germany), Terumo BCT (Lakewood, Colo.) and Sartorius GmbH (Gottingen, Germany).

FIG. 5A shows one embodiment of a bioreactor assembly 500 for cell growth, transfection, and editing in the automated multi-module cell processing instruments described herein. Unlike most bioreactors that are used to support fermentation or other processes with an eye to harvesting the products produced by organisms grown in the bioreactor, the present bioreactor (and the processes performed therein) is configured to grow cells, monitor cell growth (via, e.g., optical means or capacitance), passage cells, select cells, transfect cells, and support the growth and harvesting of edited cells. Bioreactor assembly 500 comprises cell growth, transfection, and editing vessel 501 comprising a main body 504 with a lid assembly 502 comprising ports 508, including an optional motor integration port 510 driving impeller 506 via impeller shaft 552. Bioreactor assembly 500 comprises a growth vessel 501 comprising tapered a main body 504 with a lid assembly 502 comprising ports 508, including an optional motor integration port 510 driving impeller 506 via impeller shaft 552. The tapered shape of main body 504 of the vessel 501 along with, in some embodiments, dual impellers allows for working with a larger dynamic range of volumes, such as, e.g., up to 500 ml and as low as 100 ml for rapid sedimentation of the microcarriers. In addition, the low volume is useful for magnetic bead separation or enrichment as described above.

Bioreactor assembly 500 further comprises bioreactor stand assembly 503 comprising a main body 512 and vessel holder 514 comprising a heat jacket or other heating means (not shown, but see FIG. 5E) into which the main body 504 of vessel 501 is disposed in operation. The main body 504 of vessel 501 is biocompatible and preferably transparent—in some embodiments, in the UV and IR range as well as the visible spectrum—so that the growing cells can be visualized by, e.g., cameras or sensors integrated into lid assembly 502 or through viewing apertures or slots in the main body 512 of bioreactor stand assembly 503 (not shown in this FIG. 5A, but see FIG. 5E).

Bioreactor assembly 500 supports growth of cells from a 500,000 cell input to a 10 billion cell output, or from a 1 million cell input to a 25 billion cell output, or from a 5 million cell input to a 50 billion cell output or combinations of these ranges depending on, e.g., the size of main body 504 of vessel 501, the medium used to grow the cells, whether the cells are adherent or non-adherent. The bioreactor that comprises assembly 500 supports growth of both adherent and non-adherent cells, wherein adherent cells are typically grown of microcarriers as described in detail above and supra or as spheroids. Alternatively, another option for growing mammalian cells in the bioreactor described herein is growing single cells in suspension using a specialized medium such as that developed by ACCELLTA™ (Haifa, Israel). As described above, cells grown in this medium must be adapted to this process over many cell passages; however, once adapted the cells can be grown to a density of >40 million cells/ml and expanded 50-100× in approximately a week, depending on cell type.

Main body 504 of vessel 501 preferably is manufactured by injection molding, as is, in some embodiments, impeller 506 and the impeller shaft (not shown). Impeller 506 also may be fabricated from stainless steel, metal, plastics or the polymers listed infra. Injection molding allows for flexibility in size and configuration and also allows for, e.g., volume markings to be added to the main body 504 of vessel 501. Additionally, material from which the main body 504 of vessel 501 is fabricated should be able to be cooled to about 4° C. or lower and heated to about 55° C. or higher to accommodate cell growth. Further, the material that is used to fabricate the vial preferably is able to withstand temperatures up to 55° C. without deformation. Suitable materials for main body 504 of vessel 501 include those described for the rotating growth vial described in relation to FIGS. 3A and 3B and the TFF device described in relation to FIG. 4A-4E, including cyclic olefin copolymer (COC), glass, polyvinyl chloride, polyethylene, polyetheretherketone (PEEK), polypropylene, polycarbonate, poly(methyl methacrylate (PMMA)), polysulfone, poly(dimethylsiloxane), cyclo-olefin polymer (COP), and co-polymers of these and other polymers. Preferred materials include polypropylene, polycarbonate, or polystyrene. The material used for fabrication may depend on the cell type to be grown, transfected and edited, and is conducive to growth of both adherent and non-adherent cells and workflows involving microcarrier-based transfection. The main body 504 of vessel 501 may be reusable or, alternatively, may be manufactured and configured for a single use. In one embodiment, main body 504 of vessel 501 may support cell culture volumes of 25 ml to 500 ml, but may be scaled up to support cell culture volumes of up to 3 L.

The bioreactor stand assembly comprises a stand or frame 550, a main body 512 which holds the vessel 501 during operation. The stand/frame 550 and main body 512 are fabricated from stainless steel, other metals, or polymer/plastics. The bioreactor main body further comprises a heat jacket (not seen in FIG. 5A, but see FIG. 5E) to maintain the bioreactor main body 504—and thus the cell culture—at a desired temperature. Essentially, the stand assembly can host a set of sensors and cameras to monitor cell culture.

FIG. 5B depicts a top-down view of one embodiment of vessel lid assembly 502. Vessel lid assembly 502 is configured to be air-tight, providing a sealed, sterile environment for cell growth, transfection and editing as well as to provide biosafety maintaining a closed system. Vessel lid assembly 502 and the main body 504 of vessel 501 can be sealed via fasteners such as screws, using biocompatible glues, or the two components may be ultrasonically welded. Vessel lid assembly 502 is some embodiments is fabricated from stainless steel such as S316L stainless steel but may also be fabricated from metals, other polymers (such as those listed supra) or plastics. As seen in this FIG. 5B—as well as in FIG. 5A—vessel lid assembly 502 comprises a number of different ports to accommodate liquid addition and removal; gas addition and removal; for insertion of sensors to monitor culture parameters (described in more detail infra); to accommodate one or more cameras or other optical sensors; to provide access to the main body 504 of vessel 501 by, e.g., a liquid handling device; and to accommodate a motor for motor integration to drive one or more impellers 506. Exemplary ports depicted in FIG. 5B include three liquid-in ports 516 (at 4 o'clock, 6 o'clock and 8 o'clock), one liquid-out port 522 (at 11 'clock), a capacitance sensor 518 (at 9 o'clock), one "gas in" port 524 (at 12 o'clock), one "gas out" port 520 (at 10 o'clock), an optical sensor 526 (at 1 o'clock), a rupture disc 528 at 2 o'clock, a self-sealing port 530 (at 3 o'clock) to provide access to the main body 504 of growth vessel 501; and (a temperature probe 532 (at 5 o'clock).

The ports shown in vessel lid assembly 502 in this FIG. 5B are exemplary only and it should be apparent to one of ordinary skill in the art given the present disclosure that, e.g., a single liquid-in port 516 could be used to accommodate addition of all liquids to the cell culture rather than having a liquid-in port for each different liquid added to the cell culture. Similarly, there may be more than one gas-in port 524, such as one for each gas, e.g., $O_2$, $CO_2$ that may be added. In addition, although a temperature probe 532 is shown, a temperature probe alternatively may be located on the outside of vessel holder 514 of bioreactor stand assembly 503 separate from or integrated into heater jacket 548 (not seen in this FIG. 5B, but see FIG. 5E). A self-sealing port 530, if present, allows access to the main body 504 of vessel 501 for, e.g., a pipette, syringe, or other liquid delivery system via a gantry (not shown). As shown in FIG. 5A, additionally there may be a motor integration port to drive the impeller(s), although in other configurations of vessel 501 may alternatively integrate the motor drive at the bottom of the main body 504 of vessel 501. Vessel lid assembly 502 may also comprise a camera port for viewing and monitoring the cells.

Additional sensors include those that detect $O_2$ concentration, a $CO_2$ concentration, culture pH, lactate concentration, glucose concentration, biomass, and optical density. The sensors may use optical (e.g., fluorescence detection), electrochemical, or capacitance sensing and either be reusable or configured and fabricated for single-use. Sensors appropriate for use in the bioreactor are available from Omega Engineering (Norwalk Conn.); PreSens Precision Sensing (Regensburg, Germany); C-CIT Sensors AG (Waedenswil, Switzerland), and ABER Instruments Ltd. (Alexandria, Va.). In one embodiment, optical density is measured using a reflective optical density sensor to facilitate sterilization, improve dynamic range and simplify mechanical assembly. The rupture disc, if present, provides safety in a pressurized environment, and is programmed to rupture if a threshold pressure is exceeded in the bioreactor. If the cell culture in the bioreactor vessel is a culture of adherent cells, microcarriers may be used as described supra.

In such an instance, the liquid-out port may comprise a filter such as a stainless steel or plastic (e.g., polyvinylidene difluoride (PVDF), nylon, polypropylene, polybutylene, acetal, polyethylene, or polyamide) filter or frit to prevent microcarriers from being drawn out of the culture during, e.g., medium exchange, but to allow dead cells to be withdrawn from the vessel. The microcarriers used for initial cell growth can be nanoporous (where pore sizes are typically <20 nm in size), microporous (with pores between >20 nm to <1 μm in size), or macroporous (with pores between >1 μm in size, e.g. 20 μm) and the microcarriers are typically 50-200 μm in diameter; thus the pore size of the filter or frit in the liquid-out port will differ depending on microcarrier size.

The microcarriers used for cell growth depend on cell type and desired cell numbers, and typically include a coating of a natural or synthetic extracellular matrix or cell adhesion promoters (e.g., antibodies to cell surface proteins or poly-L-lysine) to promote cell growth and adherence. Microcarriers for cell culture are widely commercially available from, e.g., Millipore Sigma, (St. Louis, Mo., USA); ThermoFisher Scientific (Waltham, Mass., USA); Pall Corp. (Port Washington, N.Y., USA); GE Life Sciences (Marlborough, Mass., USA); and Corning Life Sciences (Tewkesbury, Mass., USA). As for the extracellular matrix, natural matrices include collagen, fibrin and vitronectin (available, e.g., from ESBio, Alameda, Calif., USA), and synthetic matrices include MATRIGEL® (Corning Life Sciences, Tewkesbury, Mass., USA), GELTREX™ (ThermoFisher Scientific, Waltham, Mass., USA), CULTREX® (Trevigen, Gaithersburg, Md., USA), biomemetic hydrogels available from Cellendes (Tubingen, Germany); and tissue-specific extracellular matrices available from Xylyx (Brooklyn, N.Y., USA); further, denovoMatrix (Dresden, Germany) offers screenMATRIX™, a tool that facilitates rapid testing of a large variety of cell microenvironments (e.g., extracellular matrices) for optimizing growth of the cells of interest.

FIG. 5C is a side view of the main body 504 of vessel 501. A portion of vessel lid assembly 502 can be seen, as well as two impellers 506a and 506b. Also seen are a lactate/glucose sensor probe 534, a pH, $O_2$, $CO_2$ sensor 536 (such as a PRESENS™ integrated optical sensor (Precision Sensing GmbH, (Regensburg, Germany)), and a viable biomass sensor 538 (such as, e.g., the FUTURA PICO™ capacitance sensor (ABER, Alexandria, Va.)). In some embodiments, flat regions are fabricated onto the main body 504 of vessel 501 to reduce optical loss, simplify spot placement and simplify fluorescent measurement of pH, $dO_2$, and $dCO_2$.

FIG. 5D shows exemplary design guidelines for a one-impeller embodiment (left) and a two-impeller embodiment (right) of the main body 504 of vessel 501, including four exemplary impeller configurations. The embodiment of the INSCRIPTA™ bioreactor vessel 501 main body 504 as shown in this FIG. 5D has a total volume of 820 ml and supports culture volumes from 25 ml to 500 ml. As mentioned above, the impellers (and impeller shaft) may be injection molded or may be fabricated from stainless steel, other biocompatible metals, polymers or plastics and preferably comprised polished surfaces to facilitate sterilization. The impeller may be configured as a turbine-, pitched-blade-, hydrofoil- or marine-type impeller. In a two-impeller configuration, the impellers may be of the same type or different types. In the bioreactors described herein (the "INSCRIPTA™ bioreactors") and used to generated the data in Examples IV-XI, agitation is provided at 0-100 rpm, or 40-80 rpm, or approximately 70 rpm during cell growth (depending on the cell type being cultured); however, lower or higher revolutions per minute may be used depending on the volume of the main body 504 of vessel 501, the type of cells being cultured, whether the cells are adherent and being grown on microcarriers or the cells are non-adherent, and the size and configuration of the impellers. The impeller may turn in a clockwise direction, a counter-clockwise direction or the impeller may change direction (oscillate) or stop at desired intervals, particularly during cell detachment from the microcarriers. Also, intermittent agitation may be applied, e.g., agitating for 10 minutes every 30 minutes, or agitating for 1 minute every 5 minutes or any other desired pattern. Additionally, impeller rpm is often increased (e.g., up to 4000 rpm) when the cells are being detached from microcarriers. Although the present embodiment of INSCRIPTA™ bioreactor utilizes one or more impellers for cell growth, alternative embodiments of the INSCRIPTA™ bioreactor described herein may utilize bubbling or other physical mixing means.

Also seen in FIG. 5D is an equation that gives a range for exemplary bioreactor dimensions base on the height (H) and thickness (T) of the main body of vessel 504. For example, D=0.25–05*T means the impeller diameter could be one quarter or one half of the main body of vessel 504 thickness, T. C is the clearance of the impeller from the bottom of the main body of vessel 504, which can be 0.15 to 0.5 times the thickness. It should be apparent to one of ordinary skill in the art given the present disclosure that these numbers are just one embodiment and the ranges may be larger. The bioreactor vessel 501 main body 504 comprises an 8-10 mm clearance from the bottom of the main body 504 of vessel 501 to the lower impeller 506b and the lower impeller 506b and the upper impeller 506a are approximately 40 mm apart.

FIG. 5E is a side view of the vessel holder portion 514 of the bioreactor stand main body 512 of the bioreactor stand assembly 503. Inner surface 540 of vessel holder 514 is indicated and shown are camera or fiber optic ports 546 for monitoring, e.g., cell growth and viability; $O_2$ and $CO_2$ levels, and pH. The vessel holder portion 514 of the bioreactor stand main body 512 may also provide illumination using LED lights, such as a ring of LED lights (not shown). FIG. 5F is a side perspective view of the assembled bioreactor without sensors 542. Seen are vessel lid assembly 502, bioreactor stand assembly 503, bioreactor stand main body 512 into which the main body 504 of vessel 501 (not seen in FIG. 5E) is inserted. FIG. 5G is a lower side perspective view of bioreactor assembly 500 showing bioreactor stand assembly 503, bioreactor stand main body 512, vessel lid assembly 502 and two camera mounts 544. Surrounding bioreactor stand main body 512 is heater jacket 548.

FIG. 5H is an exemplary diagram of the bioreactor fluidics. Fluidics and pneumatics are designed to establish a cell culture environment conducive for mammalian cell growth, including iPSCs. Fluidic circuits are designed to deliver and/or remove cell medium, buffers, microcarriers and additional reagents needed for growth, maintenance, selection and passaging of the cells in the automated closed culture instrument. The pneumatic circuits are designed to deliver the appropriate gas mixture and humidity for the chosen cell type, and may comprise line-in filters to prevent any contaminants from reaching the bioreactor.

FIG. 5I is a block diagram for an exemplary bioreactor control system. The control system is designed to control and automate the fluidics, pneumatics and sensor function in a closed system and without human intervention. In one embodiment, the control system is based on state-machines with a user editable state order and parameters using Json and jsonette config files. State-machines allow for dynamic control of several aspects of the bioreactor with a single computer.

Figure 14:
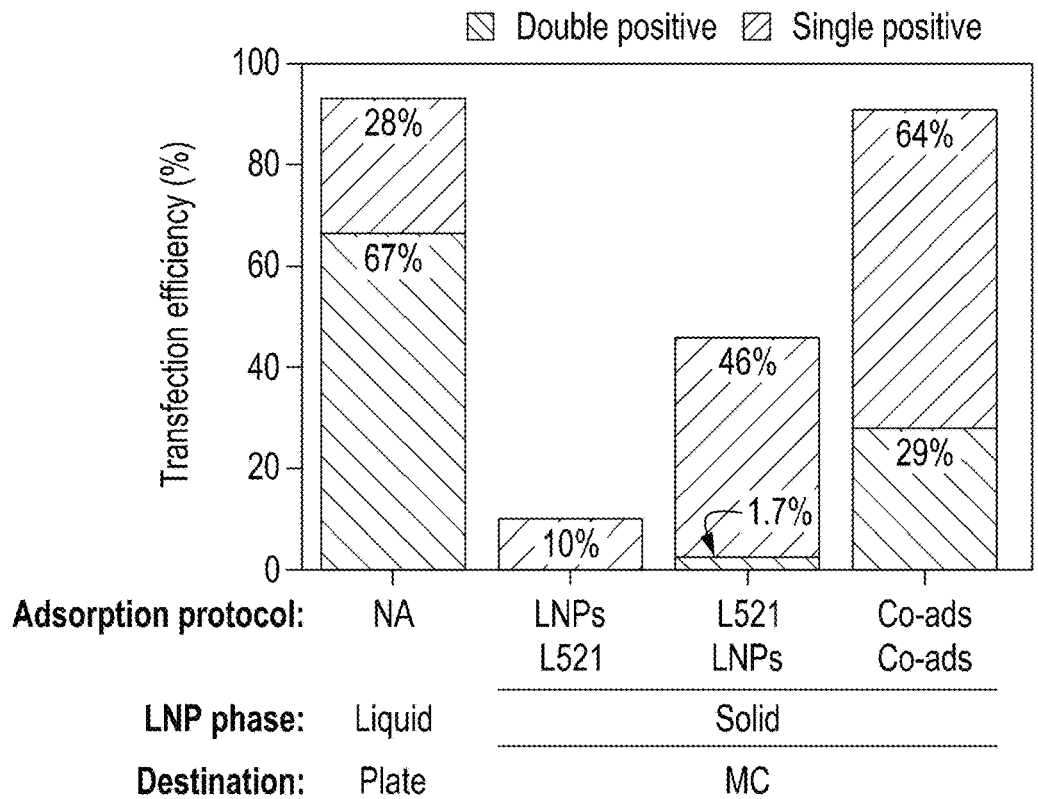
FIG. 14 is a bar graph showing data demonstrating that microcarrier fidelity is tunable by the adsorption protocol used.

In use, the bioreactor described herein is used for cell growth and expansion—either before or after the cells are transfected in droplets—as well as for medium exchange and cell concentration. Medium/buffer exchange is in one embodiment accomplished using gravitational sedimentation and aspiration via a filter in the liquid-out port where the filter is of an appropriate size to retain microcarriers (see, e.g., Example VII, infra). In one embodiment used with the present bioreactor, a frit with pore size 100 μm was used and microcarriers with diameters or 120-225 μm were used in the cell culture. Sedimentation was accomplished in approximately 2-3 minutes for a 100 ml culture and 4-5 minutes for a 500 ml culture. The medium was aspirated at >100 ml/min rate. In addition to clearing the medium from the main body 504 of vessel 501, dead cells were removed as well. If sedimentation is used, the microcarriers do not typically accumulate on the filter; however, if accumulation is detected, the medium in the liquid-out port can be pushed back into main body 504 of vessel 501 in a pulse. In some embodiments—particularly those where sedimentation is not used—a cycle of aspiration, release (push back), aspiration and release (push back) may be performed. Experimental results show that medium exchange (aspiration) at ~200 ml/min does not impact cell growth (see FIG. 14).

Workflows in the Automated Instrument

Figure 6A:
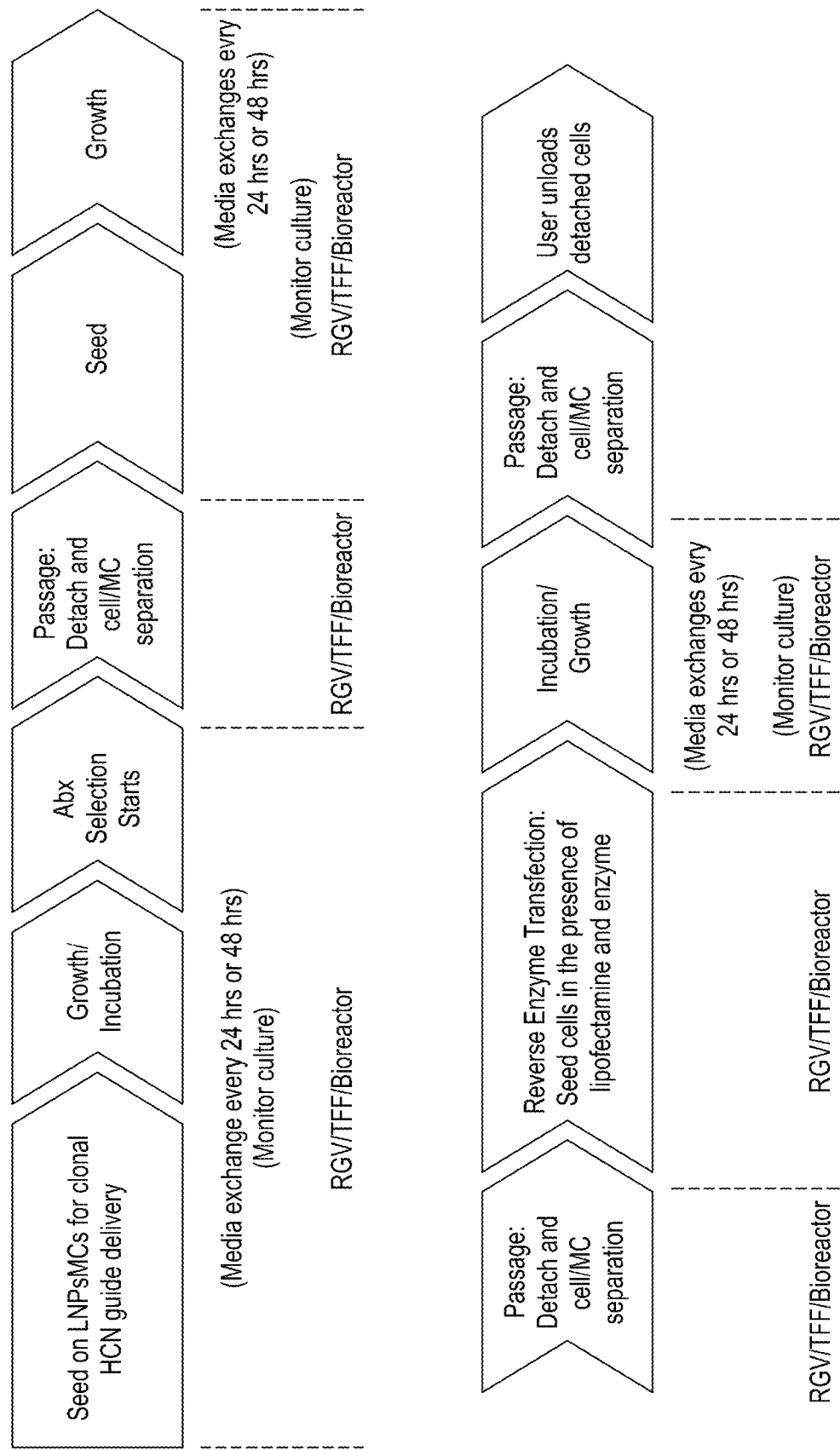
FIG. 6A depicts a first option for growing, passaging, transfecting and editing iPSCs involving sequential transfection of editing cassettes and nuclease.

FIG. 6A depicts a first exemplary option for growing, passaging, transfecting and editing iPSCs, where there is sequential delivery of clonal high copy number (HCN) LNPsMCs—i.e., lipid nanoparticle-coated microcarriers, where each microcarrier is coated with many copies of delivery vehicles (e.g., RNA, DNA, plasmid, or ribonucleoprotein) carrying a single clonal editing cassette—followed by bulk enzyme delivery. Note that the three growth modules described supra may be used for all processes or a combination of modules may be used. Following the workflow of FIG. 6A, first cells are seeded on the LNPsMCs to deliver clonal copies of nucleic acids to the cells. Again, the LNPsMCs (i.e., RBMCs) are typically fabricated or manufactured off-instrument. The cells are allowed to grow and after 24-48 hours, medium is exchanged for medium containing antibiotics to select for cells that have been transfected. The cells are passaged, re-seeded and grown again, and then passaged and re-seeded, this time onto microcarriers comprising LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) with the enzyme, e.g., provided in solution in bulk or as a coding sequence under the control of a promoter, or as a protein on the surface of a microcarrier. The enzyme is taken up by the cells on the microcarriers, and the cells are incubated and allowed to grow. Medium is exchanged as needed and the cells are detached from the microcarriers for subsequent growth and analysis.

Figure 6B:
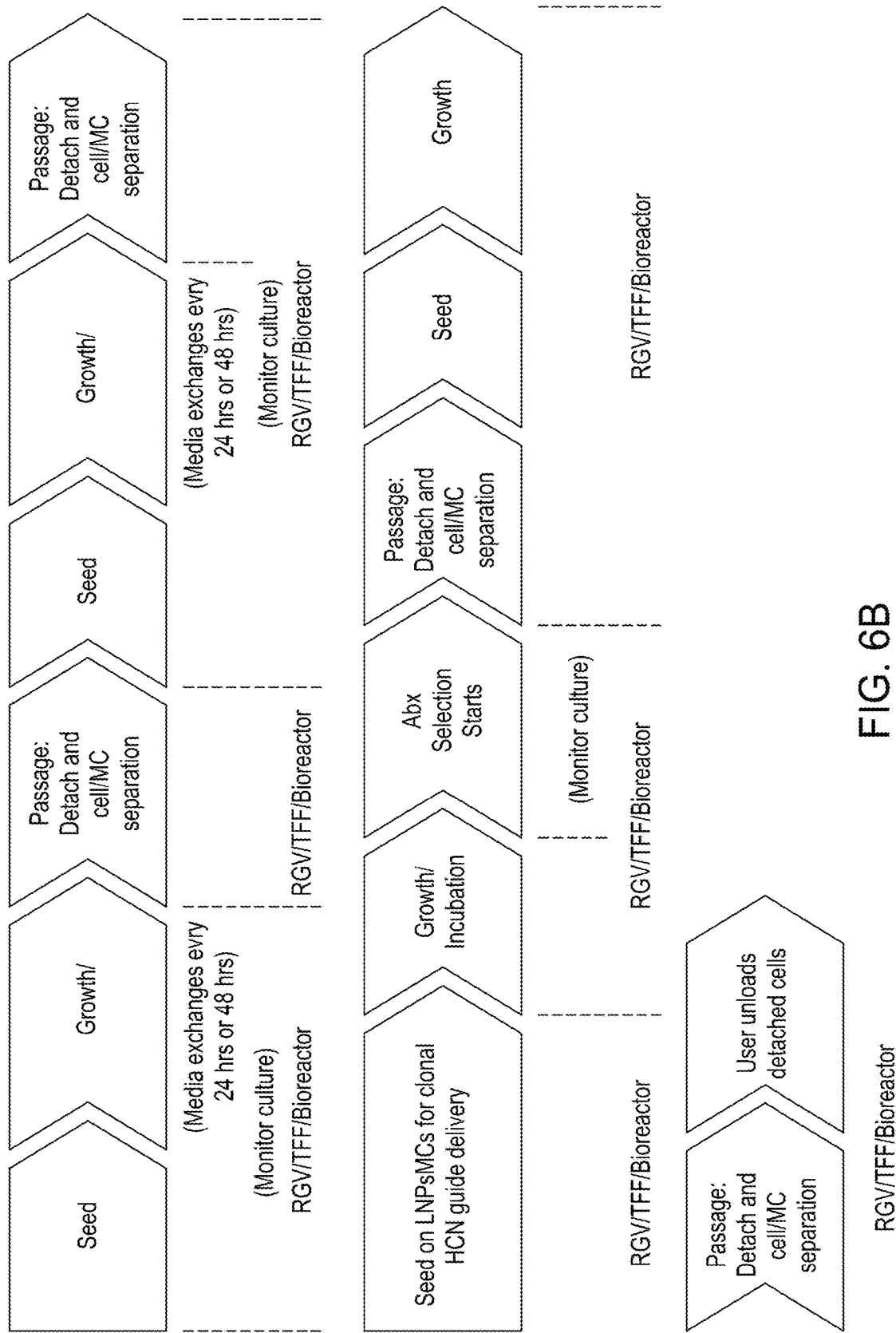
FIG. 6B depicts a second option for growing, passaging, transfecting and editing iPSCs involving simultaneous transfection of editing cassettes and nuclease.
Figure 6C:
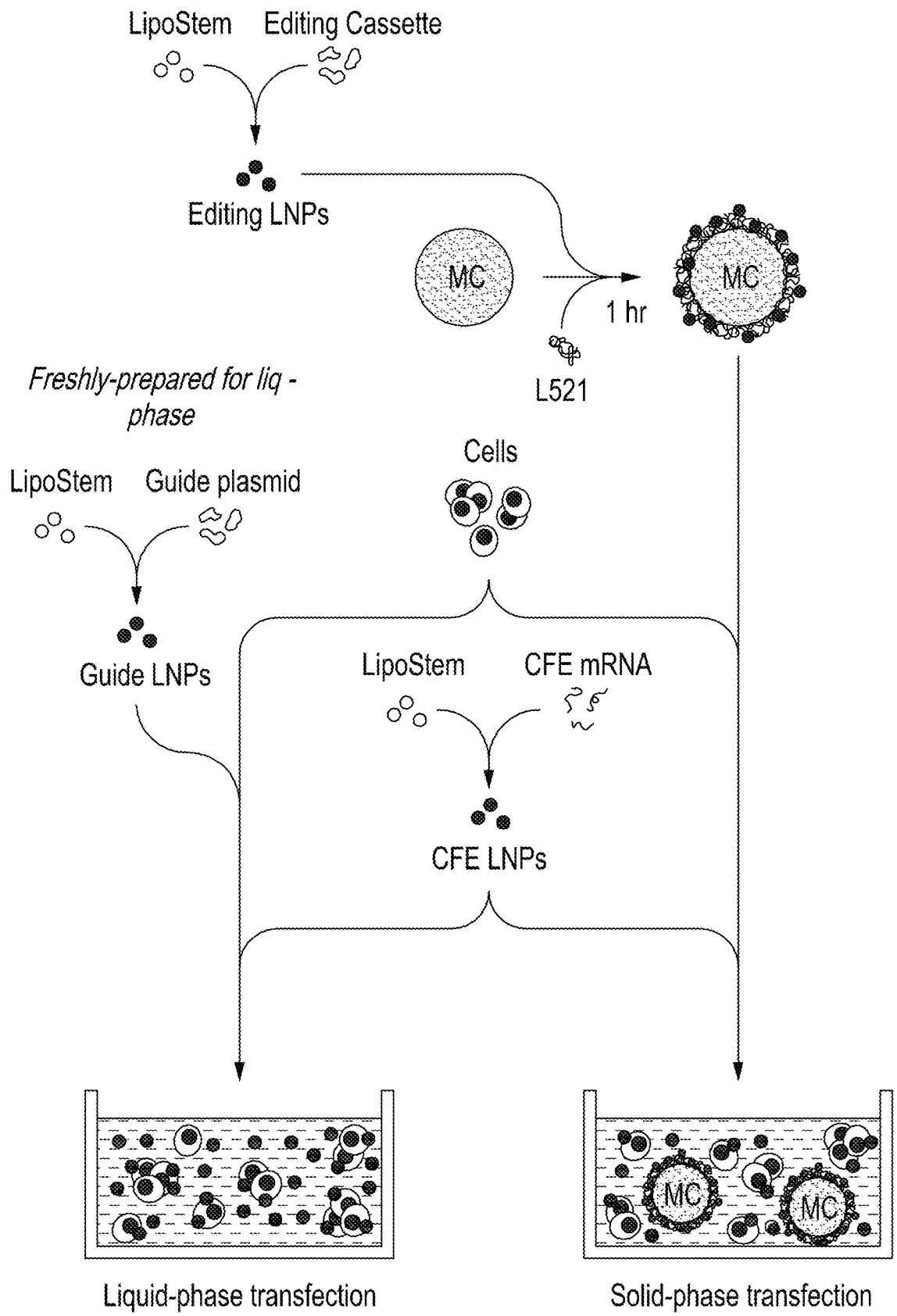
FIG. 6C illustrates the processes of solid phase transfection (as described in relation to FIGS. 6A and 6B) and liquid phase transfection. Note that the three growth modules described supra may be used for all processes.

FIG. 6B depicts a second option for growing, passaging, transfecting and editing iPSCs where there is simultaneous delivery of clonal high copy number (HCN) LNPsMCs—i.e., lipid nanoparticle-coated microcarriers, where each microcarrier is coated with many copies of delivery vehicles (e.g., RNA, DNA, plasmid, or ribonucleoprotein) carrying a single clonal editing cassette—and enzyme (e.g., as a coding sequence under the control of a promoter therefor, as a ribonucleoprotein complex, or as a protein). Again, the LNPsMCs (i.e., RBMCs) are typically fabricated or manufactured off-instrument. Note that the three growth modules described supra may be used for all processes or a combination of modules may be employed. Following the workflow of FIG. 6B, first cells are seeded on microcarriers to grow. The cells are passaged, detached, re-seeded, grown and detached again to increase cell number, with medium exchanged every 24-48 hours as needed. Following detachment, the cells are seeded on LNPsMCs for clonal delivery of the editing cassette and enzyme in a co-transfection reaction. Following transfection, the cells grown for 24-48 hours after which medium is exchanged for medium containing antibiotics for selection. The cells are selected and passaged, re-seeded and grown again. Medium is exchanged as needed and the cells are detached from the microcarriers for subsequent growth and analysis.

FIG. 6C illustrates the processes of solid phase transfection (as described in relation to FIGS. 6A and 6B) and liquid phase transfection. Note that the three growth modules described supra may be used for all processes or a combination of modules may be employed. At top and down the right side of FIG. 6C shows the sequential delivery of editing cassettes and enzyme with transfection accomplished in solid phase and at left side of FIG. 6C is the delivery of editing cassettes and enzyme with transfection accomplished in liquid phase not involving microcarriers. Following the solid phase workflow, LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) and editing cassettes are combined to form editing LNP complexes. The LNP complexes are combined with laminin-coated microcarriers, where the LNP complexes are adsorbed onto the laminin-coated surface of the microcarriers. In a next step, cells are seeded on the microcarriers and then CREATE fusion enzyme (CFE) mRNA is combined with LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) to form complexes which are then delivered to the microcarriers comprising the LNP complexes and cells. Following the liquid workflow, LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) and editing cassettes are combined to form editing LNP complexes. These complexes are combined with cells in liquid phase. Next, CREATE fusion enzyme (CFE) mRNA is combined with LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) to form complexes which are then delivered to the cells LNP complexes in liquid phase.

Figure 7A:
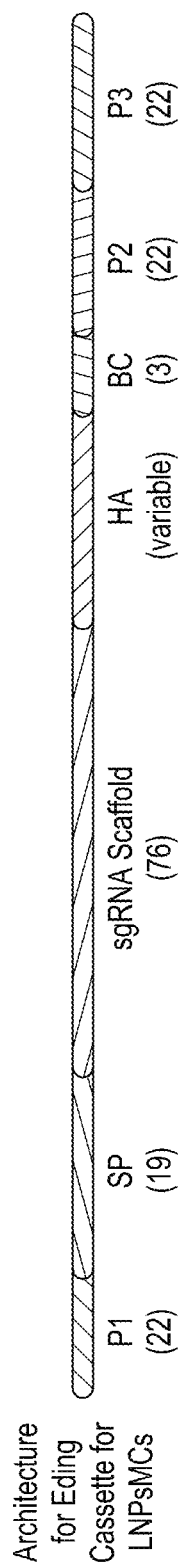
FIG. 7A depicts an exemplary architecture for editing cassettes to be delivered as LNPsMCs.

FIG. 7A depicts an exemplary architecture for editing cassettes to be delivered as LNPsMCs. This architecture comprises from 5' to 3', primer binding sequence 1; a gRNA spacer sequence; a gRNA scaffold sequence; the donor DNA—the nucleic acid that is designed to introduce a DNA sequence modification (insertion, deletion, substitution) into a locus by homologous recombination using nucleic acid-guided nucleases or a nucleic acid that serves as a template (including a desired edit) to be incorporated into target DNA by reverse transcriptase in a CREATE fusion editing (CFE) system); a barcode, a second primer binding sequence; and a third primer binding sequence. The third primer binding sequence facilitates clonal isolation of the editing cassette from a pool of editing cassettes.

Figure 7B:
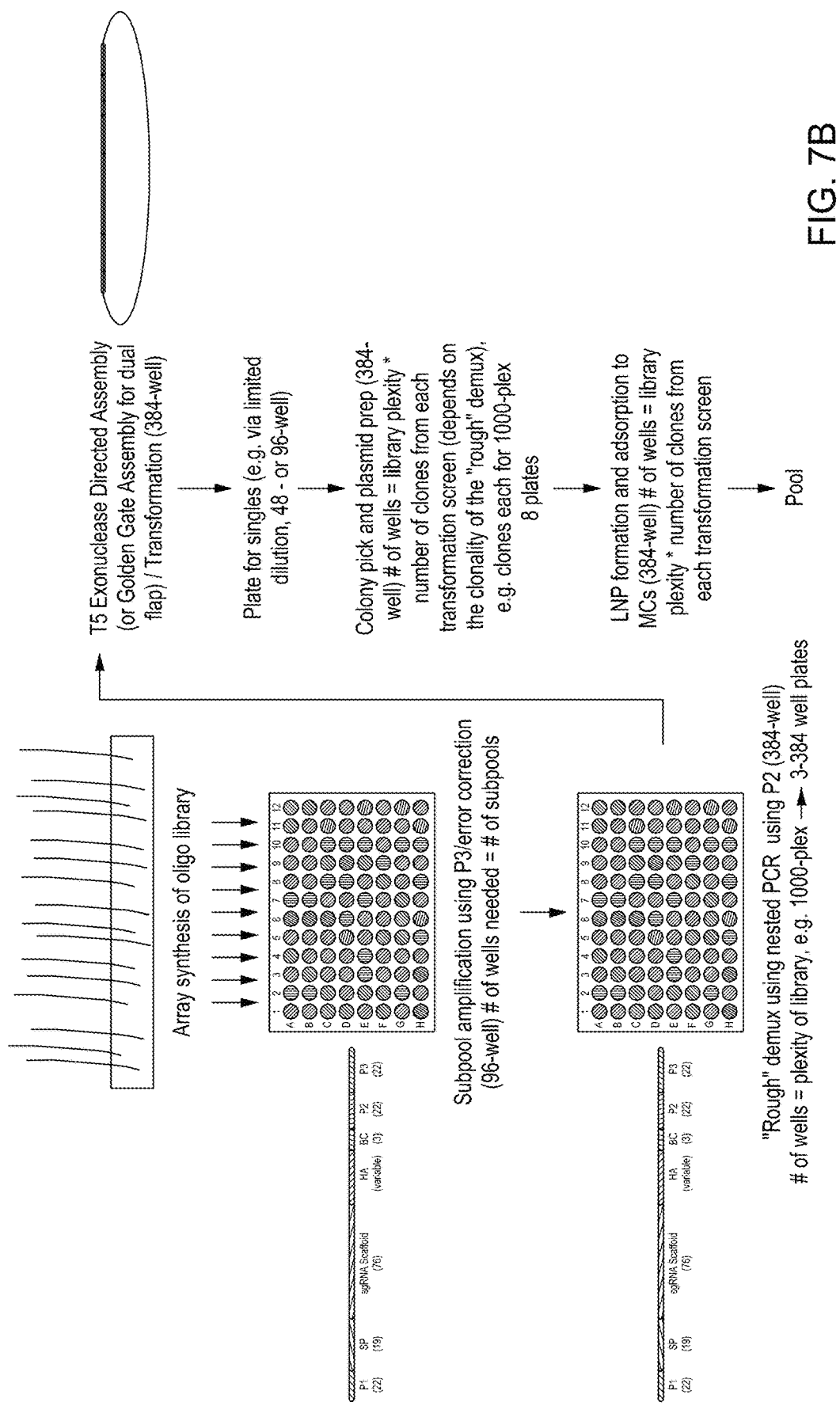
FIG. 7B depicts an exemplary workflow for creating LNPsMCs.

FIG. 7B depicts an exemplary workflow for creating LNPsMCs for pooled delivery. At top left, editing cassettes are synthesized as oligonucleotides on a substrate. The oligonucleotides are removed from the substrate and sub-pooled for amplification using the P3 primer binding site. These editing cassettes are then error corrected. As described supra, during most oligonucleotide synthesis procedures, some oligonucleotides will comprise one or more sequence errors. As described in relation to FIG. 1C, FIG. 2D-1, FIG. 2H and FIG. 2I, oligonucleotides are processed so as to remove oligonucleotides with errors, leaving only oligonucleotides, e.g., error-corrected editing cassettes, which were synthesized properly. The error-corrected editing cassettes are amplified to produce a pool of error-corrected editing cassettes.

In a next step, the subpooled, amplified editing cassettes are de-multiplexed using the P2 primer binding site with the number of wells needed equal to the plexity of the library of editing cassettes; e.g., 1000-plex library requires 3×384-well plates. Following demultiplexing, the editing cassettes are inserted into a vector backbone via T5 exonuclease- or Golden Gate-directed assembly and the vectors are transformed into *E. coli*, plated, selected and allowed to grow. Colonies are picked and plasmids are prepared. Following plasmid prep, LNPs are formed in each well and the LNPs are adsorbed onto microcarriers and pooled for transfection.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: Diffusion, Payload, and Cell Load Calculations

Figure 8A:
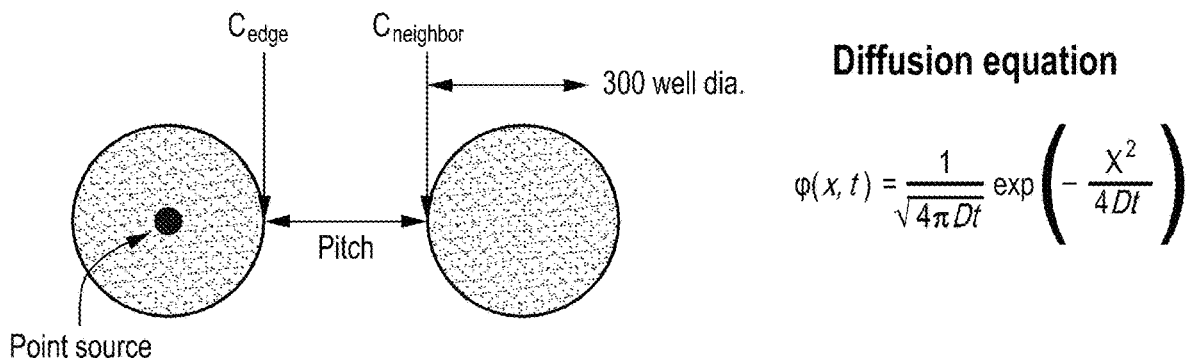
FIG. 8A shows an equation for calculating diffusion for reagents in microwells or for reagent bundles in microcarriers.
Figure 8B:
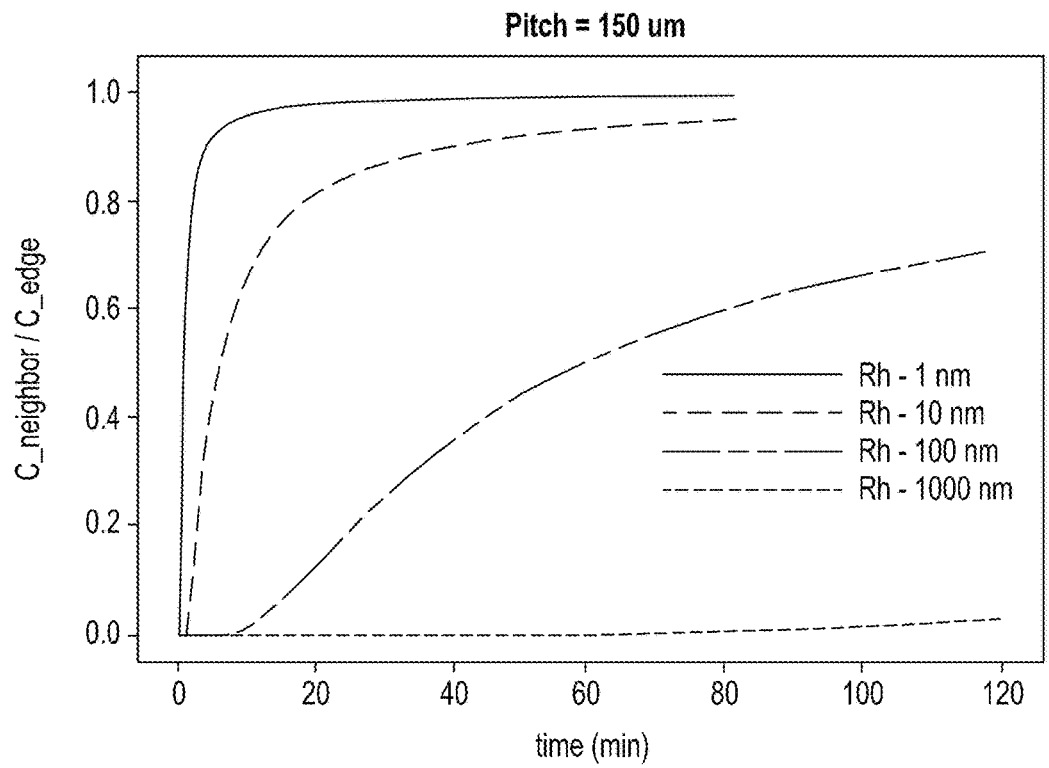
FIGS. 8B-8D are three graphs showing reagent diffusion times calculated for various neighbor-edge distances and different pitches (150 µm, 300 µm and 600 µm) over time (0-120 minutes).
Figure 8C:
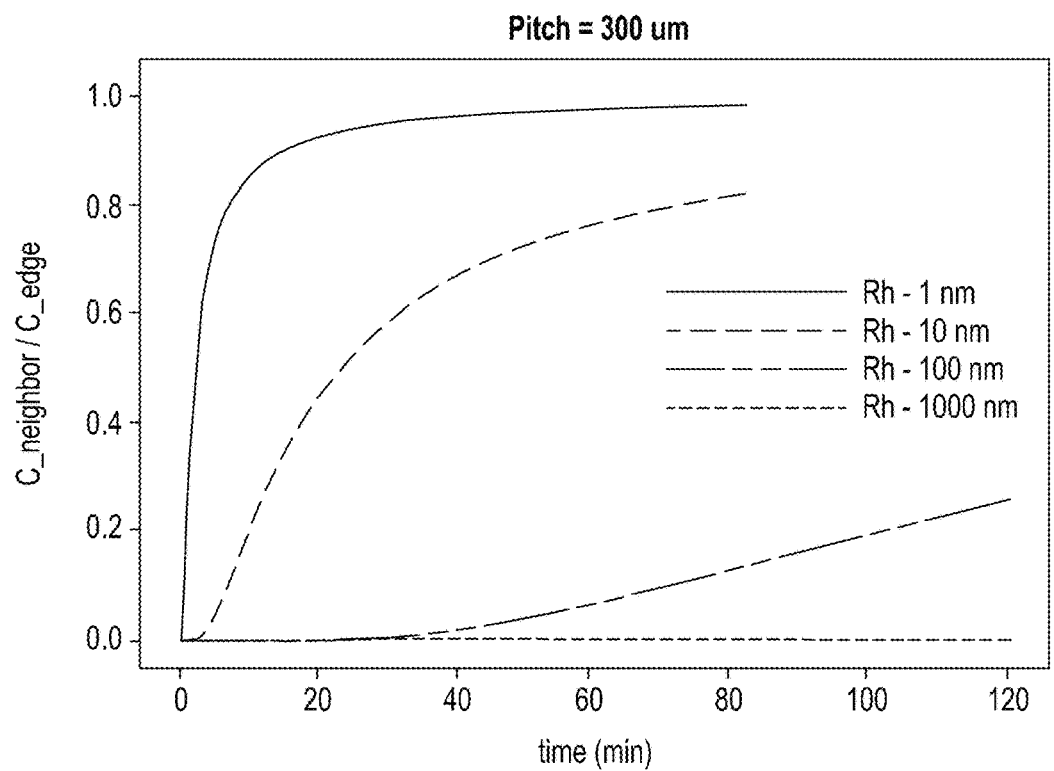
Figure 8D:
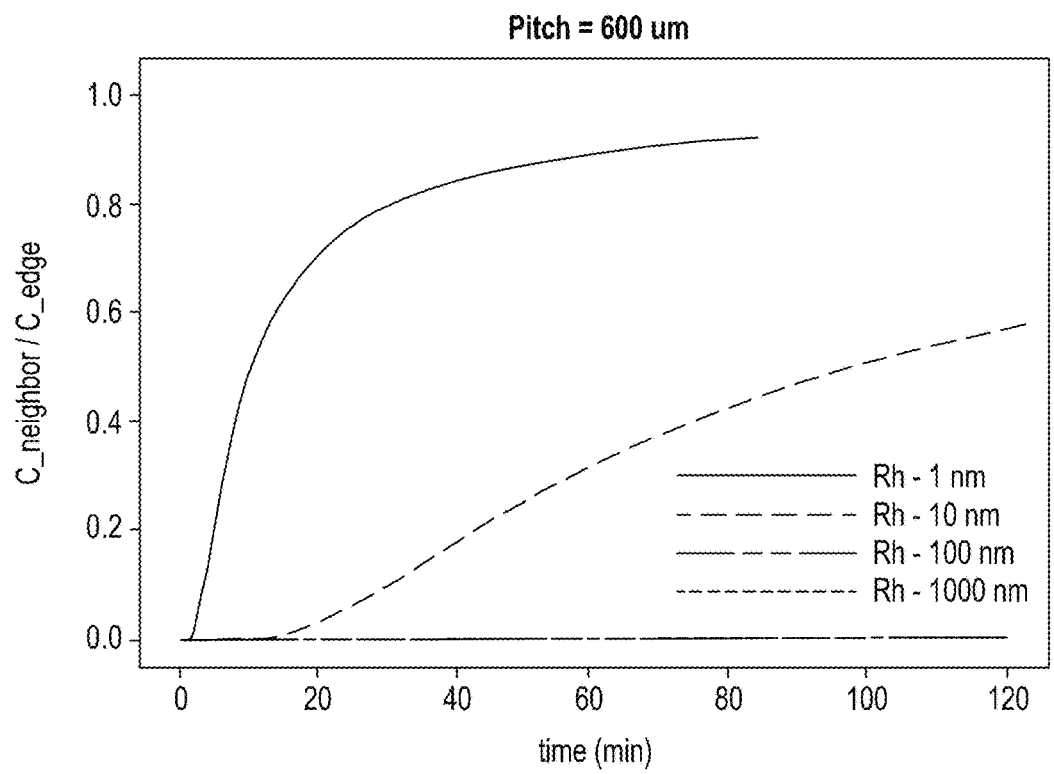

FIG. 8A shows an equation for calculating diffusion for reagents in microwells or for reagent bundles in microcarriers, which can be used to approximate reagent concentrations at on-target or potential off-target locations. FIGS. 8B-8D are three graphs for reagent diffusion at different distances from a source site (150 μm, 300 μm and 600 μm) over time (0-120 minutes) as a function of reagent size.

Figure 9:
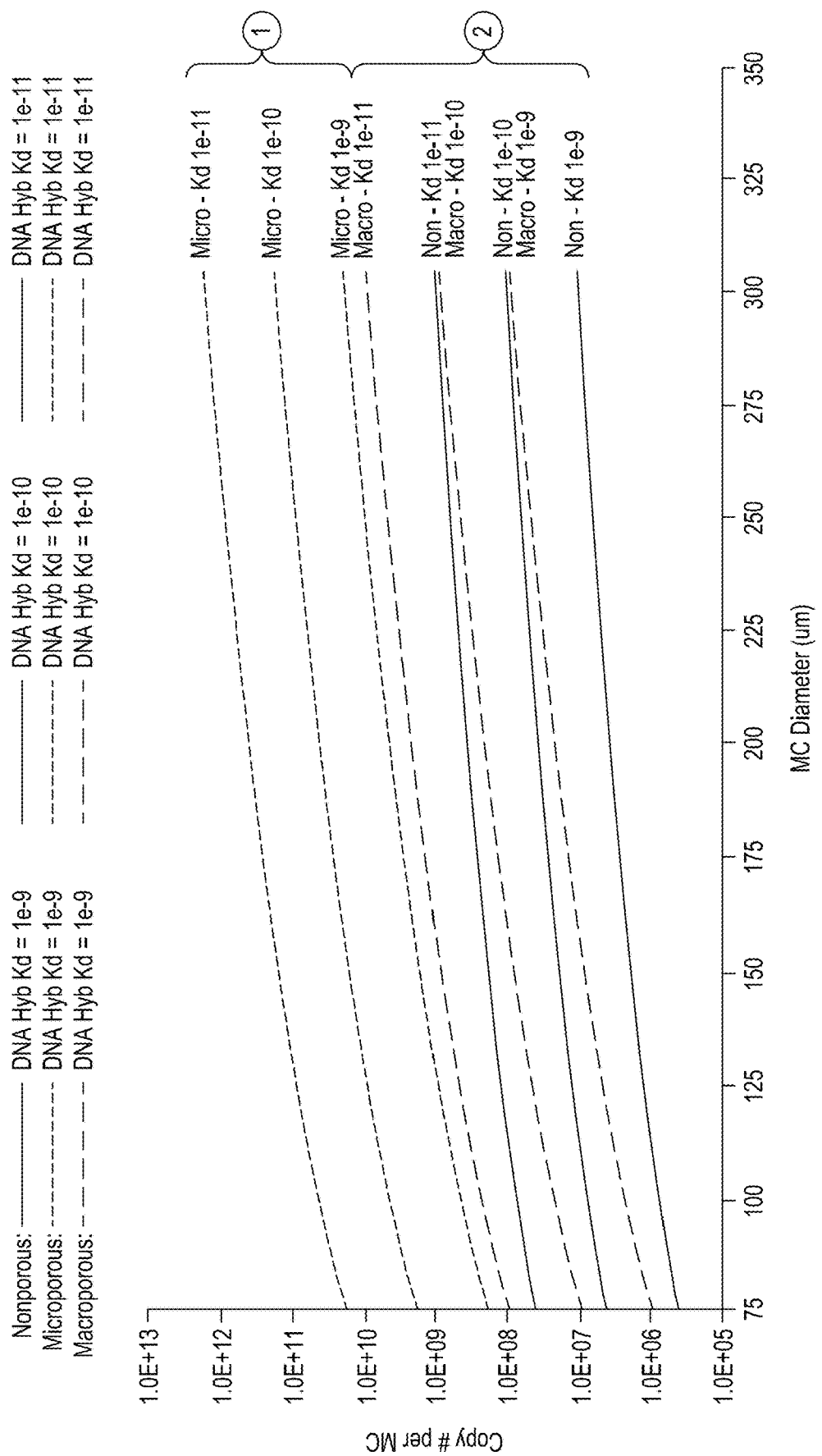
FIG. 9 is a graph plotting the predicted copy numbers of amplified editing cassettes that can be pulled down by reagent bundle microcarriers for varying-sizes and -types of microcarriers.

FIG. 9 is a graph plotting the predicted copy numbers of amplified editing cassettes that can be "pulled down" by the method depicted in FIG. 1C by reagent bundle microcarriers for varying sizes (e.g., diameters ranging from 75-350 μm) and varying types (e.g., non-, micro-, and macroporous) of microcarriers. Assuming a DNA hybridization of Kd=1e-9 to 1e-11, a microporous microcarrier pore size of 100 nm and a macroporous microcarrier pore size of 20 μm, microporous microcarriers can pull down a higher payload copy number of editing cassette amplicons due to higher surface area per diameter microcarrier. Macroporous and nonporous microcarriers have similar payload per copy number for relatively smaller microcarriers, but payload copy number increases more for macroporous microcarriers with increasing size compared to nonporous microcarriers.

Figure 10:
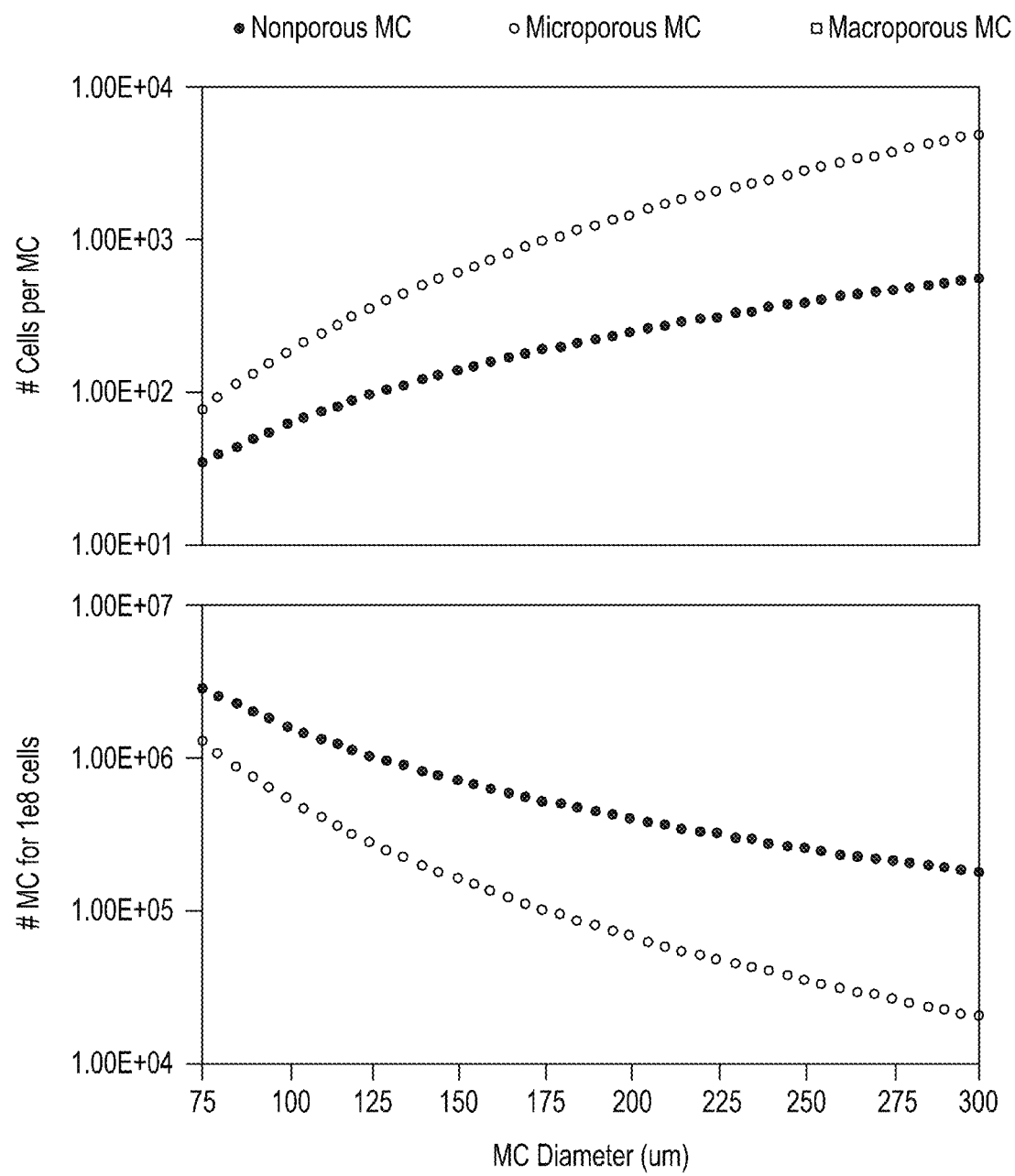
FIG. 10 shows at top a graph plotting the number of cells that may be carried per microcarrier for varying-sizes and -types of microcarriers; and at bottom the number of microcarriers and microcarrier cell diameter needed to carry 1e8 cells.

FIG. 10 shows at top a graph plotting the number of cells that may be carried per microcarrier for varying sizes (e.g., diameters ranging from 75-350 μm) and varying types (e.g., non-, micro-, and macroporous) of microcarriers. Assuming that cells grow only on the surface of nonporous and microporous microcarriers, macroporous microcarriers can grow more cells per microcarrier due to higher surface area (e.g., larger pores, e.g., approximately 20 μm, with pore volume at 60% of total bead volume) for cells to adhere and grow (assuming a cell footprint of approximately 400 μm$^2$ at 75% confluency). Nonporous and microporous microcarriers have the same number of cells carried per microcarrier due to cells growing only on the surface of the microcarrier, as the cells cannot fit into and populate the pores of the microporous microcarriers. FIG. 10 at bottom shows the number of microcarriers and microcarrier cell diameter needed to carry 1e8 cells. To reach 1e8 cells, the number of macroporous microcarriers needed is an order of magnitude less compared to nonporous and microporous microcarriers, and the difference increases with increasing microcarrier size.

Figure 11:
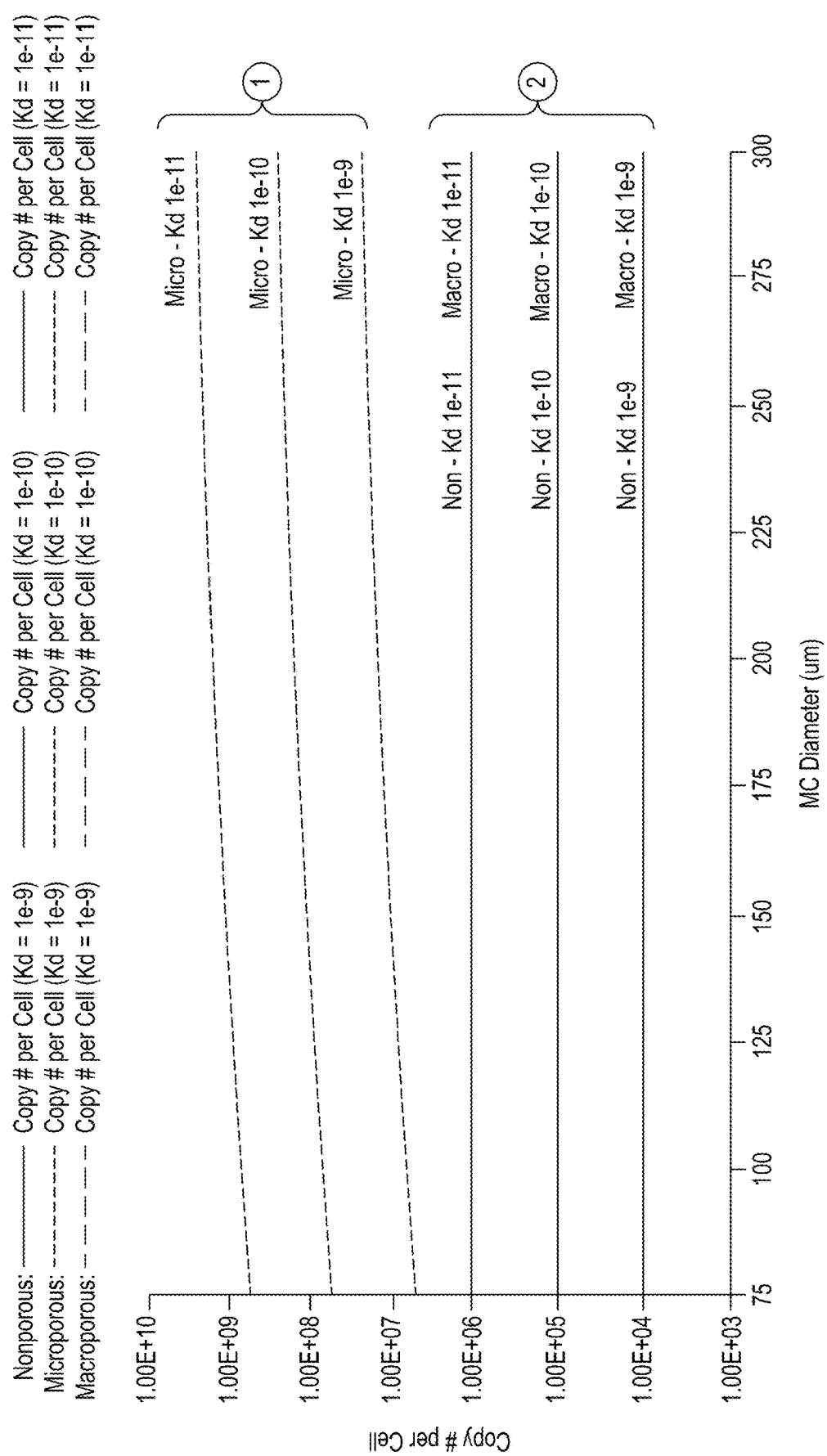
FIG. 11 is a graph plotting the microcarrier diameter and type needed to carry 1e6 copies of editing cassettes per cell per microcarrier.

FIG. 11 is a graph plotting the microcarrier diameter and type needed to carry 1e6 copies of editing cassettes per cell per microcarrier. Microporous RBMCs can reach 1e6 copy numbers of editing cassette amplicons per cell for three DNA hybridization Kds (1e-9 to 1e-11) for pull down demultiplexing (such as shown in FIG. 1C). Macro- and nonporous RBMCs may not reach the desired copy number if the Kd is in the range of 1e-9 to 1e-10. Table 1 shows various RBMC types and surface functionalization options.

TABLE 1

Microcarrier and RBMC Surface Functionalization Options

| Matrix | Examples | Surface Modifications | Coupling Reaction for DNA Barcode | Payload Cleavable Group | Payload Release Chemistry | Biofunctionalization Modifications For Cell Adhesion | Matrix Degradable?* |
|---|---|---|---|---|---|---|---|
| Hydrogel Beads (synthesized in-house) | Synthetic polymer | Polyacrylamide, PAA, PMMA, PEG (acrylate, thiol, maleimide), PHEMA, PNIPAM | Amine (—NH3) Carboxylic (—COOH) Hydroxyl (—OH) Azide (—N3) Alkyne (C≡C) Maleimide Streptavidin Biotin | EDC NHS (amine and carboxyl) Click Rxn: CuACC (azide and alkyne), Michael Addition (thiol and C═C, e.g. acrylate, maleimide) Protein binding (streptavidin and biotin) | Chemical: disulfide (—SS—), nitrobenzyl Biological: biotin/streptavidin, dU, peptide, RNA, | UV light Chemical Trigger: reductant, free biotin Enzyme Trigger: USER, proteinase, RNAse | Cationic groups: lysine, amine Bio-matrix: gelatin, collagen, Matrigel Others: PNIPAM | Yes - cleavable x-linker (e.g. disulfide, peptide, metal ion), cleaved by reductant, enzymes, EDTA |
| | Bio-polymer | Agarose, alginate, chitin, gelatin, collagen | | | | Enzyme digestion | Bio-matrix: gelatin, collagen, Matrigel | Yes - enzyme digestion |

TABLE 1-continued

Microcarrier and RBMC Surface Functionalization Options

| | Matrix | Examples | Surface Modifications | Coupling Reaction for DNA Barcode | Payload Cleavable Group | Payload Release Chemistry | Biofunctionalization Modifications For Cell Adhesion | Matrix Degradable?* |
|---|---|---|---|---|---|---|---|---|
| Commercial Microcarriers | X-linked poly styrene | Solohill Hillex (Pall), Corning Microcarriers (Corning) | DEAE amine | EDC NHS (amine and carboxyl) | Chemical: disulfide (—SS—), nitrobenzyl Biological: biotin/streptavidin, dU, peptide, RNAse | UV light Chemical Trigger: reductant, free biotin Enzyme Trigger: USER, proteinase, RNAse | Cationic groups: DEAE amine Bio-matrix: Collagen, CellBIND, Systemax | No |
| | X-linked Dextran | Cytodex (GE) | DEAE amine | EDC NHS (amine and carboxyl) | Chemical: disulfide (—SS—), nitrobenzyl Biological: biotin/streptavidin, dU, peptide, RNAse | UV light Chemical Trigger: reductant, free biotin Enzyme Trigger: USER, proteinase, RNAse | Cationic groups: DEAE amine Bio-matrix: Collagen, gelatin | No |
| | X-linked Cellulose | Cytopore (GE) | DEAE amine | EDC NHS (amine and carboxyl) | Chemical: disulfide (—SS—), nitrobenzyl Biological: biotin/streptavidin, dU, peptide, RNAse | UV light Chemical Trigger: reductant, free biotin Enzyme Trigger: USER, proteinase, RNAse | Cationic groups: DEAE amine | No |
| | Gelatin/ Collagen ** | Cultisphere (Percell) | Gelatin | | | | Bio-matrix: gelatin | Yes - enzyme digestion |
| Commercial Porous Resin | X-linked Polyacrylamide | Ultralink Resin (Thermo) | Amine (—NH3) NHS-activated carboxy Sulfhydryl (—SH) Azide (—N3) Alkyne Maleimide Streptavidin Lysine Hydrazine (—CONHNH2) Epoxy | EDC NHS (amine and carboxyl) Click Rxn: CuACC (azide and alkyne), Michael Addition (thiol and C=C, e.g. acrylate, maleimide) Protein binding (streptavidin and biotin) Wolff-Kishner rxn (hydrazide and aldehyde —CHO) Expoxy with —SH, —NH2, —OH | Chemical: disulfide (—SS—), nitrobenzyl Biological: biotin/streptavidin, dU, peptide, RNAse | UV light Chemical Trigger: reductant, free biotin Enzyme Trigger: USER, proteinase, RNAse | Cationic groups: lysine, amine Bio-matrix: gelatin, collagen, Matrigel | No |
| | X-linked agarose | Pierce Coupling Resin (Thermo), Sepharose (GE) | Amine (—NH3) NHS-activated carboxy Sulfhydryl (—SH) Azide (—N3) Alkyne Maleimide Streptavidin Lysine Hydrazine | EDC NHS (amine and carboxyl) Click Rxn: CuACC (azide and alkyne), Michael Addition (thiol and C=C, e.g. acrylate, maleimide) Protein | Chemical: disulfide (—SS—), nitrobenzyl Biological: biotin/streptavidin, dU, peptide, RNAse | UV light Chemical Trigger: reductant, free biotin Enzyme Trigger: USER, proteinase, RNAse | Cationic groups: lysine, amine Bio-matrix: gelatin, collagen, Matrigel | No |

TABLE 1-continued

Microcarrier and RBMC Surface Functionalization Options

| Matrix | Examples | Surface Modifications | Coupling Reaction for DNA Barcode | Payload Cleavable Group | Payload Release Chemistry | Biofunctionalization Modifications For Cell Adhesion | Matrix Degradable?** |
|---|---|---|---|---|---|---|---|
| | | (—CONHNH2) | binding (streptavidin and biotin) Wolff-Kishner rxn (hydrazide and aldehyde —CHO) | | | | |

*Payload release chemistry and matrix degradation chemistry must be compatible conditions where cells will be viable; no harsh chemicals, reaction temperatures (4° C. to 40° C.) in OptiMEM to full serum medium
** Macroporous microcarrier Example II: Characterization of RPMCs and iPSC Transfection Efficiency

TABLE 2

| Term | Definition |
|---|---|
| rvMC | Reagent vehicle microcarrier, or RBMC (reagent bundle microcarrier) or LNPsMCs |
| LNP | Lipid nanoparticle. The transfection reagent resulting from the incubation of the nucleic acid payload with the lipofection reagent (LIPOFECTAMINE ™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) Stem Transfection Reagent (ThermoFisher Scientific, Waltham MA). |
| L521 | Laminin 521. The extracellular matrix protein adsorbed to MCs that enables cell adherence. |
| mTeSR | iPSC growth medium (STEMCELL Technologies Canada INC., Vancouver, BC) |
| CloneR | Growth supplement added to mTeSR for the first 24 hr post-seeding to improve seeding efficiency and viability (STEMCELL Technologies Canada INC., Vancouver, BC) |
| TE | Transfection efficiency |

Figure 12:
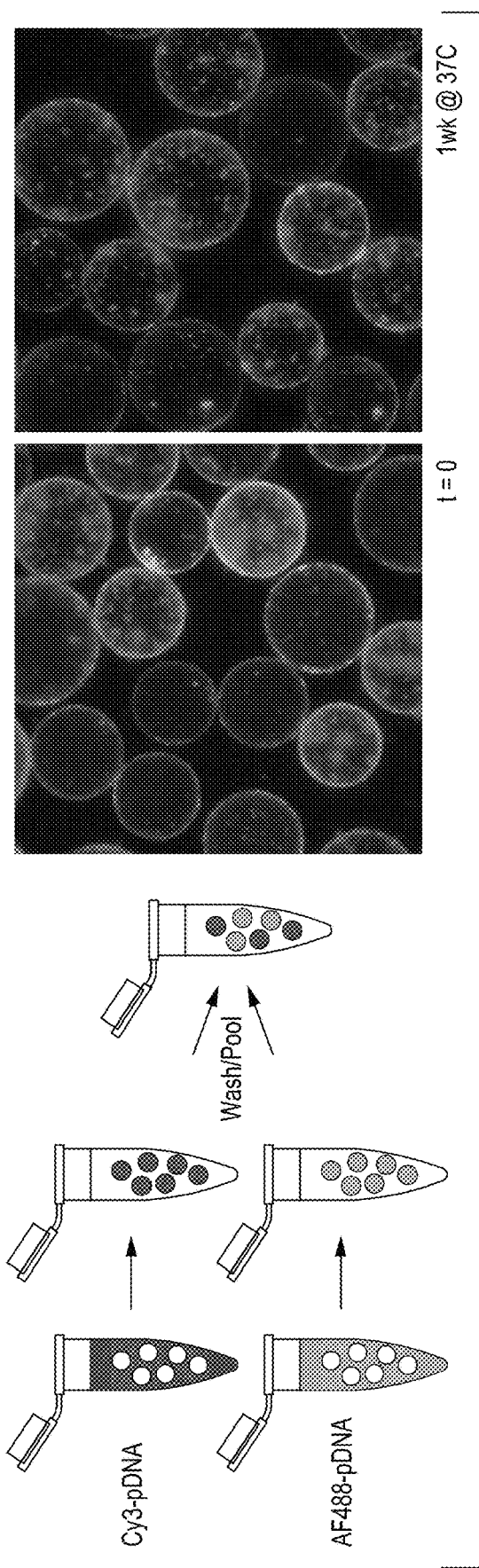
FIG. 12 is a simplified workflow and two photographs of fluorescent cells on microcarriers demonstrating the integrity of nucleic acids loaded on laminin-coated microcarriers when mixed.

Plasmid DNA was labeled with either Cy3 or Alexa Fluor 488 using a Mirus Label IT nucleic acid labeling kit according to the manufacturer's protocol. This labeled payload was used to prepare rvMCs. First, Enhanced Attachment MCs (Corning) were autoclaved. These MCs were then washed with OptiMEM, allowed to settle, and the supernatant was aspirated. Two separate LNPs were formed by mixing a 5% v/v solution of LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) Stem in OptiMEM with a 10 ng/μL solution of the separate DNA payloads in OptiMEM and incubating at room temperature for 10 minutes. After the incubation, a stock of 100 μg/mL L521 was added to the LNP suspension to a final concentration of 10 μg/ml. The MCs were then suspended in this solution and placed in a 37° C. liquid bath. During this incubation, the MCs were suspended every five minutes by gently spinning the tube back and forth. These rvMCs were then washed three times with mTeSR+CloneR and the two batches of rvMCs with unique payloads were pooled together. Finally, the rvMCs were imaged by performing a z-scan with an epifluorescence microscope. The images in FIG. 12 are maximum intensity z-projections of these scans. The green and red puncta are LNPs adsorbed to the rvMC surface. After washing (t=0), the LNP populations are segregated between MCs. After incubating the rvMCs for one week at 37° C., puncta are still visible with minimal cross-contamination.

Figure 13:
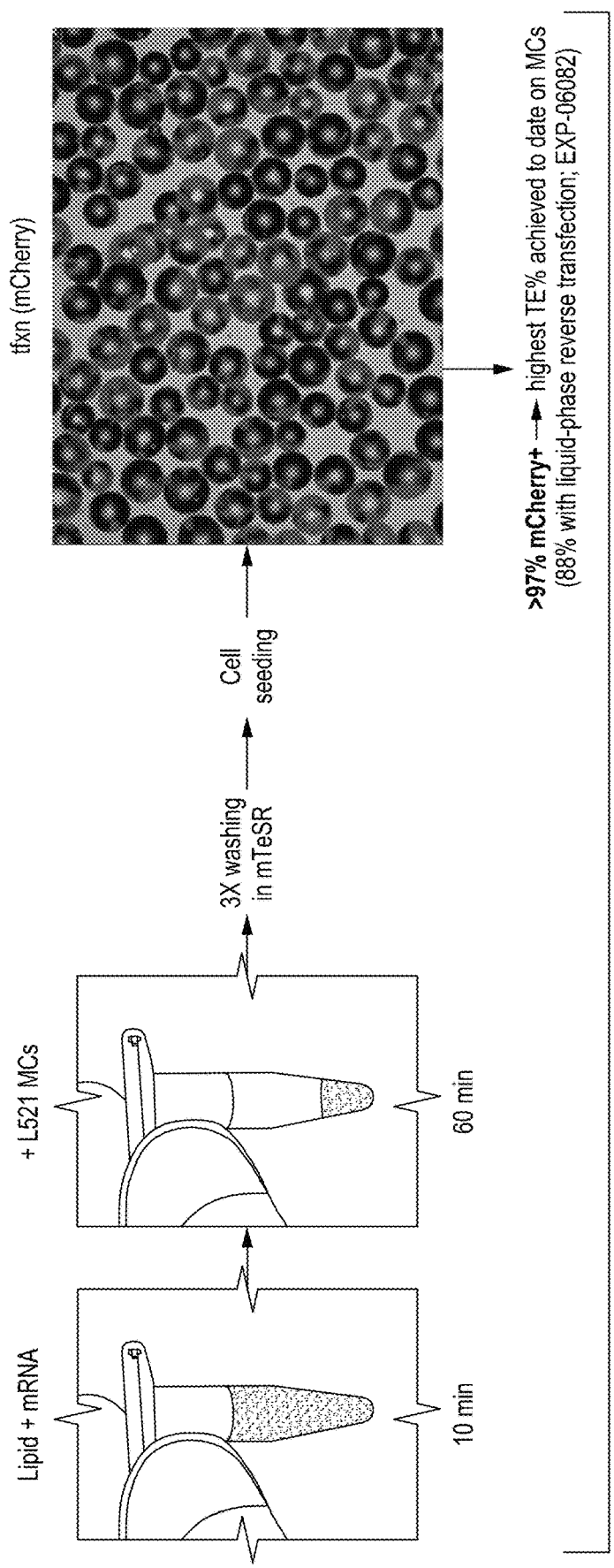
FIG. 13 is a simplified workflow and a photograph of fluorescent cells demonstrating that LNPs absorb onto L521 microcarriers and remain functional for transfection after washing.

For solid phase transfection of cells with mRNA encoding for mCherry, rvMCs were prepared using a two-step assembly protocol. First, MCs were washed with DPBS+calcium+ magnesium and then coated with L521 by incubating in a 10 μg/mL solution of L521 at 37° C. for 1 hour with inversions every 15 minutes. After the incubation, MCs were washed twice with OptiMEM, allowed to settle, and the supernatant was aspirated. LNPs were then assembled with the mCherry mRNA payload as described above. The LNPs form an optically-dense suspension after 10 min (FIG. 13 at left). Then, the L521-coated MCs were suspended with the LNPs and incubated in a 37° C. water bath for 60 minutes. During the incubation, the tube was gently spun every 5 minutes to resuspend the MCs. The supernatant was clear after the rvMCs settled to the bottom of the tube, indicating that the LNPs had attached to and been pulled down with the rvMCs (FIG. 13 middle). The rvMCs were washed three times in mTeSR+CloneR and iPSCs were seeded at 2×105 cells/ml. The cell and rvMC suspension was placed in a non-treated 6-well plate and shaken at 70 RPM in an incubator (37° C., 5% $CO_2$) overnight. Transfected cells expressed mCherry and were visualized on the surface of rvMCs using an epifluorescence microscope (FIG. 13 photograph at right). Cells were then detached from rvMCs and analyzed by flow cytometry, which revealed that the TE using rvMCs was >97%.

Pools consisting of two populations of rvMCs with distinct payloads were prepared using three adsorption protocols (see FIG. 12 and protocol described above in this Example). Instead of plasmid payloads, one population of rvMCs contained mRNA encoding for mCherry and the other contained mRNA encoding for GFP. In one adsorption protocol, MCs washed with OptiMEM were suspended in an LNP suspension prepared as described above. The MCs were incubated at 37° C. in a liquid bath for 1 hour with gentle agitation every 5 minutes. Next, the MCs were washed and resuspended in a 10 μg/ml solution of L521. The MCs were then incubated for an hour at 37° C. for 1 hour with gentle agitation every 5 minutes. Another set of MCs were first incubated with L521 following the protocol above and were then incubated with LNPs in the second incubation. In the final set of MCs, L521 and LNPs were coadsorbed on the surfaces of MCs for 1 hour at 37° C. with gentle agitation every 5 minutes.

After the final incubation, the mCherry mRNA and GFP mRNA samples prepared by the same protocol were pooled together. Cells were seeded on the rvMCs in a non-treated 6-well plate and shaken at 70 RPM in an incubator (37° C., 5% $CO_2$) overnight. Cells were detached from rvMCs and were analyzed by flow cytometry. Cells that had a signal above background for both colors were considered double positive and cells with a signal above background for one of the two colors were counted as single positive. The adsorption protocol used impacted both the total transfection efficiency as well as the fraction of cross contamination (indicated by the fraction of double positive cells). The co-adsorption protocol, for example, had a total transfection efficiency of 93%, which was equivalent to the liquid-phase delivery of LNPs to cells seeded onto a Matrigel-coated plate (see FIG. 14). The number of double positive cells was lower with the solid phase delivery (29% vs. 67% with liquid-phase delivery). By adsorbing L521 first and then adsorbing LNPs, a lower transfection efficiency of 48% was achieved, but the fraction of double positive cells was only 1.7%. Thus, the performance of the rvMC solid phase delivery system is tunable by the adsorption protocol.

Example III: iPSC Editing Efficiency

To evaluate editing on rvMCs, a batch of rvMCs were assembled using the co-adsorption method described above. The payload was a plasmid coding for a CFE guide RNA that converts the GFP gene to a BFP gene. The expression of BFP is used as an indicator of editing in iPSCs that have a lentiviral-integrated GFP gene. Different concentrations of this DNA payload (10-30 ng/μL) were used during the initial LNP complexation before adsorption on MCs. In a separate reaction, CFE mRNA was complexed into LNPs. In this reaction, the concentration of mRNA was 25 ng/μL and the LIPOFECTAMINE™ (a composition of 3:1 DOSPA (2,3-dioleoyloxy-N-[2(sperminecarboxamido)ethyl]-N,N-dimethyl-1-propaniminium trifluoroacetate) to DOPE (1,2-dioleoyl-sn-glycerophosphotheanolamine)) Stem concentration was 5% v/v. At the time of transfection, iPSCs were seeded on rvMCs containing the plasmid payload and were co-transfected with liquid-phase LNPs containing CFE mRNA. In the control sample, cells were seeded on a Matrigel-coated plate in the presence of LNPs containing plasmid and LNPs containing CFE mRNA (see depiction of method in FIG. 6C). With 10 ng/μL of plasmid DNA, the fraction of edited cells (as indicated by the expression of BFP) was equivalent to the fraction observed after a standard reverse co-transfection in a plate (see FIG. 15).

Example IV: Biocompatibility of Bioreactor Materials

The bioreactor disclosed herein is one embodiment of a fully-automated, end-to-end closed instrument that does not require human hands or intervention. Such automated, closed instruments establish and provide consistent results in a workflow and enhance uniformity of processing between "batches" while further maintaining sample integrity. Biocompatibility of bioreactor relevant materials were screened in plate cultures using conditioned media. mTeSR™Plus serum-free, feeder-free cell culture medium (STEMCELL Technologies Canada INC., Vancouver, BC) was incubated with the material of interest (i.e., stainless steel and polycarbonate) for at least 72 hours at 4° C. for conditioning the cell culture media. WTC11 iPSCs were seeded on 6-well plates and conditioned media was used to grow cells in standard incubators at 37° C., 5% $CO_2$ and >95% relative humidity. Control cultures were grown similarly to the tested conditions except the medium was not conditioned with any materials and the medium was kept at 4° C. for 72 hours before the start of cultures.

Cells were seeded on Matrigel coated 6-well plates (CORNING® BIOCOAT™ MATRIGEL® 6-well plates (Corning, Inc., Glendale, Ariz.)) and cultured with their respective conditioned (tested sample) or unconditioned media (control) and CloneR™ (STEMCELL Technologies Canada INC., Vancouver, BC) for the first 24 hours. After the first 24 hours, cell media was exchanged with fresh conditioned (tested sample) or unconditioned media (control) without CloneR, and maintained up to 72 hours where cells reached confluency. Cell counts and viabilities were assessed at 12-hours, 36-hour and 60-hour time points after lifting cells from the Matrigel CORNING® BIOCOAT™ MATRIGEL® 6-well plates (Corning, Inc., Glendale, Ariz.)) plates using RelesR™ reagent (following the manufacturer's instructions) (STEMCELL Technologies Canada INC., Vancouver, BC) and the cells were quantified on a NucleoCounter NC-200 (Chemometec, Allerod, Denmark) automated cell counting instrument following the manufacturer's instructions.

Figure 16A:
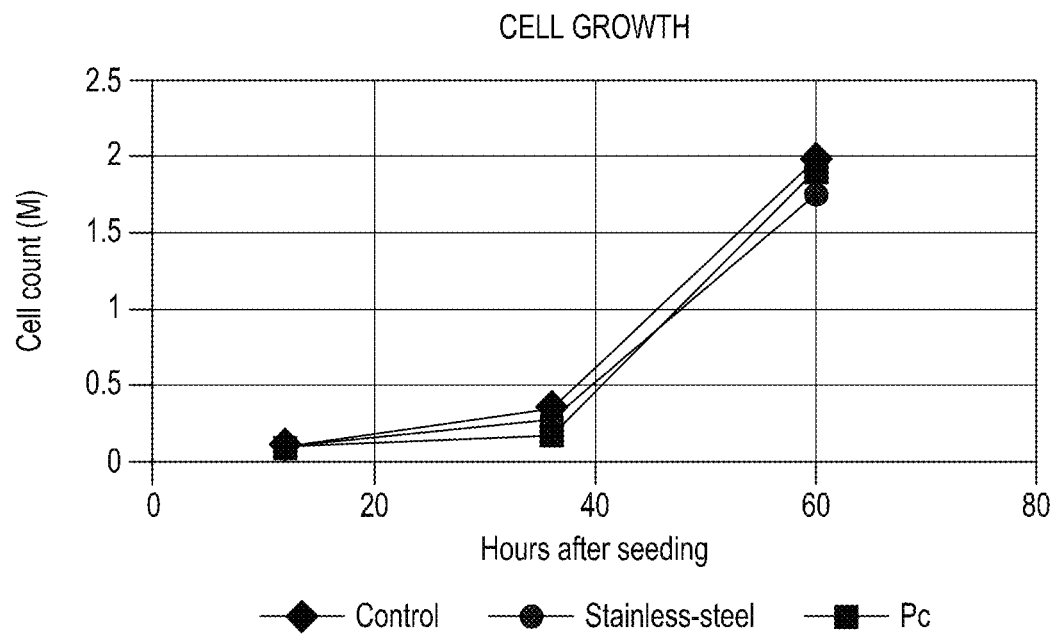
FIGS. 16A and 16B are graphs demonstrating that the materials comprising the components of the bioreactor are biocompatible.
Figure 16B:
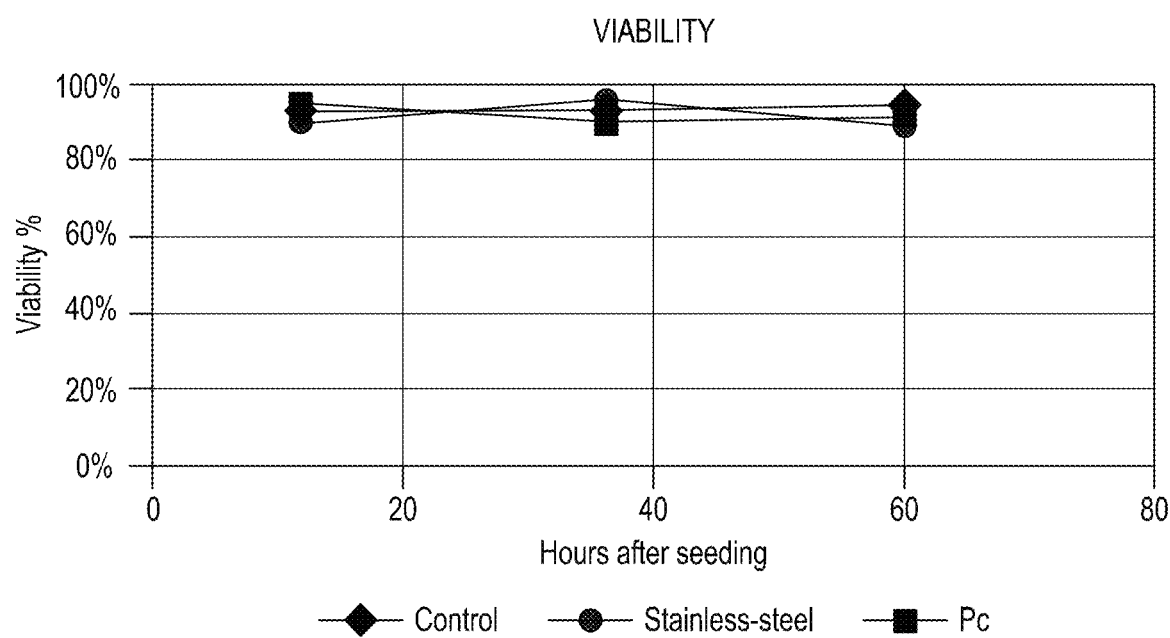

FIGS. 16A and 16B show the results of these experiments. FIGS. 16A and 16B demonstrate neither growth nor viability is impacted by the choice of materials for fabrication of the main body 504 of vessel 501 (polycarbonate), vessel lid assembly 502 (stainless steel), impeller 506 (stainless steel or polycarbonate), or medium exchange frit (stainless steel). All components were sterilized before conditioning.

Example V: Optimal Working Volume

The bioreactor described herein was tested for optimal working volume. For sensor operation, minimum optimal volume was set to 100 ml with sensor clearance at 10 mm from the bottom of the main body of the vessel. 10 million WTC11 iPSCs were seeded on 0.5 g of 10m/ml laminin L-521 coated Enhanced Attachment microcarriers (Corning, Inc., Glendale, Ariz.) in 40 ml and 100 ml mTeSR™Plus serum-free, feeder-free cell culture medium (STEMCELL Technologies Canada INC., Vancouver, BC) and CloneR (STEMCELL Technologies Canada INC., Vancouver, BC in CORNING® spinner flasks (Corning, Inc., Glendale, Ariz.). Impeller agitation was set to 70 rpm using a CHIMAREC™ direct stirrer (ThermoFisher Scientific, Waltham Mass.). A first media exchange was performed at 24 hours, and then at every 48th hour with fresh mTeSR™Plus serum-free, feeder-free cell culture medium (STEMCELL Technologies Canada INC., Vancouver, BC) (no CloneR). The cells attached to the microcarriers were quantified at 12-hour and 36-hour time points on a NucleoCounter NC-200 (Chemometec, Allerod, Denmark) automated cell counting instrument following the manufacturer's instructions. Cell counts indicated similar cell seeding efficiencies at 40 ml and 100 ml seeding volumes (data not shown).

Example VI: Assessing Growth in Bioreactor to Traditional Plating and Spinner Flask Culture Experiments were performed to assess whether cell growth in the INSCRIPTA™ bioreactor described herein is equivalent to traditional plate and spinner flask culture conditions. Ten million WTC11 iPSCs were seeded on 0.5 g of 10 µg/ml laminin L-521 coated Enhanced Attachment microcarriers (Corning, Inc., Glendale Ariz.) in 100 ml mTeSR™Plus serum-free, feeder-free cell culture medium (STEMCELL Technologies Canada INC., Vancouver, BC) and CloneR (STEMCELL Technologies Canada INC., Vancouver, BC) in the INSCRIPTA™ bioreactor and in CORNING® spinner flasks (Corning, Inc., Glendale, Ariz.). Impeller agitation was performed at 70 rpm for both the INSCRIPTA™ bioreactor and CORNING® spinners. A control culture was also seeded on Matrigel coated 6-well plates (CORNING® BIOCOAT™ MATRIGEL® 6-well plates (Corning, Inc., Glendale, Ariz.)) using 500 k cells per one well. The cells were maintained at 37° C., 5% $CO_2$ and >95% relative humidity throughout the culture period. The first media exchange was performed at 24 hours, and then at every 48th hour with fresh mTeSR™Plus serum-free, feeder-free cell culture medium (STEMCELL Technologies Canada INC., Vancouver, BC) (no CloneR) using 100 ml for microcarrier cultures and 2 ml per well for 6-well plates. Cell counts were quantified at 12-hour, 36-hour and 60-hour time points on a NucleoCounter NC-200 (Chemometec, Allerod, Denmark) automated cell counting instrument following the manufacturer's instructions.

Figure 17:
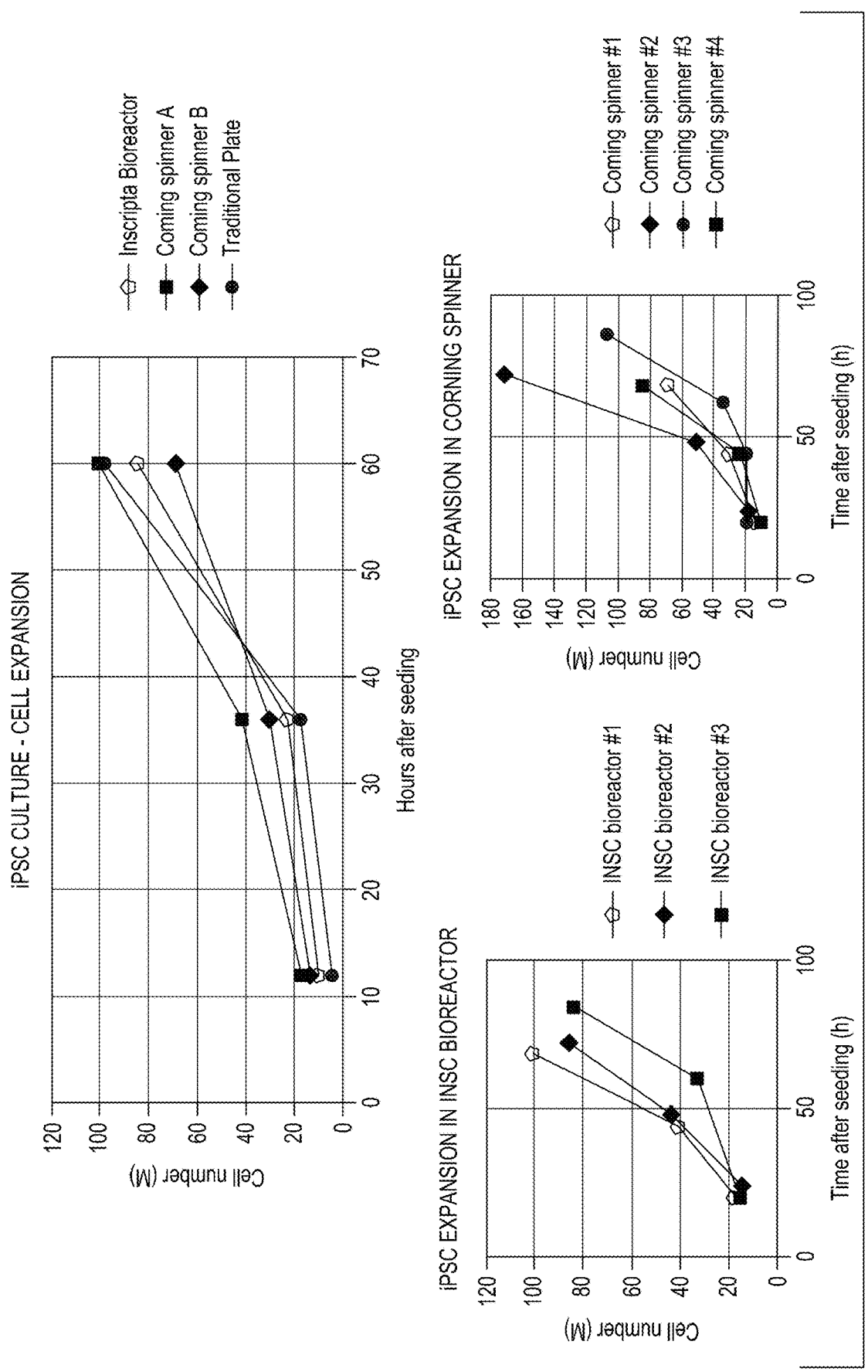
FIG. 17 comprises three graphs demonstrating that iPSC culture and cell expansion in the bioreactor described herein is comparable to cell culture and expansion in a CORNING® spinner flask and in a traditional cell culture plate.

The results are shown in FIG. 17. The graph at top shows similar numbers of iPSC cells at 10, 20, 30, 40, 50, 60, and 70 hours after seeding. The graph at bottom right shows similar results were obtained for iPSC cell expansion in three different INSCRIPTA™ bioreactors. The graph at bottom left shows the results obtained for iPSC cell expansion in four different CORNING® spinner flasks. Growth curves plotted using these cell counts indicated similar cell growth curves under the conditions tested. The 6-well plate control counts were scaled assuming an initial cell seeding number of 10 million cells for comparison. Additional INSCRIPTA™ bioreactors and CORNING® spinner flasks were seeded on different days using the same methods to compare cell growth curve variations and showed similar variation across INSCRIPTA™ bioreactors and CORNING® spinners.

Example VII: Effect of Medium Exchange

Figure 18:
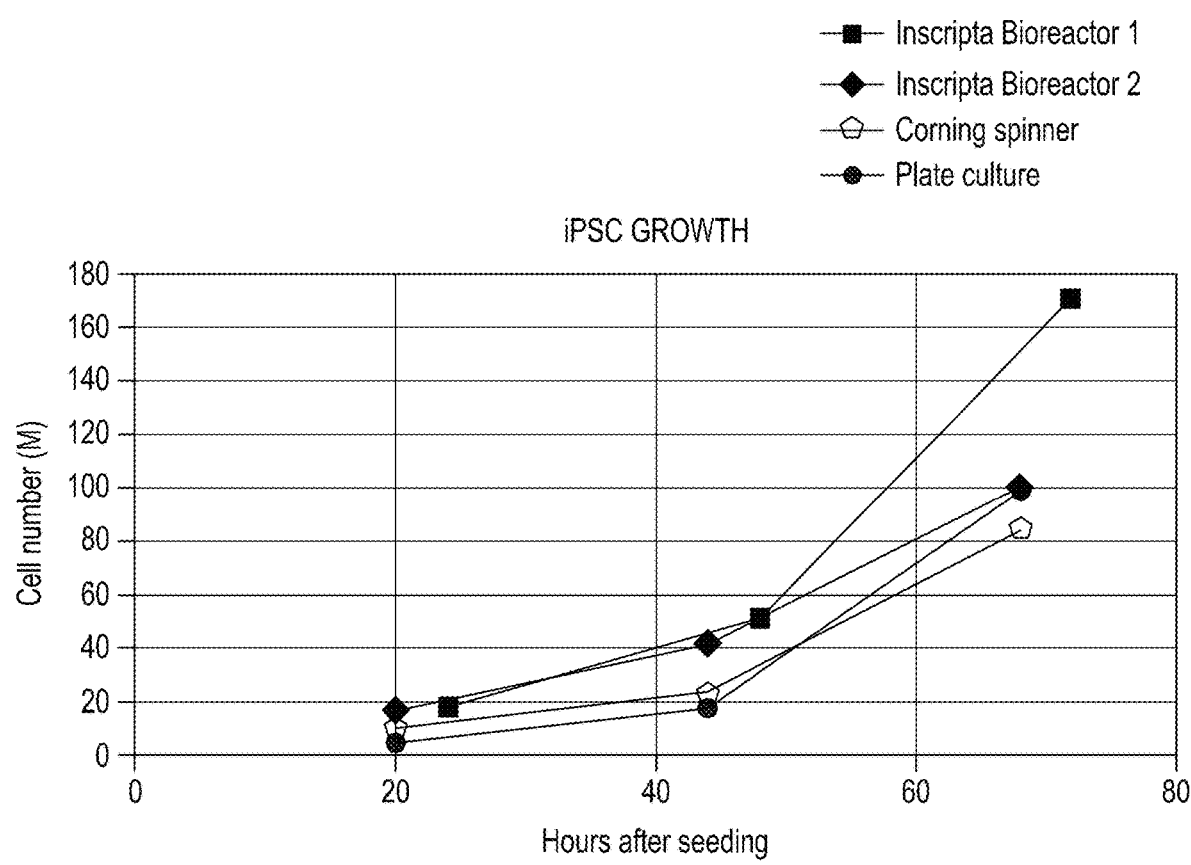
FIG. 18 is a graph demonstrating that media exchange at ~200 ml/minute does not impact cell growth.

Ten million WTC11 iPSCs were seeded on 0.5 g of 10 µg/ml laminin L-521 coated Enhanced Attachment microcarriers (Corning, Inc., Glendale, Ariz.) in 100 ml mTeSR-™Plus serum-free, feeder-free cell culture medium (STEMCELL Technologies Canada INC., Vancouver, BC) and CloneR (STEMCELL Technologies Canada INC., Vancouver, BC) in INSCRIPTA™ bioreactors and CORNING® spinner flasks. Impeller agitation was performed at 70 rpm for both the INSCRIPTA™ bioreactors and the CORNING® spinners. A 6-well plate control culture was also seeded on CORNING® BIOCOAT™ MATRIGEL® 6-well plates (Corning, Inc., Glendale, Ariz.) was also seeded using 500 k cells per one well. The cells were maintained at 37° C., 5% $CO_2$ and >95% relative humidity throughout the culture period. A first media exchange was performed at 24 hours, and then at every 48th hour with fresh mTeSR™Plus serum-free, feeder-free cell culture medium (STEMCELL Technologies Canada INC., Vancouver, BC) (no CloneR) using 100 ml for microcarrier cultures and 2 ml per well for 6-well plates. Media exchanges on the INSCRIPTA™ bioreactors were performed using a frit system as follows: Impeller agitation was stopped and the microcarriers were allowed to settle gravitationally for 5 minutes. After settling, >90% of the spent media was aspirated from the INSCRIPTA™ bioreactor through a frit connected to a peristaltic pump operating at 200 ml/min flow rate. The frit consisted of ~100 micron pores while the microcarriers ranged from 120-225 micron in diameter. As such, microcarriers were retained in the bioreactor but spent media and dead cells were aspirated out of the bioreactor vessel. As a comparison, media exchange in CORNING® spinner flasks and 6-well plates were performed using a serological pipette connected to an aspirator (BVC Professional Aspiration System (Vacuubrand, Essex Conn.)). In all conditions, fresh media was added manually using a serological pipette. Cell counts were quantified at 20-hour, 44-hour and 68-hour time points on a NucleoCounter NC-200 (Chemometec, Allerod, Denmark) automated cell counting instrument following the manufacturer's instructions. The results are shown in FIG. 18. Growth curves plotted using these cell counts indicated that the media exchange approach through a frit does not have any noticeable impact on cell growth. The 6-well plate control counts were scaled assuming an initial cell seeding number of 10 million cells for comparison. During the process there was no accumulation of microcarriers on the frit in the liquid-out port.

Example VIII: Effect of Impeller Shear on Cell Viability and Reproducibility

Cell detachment from microcarriers may be achieved using an impeller agitation-based approach as follows: 10M cells were seeded on 0.5 g of 10 µg/ml laminin L-521 coated microcarriers (Corning, Inc., Glendale Ariz.), and expanded in the INSCRIPTA™ bioreactor at 100 ml mTeSR™Plus serum-free, feeder-free cell culture medium (STEMCELL Technologies Canada INC., Vancouver, BC) at 37° C., 5% $CO_2$, and >95% relative humidity as described above. Once the cells reached >50 million cells as determined by cell counting, the microcarriers were allowed to settle gravitationally for 5 minutes, and >90% of the spent media was aspirated. 100 ml phosphate buffered saline (PBS) was added to microcarriers for washing and aspirated after 5 minutes. 100 ml RelesR (STEMCELL Technologies Canada INC., Vancouver, BC) was added to the microcarriers and incubated at 37° C. for 6 minutes. After 6 minutes, >90% of the RelesR (STEMCELL Technologies Canada INC., Vancouver, BC) was aspirated and 100 ml of cell media was added to the microcarriers to quench any RelesR.

At this stage, impeller agitation was performed by rotating the impeller at 2700 rpm in the clockwise direction for 15 seconds first, and then at 2700 rpm in the counter-clockwise direction for 15 seconds. This bi-directional agitation for a total of 30 seconds duration was defined as "one round" or "one cycle". Up to five rounds/cycles of impeller agitation was tested in terms of cell detachment efficiency. After detachment, the cell and microcarrier suspension was transferred to a conical vessel. Cells and microcarriers were separated using gravitational settling where the microcarriers settle faster than the cells due to their larger diameter. In another approach, the cell and microcarrier suspension was passed through a strainer with 100 micron mesh size (e.g., CORNING® Sterile Cell strainer-100 micron, Corning, Inc., Glendale Ariz.) to separate the cells from the microcarriers. As control, a 1 ml aliquot of microcarrier culture was detached using a P1000 pipette (PIPETMAN®) by passing the microcarriers through the pipette 5 times. After detachment, post detachment viability and the number of detached cells were quantified for assessing detachment efficiency.

Figure 19:
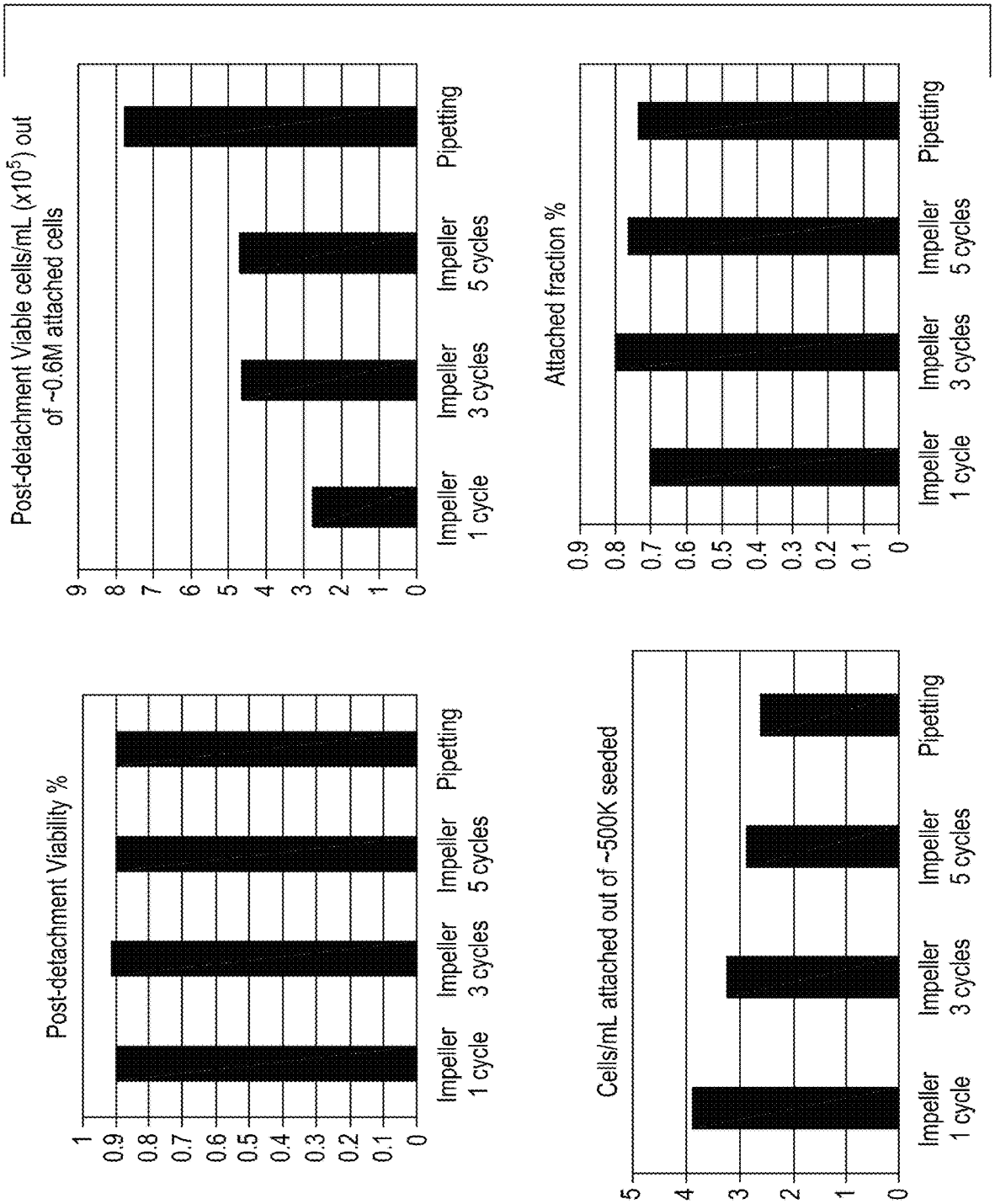
FIG. 19 is a series of four graphs demonstrating that up to five rounds of impeller shear is tolerated by iPSCs with no negative effects on re-seeding.
Figure 21:
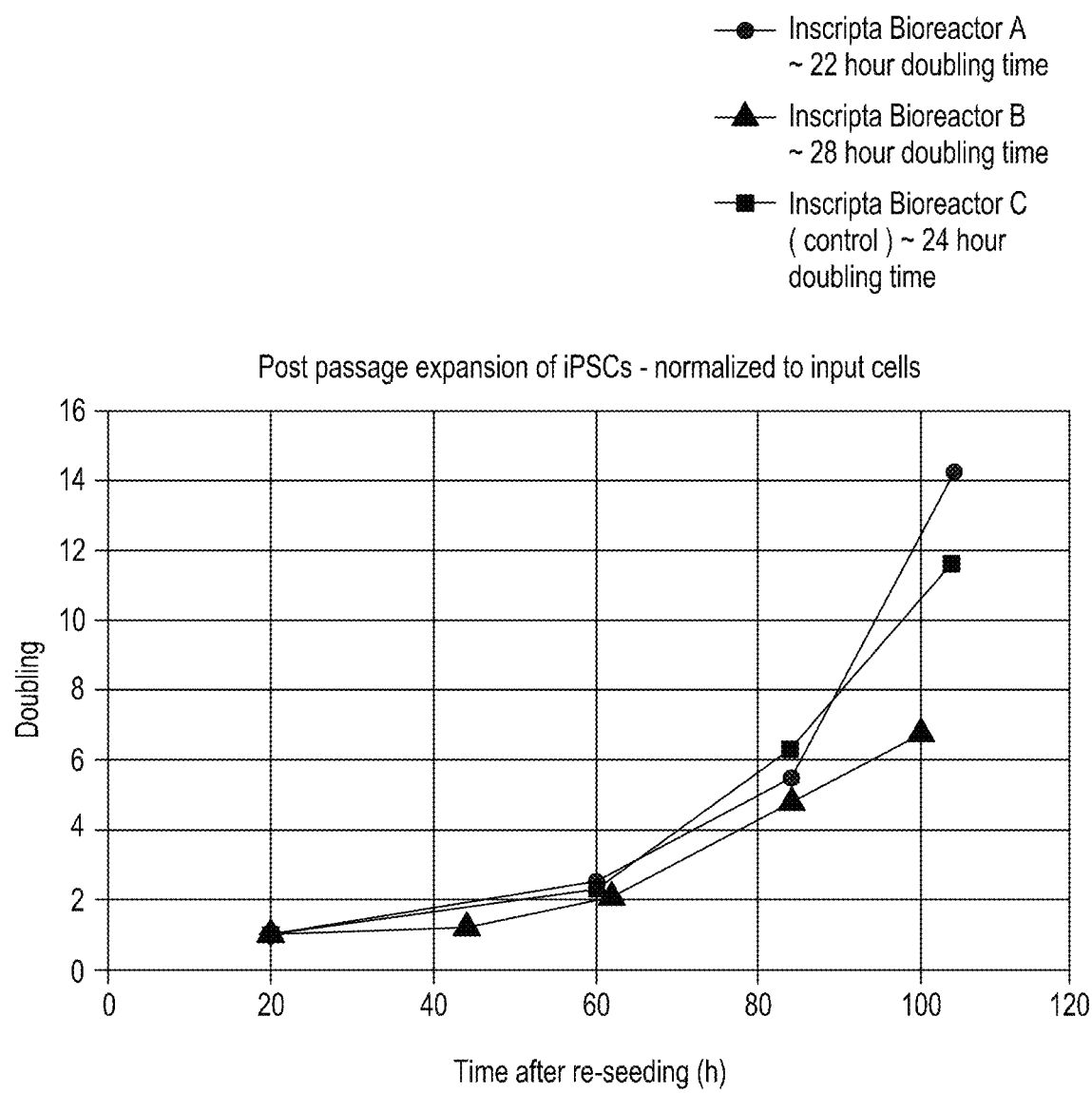

The results are shown in FIG. 19. The graph at top left of FIG. 19 shows the percent post-detachment of the cells. The graph at top right in FIG. 19 shows the number of viable cells/ml (×10$^5$) out of ~0.6M attached cells. The graph at bottom left in FIG. 19 shows the number of cells/ml attached out of ~500K seeded. Finally, the graph at bottom right in FIG. 19 shows the attached fraction of cells after each cycle. Note that viability remained around 90% after all of the first, third and fifth cycles. The cells were effectively detached from the microcarriers using the impeller agitation approach and showed >90% post-detachment viability after up to five rounds of impeller agitation, which was similar to the control. The re-seeding efficiency of cells detached with impeller agitation were also similar to the control case where >70% of the detached cells were able to re-seed.

Reproducibility of impeller agitation-based passaging was tested. Ten million cells were seeded on 0.5 g of 10 µg/ml laminin L-521 coated microcarriers (Corning, Inc., Glendale Ariz.), and expanded in the INSCRIPTA™ bioreactor in 100 ml mTeSR™Plus serum-free, feeder-free cell culture medium (STEMCELL Technologies Canada INC., Vancouver, BC) at 37° C., 5% $CO_2$, and >95% relative humidity as described above. Once the cells reached >50 million cells as determined by cell counting, the microcarriers were allowed to settle gravitationally for 5 minutes and >90% spent media was aspirated. 100 ml phosphate buffered saline (PBS) was added to the microcarriers for washing and was aspirated after 5 minutes. 100 ml ReleSR (STEMCELL Technologies Canada INC., Vancouver, BC) were added to the microcarriers and incubated at 37° C. for 6 minutes. After 6 minutes, >90% of the ReleSR was aspirated and 100 ml of cell media was added to the microcarriers to quench any ReleSR. At this stage impeller agitation was performed by rotating the impeller at 2700 rpm in clockwise direction for 15 seconds first, and then at 2700 rpm in counter-clockwise direction for 15 seconds. This bi-directional agitation for a total of 30 seconds duration was defined as "one round" or "one cycle". Three rounds/cycles of impeller agitation was used to detach the cells from microcarriers. After detachment, the cell and microcarrier suspension was transferred to a conical vessel. The cells and the microcarriers were separated using gravitational settling where the microcarriers settle faster than cells due to their larger diameter. Detached cells were re-seeded on fresh microcarriers at 10 million cells per 0.5 g of CORNING® laminin coated microcarriers (Corning, Inc., Glendale, Ariz.), and re-seeding efficiencies were determined based on cell counts at 24 hours after seeding. Passaging and re-seeding efficiencies are quantified and shown in the FIG. 20. FIG. 20 at top shows a simplified workflow for this process, as well as a table showing the efficiency of each step (middle), and at bottom a bar graph of passaging statistics for the indicated steps. The results indicate that impeller-based passaging is reproducible and allows for re-seeding of 30-65% of cells that were on the microcarriers prior to detachment.

Example IX: Cell Re-Seeding and Expansion after Impeller Passaging

Figure 21:
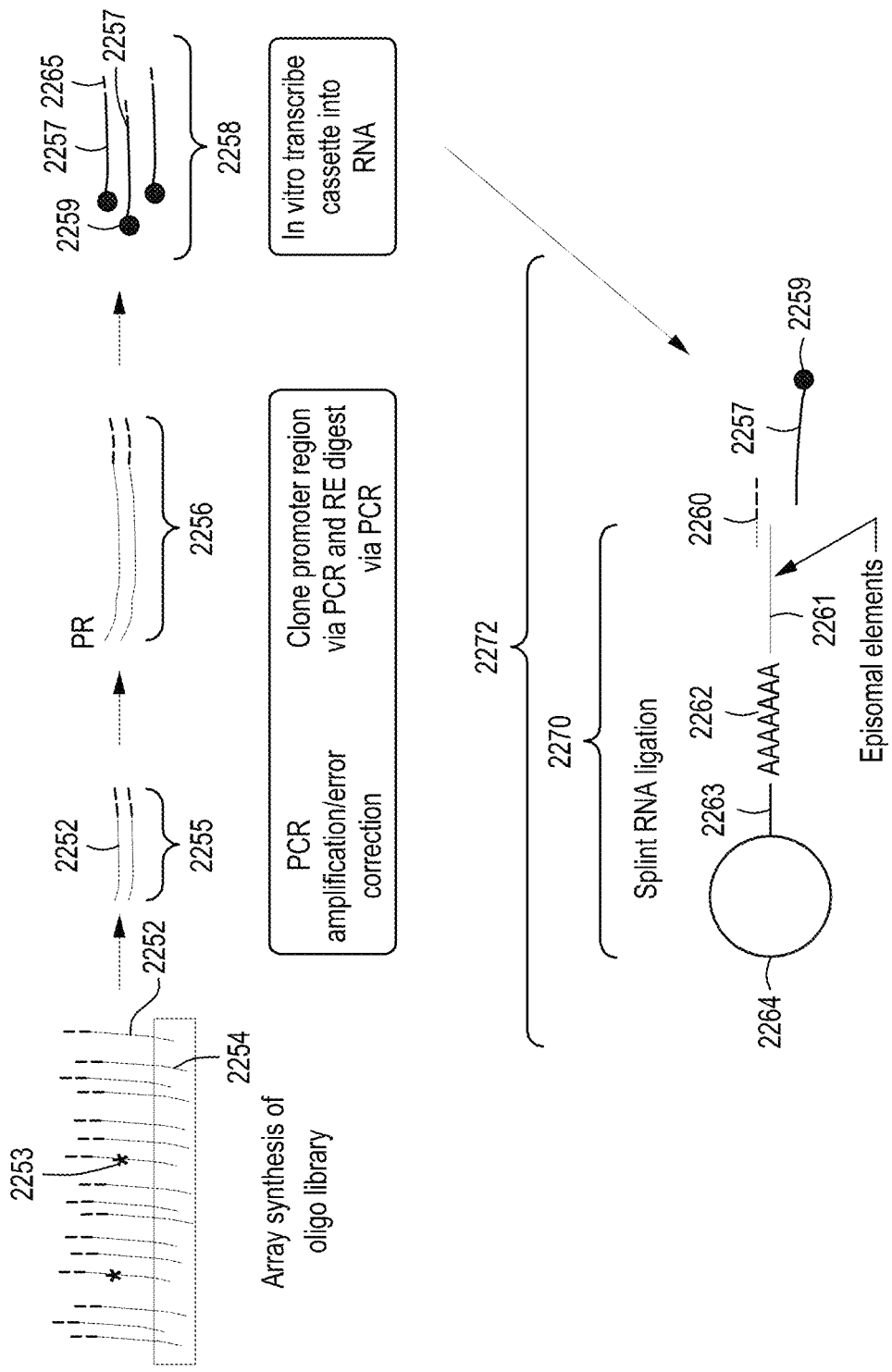
FIG. 21 is a graph showing that cell seeding and expansion are both unaffected by the impeller-shear based passaging protocol.

Cell seeding and expansion after impeller passaging was tested. Ten million WTC11 cells were seeded on 0.5 g of 10 µg/ml laminin L-521 coated microcarriers (Corning, Inc., Glendale, Ariz.), and expanded in the INSCRIPTA™ bioreactor in 100 ml mTeSR™Plus serum-free, feeder-free cell culture medium (STEMCELL Technologies Canada INC., Vancouver, BC) at 37° C., 5% $CO_2$, and >95% relative humidity as described above. Once the cells reached >50 million cells as determined by cell counting, the impeller passaging protocol was implemented as described above. After detachment, 10M detached cells were re-seeded on 0.5 g of fresh laminin coated microcarriers (Corning, Inc., Glendale, Ariz.) and expanded as described above. As a control, an INSCRIPTA™ bioreactor was seeded with cells detached from T75 flasks detached using standard protocols. Cell counts were quantified at 20-hour, 44-hour and 68-hour time points on a NucleoCounter NC-200 (Chemometec, Allerod, Denmark) automated cell counting instrument following the manufacturer's instructions. The results are shown in FIG. 21. FIG. 21 is a graph of triplicate results demonstrating that cell seeding and expansion are unaffected by impeller-shear passaging.

Example X: Ability of Cells to Maintain Stemness

The ability of the iPSCs to retain stemness during culture and passaging was tested. Ten million cells were seeded on 0.5 g of 10m/ml laminin L-521 coated microcarriers (Corning, Inc., Glendale, Ariz.), and expanded in an INSCRIPTA™ bioreactor in mTeSR™Plus serum-free, feeder-free cell culture medium (STEMCELL Technologies Canada INC., Vancouver, BC) at 37° C., 5% $CO_2$, and >95% relative humidity as described above. Once the cells reached >50 million cells as determined by cell counting, the impeller passaging protocol was implemented and 10M detached cells were re-seeded onto fresh 0.5 g laminin coated microcarriers (Corning, Inc., Glendale, Ariz.). This process was repeated two more times and the cells were stained after final detachment using antibodies (BIOLEGEND®, San Diego, Calif.) specific to three stemness expression markers (TRA-1-60, OCT-3/4 and SOX-2) following the manufacturer's instructions, followed by analysis using flow cytometry (BD FACSMelody™) (Becton Dickinson, Inc., Franklin Lakes, N.J.). Cells grown and impeller passaged on the INSCRIPTA™ bioreactors showed expression of stemness markers similar to the cells grown on Matrigel (CORNING® BIOCOAT™ MATRIGEL® 6-well plates (Corning, Inc., Glendale, Ariz.)) and laminin coated plates (CORNING® BIOCOAT™ laminin plates (Corning, Inc., Glendale, Ariz.)).

Stemness antibody staining was performed in the following manner, with the equipment and materials listed in Table 3:

TABLE 3

Foxp3/Transcription Factor Fixation/Permeabilization Concentrate and Diluent, ThermoFisher Scientific, cat. # 00-5521-00
eBioscience ™ Flow Cytometry Staining Buffer, ThermoFisher Scientific, cat. # 00-4222-26
Anti-SOX2 (Brilliant Violet 421): Biolegend, cat. # 656114
Anti-OCT3/4 (Alexa488): Biolegend, cat. # 653706
Anti-TRA-1-60 (PE-Cy7): Biolegend, cat. # 330620
Anti-CD44 (PE-Cy5): ThermoFisher Scientific, cat. # 15-0441-82
Anti-CD13 (PE-Cy7): Biolegend, cat. # 301712
Anti-NESTIN (Alexa488): Biolegend, cat. # 656812
Anti-SSEA4 (V450): BD Biosciences, cat. # 561156
FACSMelody ™ flow cytometer (Becton Dickinson, Inc., Franklin Lakes, NJ)

In a first step, a single-cell suspension was prepared and centrifuged 5 minutes at 200×g. The cells were then washed in an appropriate volume of DPBS and centrifuged again for 5 minutes at 200×g. The supernatant was discarded and the pellet was vortexed to dissociate the pellet. Fresh Foxp3 fixation/permeabilization working solution (ThermoFisher Scientific, Waltham Mass.) was prepared by mixing one part Foxp3 fixation/permeabilization concentrate with three parts Foxp3 fixation/permeabilization diluent and 1 ml was added to each tube and each tube was then vortexed. The vortexed cells and fixation/permeabilization working solution were incubated for 30-60 minutes in the dark at room temperature. A 1× working solution of permeabilization buffer was prepared by mixing one part 10× permeabilization buffer with nine parts dH$_2$O and 2 ml was added to each sample. The cells were centrifuged at 400-600×g for 5 minutes at room temperature and the supernatant was discarded. The cell pellet was resuspended in 1× permeabilization buffer for a total volume of approximately 100 μl. The cells were diluted so that there were no more than 10,000 cells/μl, and 1M cells were transferred to a fresh tube. The appropriate amount of directly-conjugated antibody was dispensed into each tube. The cells were incubated for >30 minutes in the dark at room temperature. Two ml of 1× permeabilization buffer was added to each tube and the samples were centrifuged at 400-600×g for 5 minutes at room temperature and the supernatant was discarded. The stained cells were suspended in flow cytometry staining buffer.

Figure 22:
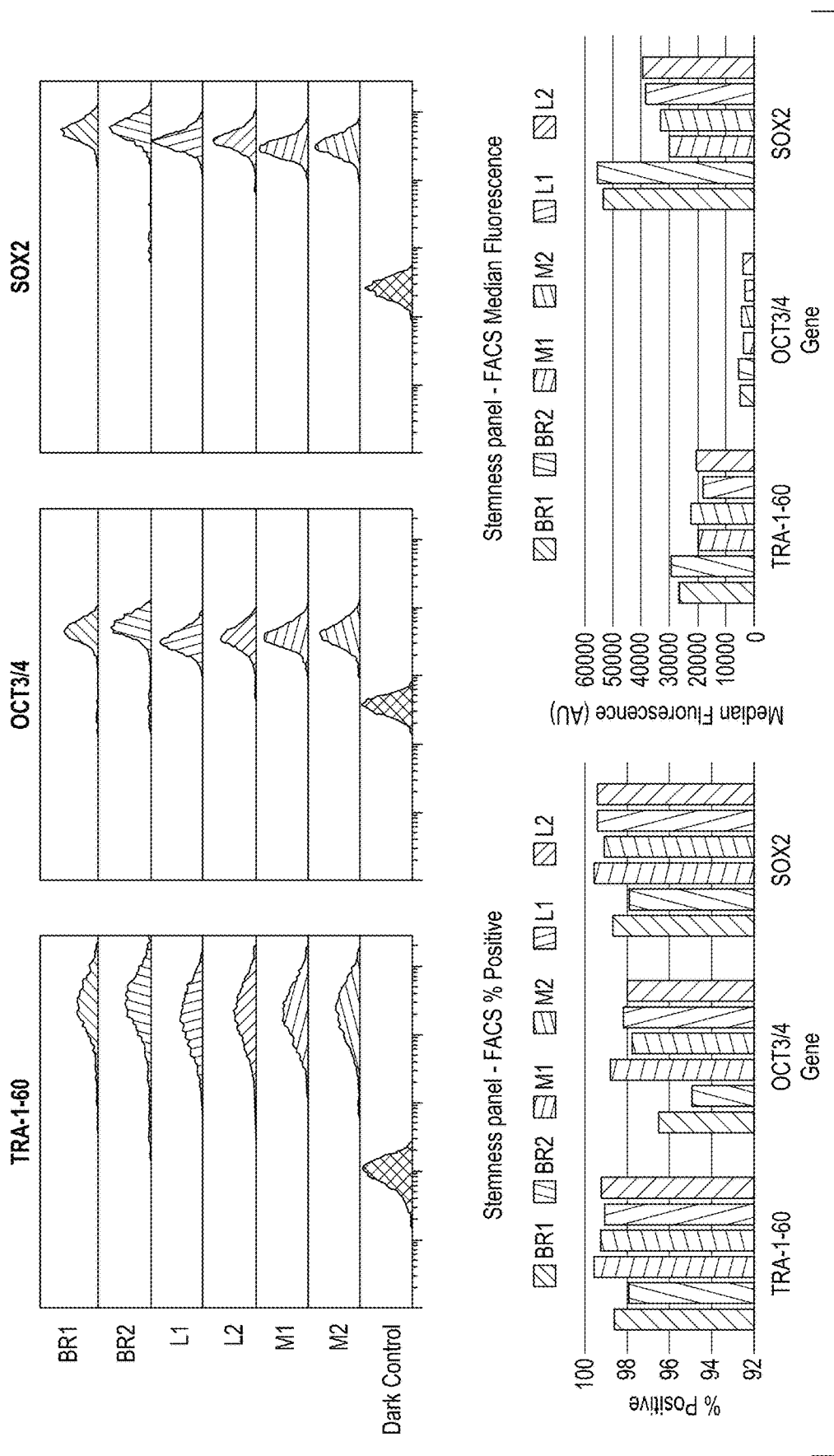
FIG. 22 at top are histograms showing the fluorescent expression distribution measured via flow cytometry of the cell population for individual stemness marker expression.

The results are shown in FIG. 22. FIG. 22 at top are histograms showing the fluorescent expression distribution measured via flow cytometry of the cell population for individual stemness marker expression. The x-axis shows the fluorescence signal and the y-axis shows cell count. BR1 indicates results for INSCRIPTA™ bioreactor 1, BR2 indicates results for INSCRIPTA™ bioreactor 2 (replicate), L1 indicates CORNING® BIOCOAT™ laminin plates (Corning, Inc., Glendale, Ariz.), L2 indicates CORNING® BIOCOAT™ laminin plates (Corning, Inc., Glendale, Ariz.) (replicate), M1 indicates CORNING® BIOCOAT™ MATRIGEL® 6-well plates (Corning, Inc., Glendale, Ariz.), and M2 indicates CORNING® BIOCOAT™ MATRIGEL® 6-well plates (Corning, Inc., Glendale, Ariz.) (replicate). A dark control was used for comparison where the cells in one well from the M1 6-well plate are prepared as the experimental cells but were not stained with antibodies. Looking at the graph at bottom left of FIG. 22, note that the percent of cells positive for the TRA-1-60 and SOX2 cell surface markers was similar across culture conditions. Cell surface marker OCT3/4 was a little lower (94-96%) in the cells grown in the INSCRIPTA™ bioreactors than in the laminin plates (98%) and in the MATRIGEL® plates (98%). The graph at right of FIG. 22 shows the median fluorescence obtained for each of TRA 1-60, OCT3/4 and SOX2 markers for each bioreactor, laminin plate and MATRIGEL® plate replicate.

Example XI: Ability of Cells to Maintain Differentiation Potential

To test whether cells grown in the INSCRIPTA™ bioreactor would retain differentiation potential, ten million cells were seeded on 0.5 g of 10 μg/ml laminin L-521 coated microcarriers (Corning, Inc., Glendale Ariz.), and expanded in INSCRIPTA™ Bioreactor in 100 ml mTeSR™Plus serum-free, feeder-free cell culture medium (STEMCELL Technologies Canada Inc., Vancouver, BC) at 37° C., 5% CO$_2$, and >95% relative humidity as described above. Once the cells reached >50 million cells as determined by cell counting, the impeller passaging protocol as described above in Example VII was implemented and 10M detached cells were re-seeded onto 0.5 g fresh laminin coated microcarriers. This process was repeated two more times, and after the final detachment the cells were seeded on 12-well plates for trilineage differentiation using a commercial protocol (STEMDIFF™ Trilineage Differentiation Kit, STEMCELL Technologies Canada Inc., Vancouver, BC). After trilineage differentiation, the cells from each lineage were stained with antibodies specific to markers specific to that lineage (available from BIOLEGEND®, San Diego Calif. and Miltenyi Biotec, San Diego, Calif.) following the manufacturer's instructions. The cells grown and impeller-passaged on the INSCRIPTA™ bioreactors showed expression of lineage-specific markers similar to the cells grown on Matrigel and laminin coated plates.

The tri-lineage differentiation antibody staining protocol was performed in the following manner, with the equipment listed in Table 4 and the antibodies listed in Table 4:

TABLE 4

Foxp3/Transcription Factor Fixation/Permeabilization Concentrate and Diluent, ThermoFisher Scientific, cat. # 00-5521-00
eBioscience ™ Flow Cytometry Staining Buffer, ThermoFisher Scientific, cat. # 00-4222-26
FACS staining buffer (2% FBS, 1 mM EDTA, 0.5% BSA)
FACS buffer (2% FBS, 1 mM EDTA)
FACSMelody ™ flow cytometer (Becton Dickinson, Inc., Franklin Lakes, NJ)

TABLE 5

| Marker | Cell Type | Antibody Link | Catalog # | Conjugate | Isotype | Isotype | Conc. |
|---|---|---|---|---|---|---|---|
| CXCR4 | Mesoderm | BioLegend | 306518 | BV421 | Mouse IgG2a, κ | BioLegend | 1:200 |
| NCAM1 | Mesoderm | BioLegend | 362510 | PE-Cy7 | Mouse IgG1, κ | BioLegend | 1:200 |
| Brachyury | Mesoderm | SantaCruz | sc-374321 AF488 | AF488 | Mouse IgG2b, κ | BioLegend | 1:25 |
| Nestin | Ectoderm | BioLegend | 656808 | BV421 | Mouse IgG2a, κ | BioLegend | 1:400 |
| Otx-2 | Ectoderm | Miltenyi | 130-121-202 | Vio B515 | recombinant hs IgG1 | Miltenyi | 1:100 |
| PAX6 | Ectoderm | Miltenyi | 130-123-250 | PE | recombinant hs IgG1 | Miltenyi | 1:400 |
| CXCR4 | Endoderm | BioLegend | 306518 | BV421 | Mouse IgG2a, κ | BioLegend | 1:400 |
| SOX17 | Endoderm | Miltenyi | 130-111-147 | Vio B515 | recombinant hs IgG1 | Miltenyi | 1:600 |
| FOXA2 | Endoderm | BD Biosciences | 561589 | PE | Mouse IgG1, κ | BD Biosciences | >1:20 |

A single-cell suspension was prepared by lifting cells with TrypLE™ SELECT (ThermoFisher Scientific, Waltham, Mass., USA) and was centrifuged for 5 minutes at 200×g. The cells were washed in DPBS and centrifuged a second time. The cells were fixed with a Foxp3 kit (ThermoFisher Scientific, Waltam Mass.) according to the manufacturer's instructions. Following incubation at room temperature in the dark for 30-60 minutes, 1 ml Foxp3 fixation/permeabilization working solution was added. Each sample contained ≤10M cells. A 1× working solution of permeabilization buffer was prepared by mixing one part of 10× Permeabilization Buffer with nine parts of distilled water and 2 ml of 1× permeabilization buffer was added to each tube. The samples were centrifuged at 400-600×g for 5 minutes at room temperature. The supernatant was discarded and the pellet was resuspended in residual volume of 1× permeabilization buffer for a total volume of approximately 100 µl. The cells were diluted so that there were no more than 10,000 cells/µl in a 96-well V- or U-bottom plate. A master mix of antibodies per cell lineage in FACS staining buffer was prepared. Approximately 500,000 cells were stained in 50 µl of staining solution. The cells were incubated on ice in the dark for at least 30 minutes. 150 µl of FACS buffer was added to each well. The cells were then centrifuged at 500×g for 5 minutes at room temperature and the supernatant was discarded. The cells were resuspended in FACS buffer and analyzed by a flow cytometer on the FACSMelody™ flow cytometer.

Figure 23A:
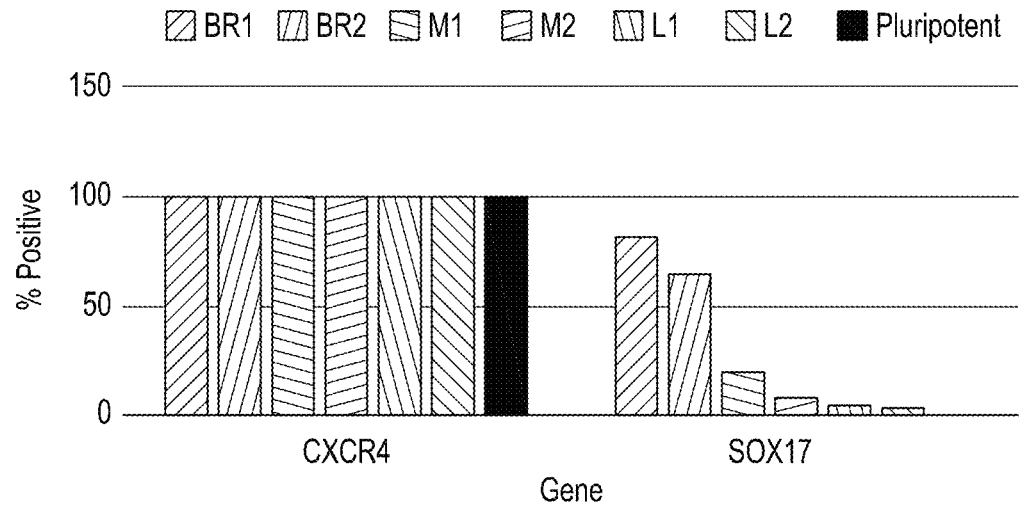
FIGS. 23A-23F shows a series of panels, both % positive and median fluorescence, demonstrating that iPSCs grown in the bioreactor described herein maintain differentiation potential comparable to iPSCs cultured on laminin plates and in MATRIGEL® plates (CORNING® BIOCOAT™ MATRIGEL® 6-well plates (Corning, Inc., Glendale, Ariz.)).
Figure 23B:
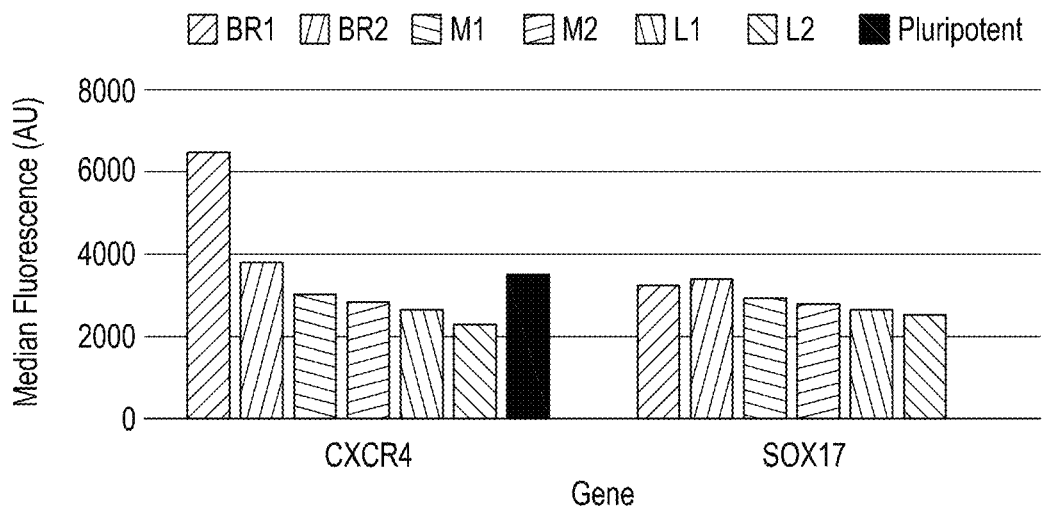
Figure 23C:
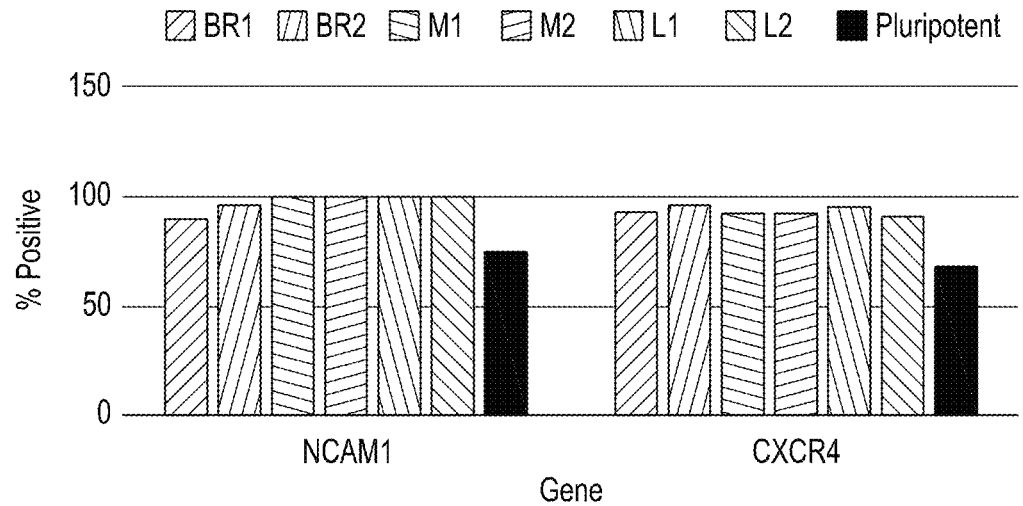
Figure 23D:
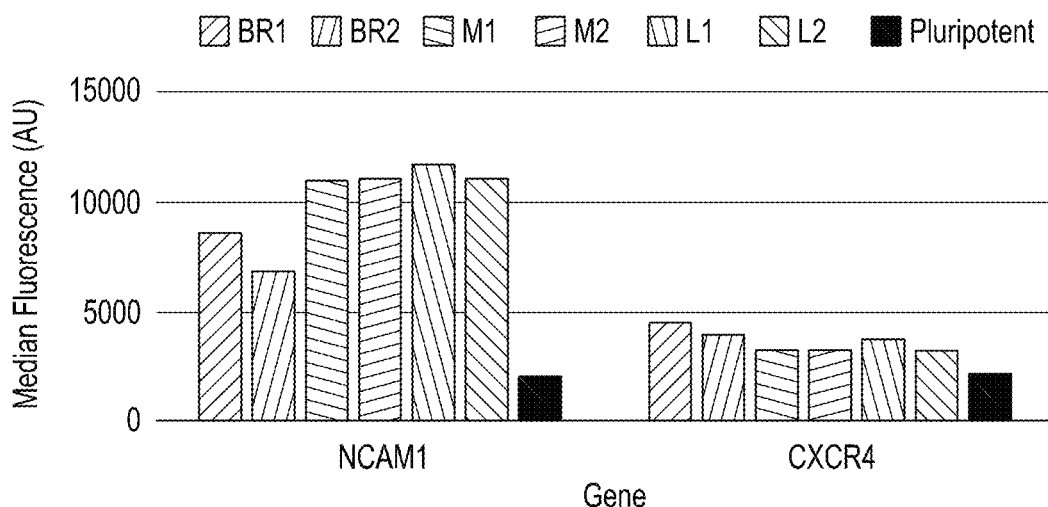
Figure 23E:
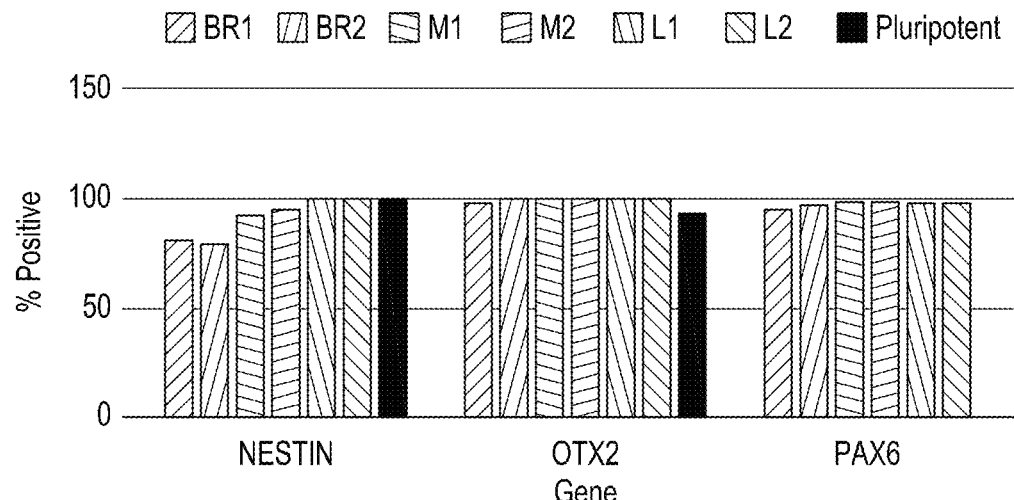
Figure 23F:
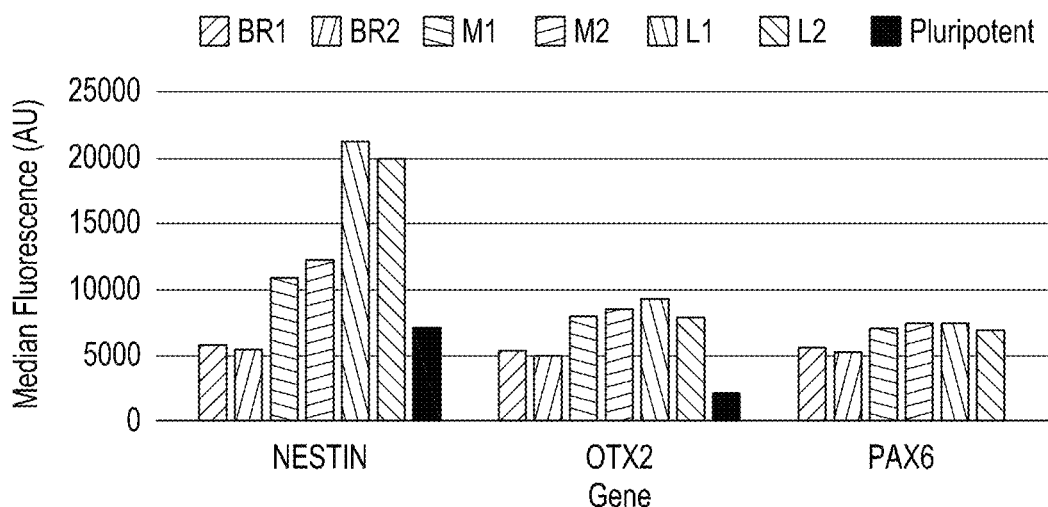

The results are shown in FIG. 23A-23F. FIGS. 23A, 23C and 23E are bar graphs showing % positive cells for endoderm markers CXCR4 and SOX17; mesoderm markers NCAM1 and CXCR4; and ectoderm markers NESTIN, OTX2 and PAX6. FIGS. 23B, 23D and 23F are bar graphs showing median fluorescence obtained for the endoderm, mesoderm and ectoderm markers. BR1 indicates results for INSCRIPTA™ bioreactor 1, BR2 indicates results for INSCRIPTA™ bioreactor 2 (replicate), L1 indicates CORNING® BIOCOAT™ laminin plates (Corning, Inc., Glendale, Ariz.), L2 indicates CORNING® BIOCOAT™ laminin plates (Corning, Inc., Glendale, Ariz.) (replicate), M1 indicates CORNING® BIOCOAT™ MATRIGEL® 6-well plates (Corning, Inc., Glendale, Ariz.), and M2 indicates CORNING® BIOCOAT™ MATRIGEL® 6-well plates (Corning, Inc., Glendale, Ariz.) (replicate). Note that the cells grown in the bioreactors maintain differentiation potential roughly equivalent to cells grown in the laminin plates and MATRIGEL® plates. A pluripotent control was used, where the pluripotent control were cells that were not differentiated using the STEMDIFF medium (STEMDIFF™ Trilinage Differentiation Kit, STEMCELL Technologies Canada Inc., Vancouver, BC) but were maintained in mTeSRPlus medium (STEMCELL Technologies Canada INC., Vancouver, BC).

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are snot to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A method for transfecting and performing nucleic acid-guided nuclease editing in mammalian iPSCs or primary cells in an automated closed cell editing instrument comprising the steps of:
   synthesizing a library of editing cassettes off instrument, wherein each editing cassette comprises a different gRNA and donor DNA pair;
   amplifying each editing cassette in the library of editing cassettes in a partition separate from other editing cassettes to form clonal copies of the editing cassettes in each partition;
   adding nuclease to each partition with amplified editing cassettes; adding transfection reagents to each partition to form a library of transfection reagent/nucleic acid/nuclease complexes;
   adding microcarriers to each partition, wherein the microcarriers are coated in extracellular matrix or a cell adhesion molecule coating and wherein the transfection reagent/nucleic acid/nuclease complexes in the partitions bind to the microcarriers;
   transferring cell growth medium, the microcarriers and the mammalian iPSCs or primary cells to a growth module in the automated closed cell editing instrument via a liquid handling system;
   maintaining suspension of the microcarriers in the growth module by stirring or bubbling;
   allowing the mammalian iPSCs or primary cells to seed on the coated microcarriers in the growth module;
   providing conditions for the mammalian iPSCs or primary cells to take-up the transfection reagent/nucleic acid/nuclease payloads in the growth module;
   providing conditions for the nucleic acids and nuclease to edit the mammalian iPSCs or primary cells in the growth module; and
   detaching the edited mammalian iPSCs or primary cells from the microcarriers, wherein the edited mammalian iPSCs or primary cells maintain stemness and differentiation potential.

2. The method of claim 1, wherein the growth module is a rotating growth module.

3. The method of claim 1, wherein the growth module is a tangential flow filtration module.

4. The method of claim 1, wherein the growth module is a bioreactor.

5. The method of claim 1, wherein the liquid handling system comprises an air displacement pipettor.

6. The method of claim 5, wherein the automated closed cell editing instrument comprises a reagent cartridge.

7. The method of claim 1, wherein the liquid handling system comprises a manifold with one or more connections to the bioreactor.

8. The method of claim 1, wherein the liquid handling system comprises reagent receptacles individually connected to the growth module.

9. The method of claim 1, wherein the mammalian iPSCs or primary cells are iPSCs.

10. The method of claim 1, wherein the mammalian iPSCs or primary cells are primary cells.

11. The method of claim 1, wherein the microcarriers are fabricated from natural organic materials, biocompatible synthetic polymers, or inorganic materials.

12. The method of claim 11, wherein the microcarriers are fabricated from polystyrene.

13. The method of claim 11, wherein the microcarriers are fabricated from a polyacrylate.

14. The method of claim 11, wherein the microcarriers are coated with laminin.

15. The method of claim 14, wherein the microcarriers are coated with laminin L-521.

16. The method of claim 1, wherein the microcarriers range in size from 30-1200 microns in diameter.

17. The method of claim 16, wherein the microcarriers range in size from 50-150 microns in diameter.

18. The method of claim 1, wherein after the edited mammalian iPSCs or primary cells are detached from the microcarriers, the cell growth medium is exchanged and fresh microcarriers are added to the growth module.

19. The method of claim 18, wherein the growth module is a rotating growth module and the mammalian iPSCs or primary cells are detached from the microcarriers by increasing rotation of the rotating growth vial.

20. The method of claim 19, wherein the growth module is a rotating growth module comprising fins, wherein the fins comprise frits.

21. The method of claim 18, wherein the growth module is a tangential flow filtration module and the mammalian iPSCs or primary cells are detached from the microcarriers by bubbling.

22. The method of claim 18, wherein the growth module is a bioreactor with at least one impeller and the mammalian iPSCs or primary cells are detached from the microcarriers by increasing revolutions per minute of the at least one impeller.

23. The method of claim 18, wherein the growth module is a bioreactor with at least two impellers and the mammalian iPSCs or primary cells are detached from the microcarriers by increasing revolutions per minute of the at least two impellers.

24. The method of claim 1, wherein the nuclease is provided as a protein.

25. The method of claim 1, wherein the nuclease is provided as a nucleic acid coding sequence under the control of a promoter.

26. The method of claim 1, wherein each different editing cassette in the library of editing cassettes comprises a different barcode.

27. The method of claim 1, wherein the steps of providing conditions for the mammalian iPSCs or primary cells to take-up the transfection reagent/nucleic acid/nuclease payloads in the growth module and providing conditions for the nucleic acids and nuclease to edit the mammalian iPSCs or primary cells in the growth module may take up to 2 days.

28. The method of claim 27, wherein the steps of providing conditions for the mammalian iPSCs or primary cells to take-up the transfection reagent/nucleic acid/nuclease payloads in the growth module and providing conditions for the nucleic acids and nuclease to edit the mammalian iPSCs or primary cells in the growth module may take up to 24 hours.

29. The method of claim 1, wherein the editing cassettes comprise from 5' to 3': a first primer binding region; a spacer region of the gRNA; a scaffold region of the gRNA; the donor DNA; a barcode; a second primer binding region; and a third primer binding region.

30. A method for transfecting and performing nucleic acid-guided nuclease editing in mammalian iPSCs or primary cells in an automated closed cell editing instrument comprising the steps of:
    synthesizing a library of editing cassettes off instrument, wherein each editing cassette comprises a different gRNA and donor DNA pair;
    amplifying each editing cassette in the library of editing cassettes in a partition separate from other editing cassettes to form clonal copies of the editing cassettes in each partition;
    adding nuclease to each partition with amplified editing cassettes;
    adding transfection reagents to each partition to form a library of transfection reagent/nucleic acid/nuclease complexes;
    adding microcarriers to each partition, wherein the microcarriers are coated in extracellular matrix or a cell adhesion molecule coating and wherein the transfection reagent/nucleic acid/nuclease complexes in the partitions bind to the microcarriers;
    transferring cell growth medium, the microcarriers and mammalian iPSCs or primary cells to a growth module in the automated closed cell editing instrument via a liquid handling system;
    maintaining suspension of the microcarriers in the growth module by stirring or bubbling;
    allowing the mammalian iPSCs or primary cells to seed on the coated microcarriers in the growth module;
    providing conditions for the mammalian iPSCs or primary cells to take-up the transfection reagent/nucleic acid/nuclease payloads in the growth module;
    providing conditions for the nucleic acids and nuclease to edit the mammalian iPSCs or primary cells in the growth module;
    detaching the edited mammalian iPSCs or primary cells from the microcarriers;
    exchanging the cell growth medium in the growth module and adding fresh microcarriers to the growth module;
    growing the edited mammalian iPSCs or primary cells; and
    detaching the edited mammalian iPSCs or primary cells from the microcarriers, wherein the edited mammalian iPSCs or primary cells maintain stemness and differentiation potential.

* * * * *